(12) United States Patent
Hatakeyama et al.

(10) Patent No.: US 12,001,139 B2
(45) Date of Patent: Jun. 4, 2024

(54) RESIST COMPOSITION AND PATTERNING PROCESS

(71) Applicant: Shin-Etsu Chemical Co., Ltd., Tokyo (JP)

(72) Inventors: Jun Hatakeyama, Joetsu (JP); Tomomi Watanabe, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 502 days.

(21) Appl. No.: 17/381,405

(22) Filed: Jul. 21, 2021

(65) Prior Publication Data

US 2022/0043343 A1 Feb. 10, 2022

(30) Foreign Application Priority Data

Aug. 4, 2020 (JP) .................................. 2020-132114
Mar. 16, 2021 (JP) .................................. 2021-041923

(51) Int. Cl.
| | |
|---|---|
| *G03F 7/004* | (2006.01) |
| *C07C 43/29* | (2006.01) |
| *C07C 43/295* | (2006.01) |
| *C07C 53/15* | (2006.01) |
| *C07C 59/115* | (2006.01) |

(Continued)

(52) U.S. Cl.
CPC ............ *G03F 7/0045* (2013.01); *C07C 43/29* (2013.01); *C07C 43/295* (2013.01); *C07C 53/15* (2013.01); *C07C 59/115* (2013.01); *C07C 63/70* (2013.01); *C07C 65/05* (2013.01); *C07C 69/63* (2013.01); *C07C 205/58* (2013.01); *C07C 229/60* (2013.01); *C07C 311/09* (2013.01); *C07D 205/04* (2013.01); *C07D 295/13* (2013.01); *C08F 220/1804* (2020.02); *C08F 220/22* (2013.01); *C08F 220/30* (2013.01); *G03F 7/0382* (2013.01); *G03F 7/0392* (2013.01)

(58) Field of Classification Search
CPC ... G03F 7/0045; C07C 381/12; C07C 311/09; C07D 295/088; C08F 220/1804; C08F 220/22; C08F 220/30
See application file for complete search history.

(56) References Cited

U.S. PATENT DOCUMENTS

| | | | |
|---|---|---|---|
| 7,468,236 B2 * | 12/2008 | Watanabe | ............. G03F 7/0046 430/281.1 |
| 8,921,026 B2 | 12/2014 | Hatakeyama et al. | |

(Continued)

FOREIGN PATENT DOCUMENTS

| | | |
|---|---|---|
| JP | 2001-166476 A | 6/2001 |
| JP | 2001-194776 A | 7/2001 |

(Continued)

OTHER PUBLICATIONS

Machine translation of JP Office Action (no date) (Year: 0000).*
Office Action dated May 6, 2022, issued in counterpart TW Application No. 110128299. (11 pages).

*Primary Examiner* — Amanda C. Walke
(74) *Attorney, Agent, or Firm* — WHDA, LLP

(57) ABSTRACT

A resist composition is provided comprising a base polymer and a quencher comprising a cyclic ammonium salt having a fluorinated saturated hydrocarbyl group or fluorinated aryl group. The resist composition has a high sensitivity and forms a pattern with improved LWR or CDU, independent of whether it is of positive or negative tone.

14 Claims, 1 Drawing Sheet

(51) Int. Cl.
*C07C 63/70* (2006.01)
*C07C 65/05* (2006.01)
*C07C 69/63* (2006.01)
*C07C 205/58* (2006.01)
*C07C 229/60* (2006.01)
*C07C 311/09* (2006.01)
*C07D 205/04* (2006.01)
*C07D 295/13* (2006.01)
*C08F 220/18* (2006.01)
*C08F 220/22* (2006.01)
*C08F 220/30* (2006.01)
*G03F 7/038* (2006.01)
*G03F 7/039* (2006.01)

(56) References Cited

U.S. PATENT DOCUMENTS

| | | | | |
|---|---|---|---|---|
| 11,415,887 B2* | 8/2022 | Hatakeyama | ......... | G03F 7/0382 |
| 11,644,753 B2* | 5/2023 | Hatakeyama | ......... | G03F 7/0392 |
| | | | | 430/286.1 |
| 11,846,884 B2* | 12/2023 | Hatakeyama | ......... | G03F 7/2004 |
| 2007/0087287 A1 | 4/2007 | Watanabe et al. | | |
| 2020/0050104 A1 | 2/2020 | Hatakeyama et al. | | |
| 2020/0272048 A1* | 8/2020 | Hatakeyama | ......... | G03F 7/0397 |
| 2021/0302838 A1* | 9/2021 | Hatakeyama | ......... | G03F 7/0045 |

FOREIGN PATENT DOCUMENTS

| | | |
|---|---|---|
| JP | 2002-363148 A | 12/2002 |
| JP | 2007-108451 A | 4/2007 |
| JP | 2012-137729 A | 7/2012 |
| TW | 200734820 A | 9/2007 |
| TW | 202012355 A | 4/2020 |
| WO | 2008/066011 A1 | 6/2008 |
| WO | WO-2018033200 A1 * | 2/2018 ........... C07C 217/08 |

* cited by examiner

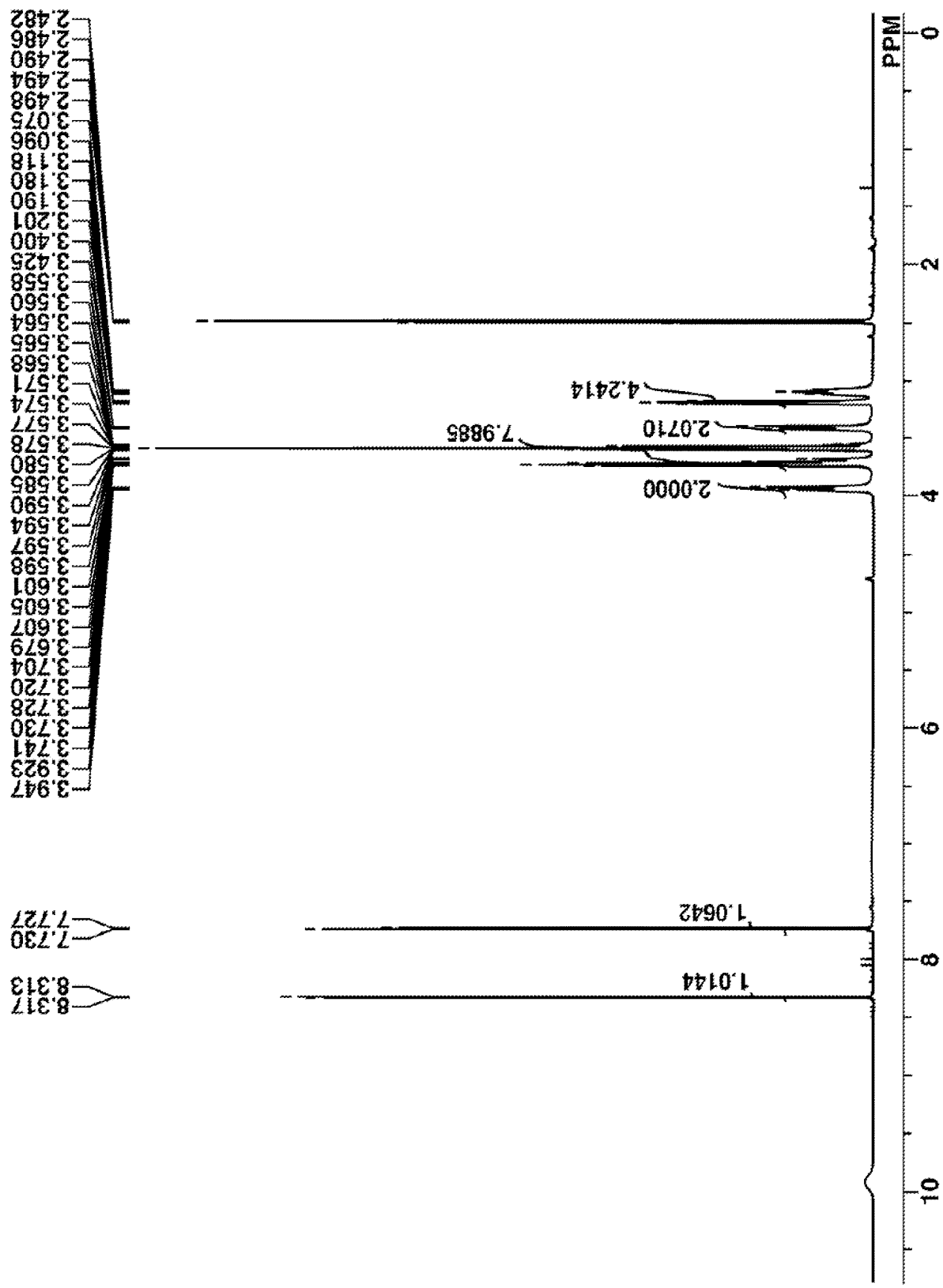

RESIST COMPOSITION AND PATTERNING PROCESS

CROSS-REFERENCE TO RELATED APPLICATION

This non-provisional application claims priority under 35 U.S.C. § 119(a) on Patent Application Nos. 2020-132114 and 2021-041923 filed in Japan on Aug. 4, 2020 and Mar. 16, 2021, respectively, the entire contents of which are hereby incorporated by reference.

TECHNICAL FIELD

This invention relates to a resist composition and a pattern forming process.

BACKGROUND ART

To meet the demand for higher integration density and operating speed of LSIs, the effort to reduce the pattern rule is in rapid progress. In particular, the enlargement of the logic memory market to comply with the wide-spread use of smart phones drives forward the miniaturization technology. As the advanced miniaturization technology, manufacturing of microelectronic devices at the 10-nm node by double patterning of the ArF immersion lithography has been implemented in a mass scale. Manufacturing of 7-nm node devices as the next generation by the double patterning technology is approaching to the verge of high-volume application. The candidate for 5-nm node devices as the next generation but one is EUV lithography.

With the progress of miniaturization in logic devices, the flash memory now takes the form of devices having stacked layers of gate, known as 3D-NAND. The capacity is increased by increasing the number of stacked layers. As the number of stacked layers increases, the hard mask used in processing of layers becomes thicker and the photoresist film also becomes thicker. While the resist for logic devices becomes thinner, the resist for 3D-NAND becomes thicker.

As the pattern feature size is reduced, approaching to the diffraction limit of light, light contrast lowers. In the case of positive resist film, a lowering of light contrast leads to reductions of resolution and focus margin of hole and trench patterns. The trend of the resist toward thicker films suggests that the thickness of resist film for previous generation devices is resumed. As more critical dimension uniformity (CDU) is required, the previous photoresist cannot accommodate the requirements. For preventing a reduction of resolution of resist pattern due to a lowering of light contrast as a result of size reduction, or for improving CDU in the trend toward thicker resist film, an attempt is made to enhance the dissolution contrast of resist film.

Chemically amplified resist compositions comprising an acid generator capable of generating an acid upon exposure to light or EB include chemically amplified positive resist compositions wherein deprotection reaction takes place under the action of acid and chemically amplified negative resist compositions wherein polarity switch or crosslinking reaction takes place under the action of acid. Quenchers are often added to these resist compositions for the purpose of controlling the diffusion of the acid to unexposed region to improve the contrast. The addition of quenchers is fully effective to this purpose. A number of amine quenchers were proposed as disclosed in Patent Documents 1 and 2.

There are known amine quenchers for inviting a polarity switch under the action of acid catalyst. Patent Document 3 proposes an amine quencher having an acid labile group. This amine compound generates a carboxylic acid via the acid-aided deprotection reaction of a tertiary ester having a carbonyl group positioned on the nitrogen atom side whereby alkaline solubility increases. In this case, however, since the molecular weight on the nitrogen atom side is not increased, the acid diffusion controlling ability is low, and the contrast improving effect is faint. Patent Document 4 describes a quencher having a tert-butoxycarbonyl group which undergoes deprotection reaction with the aid of acid, to generate an amino group. This mechanism is adapted to generate a quencher upon light exposure, achieving a reverse effect to contrast enhancement. The contrast is enhanced by the mechanism that the quencher disappears or loses its quenching ability upon light exposure or under the action of acid. Patent Document 5 discloses a quencher in the form of an amine compound which cyclizes under the action of acid to form a lactam structure. The conversion of the strong base amine compound to the weak base lactam compound causes the acid to change its activity whereby the contrast is improved.

With respect to the acid labile group used in (meth)acrylate polymers for the ArF lithography resist material, deprotection reaction takes place when a photoacid generator capable of generating a sulfonic acid having fluorine substituted at α-position (referred to "α-fluorinated sulfonic acid") is used, but not when an acid generator capable of generating a sulfonic acid not having fluorine substituted at α-position (referred to "α-non-fluorinated sulfonic acid") or carboxylic acid is used. If a sulfonium or iodonium salt capable of generating an α-fluorinated sulfonic acid is combined with a sulfonium or iodonium salt capable of generating an α-non-fluorinated sulfonic acid, the sulfonium or iodonium salt capable of generating an α-non-fluorinated sulfonic acid undergoes ion exchange with the α-fluorinated sulfonic acid. Through the ion exchange, the α-fluorinated sulfonic acid thus generated by light exposure is converted back to the sulfonium or iodonium salt while the sulfonium or iodonium salt of an α-non-fluorinated sulfonic acid or carboxylic acid functions as a quencher. Patent Document 6 discloses a resist composition comprising a sulfonium or iodonium salt capable of generating carboxylic acid as a quencher.

Sulfonium and iodonium salt type quenchers are photodecomposable like photoacid generators. That is, the amount of quencher in the exposed region is reduced. Since acid is generated in the exposed region, the reduced amount of quencher leads to a relatively increased concentration of acid and hence, an improved contrast. However, the acid diffusion in the exposed region is not suppressed, indicating the difficulty of acid diffusion control.

Since a sulfonium or iodonium salt type quencher absorbs ArF radiation of wavelength 193 nm, a resist film in which the quencher is combined with a sulfonium or iodonium salt type acid generator has a reduced transmittance to that radiation. As a result, in the case of a resist film having a thickness of at least 100 nm, the cross-sectional profile of a pattern as developed becomes tapered. For resist films having a thickness of at least 100 nm, especially at least 150 nm, a highly transparent quencher is necessary.

Lowering the PEB temperature is effective for suppressing acid diffusion. However, the dissolution contrast is reduced, inviting degradations of resolution and LWR. There is the need for a resist composition of new concept featuring controlled acid diffusion and a high contrast.

CITATION LIST

Patent Document 1: JP-A 2001-194776
Patent Document 2: JP-A 2007-108451

Patent Document 3: JP-A 2002-363148
Patent Document 4: JP-A 2001-166476
Patent Document 5: JP-A 2012-137729 (U.S. Pat. No. 8,921,026)
Patent Document 6: WO 2008/066011

DISCLOSURE OF INVENTION

For the acid-catalyzed chemically amplified resist material, it is desired to develop a quencher capable of reducing the LWR of line patterns or improving the CDU of hole patterns and increasing sensitivity. To this end, it is necessary to reduce the distance of acid diffusion significantly and to increase the contrast at the same time, that is, to improve ambivalent properties at the same time.

An object of the invention is to provide a resist composition which exhibits a high sensitivity and a reduced LWR or improved CDU, independent of whether it is of positive tone or negative tone; and a pattern forming process using the same.

The inventors have found that using a cyclic ammonium salt having a fluorinated saturated hydrocarbyl group or fluorinated aryl group (referred to as "fluorinated cyclic ammonium salt compound," hereinafter) as the quencher, a resist material having a reduced LWR, improved CDU, high contrast, improved resolution, and wide process margin is obtained.

In one aspect, the invention provides a resist composition comprising a base polymer and a quencher, the quencher comprising a salt compound having the formula (A).

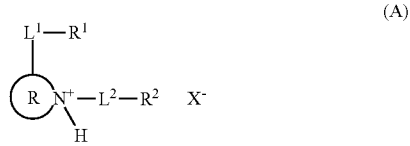

Herein the ring R is a $C_2$-$C_{12}$ alicyclic group containing the nitrogen atom, the ring may contain an ether bond, thioether bond, carbonyl group, —N(R')— or sulfonyl group, R' is hydrogen, a $C_1$-$C_6$ saturated hydrocarbyl group or -$L^3$-$R^3$.

$L^1$, $L^2$ and $L^3$ are each independently a single bond, ester bond, sulfonyl group, or $C_1$-$C_6$ alkanediyl group, some hydrogen in the alkanediyl group may be substituted by a hydroxy moiety, optionally fluorinated $C_1$-$C_{12}$ hydrocarbyloxy moiety, or optionally fluorinated $C_2$-$C_{12}$ hydrocarbylcarbonyloxy moiety, and any methylene constituent in the alkanediyl group may be replaced by an ether bond, ester bond, amide bond, sulfonyl moiety, sulfonate bond, or sulfonamide bond, with the proviso that $L^1$, $L^2$ and $L^3$ do not contain a tertiary ester structure.

$R^1$, $R^2$ and $R^3$ are each independently hydrogen, a $C_1$-$C_{16}$ saturated hydrocarbyl group, $C_6$-$C_{10}$ aryl group, $C_1$-$C_{16}$ saturated hydrocarbyl group substituted with at least three fluorine atoms, $C_6$-$C_{10}$ aryl group substituted with at least three fluorine atoms, or a combination thereof, one or both of $R^1$ and $R^2$ have at least three fluorine atoms.

$X^-$ is a carboxylate, sulfonamide, halogenated phenoxide or halide anion.

In a preferred embodiment, $X^-$ is a fluorinated or brominated carboxylate, fluorinated or brominated sulfonamide, or fluorinated or brominated phenoxide anion.

The resist composition may further comprise an acid generator capable of generating a sulfonic acid, imide acid or methide acid, an organic solvent, and/or a surfactant.

In one preferred embodiment, the base polymer comprises repeat units having the formula (a1) or repeat units having the formula (a2).

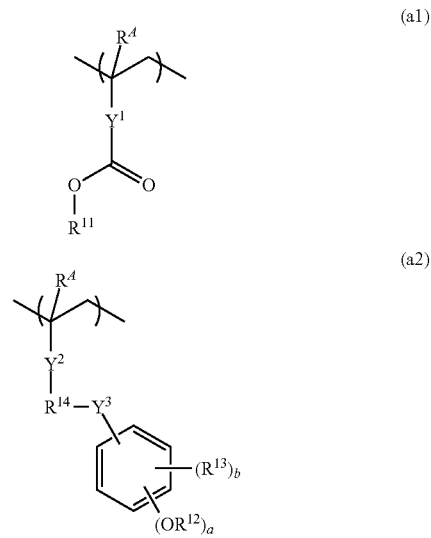

Herein $R^A$ is each independently hydrogen or methyl. $Y^1$ is a single bond, phenylene, naphthylene, or a $C_1$-$C_{12}$ linking group containing an ester bond and/or lactone ring. $Y^2$ is a single bond or ester bond. $Y^3$ is a single bond, ether bond or ester bond. $R^{11}$ and $R^{12}$ are each independently an acid labile group. $R^{13}$ is fluorine, trifluoromethyl, cyano or $C_1$-$C_6$ saturated hydrocarbyl group. $R^{14}$ is a single bond or a $C_1$-$C_6$ alkanediyl group in which some carbon may be replaced by an ether bond or ester bond, a is 1 or 2, b is an integer of 0 to 4, and 1≤a+b≤5.

In one preferred embodiment, the resist composition is a chemically amplified positive resist composition.

In another preferred embodiment, the base polymer is free of an acid labile group. Typically, the resist composition is a chemically amplified negative resist composition.

In a preferred embodiment, the base polymer comprises repeat units of at least one type selected from repeat units having the formulae (f1) to (f3).

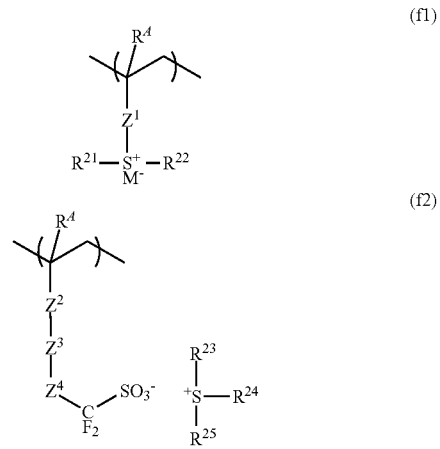

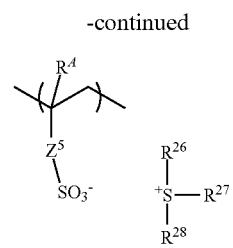

(f3)

Herein $R^A$ is each independently hydrogen or methyl. $Z^1$ is a single bond, a $C_1$-$C_6$ aliphatic hydrocarbylene group, phenylene group, naphthylene group, or $C_7$-$C_{18}$ group obtained by combining the foregoing, or —O—$Z^{11}$—, —C(=O)—O—$Z^{11}$— or —C(=O)—NH—$Z^{11}$—, wherein $Z^{11}$ is a $C_1$-$C_6$ aliphatic hydrocarbylene group, phenylene group, naphthylene group, or $C_7$-Cis group obtained by combining the foregoing, which may contain a carbonyl moiety, ester bond, ether bond or hydroxy moiety. $Z^2$ is a single bond or ester bond. $Z^3$ is a single bond, —$Z^{31}$—C(=O)—O—, —$Z^{31}$—O— or —$Z^{31}$—O—C(=O)—, wherein $Z^{31}$ is a $C_1$-$C_{12}$ hydrocarbylene group, phenylene group, or $C_7$-Cis group obtained by combining the foregoing, which may contain a carbonyl moiety, ester bond, ether bond, iodine or bromine. $Z^4$ is a methylene, 2,2,2-trifluoro-1,1-ethanediyl or carbonyl group. Z is a single bond, methylene, ethylene, phenylene, fluorinated phenylene, trifluoromethyl-substituted phenylene group. —O—$Z^{51}$—, —C(=O)—O—$Z^{51}$—, or —C(=O)—NH—$Z^{11}$—, wherein $Z^{51}$ is a $C_1$-$C_6$ aliphatic hydrocarbylene group, phenylene group, fluorinated phenylene group, or trifluoromethyl-substituted phenylene group, which may contain a carbonyl moiety, ester bond, ether bond or hydroxy moiety. $R^{21}$ to $R^{28}$ are each independently halogen or a $C_1$-$C_{20}$ hydrocarbyl group which may contain a heteroatom, a pair of $R^{23}$ and $R^{24}$ or $R^{26}$ and $R^{27}$ may bond together to form a ring with the sulfur atom to which they are attached. $M^-$ is a non-nucleophilic counter ion.

In another aspect, the invention provides a pattern forming process comprising the steps of applying the resist composition defined above to form a resist film on a substrate, exposing the resist film to high-energy radiation, and developing the exposed resist film in a developer.

Preferably, the high-energy radiation is i-line of wavelength 365 nm, ArF excimer laser of wavelength 193 nm, KrF excimer laser of wavelength 248 nm, EB, or EUV of wavelength 3 to 15 nm.

In a further aspect, the invention provides a salt compound having the formula (A').

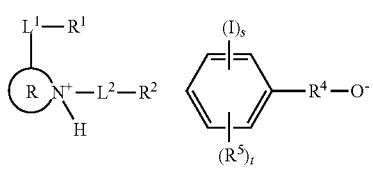

(A')

Herein R, $L^1$, $L^2$, $R^1$, and $R^2$ are as defined above. $R^4$ is a single bond or carbonyl group. $R^5$ is hydrogen, hydroxy group, optionally halogenated $C_1$-$C_6$ saturated hydrocarbyl group, optionally halogenated $C_1$-$C_6$ saturated hydrocarbyloxy group, optionally halogenated $C_2$-$C_7$ saturated hydrocarbylcarbonyloxy group, optionally halogenated $C_1$-$C_4$ saturated hydrocarbylsulfonyloxy group, fluorine, chlorine, bromine, amino group, nitro group, cyano group, —N($R^{51}$)—C(=O)—$R^{52}$, or —N($R^{51}$)—C(=O)—O—$R^{52}$. $R^{51}$ is hydrogen or a $C_1$-$C_6$ saturated hydrocarbyl group. $R^{52}$ is a $C_1$-$C_6$ saturated hydrocarbyl group or $C_2$-$C_6$ unsaturated aliphatic hydrocarbyl group. The subscript s is an integer of 1 to 5, t is an integer of 0 to 3, and $1 \leq s+t \leq 5$.

Advantageous Effects of Invention

The fluorinated cyclic ammonium salt compound is a quencher capable of suppressing acid diffusion. Since the compound has a fluorinated saturated hydrocarbyl group or fluorinated aryl group, the quencher does not agglomerate together by virtue of the electric repulsion of fluorine atoms and is uniformly distributed in a resist film. The preferred compound whose anion contains iodine or bromine is fully absorptive to exposure light, which leads to a high sensitivity, low acid diffusion, reduced LWR and improved CDU. A resist composition having a high sensitivity, low LWR and improved CDU is thus designed.

BRIEF DESCRIPTION OF DRAWINGS

FIGURE is a diagram showing the $^1$H-NMR spectrum of Quencher Q-1 in Synthesis Example 1.

DESCRIPTION OF EMBODIMENTS

As used herein, the singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation ($C_n$-$C_m$) means a group containing from n to m carbon atoms per group. The term "group" and "moiety" are interchangeable. The term fluorinated, chlorinated, brominated or iodized compound designates a fluorine, chlorine, bromine or iodine-substituted (or containing) compound. In chemical formulae, the broken line designates a valence bond, and Me stands for methyl and Ac for acetyl.

The abbreviations and acronyms have the following meaning.

EB: electron beam
EUV: extreme ultraviolet
Mw: weight average molecular weight
Mn: number average molecular weight
Mw/Mn: molecular weight dispersity
GPC: gel permeation chromatography
PEB: post-exposure bake
PAG: photoacid generator
LWR: line width roughness
CDU: critical dimension uniformity Resist Composition The resist composition of the invention is defined as comprising a base polymer and a quencher containing a fluorinated cyclic ammonium salt compound.

Fluorinated Cyclic Ammonium Salt Compound

The fluorinated cyclic ammonium salt compound has the formula (A).

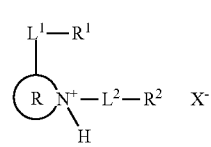

(A)

In formula (A), the ring R is a $C_2$-$C_{12}$ alicyclic group containing the nitrogen atom in the formula, and the ring may contain an ether bond, thioether bond, carbonyl group, —N(R')— or sulfonyl group. R' is hydrogen, a $C_1$-$C_6$ saturated hydrocarbyl group or -$L^3$-$R^3$. Examples of the $C_1$-$C_6$ saturated hydrocarbyl group are as will be exemplified later for the $C_1$-$C_{16}$ saturated hydrocarbyl group represented by $R^1$ to $R^3$, but of 1 to 6 carbon atoms.

Suitable alicyclic groups correspond to cyclic saturated hydrocarbons of 3 to 13 carbon atoms in which one carbon is replaced by nitrogen and in which some other carbon may be replaced by an ether bond, thioether bond, carbonyl moiety, —N(R')—, or sulfonyl moiety. Suitable cyclic saturated hydrocarbons include cyclopropane, cyclobutane, cyclopentane, cyclohexane, norbornane, and adamantane.

In formula (A), $L^1$, $L^2$ and $L^3$ are each independently a single bond, ester bond, sulfonyl group, or $C_1$-$C_6$ alkanediyl group. Some hydrogen in the alkanediyl group may be substituted by a hydroxy moiety, optionally fluorinated $C_1$-$C_{12}$ hydrocarbyloxy moiety, or optionally fluorinated $C_2$-$C_{12}$ hydrocarbylcarbonyloxy moiety, and any methylene constituent in the alkanediyl group may be replaced by an ether bond, ester bond, amide bond, sulfonyl bond, sulfonate bond, or sulfonamide bond. It is noted that $L^1$, $L^2$ and $L^3$ do not contain a tertiary ester structure.

Examples of the $C_1$-$C_6$ alkanediyl group represented by $L^1$, $L^2$ and $L^3$ include methanediyl, ethane-1,1-diyl, ethane-1,2-diyl, propane-1,2-diyl, propane-1,3-diyl, butane-1,4-diyl, pentane-1,5-diyl, and hexane-1,6-diyl.

The hydrocarbyl moiety in the optionally fluorinated $C_1$-$C_{12}$ hydrocarbyloxy group and optionally fluorinated $C_2$-$C_{12}$ hydrocarbylcarbonyloxy group may be saturated or unsaturated and straight, branched or cyclic. Examples thereof include $C_1$-$C_{12}$ alkyl groups such as methyl, ethyl, n-propyl, isopropyl, n-butyl, isobutyl, sec-butyl, tert-butyl, n-pentyl, n-hexyl, n-octyl, n-nonyl, n-decyl, undecyl and dodecyl; $C_3$-$C_{12}$ cyclic saturated hydrocarbyl groups such as cyclopropyl, cyclopentyl, cyclohexyl, cyclopropylmethyl, 4-methylcyclohexyl, cyclohexylmethyl, norbornyl and adamantyl; $C_2$-$C_{12}$ alkenyl groups such as vinyl, propenyl, butenyl, pentenyl and hexenyl; $C_6$-$C_{12}$ aryl groups such as phenyl, methylphenyl, dimethylphenyl, ethylphenyl, diethylphenyl, n-propylphenyl, isopropylphenyl, and naphthyl; $C_7$-$C_{12}$ aralkyl groups such as benzyl and phenethyl; and combinations thereof.

In formula (A). $R^1$, $R^2$ and $R^3$ are each independently hydrogen, a $C_1$-$C_{16}$ saturated hydrocarbyl group. $C_6$-$C_{10}$ aryl group, $C_1$-$C_{16}$ saturated hydrocarbyl group substituted with at least three fluorine atoms, $C_6$-$C_{10}$ aryl group substituted with at least three fluorine atoms, or a combination thereof. One or both of $R^1$ and $R^2$ have at least three fluorine atoms.

The $C_1$-$C_{16}$ saturated hydrocarbyl group represented by $R^1$, $R^2$ and $R^3$ may be straight, branched or cyclic. Examples thereof include $C_1$-$C_{16}$ alkyl groups such as methyl, ethyl, n-propyl, isopropyl, n-butyl, isobutyl, sec-butyl, tert-butyl, n-pentyl, n-hexyl, n-octyl, n-nonyl, n-decyl, undecyl, dodecyl, tridecyl, tetradecyl and pentadecyl; $C_3$-$C_{16}$ cyclic saturated hydrocarbyl groups such as cyclopropyl, cyclopentyl, cyclohexyl, cyclopropylmethyl, 4-methylcyclohexyl, cyclohexylmethyl, norbornyl and adamantyl: and combinations thereof. Examples of the $C_6$-$C_{10}$ aryl group include phenyl, methylphenyl, dimethylphenyl, ethylphenyl, diethylphenyl, n-propylphenyl, isopropylphenyl, and naphthyl.

Examples of the cation in the salt compound having formula (A) are shown below, but not limited thereto.

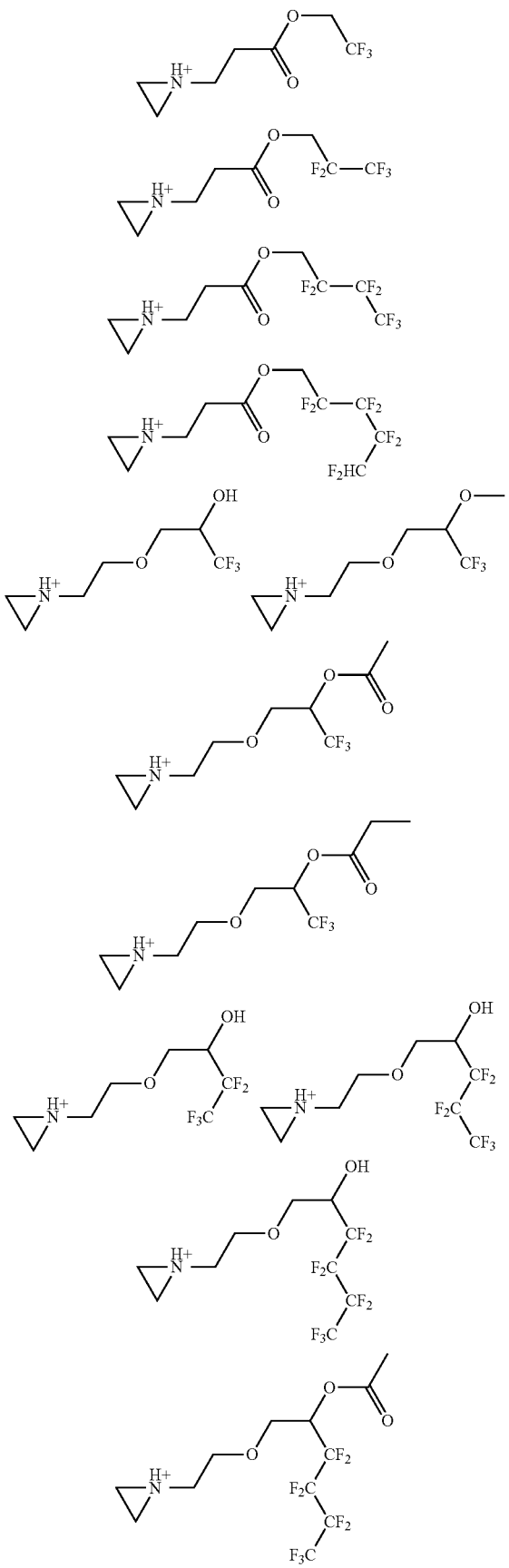

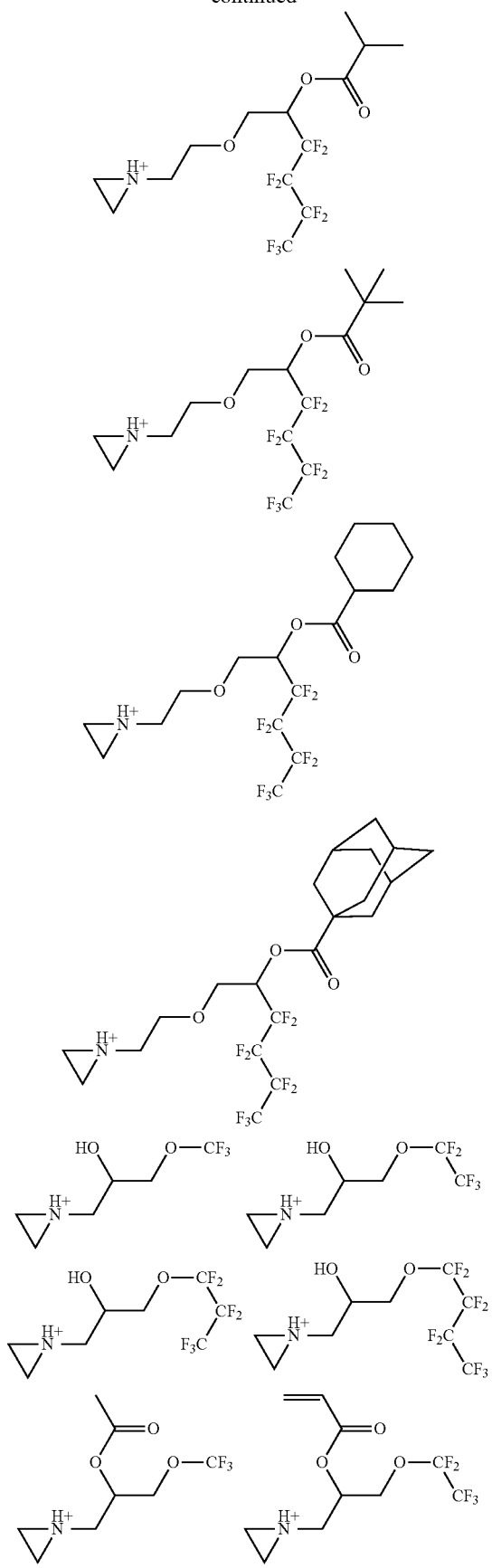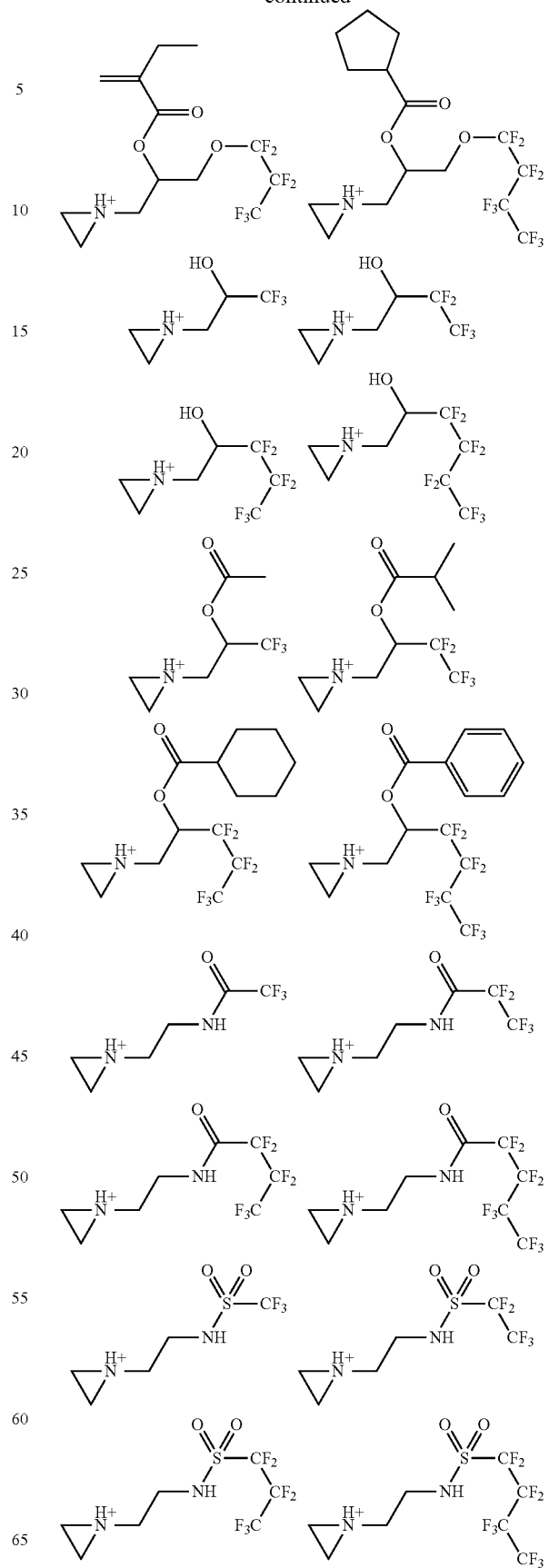

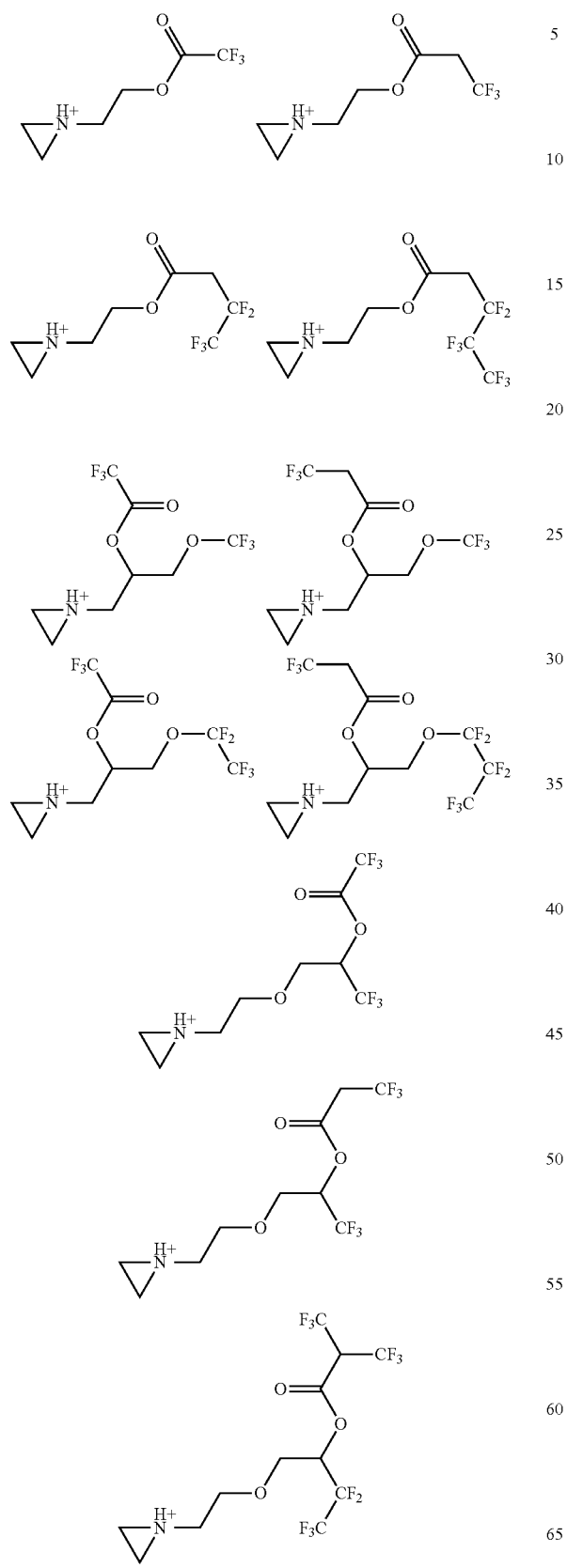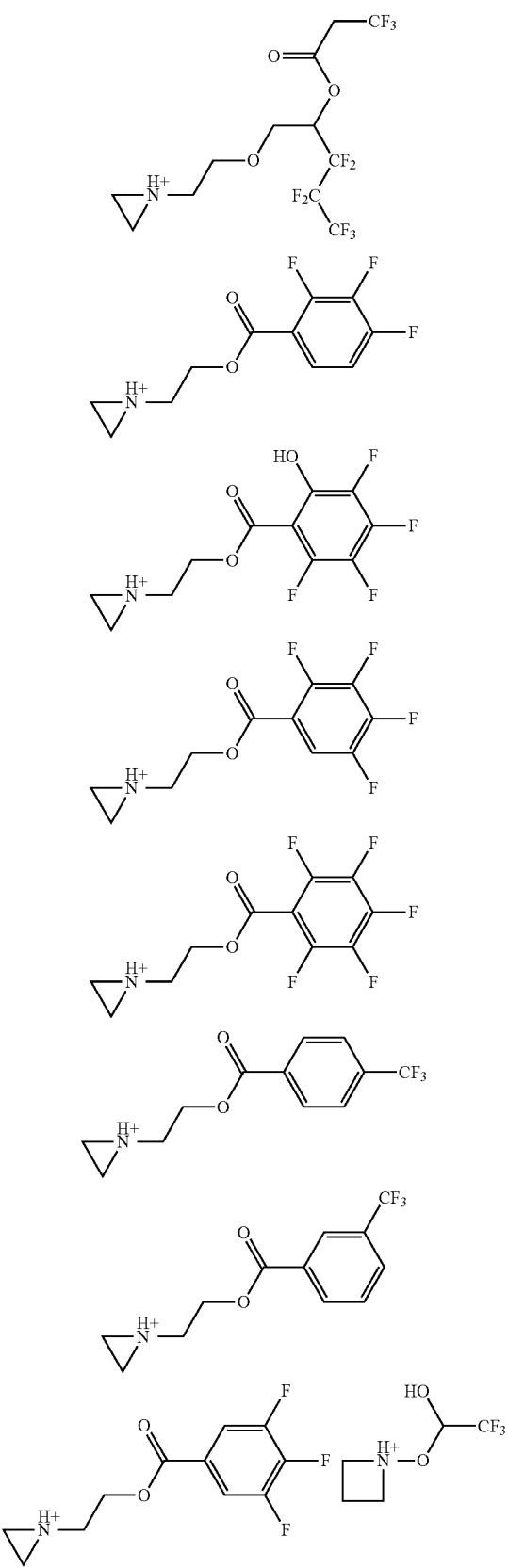

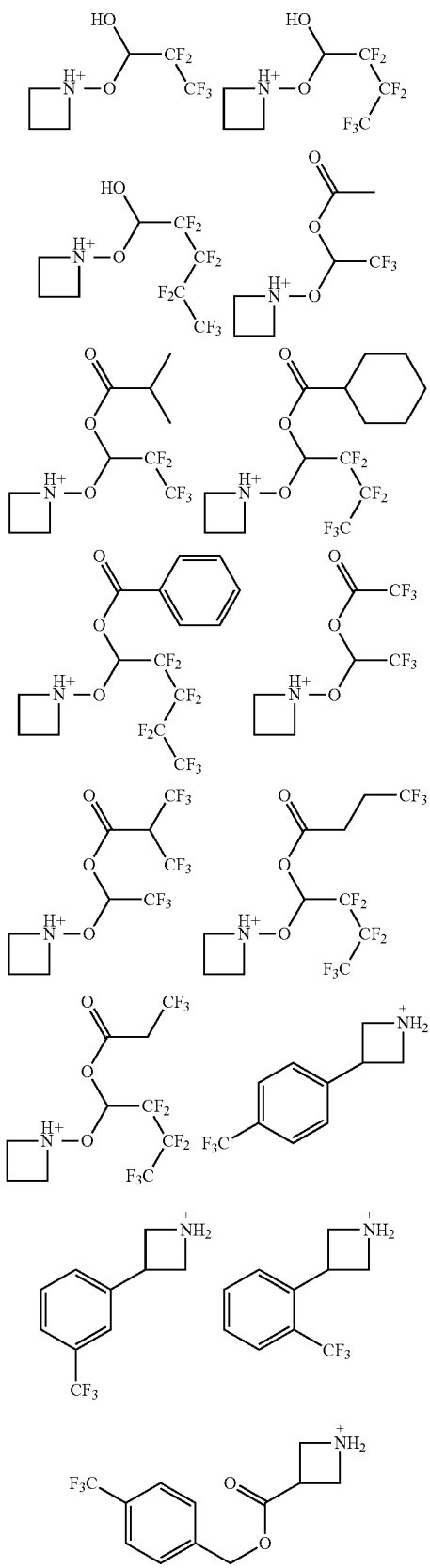
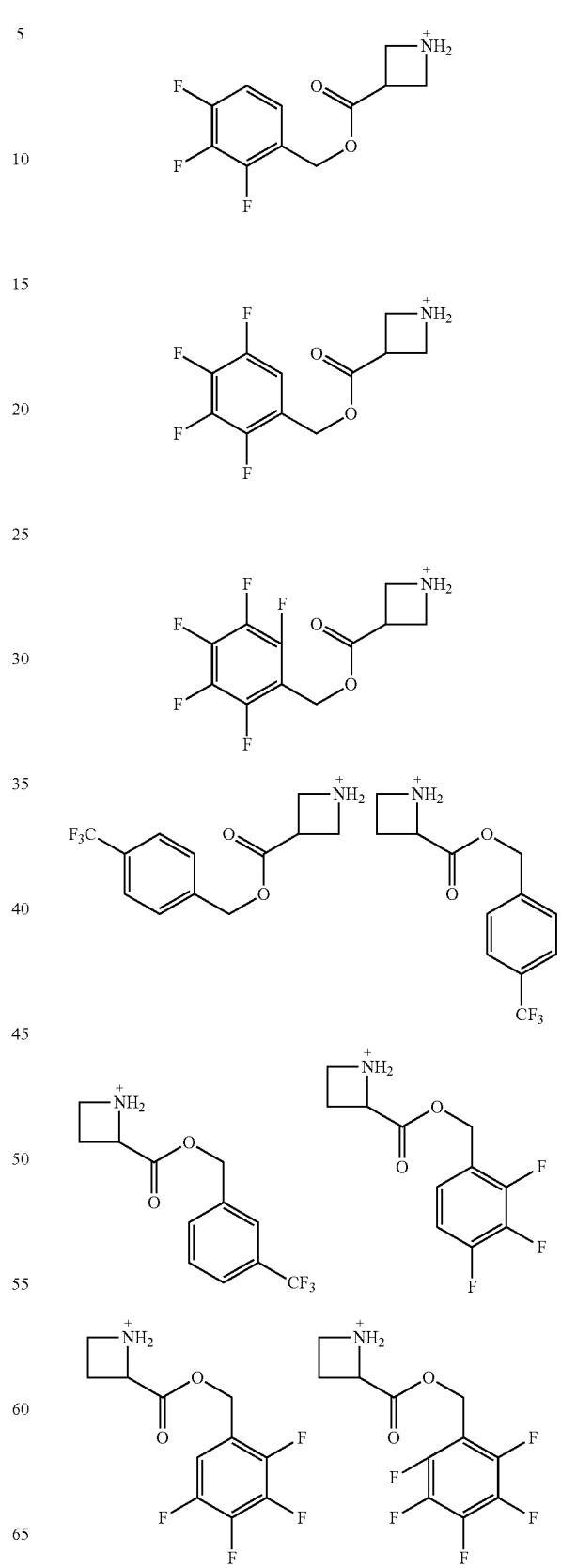

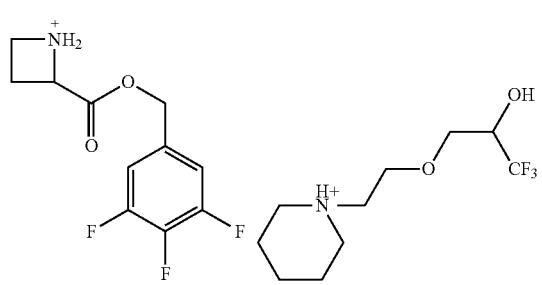
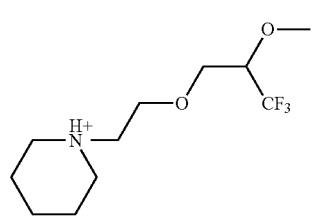
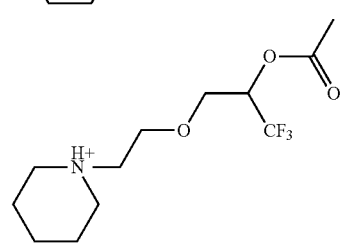
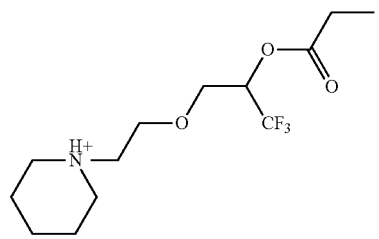
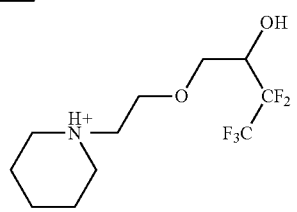
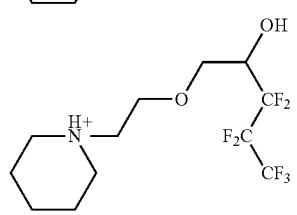
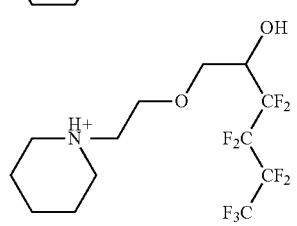
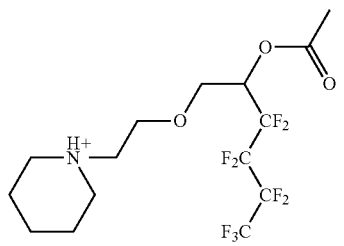
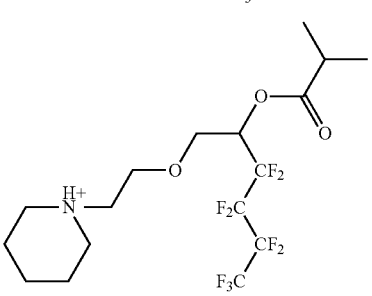
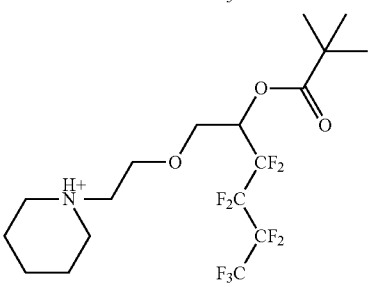
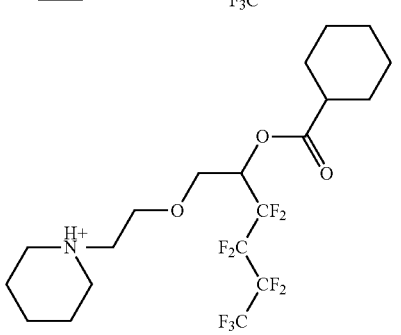
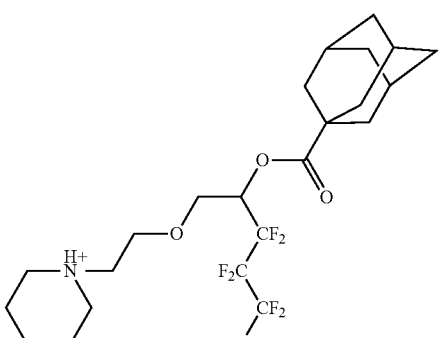
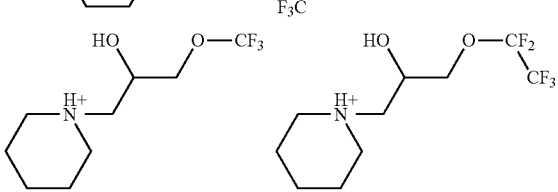

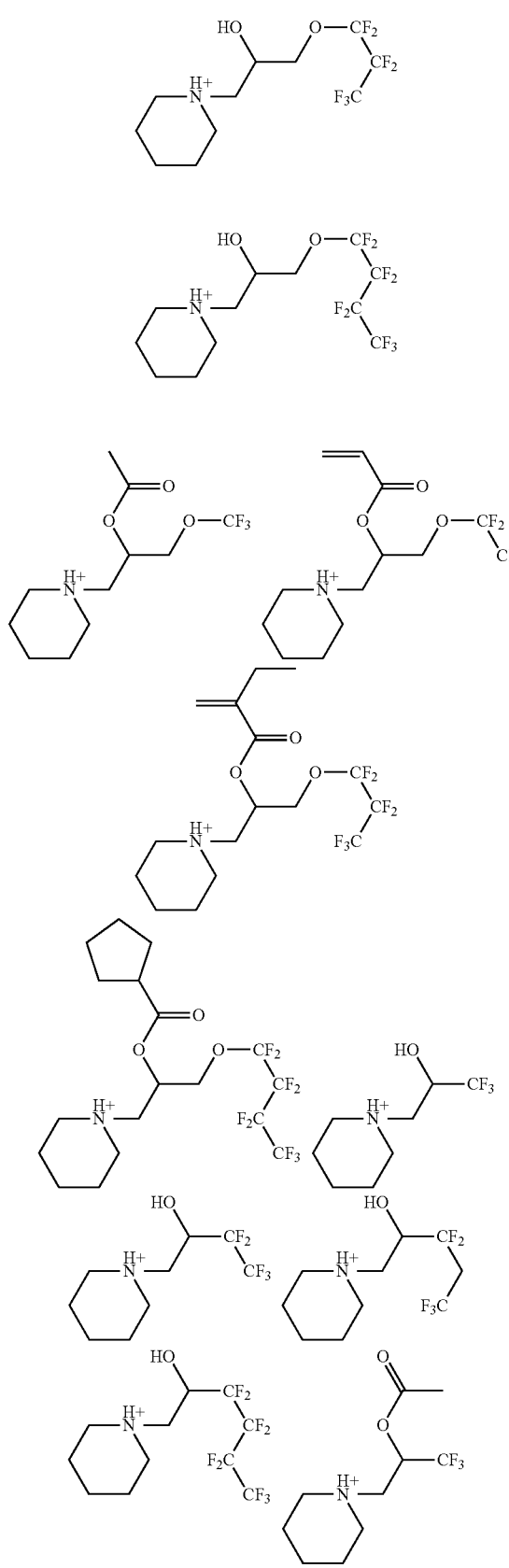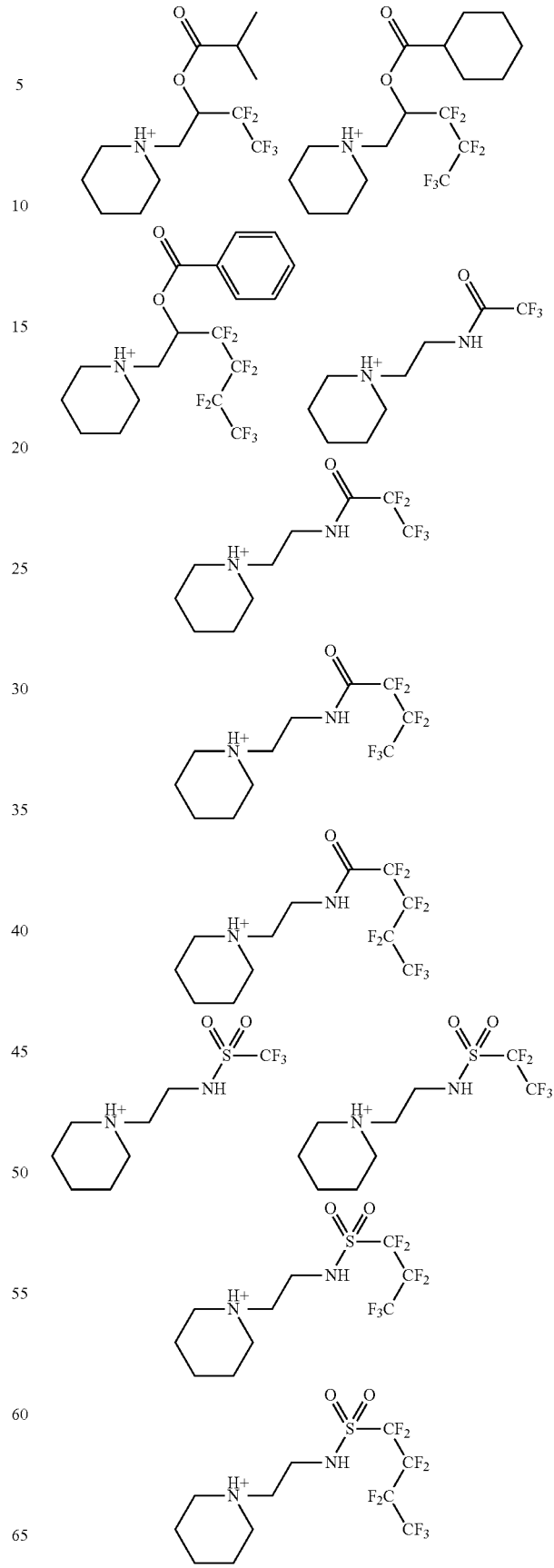

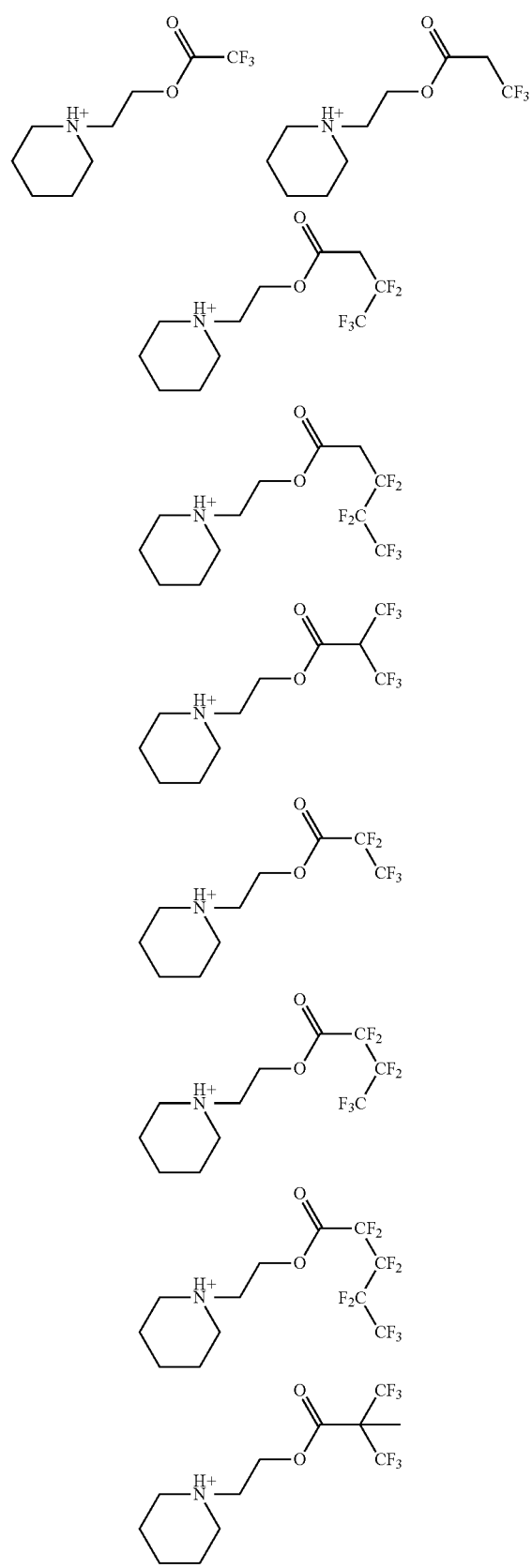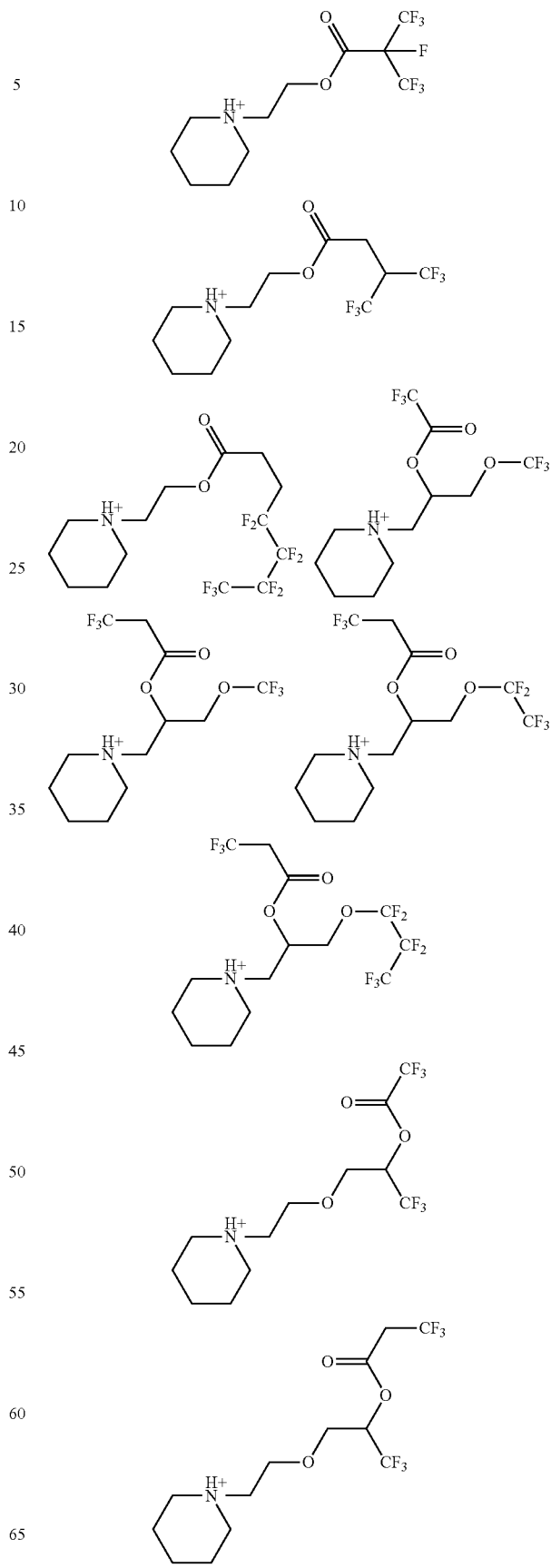

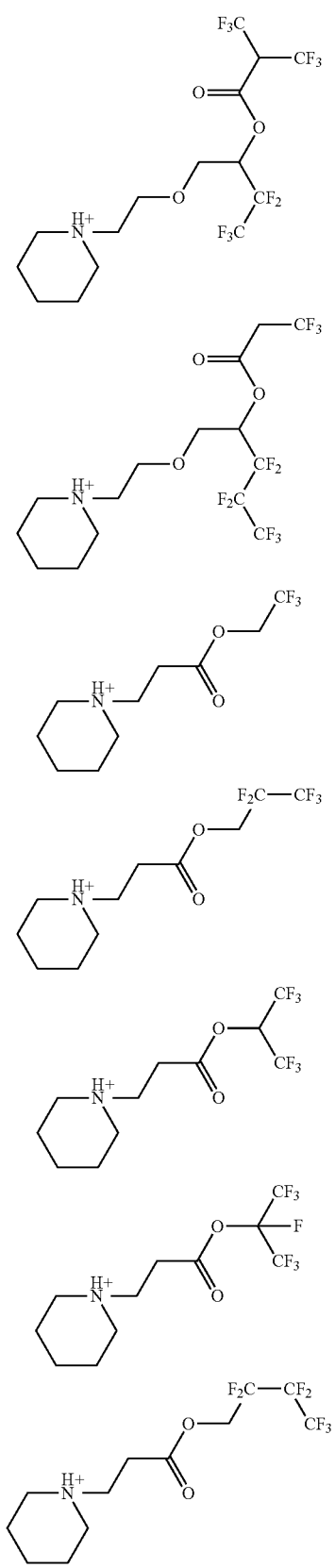
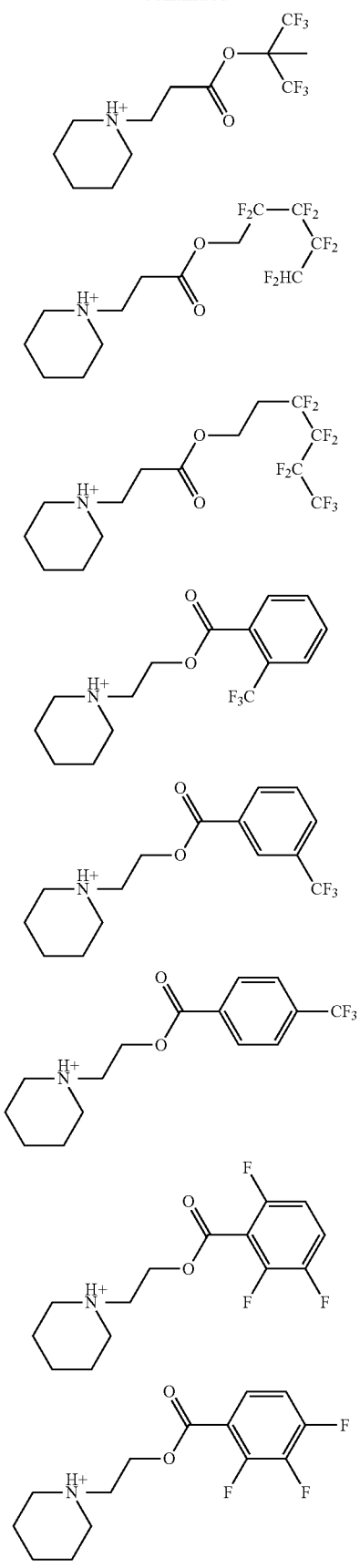

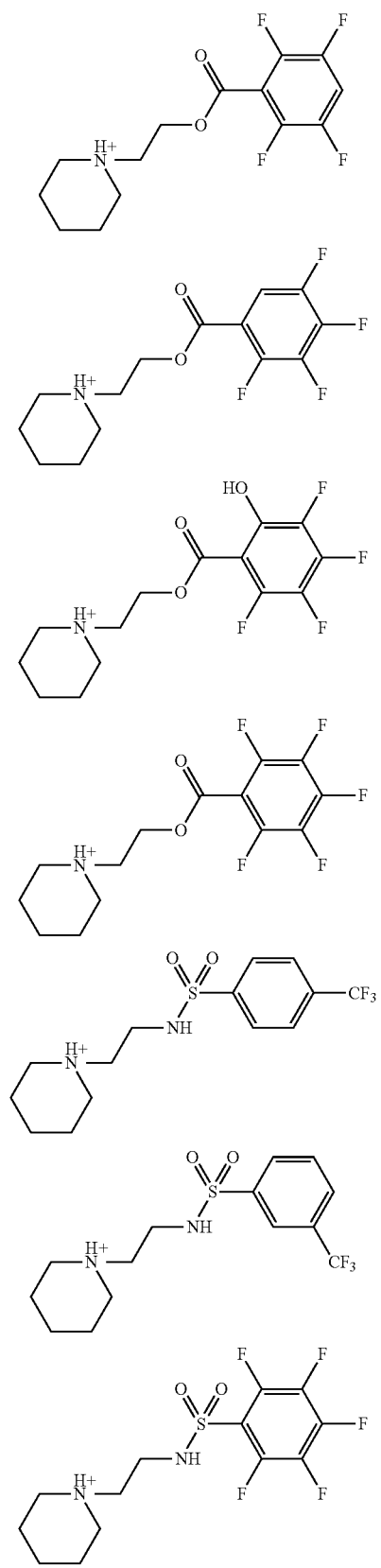
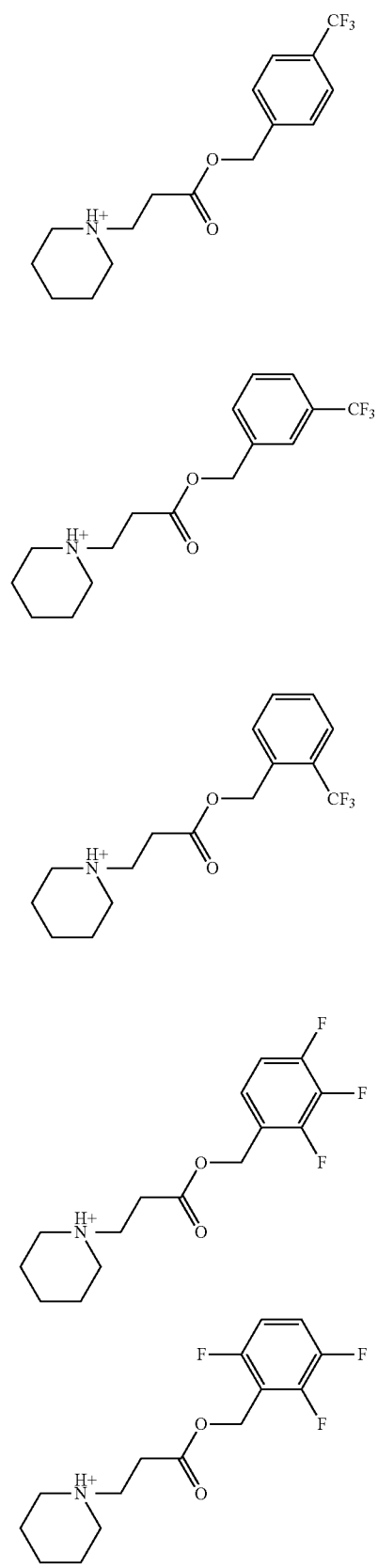

-continued
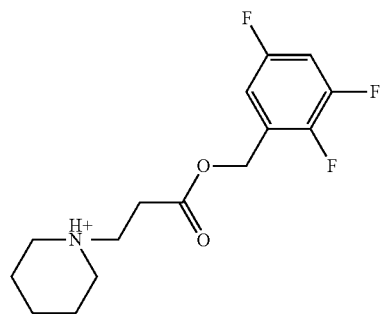
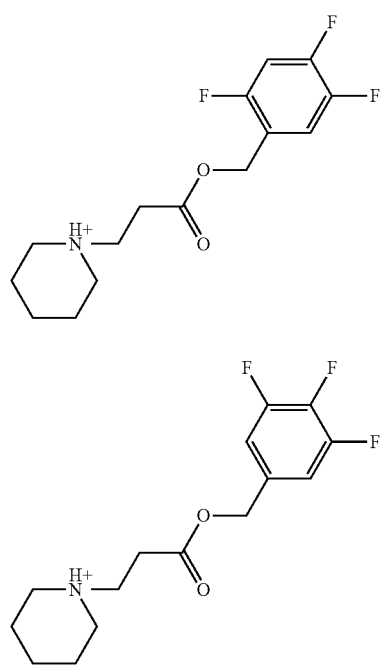
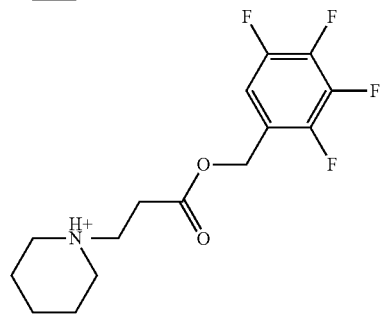
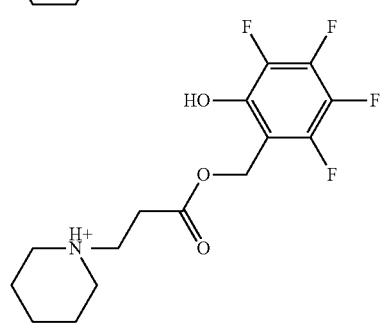
-continued
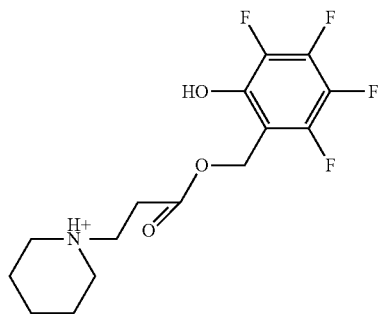
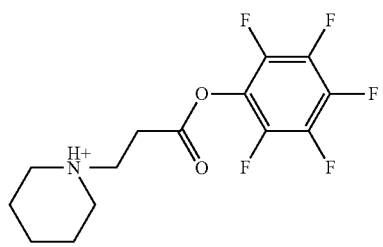
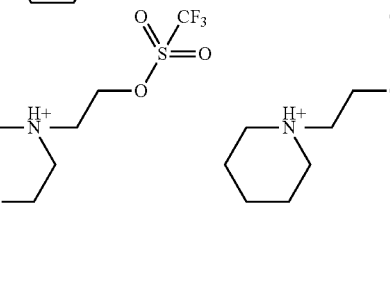
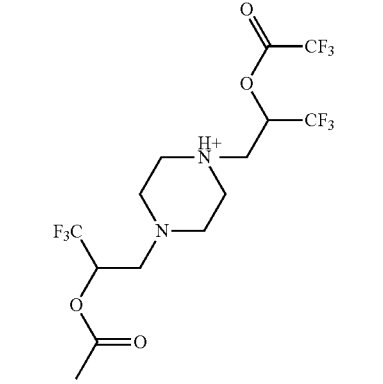
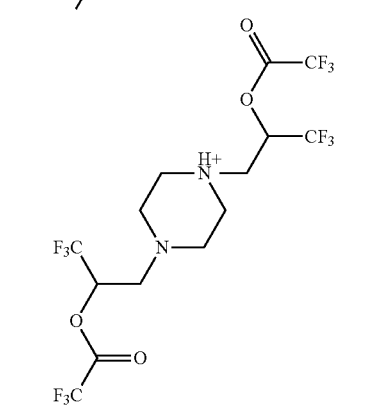

-continued
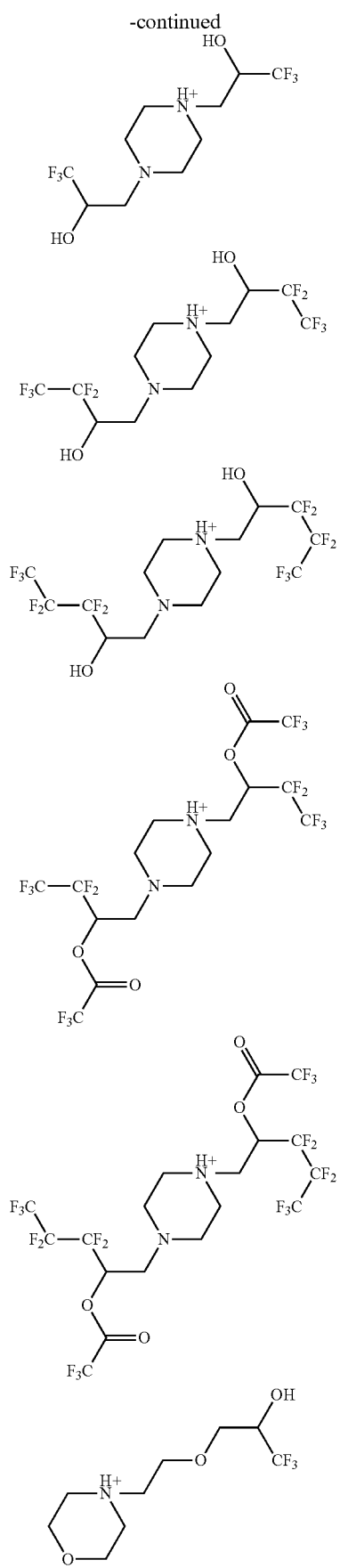
-continued
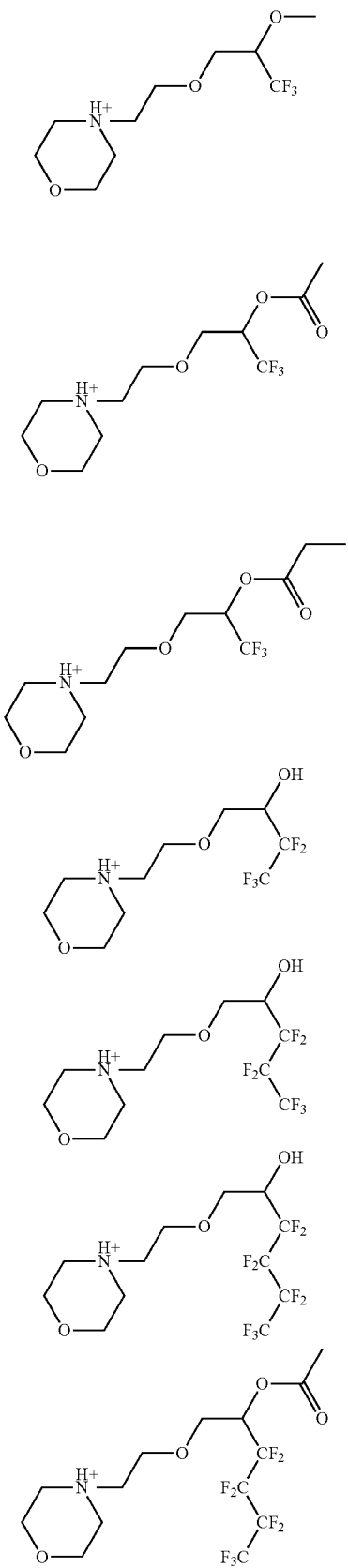

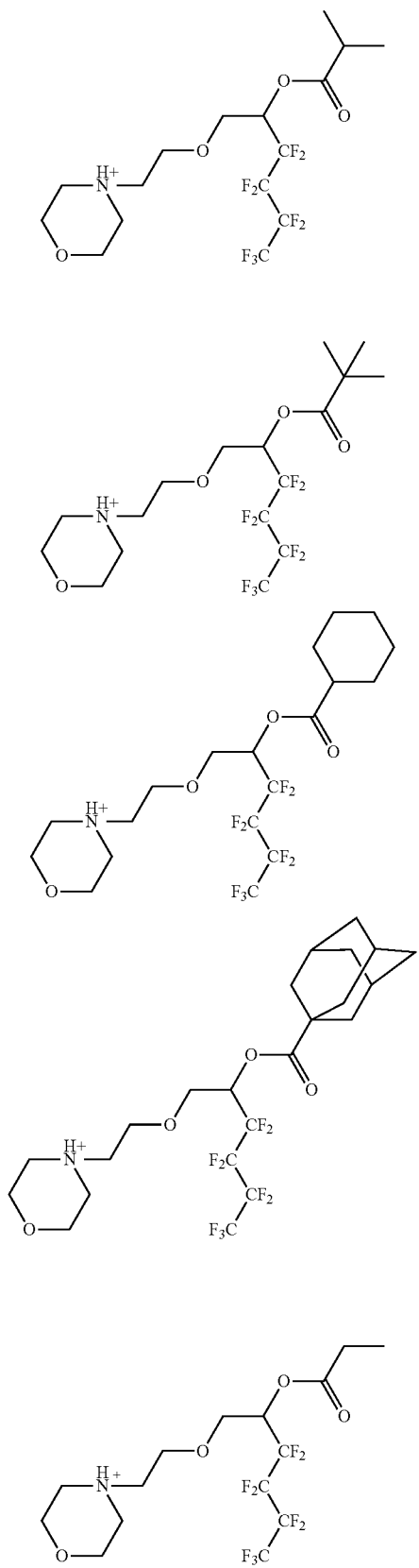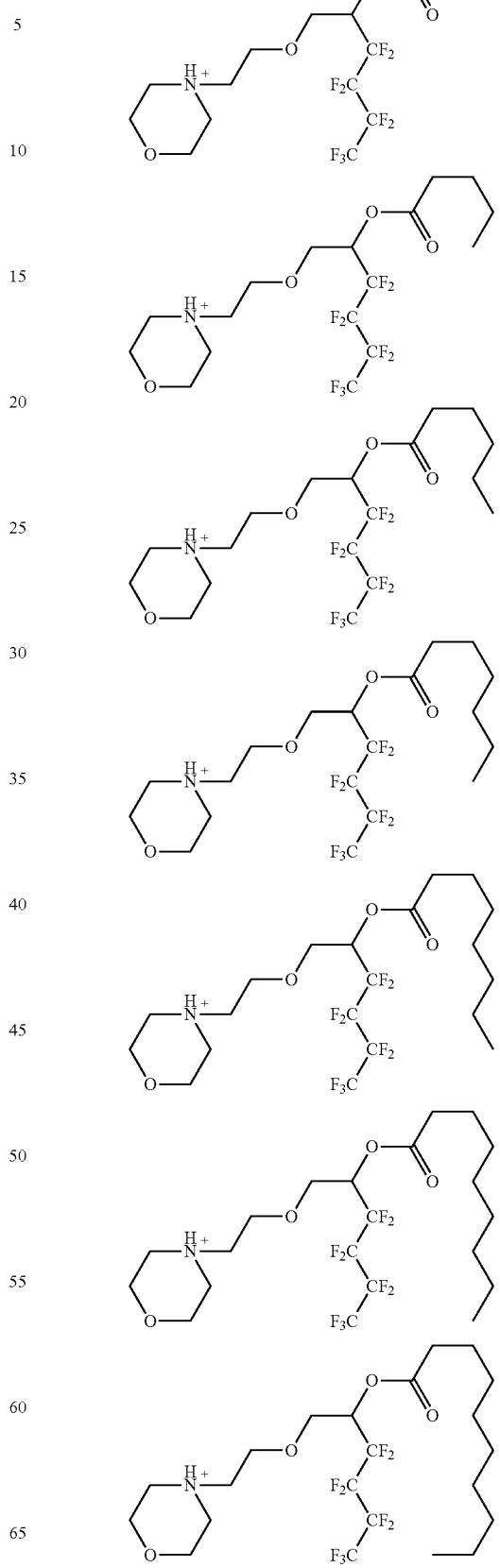

31
-continued
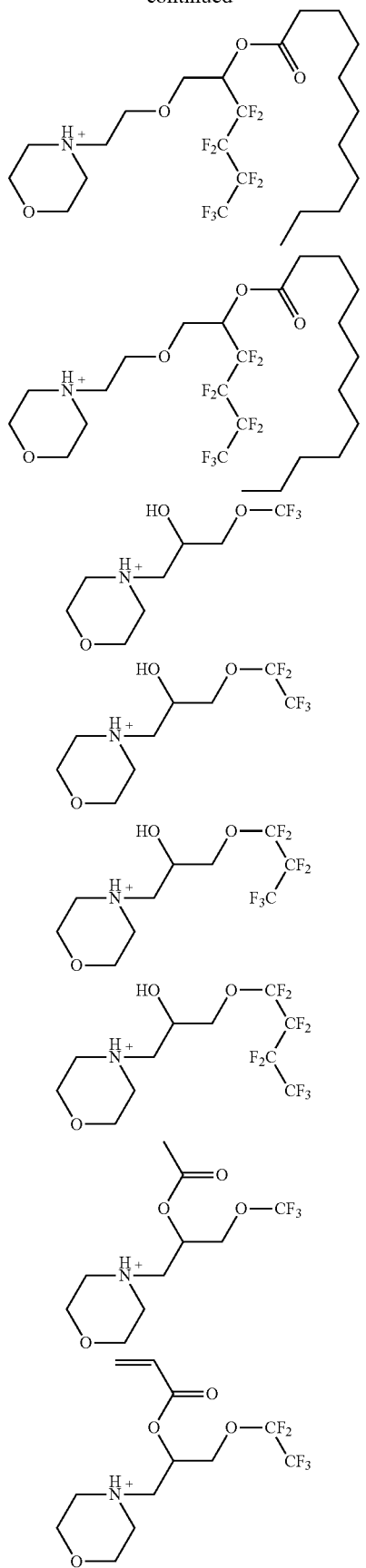
32
-continued
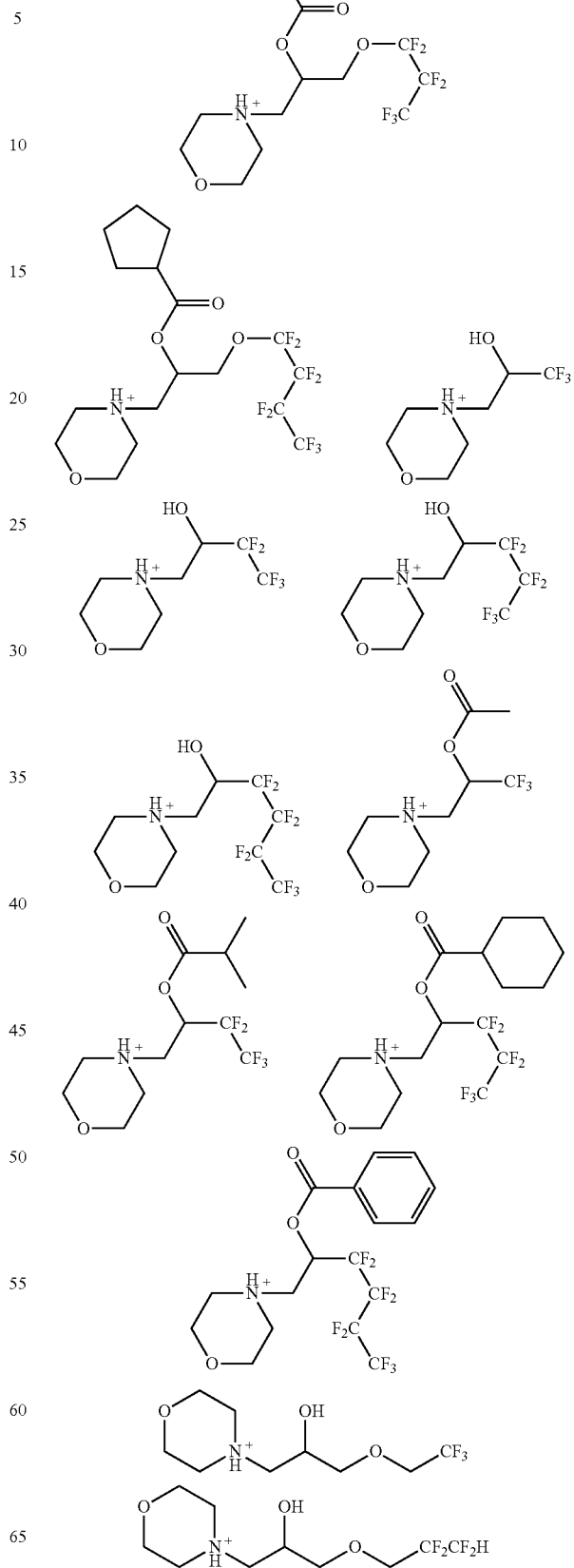

33
-continued
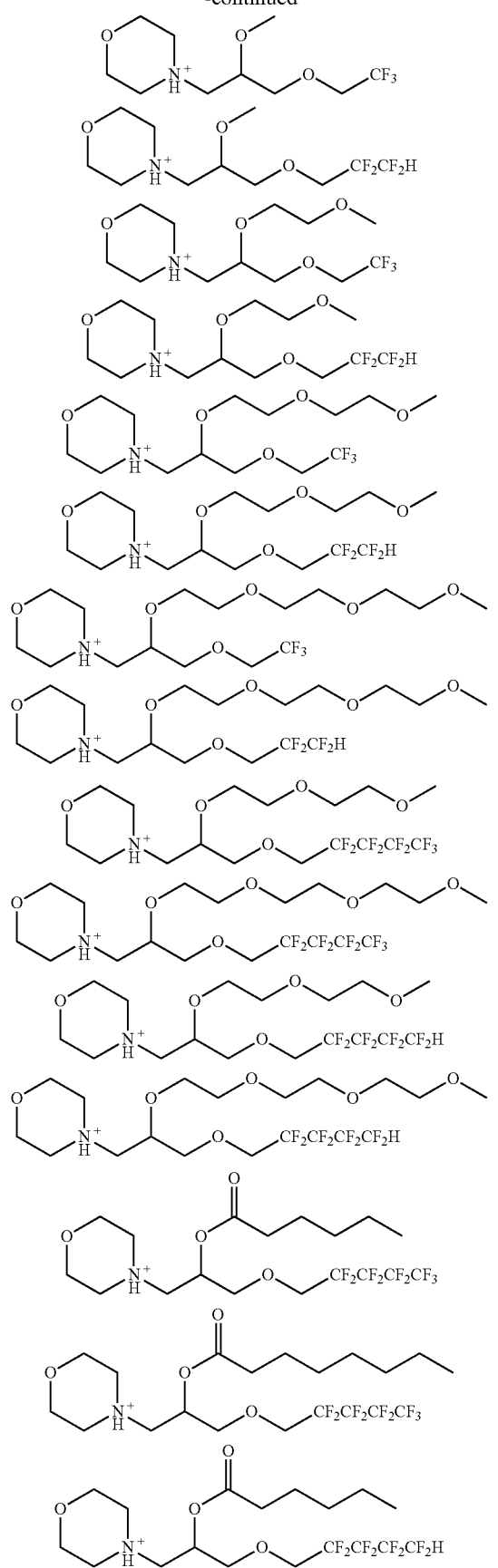
34
-continued
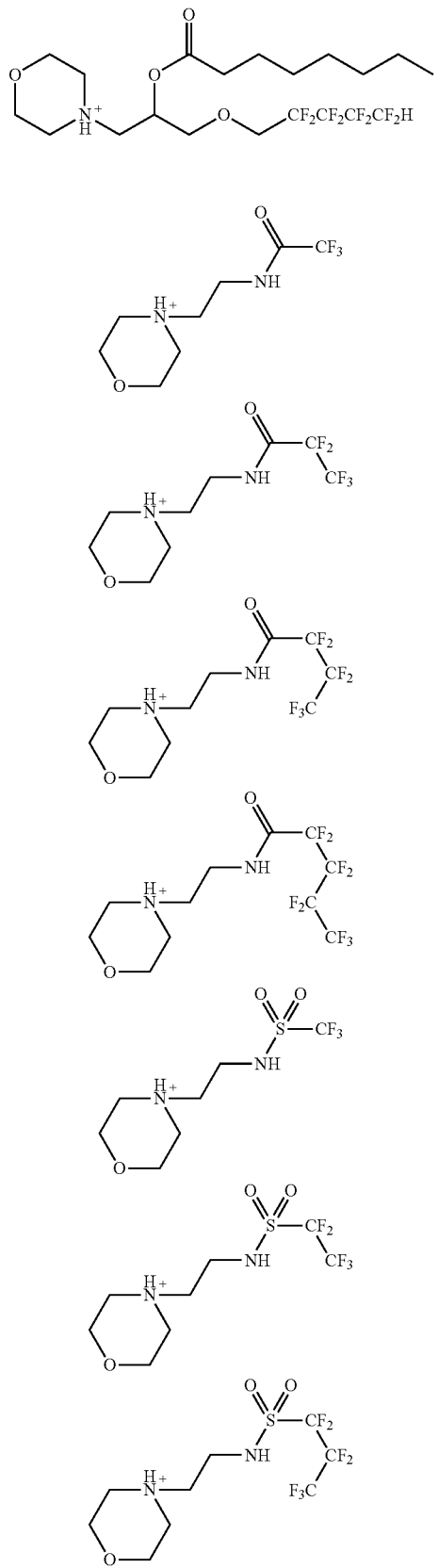

35
-continued
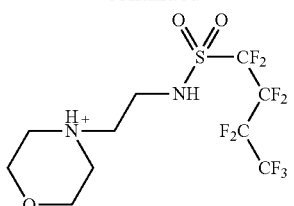
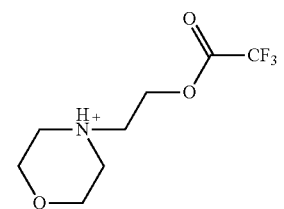
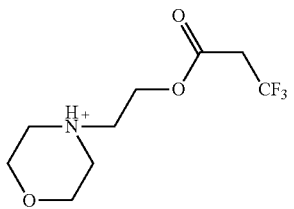
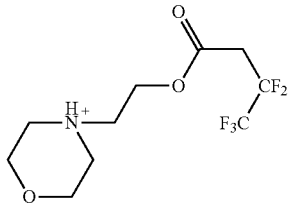
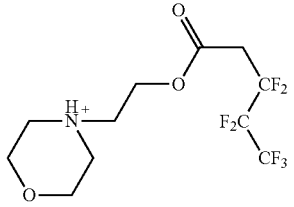
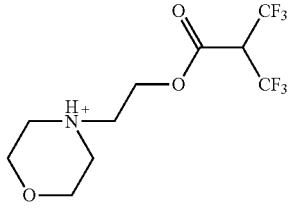
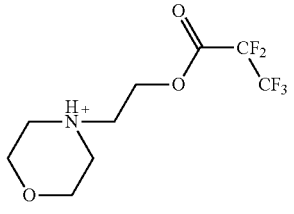
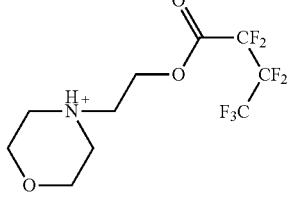
36
-continued
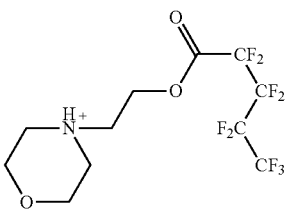
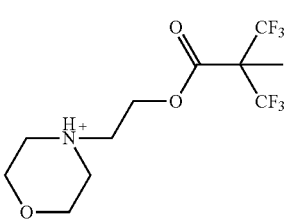
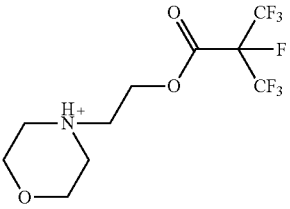
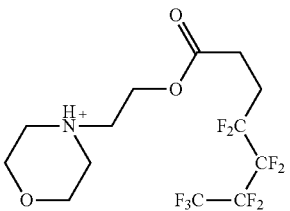
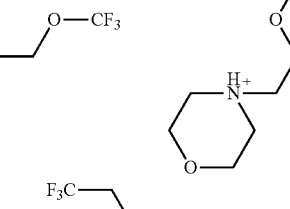
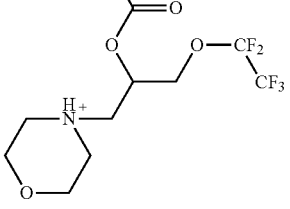

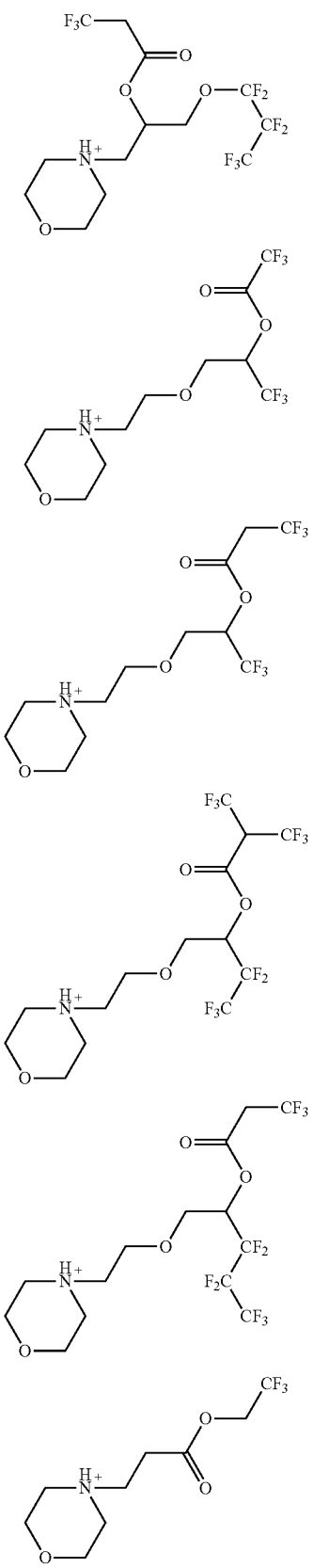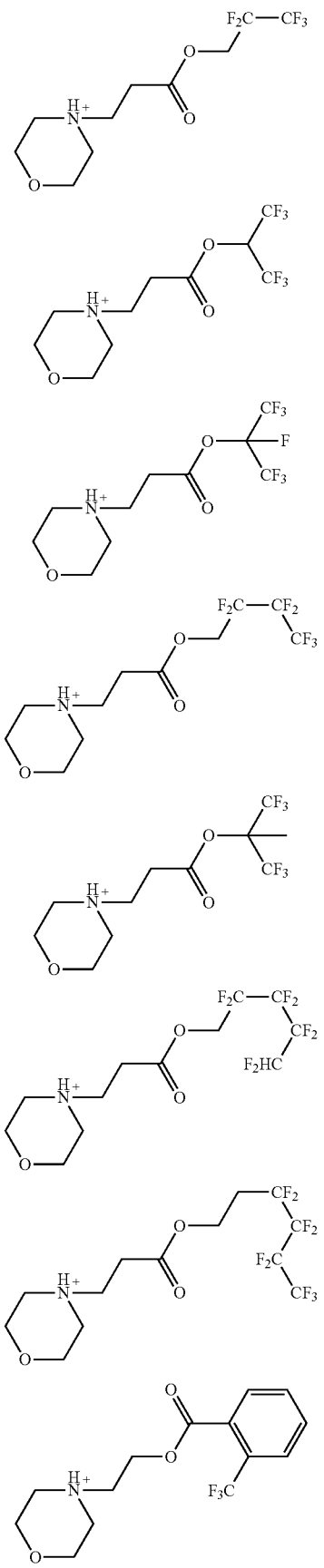

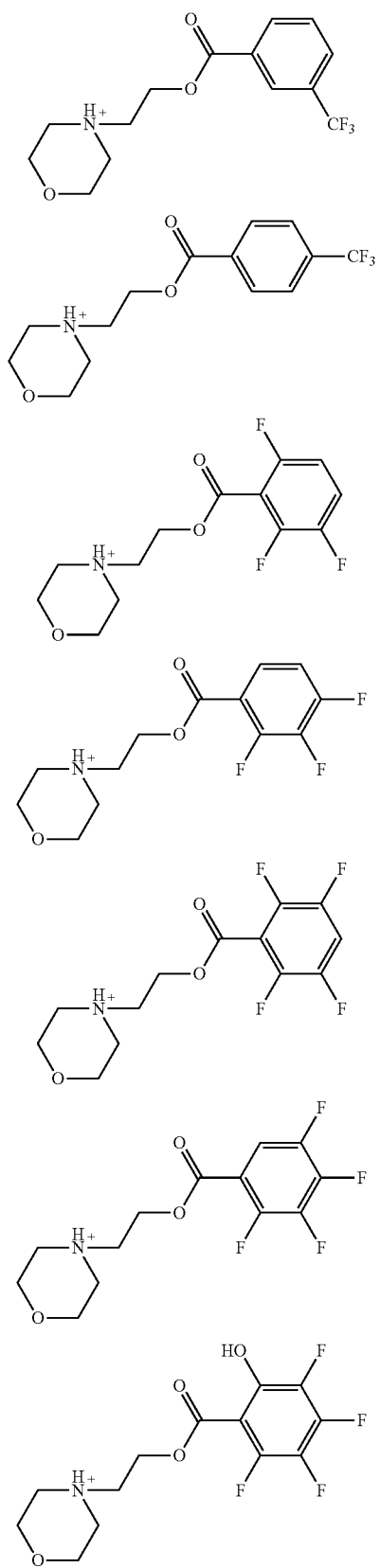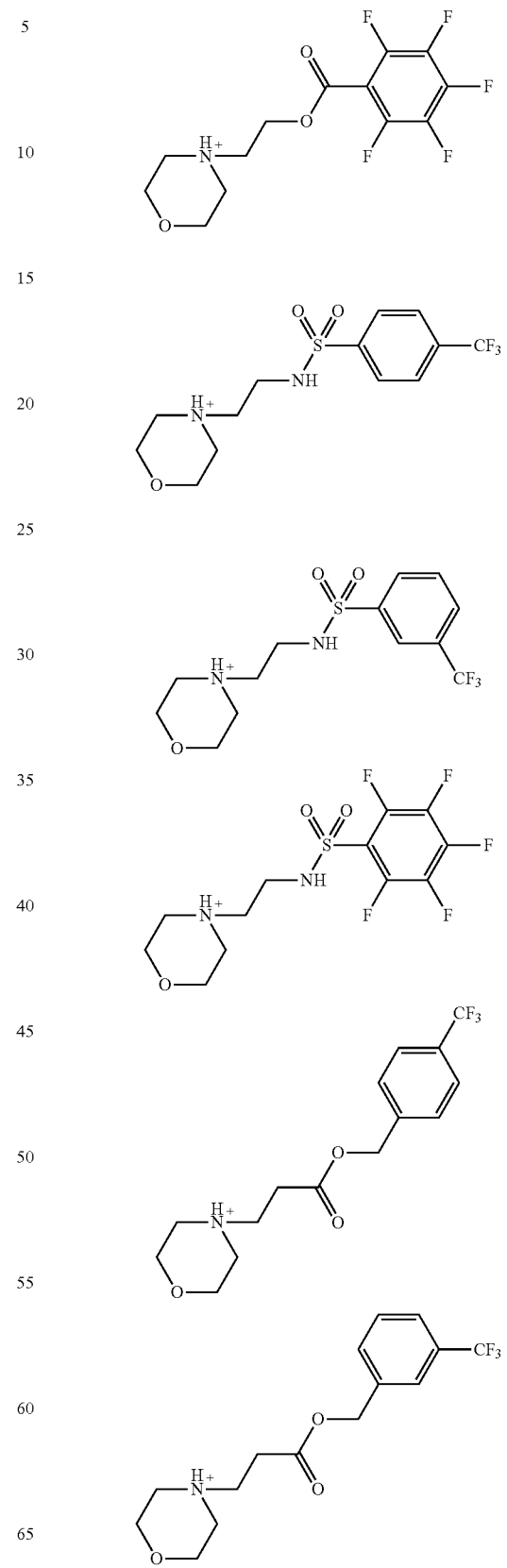

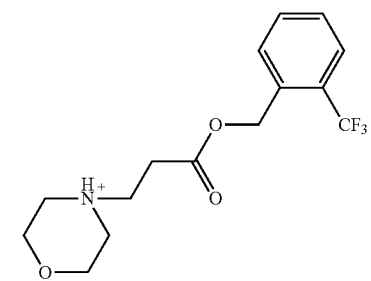
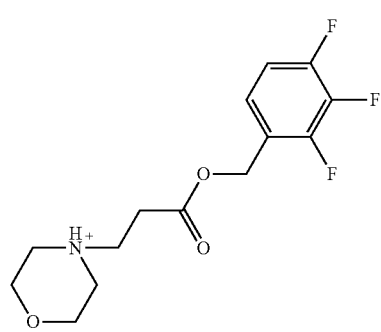
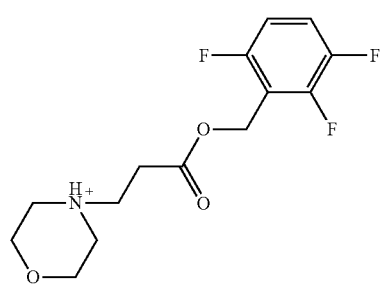
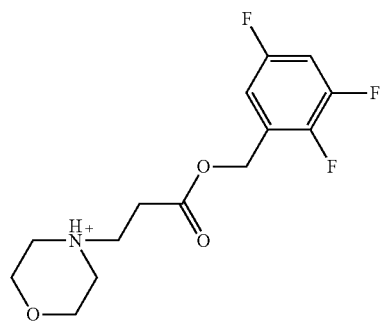
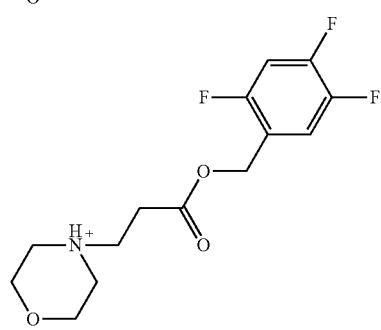
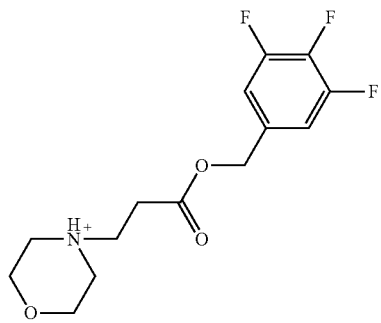
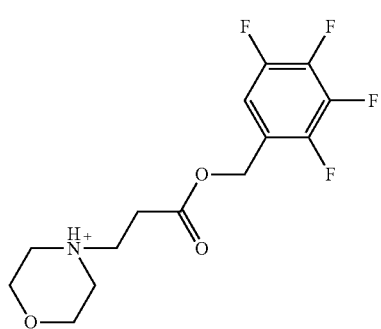
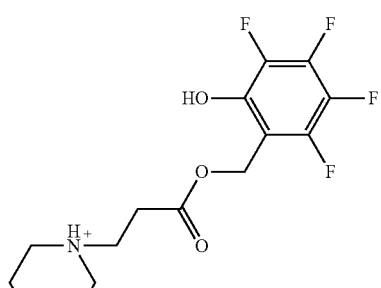
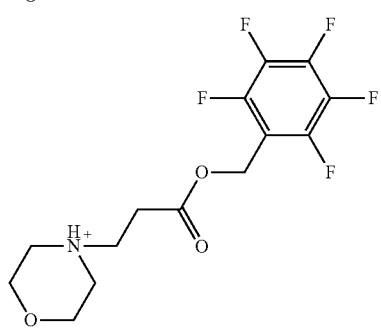
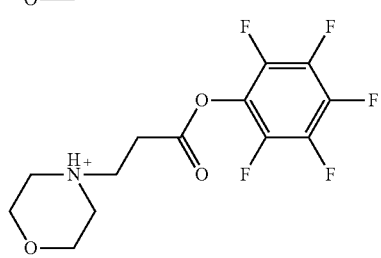

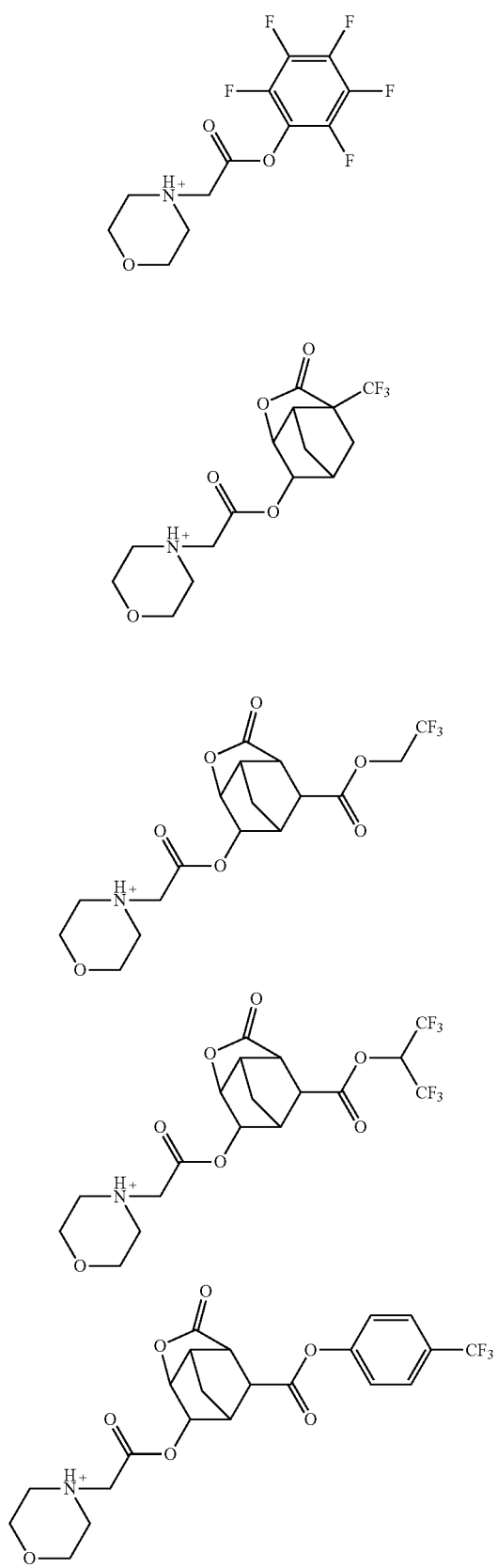
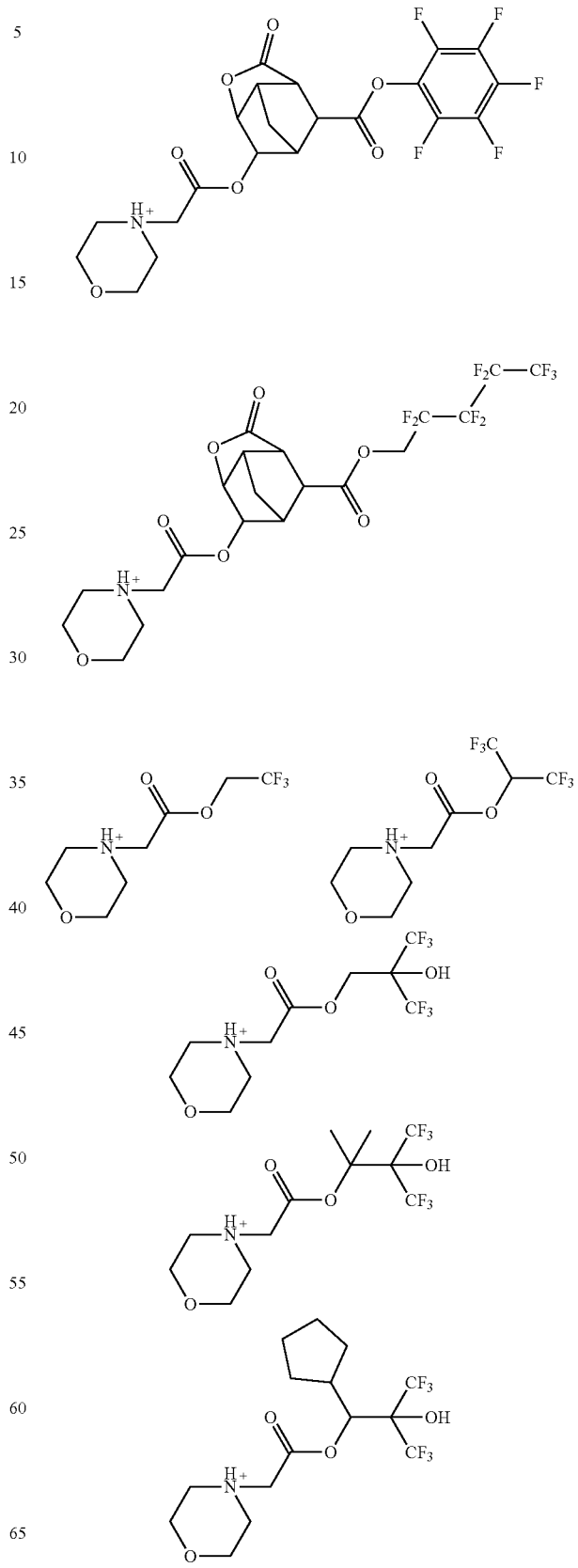

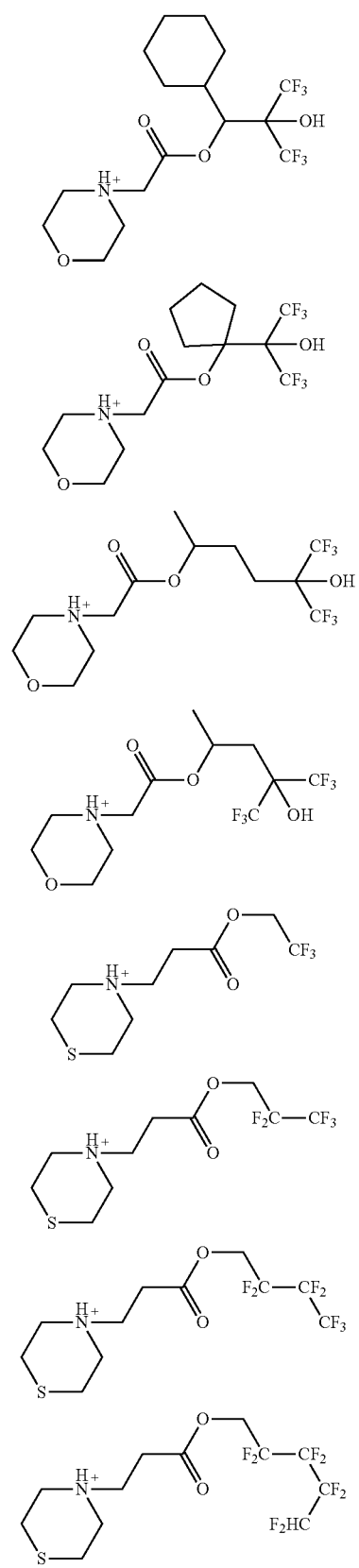
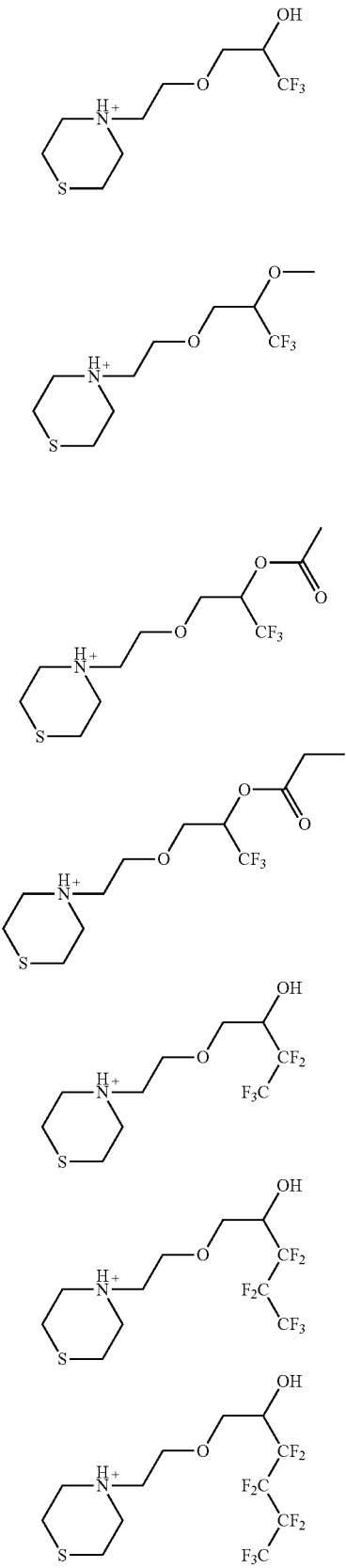

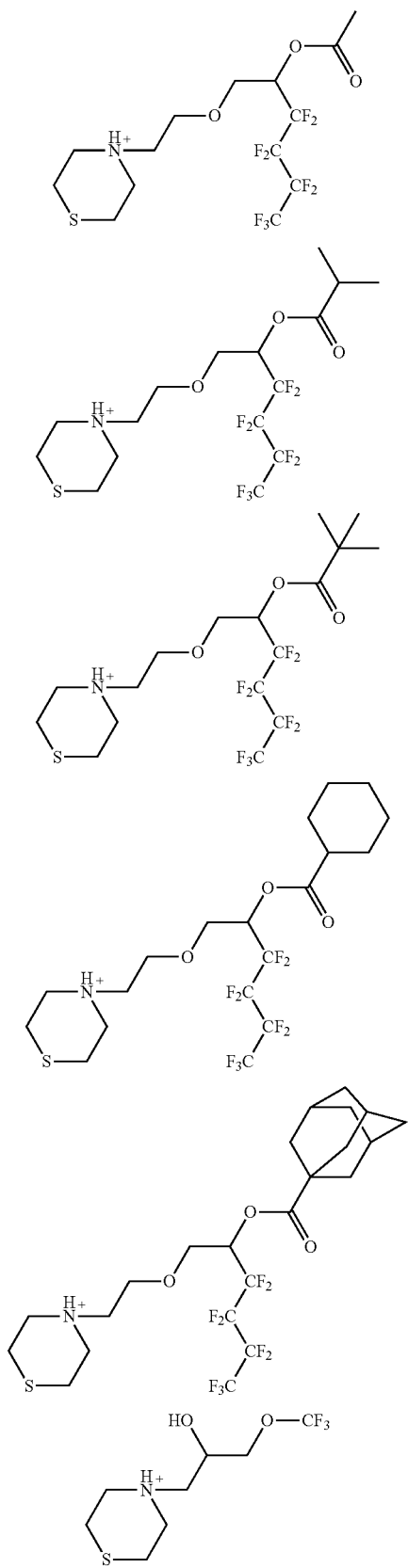
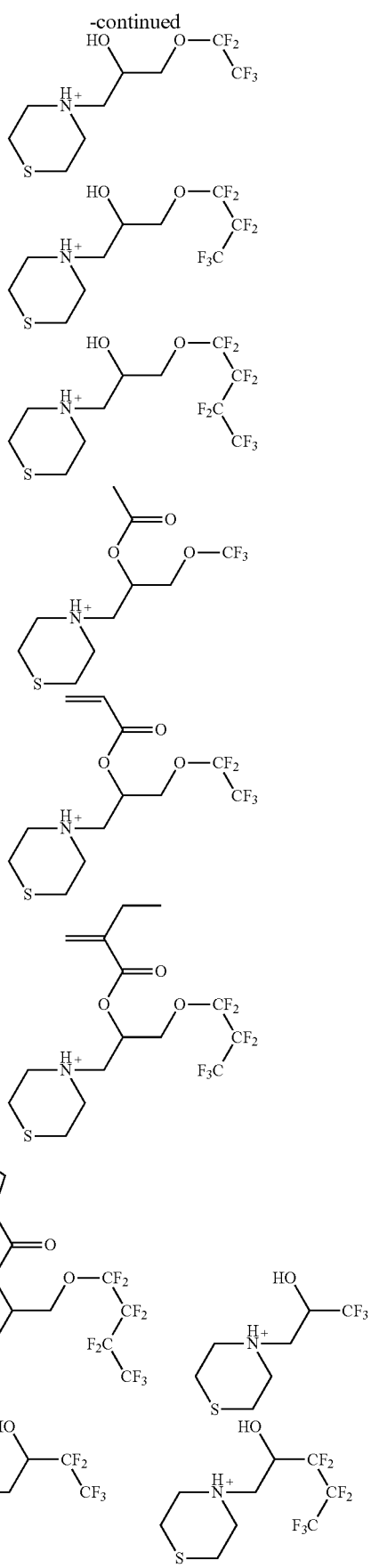

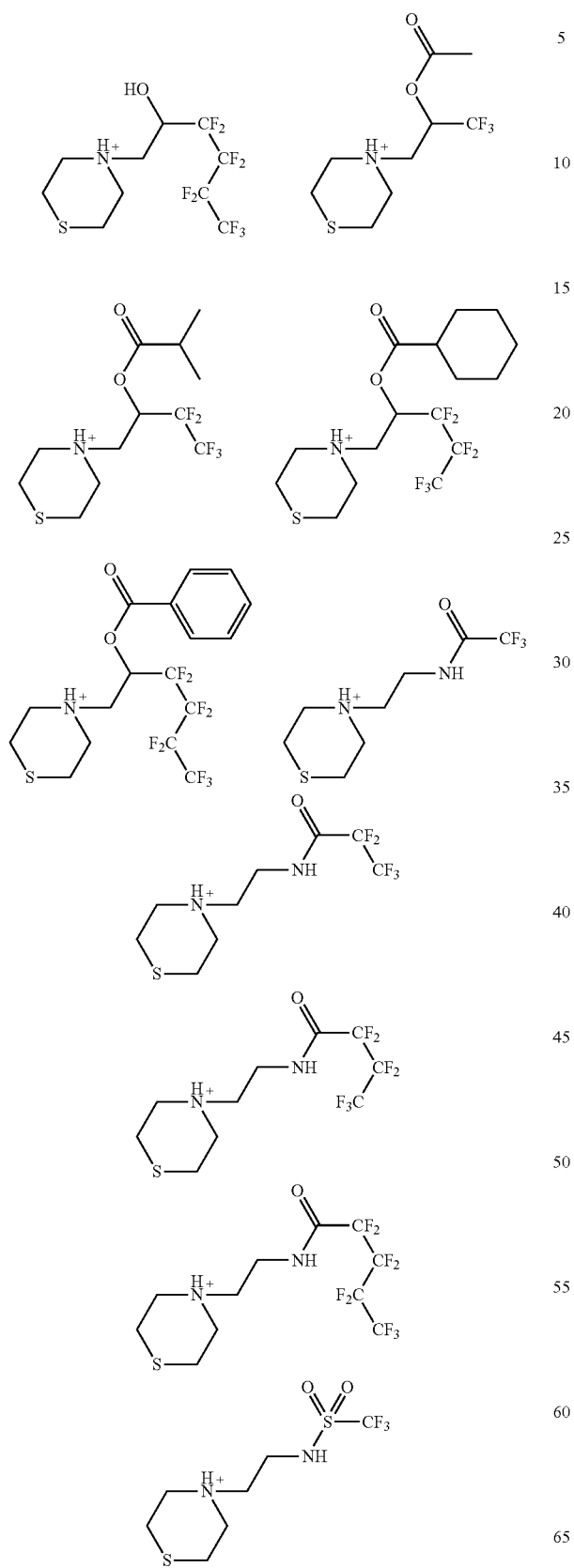
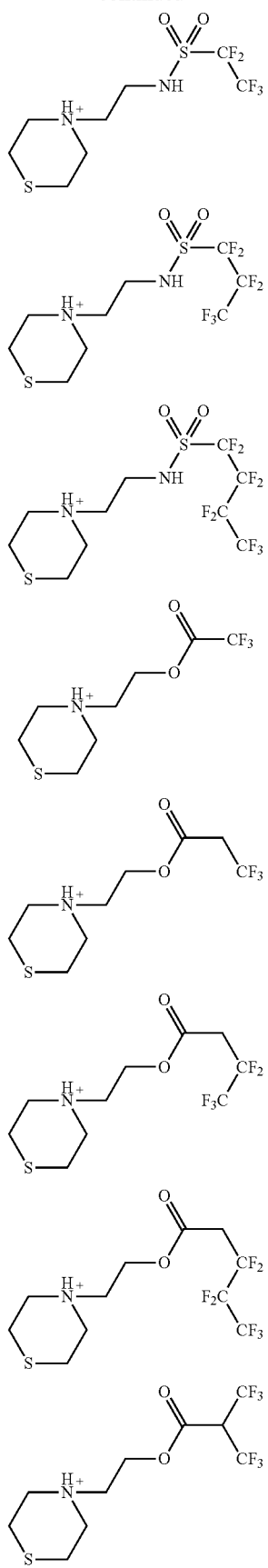

51
-continued
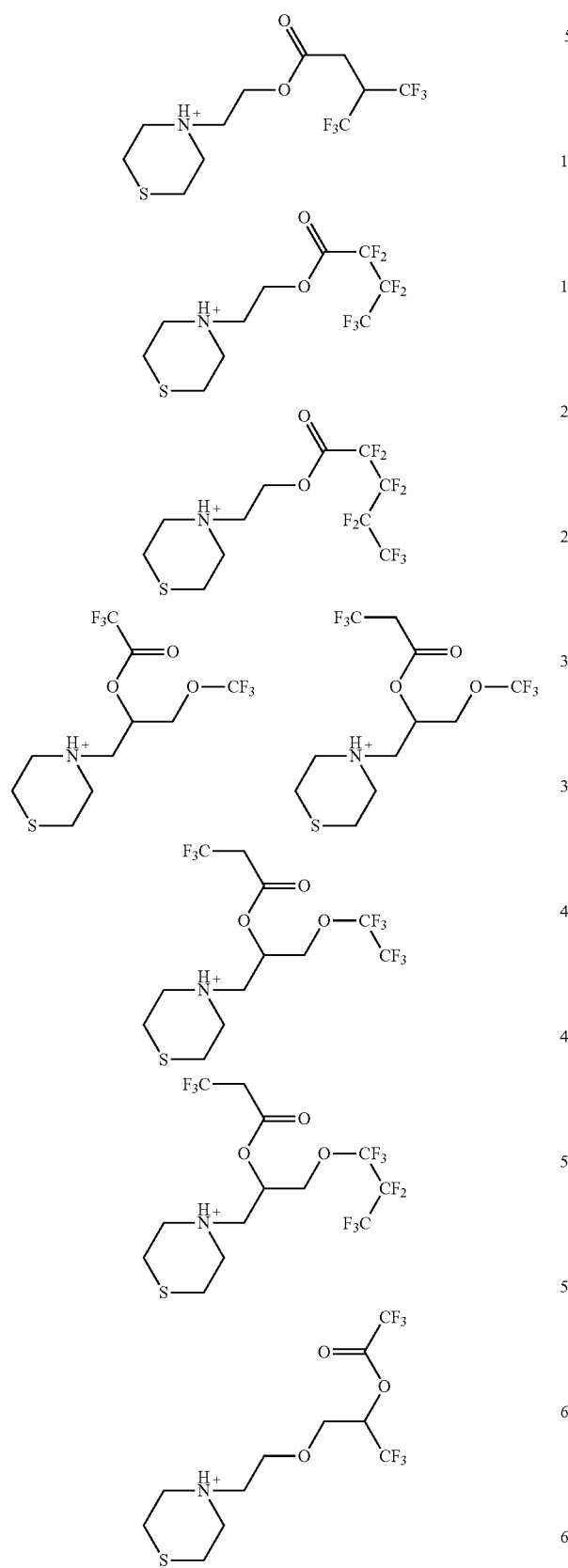
52
-continued
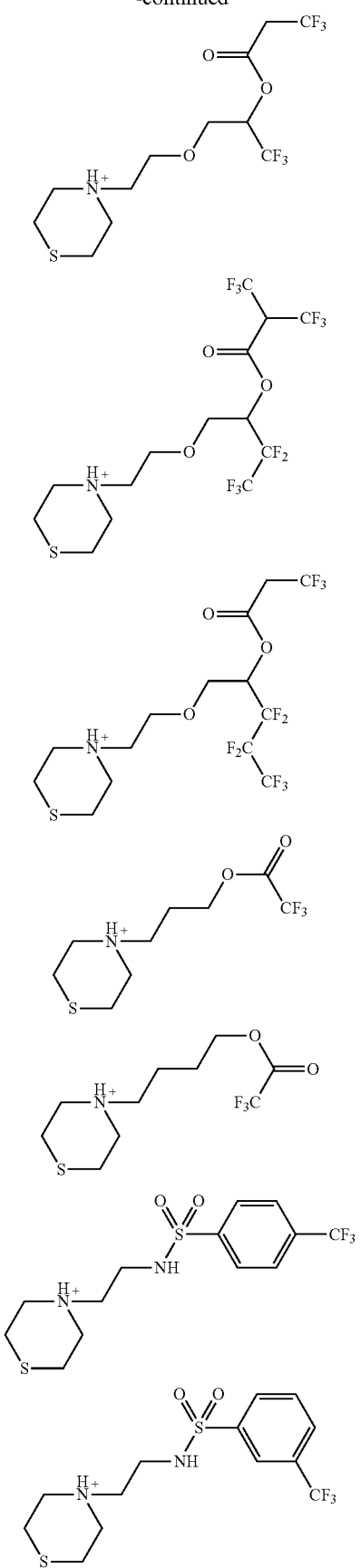

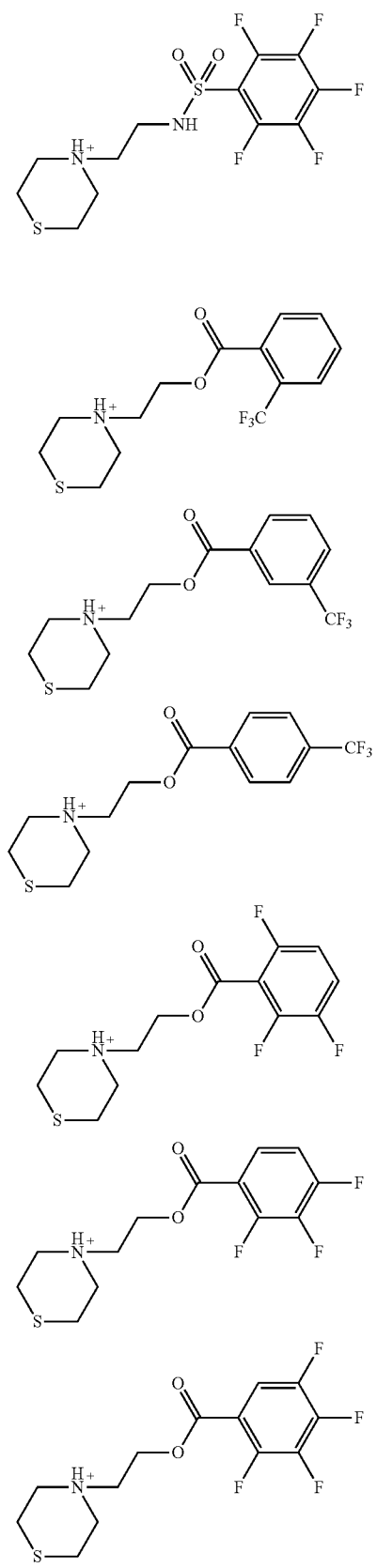
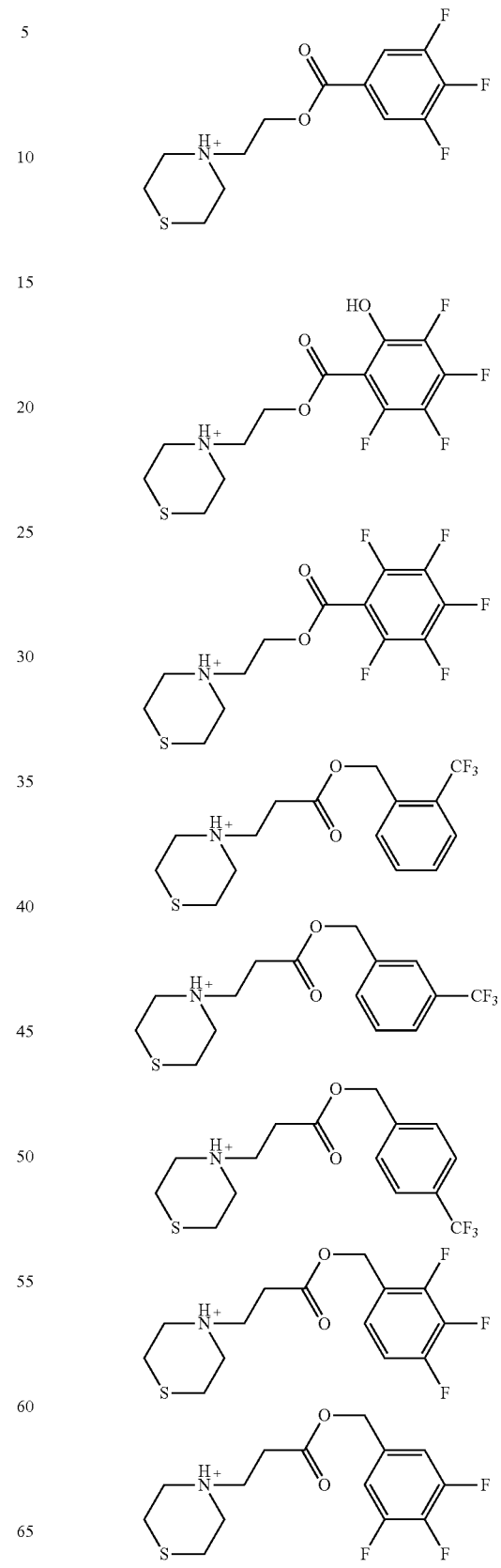

55
-continued
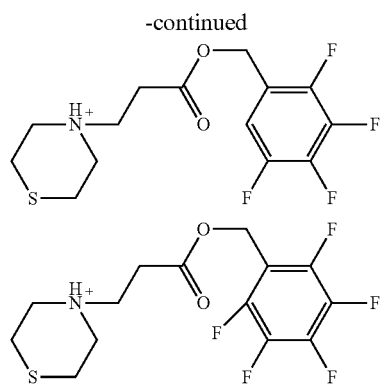
56
-continued
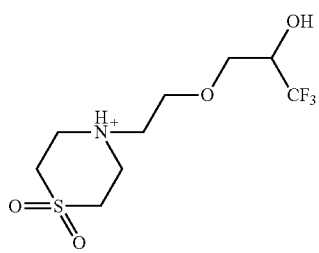
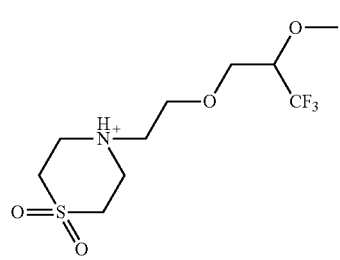
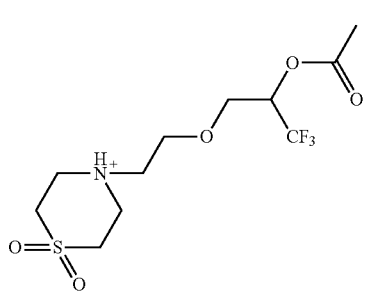
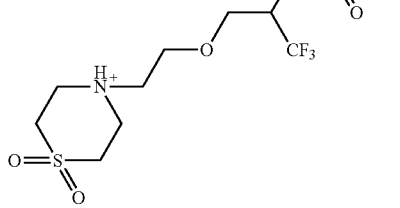
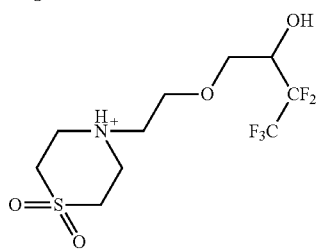
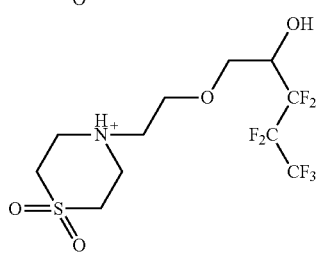

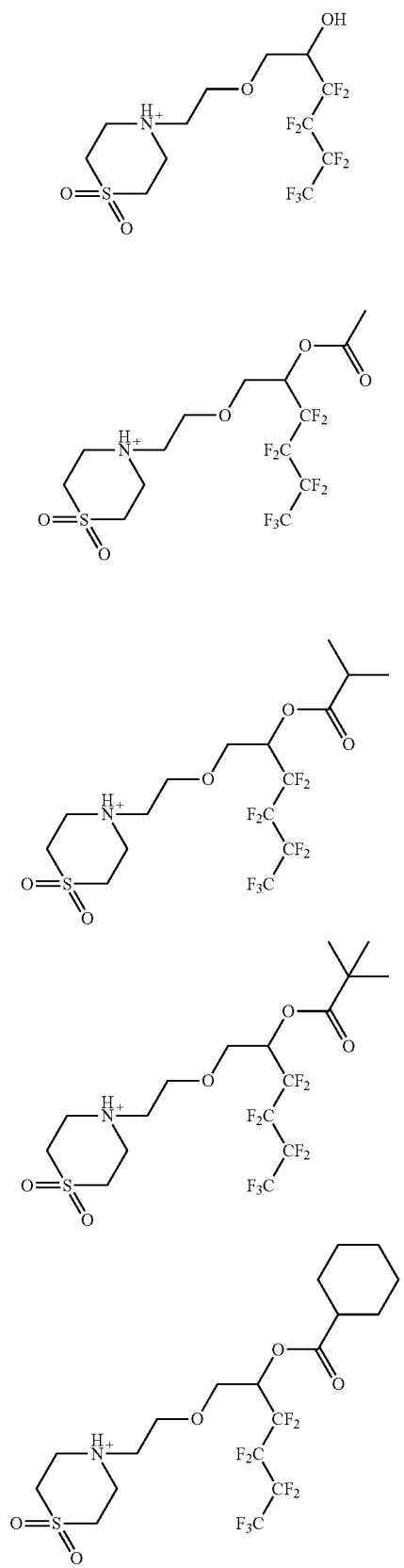
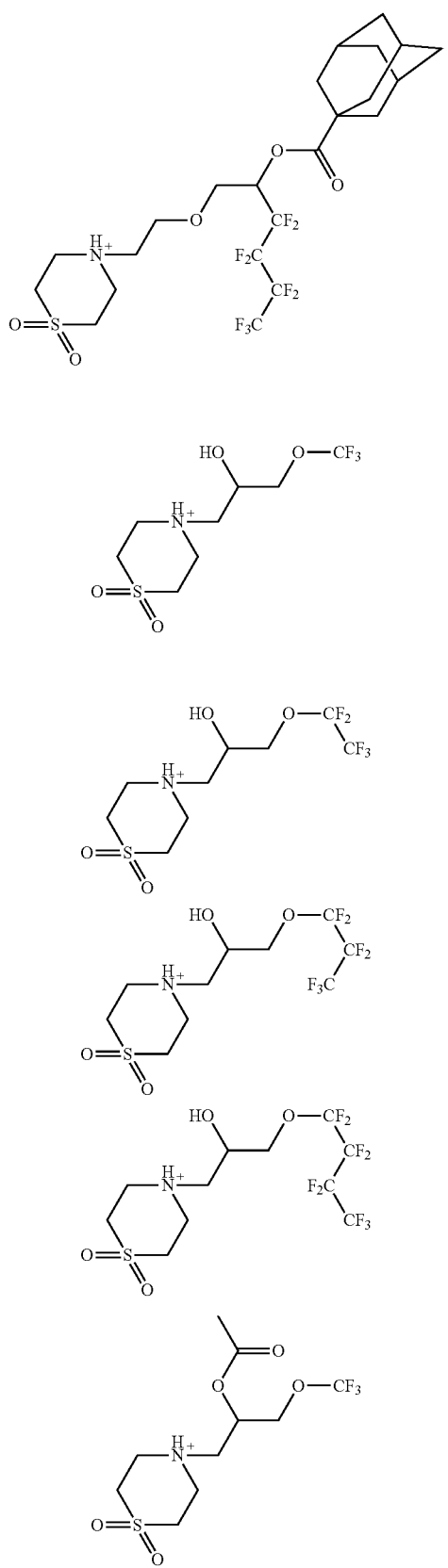

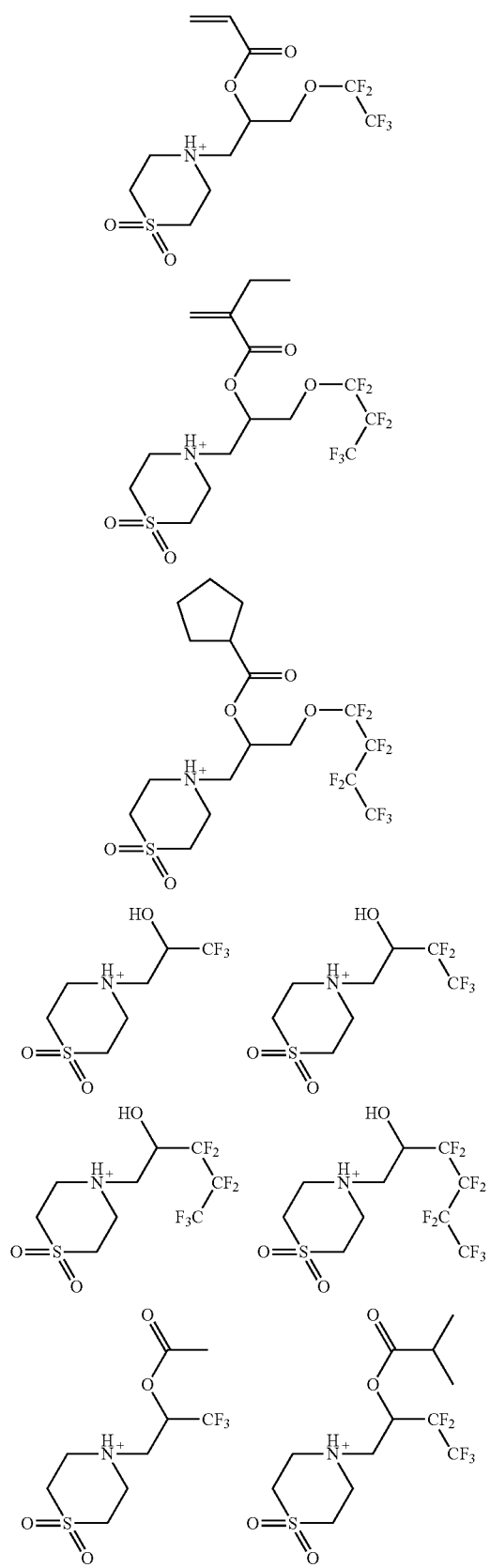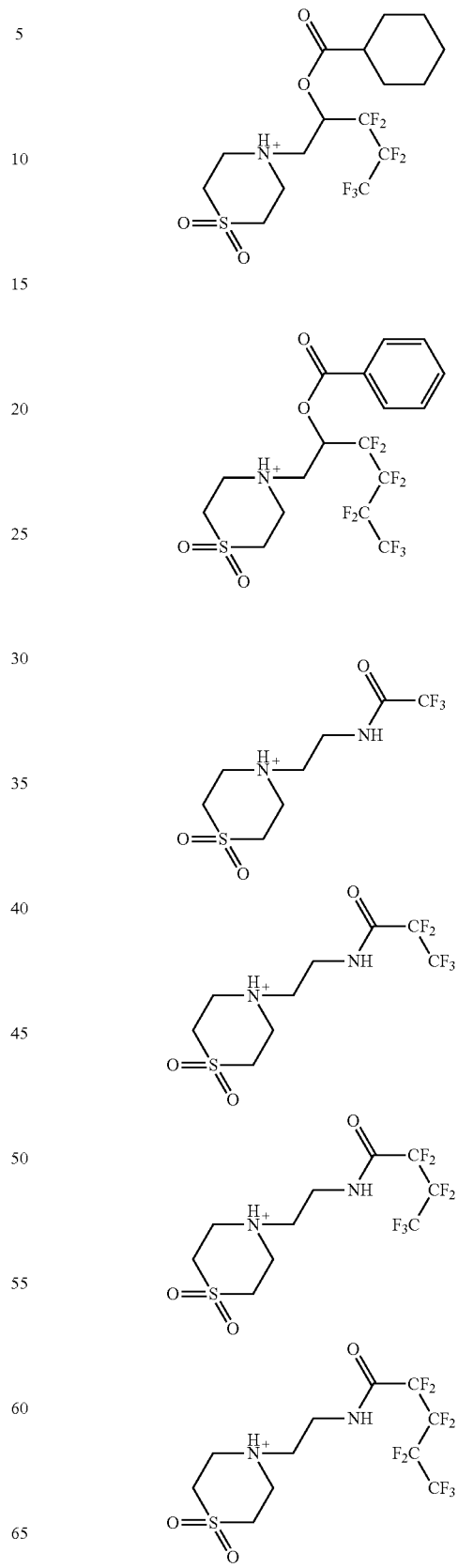

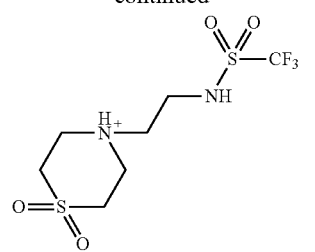
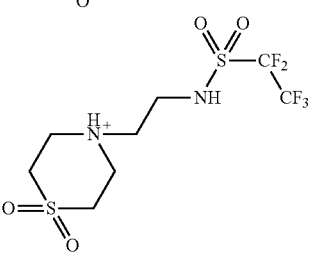
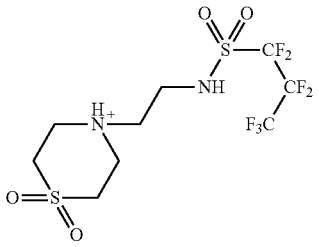
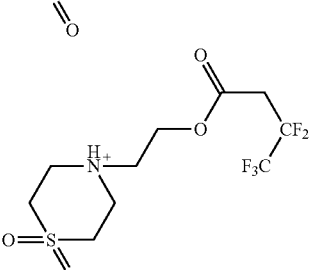
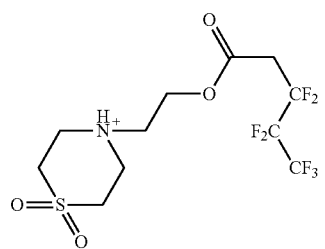
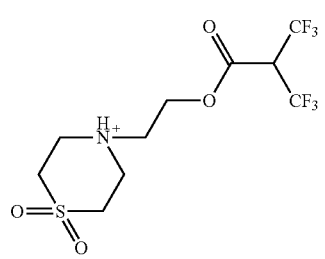
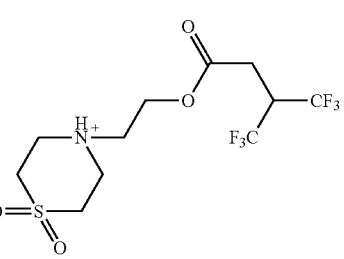
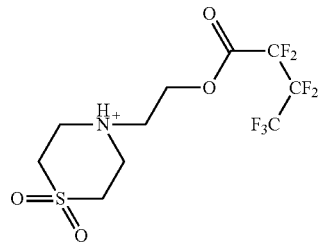
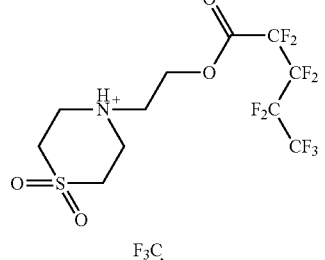
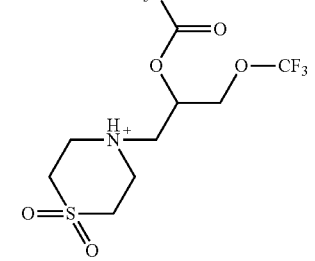

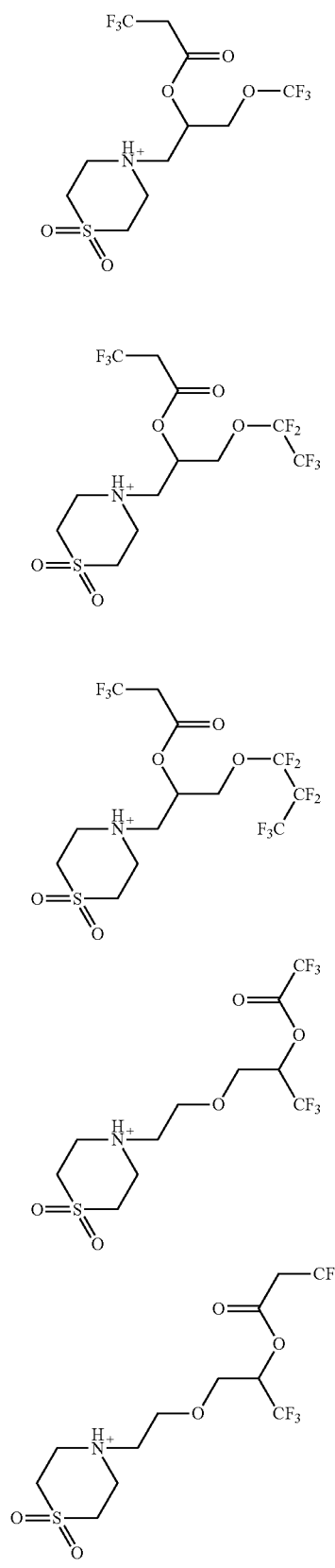
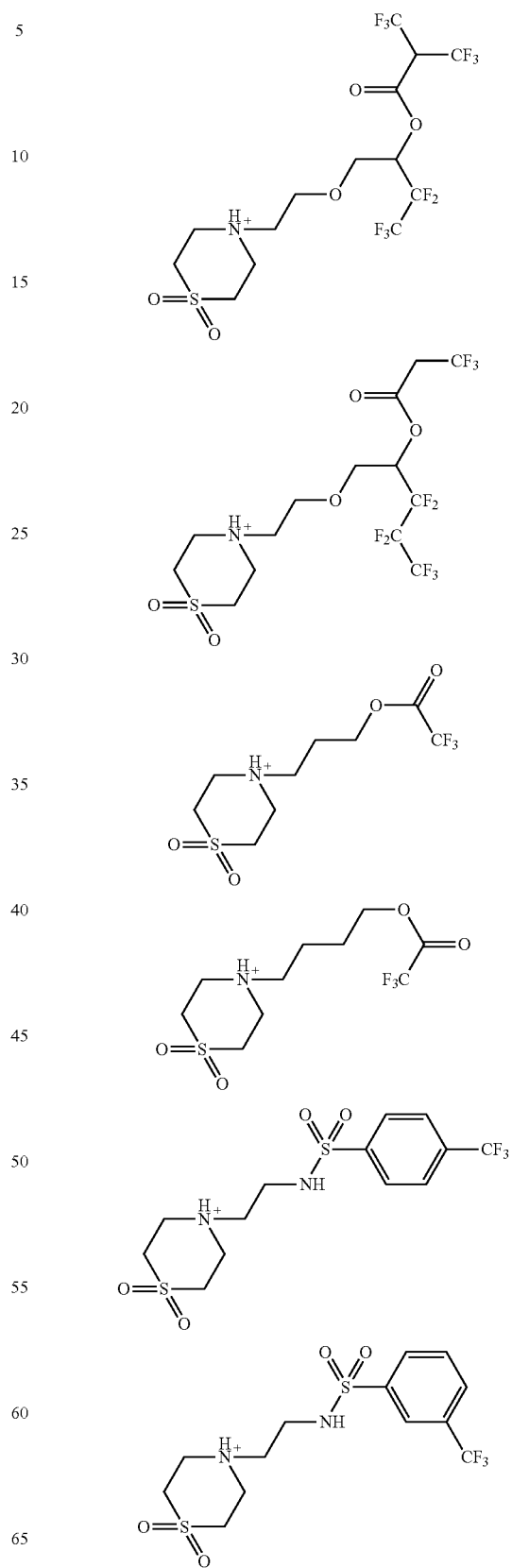

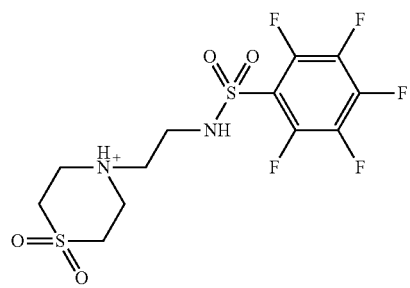
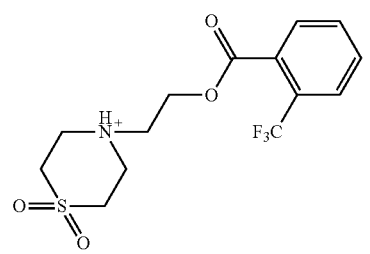
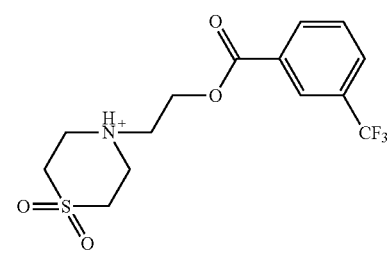
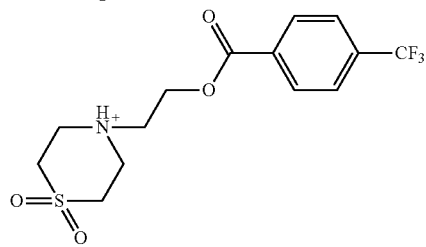
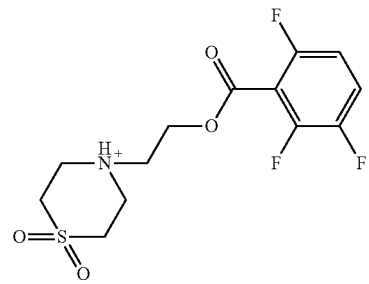
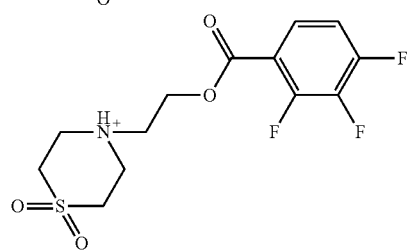
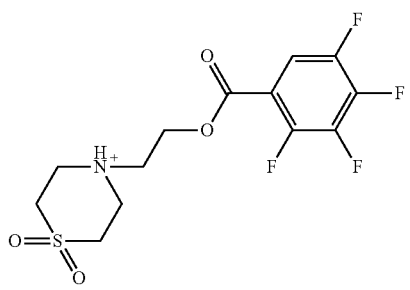
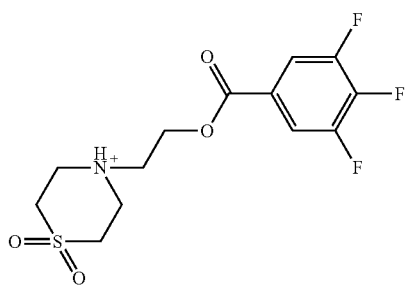
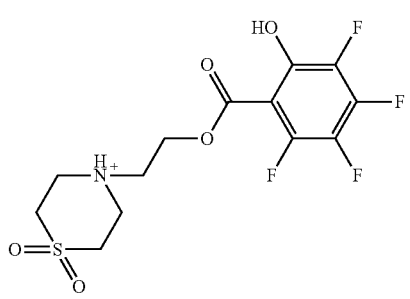
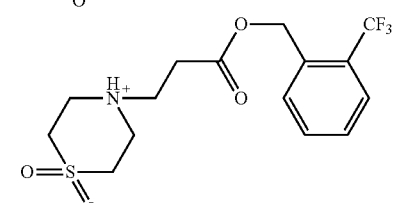
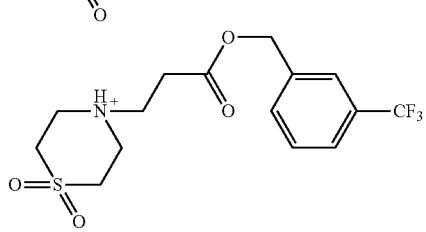

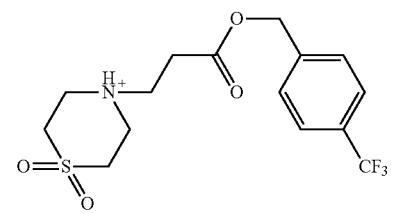
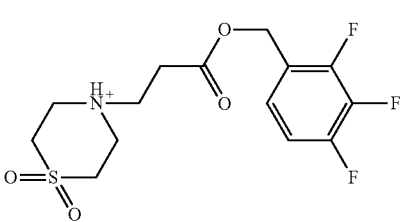
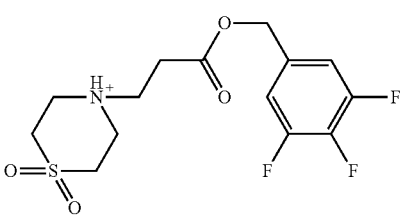
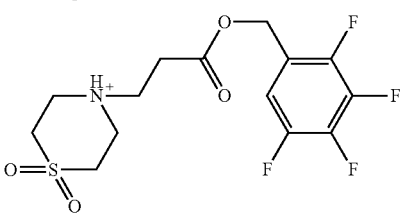
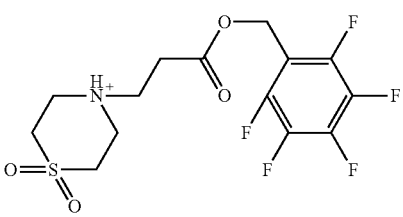
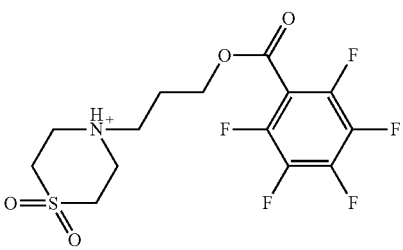
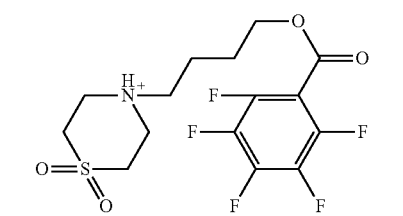
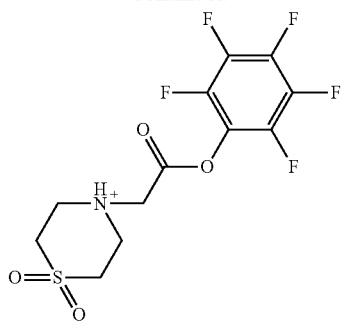
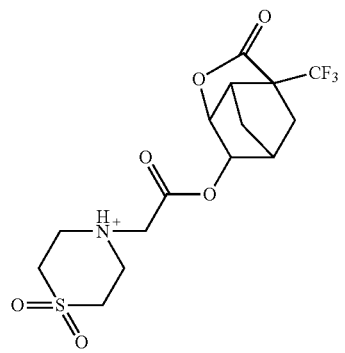
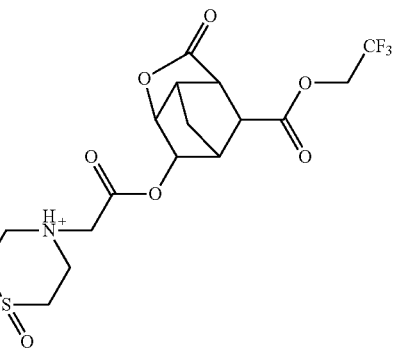
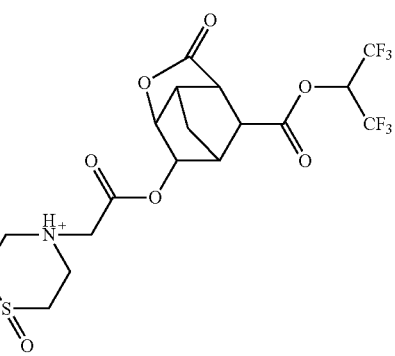
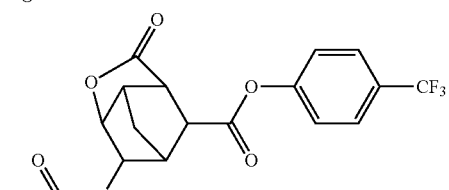

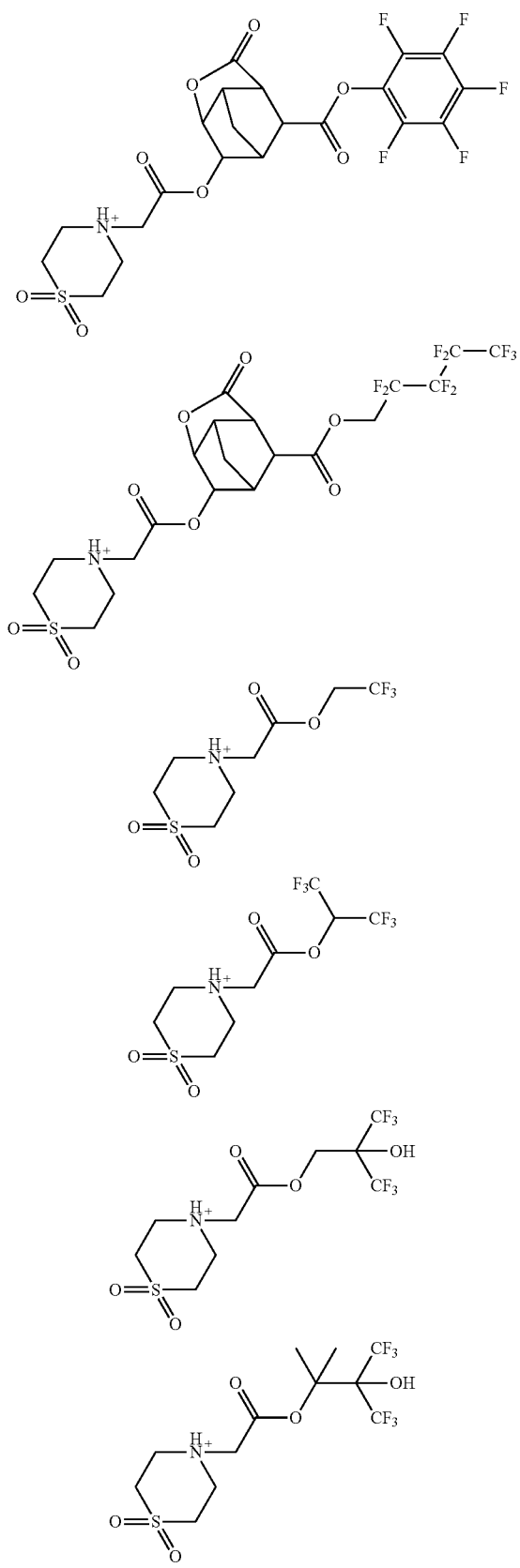
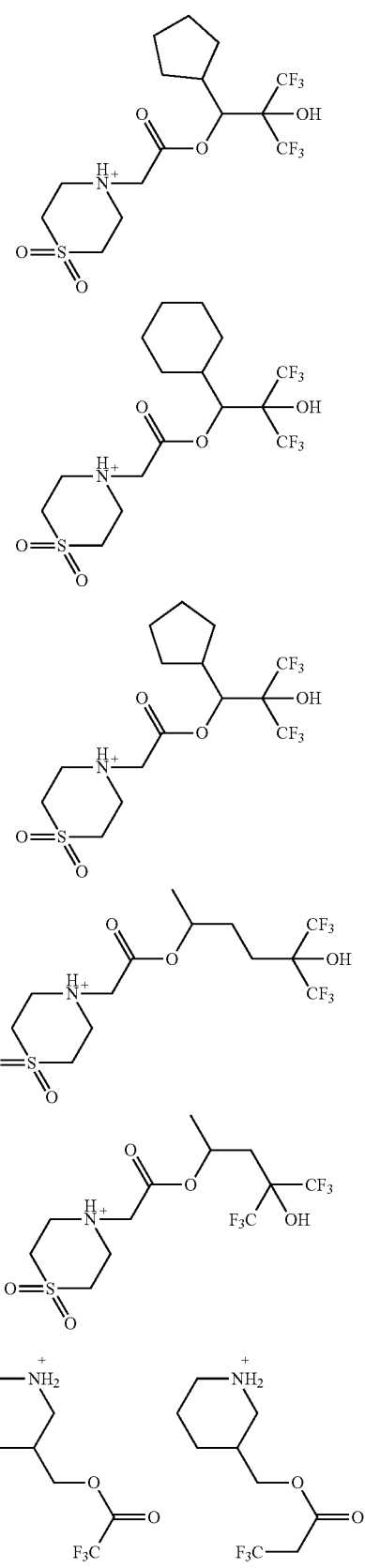

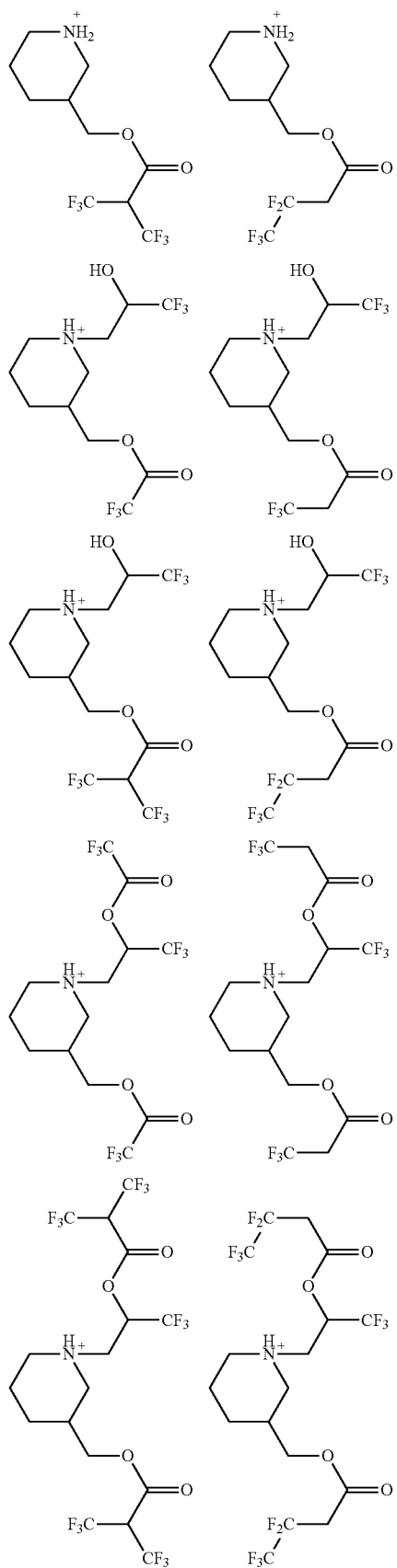
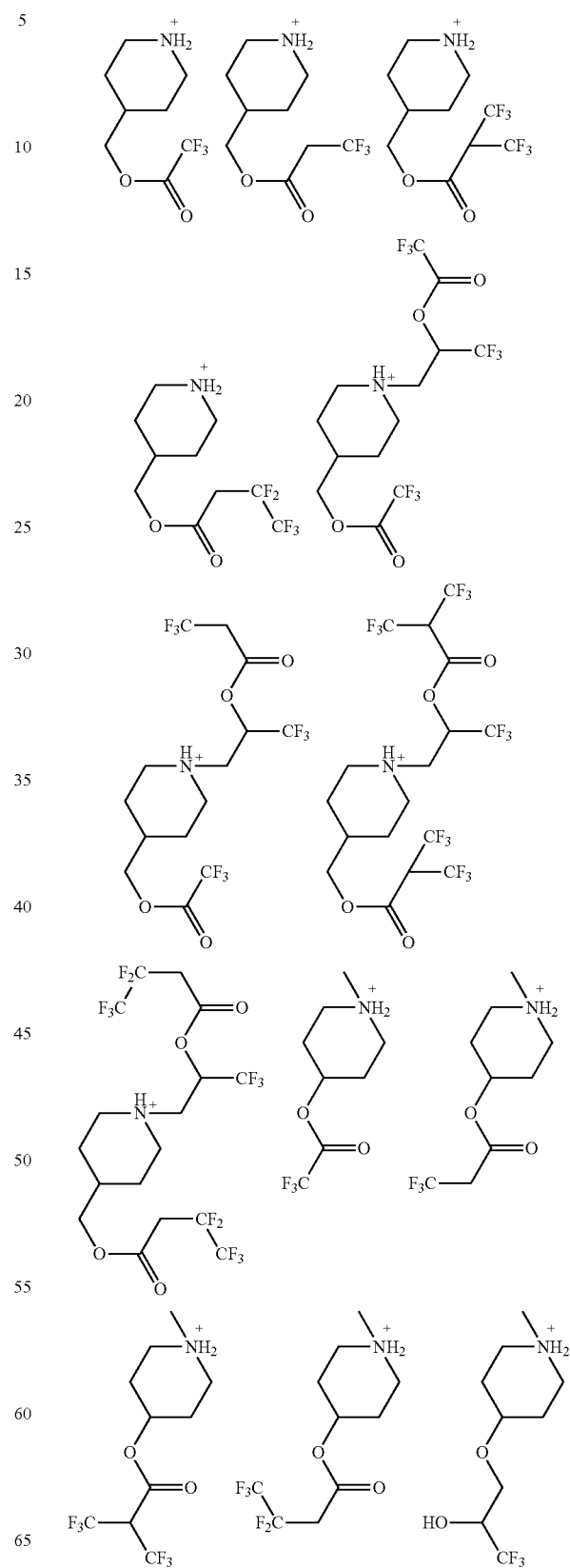

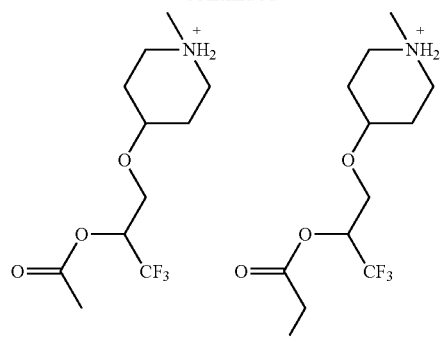
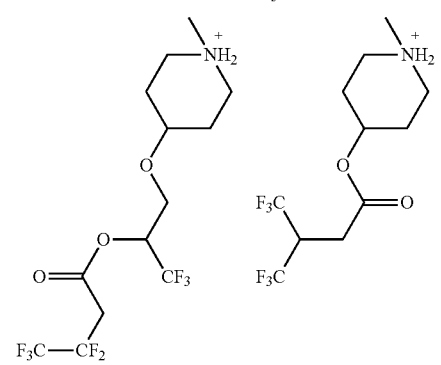
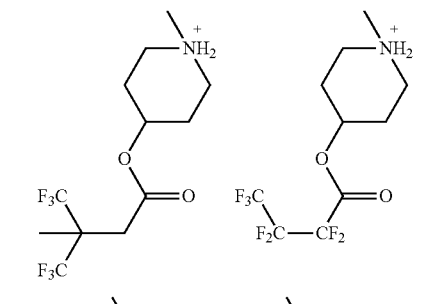
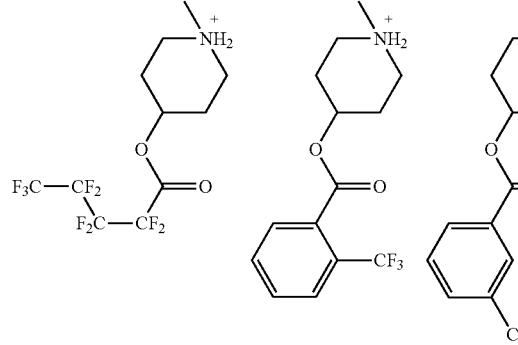
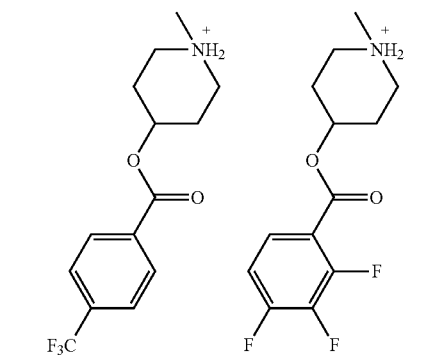
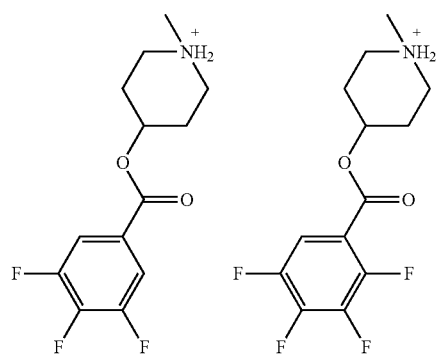
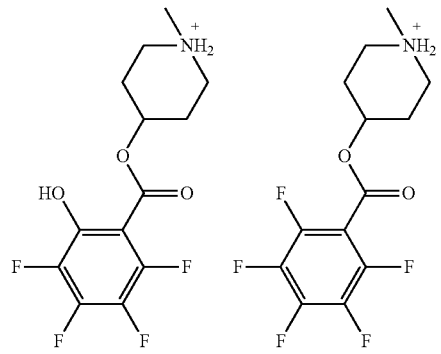
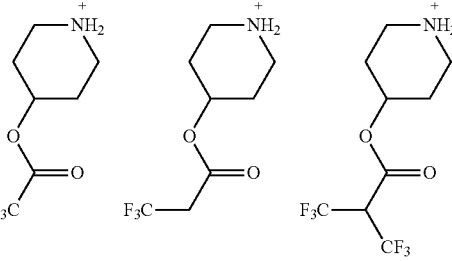
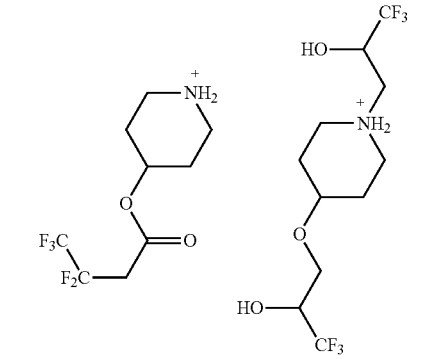

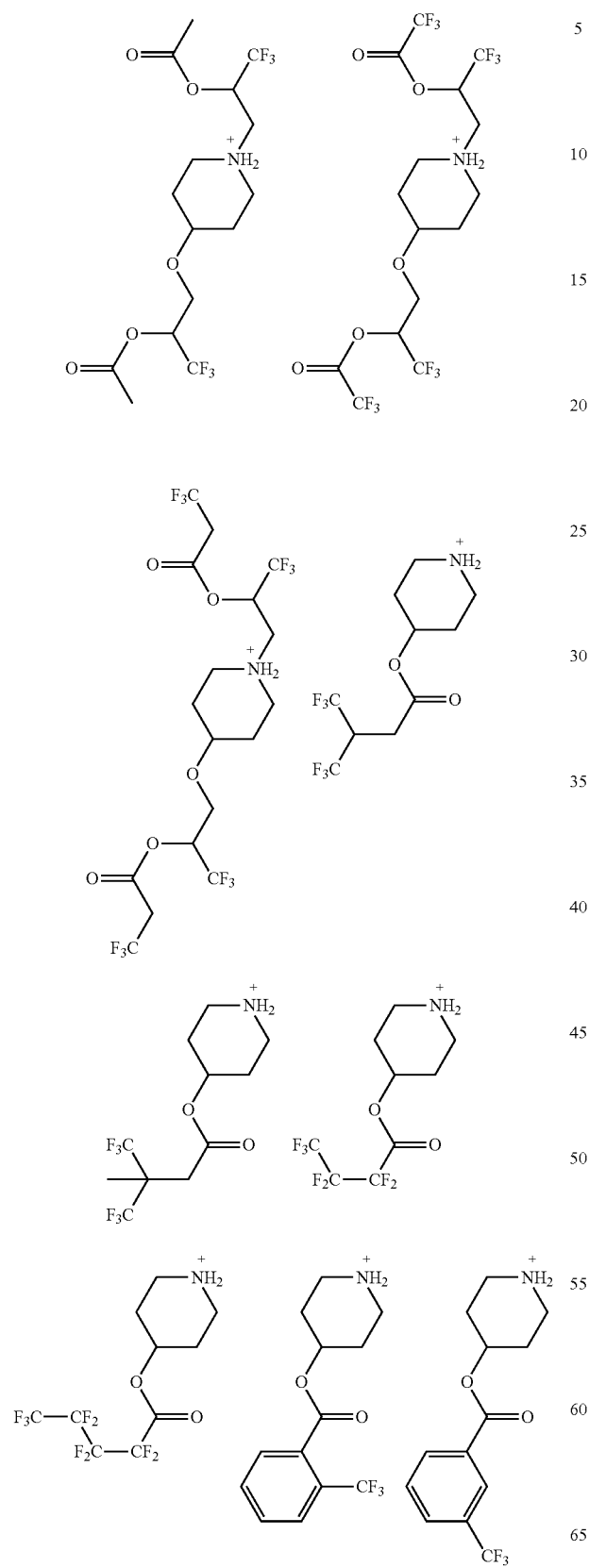

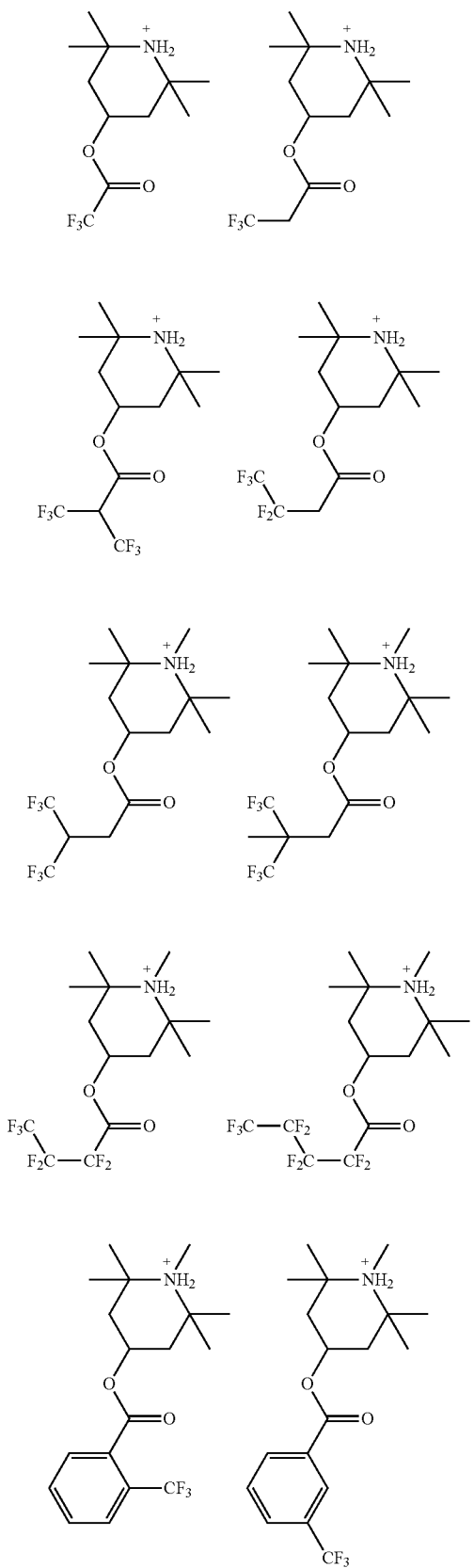
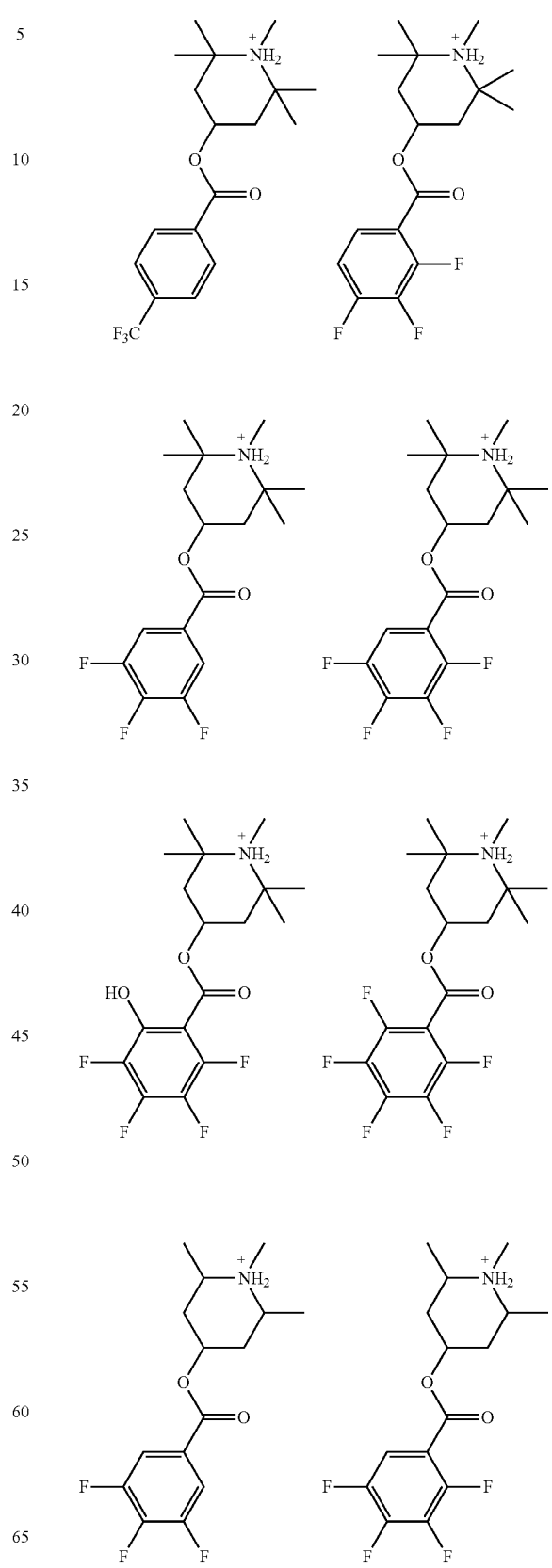

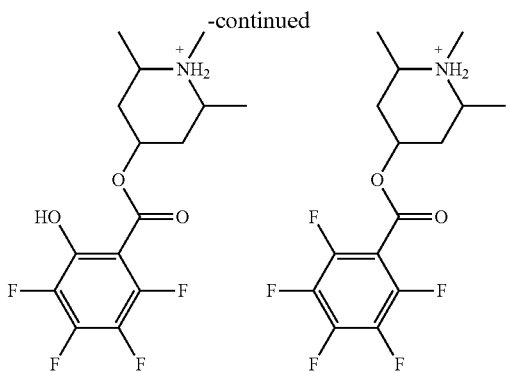

In formula (A), X⁻ is a carboxylate, sulfonamide, halogenated phenoxide or halide anion.

Preferably, the carboxylate anion has the formula (Aa); the sulfonamide anion has the formula (Ab); and the halogenated phenoxide anion has the formula (Ac), all shown below.

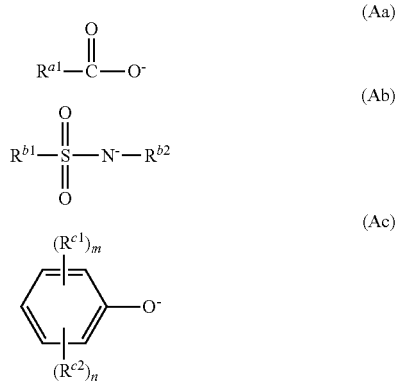

In formula (Aa), $R^1$ is hydrogen or a $C_1$-$C_{30}$ hydrocarbyl group which may contain a heteroatom. The hydrocarbyl group may be saturated or unsaturated and straight, branched or cyclic. Examples thereof include $C_1$-$C_{30}$ alkyl groups. $C_3$-$C_{30}$ cyclic saturated hydrocarbyl groups. $C_2$-$C_{30}$ alkenyl groups, $C_2$-$C_{30}$ alkynyl groups, $C_3$-$C_{30}$ cyclic unsaturated to aliphatic hydrocarbyl groups, $C_6$-$C_{30}$ aryl groups, $C_7$-$C_{30}$ aralkyl groups, and combinations thereof. In these groups, some hydrogen may be substituted by a moiety containing a heteroatom such as oxygen, sulfur, nitrogen or halogen, and some carbon may be replaced by a moiety containing a heteroatom such as oxygen, sulfur or nitrogen, so that the group may contain an ester bond, ether bond, thioether bond, carbonyl moiety, sulfonyl moiety, carbonate moiety, carbamate moiety, sulfone moiety, amino moiety, amide bond, hydroxy moiety, thiol moiety, nitro moiety, fluorine, chlorine, bromine or iodine.

In formula (Ab), $R^{b1}$ is fluorine, a $C_1$-$C_{10}$ hydrocarbyl group or a $C_1$-$C_{10}$ fluorinated hydrocarbyl group. The hydrocarbyl or fluorinated hydrocarbyl group may contain a hydroxy moiety, carboxy moiety, ether bond, ester bond or amide bond. The hydrocarbyl group may be saturated or unsaturated and straight, branched or cyclic. Examples thereof include $C_1$-$C_{10}$ alkyl groups, $C_3$-$C_{10}$ cyclic saturated hydrocarbyl groups, $C_2$-$C_{10}$ alkenyl groups, $C_2$-$C_{10}$ alkynyl groups, $C_3$-$C_{10}$ cyclic unsaturated aliphatic hydrocarbyl groups, $C_6$-$C_{10}$ aryl groups, $C_7$-$C_{10}$ aralkyl groups, and combinations thereof. The fluorinated hydrocarbyl groups are the foregoing hydrocarbyl groups in which some or all of the hydrogen atoms are substituted by fluorine atoms.

In formula (Ab), $R^{b2}$ is hydrogen or a $C_1$-$C_{20}$ hydrocarbyl group which may contain a heteroatom. Also $R^{b1}$ and $R^{b2}$ may bond together to form a ring with the atoms to which they are attached. The hydrocarbyl group may be saturated or unsaturated and straight, branched or cyclic. Examples thereof include $C_1$-$C_{20}$ alkyl groups. $C_3$-$C_{20}$ cyclic saturated hydrocarbyl groups, $C_2$-$C_{20}$ alkenyl groups, $C_2$-$C_{20}$ alkynyl groups, $C_3$-$C_{20}$ cyclic unsaturated aliphatic hydrocarbyl groups, $C_6$-$C_{20}$ aryl groups, $C_7$-$C_{20}$ aralkyl groups, and combinations thereof. In these groups, some hydrogen may be substituted by a moiety containing a heteroatom such as oxygen, sulfur, nitrogen or halogen, and some carbon may be replaced by a moiety containing a heteroatom such as oxygen, sulfur or nitrogen, so that the group may contain an ester bond, ether bond, thioether bond, carbonyl moiety, sulfonyl moiety, carbonate moiety, carbamate moiety, sulfone moiety, amino moiety, amide bond, hydroxy moiety, thiol moiety, nitro moiety, fluorine, chlorine, bromine or iodine.

In formula (Ac), $R^{c1}$ is fluorine, trifluoromethyl, 1,1,1,3,3,3-hexafluoro-2-propanol, chlorine, bromine or iodine. Preferably, $R^{c1}$ is fluorine, bromine or iodine.

In formula (Ac), $R^{c2}$ is hydrogen, hydroxy, optionally halogenated $C_1$-$C_6$ saturated hydrocarbyl group, optionally halogenated $C_1$-$C_6$ saturated hydrocarbyloxy group, optionally halogenated $C_2$-$C_7$ saturated hydrocarbylcarbonyloxy group, optionally halogenated $C_1$-$C_4$ saturated hydrocarbylsulfonyloxy group, fluorine, chlorine, bromine, amino, nitro, cyano, —N($R^{c21}$)—C(=O)—$R^{c22}$ or —N($R^{c21}$)—C(=O)—O—$R^{c22}$. $R^{c21}$ is hydrogen or a $C_1$-$C_6$ saturated hydrocarbyl group. $R^{c22}$ is a $C_1$-$C_6$ saturated hydrocarbyl group or $C_2$-$C_8$ unsaturated aliphatic hydrocarbyl group. The subscript m is an integer of 1 to 5, n is an integer of 0 to 3, meeting 1≤m+n≤5.

The saturated hydrocarbyl group represented by $R^{c2}$, $R^{c21}$ and $R^{c22}$ may be straight, branched or cyclic. Examples thereof include $C_1$-$C_6$ alkyl groups such as methyl, ethyl, n-propyl, isopropyl, n-butyl, isobutyl, sec-butyl, tert-butyl, n-pentyl and n-hexyl; cycloalkyl groups such as cyclopropyl, cyclobutyl, cyclopentyl and cyclohexyl; and combinations thereof. Examples of the saturated hydrocarbyl moiety in the $C_1$-$C_6$ saturated hydrocarbyloxy group and $C_2$-$C_7$ saturated hydrocarbylcarbonyloxy group are as exemplified above for the saturated hydrocarbyl group. Examples of the saturated hydrocarbyl moiety in the $C_1$-$C_4$ saturated hydrocarbylsulfonyloxy group are as exemplified above for the saturated hydrocarbyl group, but of 1 to 4 carbon atoms.

The $C_2$-$C_8$ unsaturated aliphatic hydrocarbyl group represented by $R^2$ may be straight, branched or cyclic. Examples thereof include alkenyl groups such as vinyl, 1-propenyl, 2-propenyl, butenyl and hexenyl, and cyclic unsaturated aliphatic hydrocarbyl groups such as cyclohexenyl.

Among others, $R^{c2}$ is preferably fluorine, chlorine, bromine, hydroxy, amino, $C_1$-$C_3$ alkyl, $C_1$-$C_3$ alkoxy, $C_2$-$C_4$ acyloxy, —N($R^{c21}$)—C(=O)—$R^{c22}$, or —N($R^{c21}$)—C(=O)—O—$R^{c22}$.

Examples of the carboxylate anion are shown below, but not limited thereto.

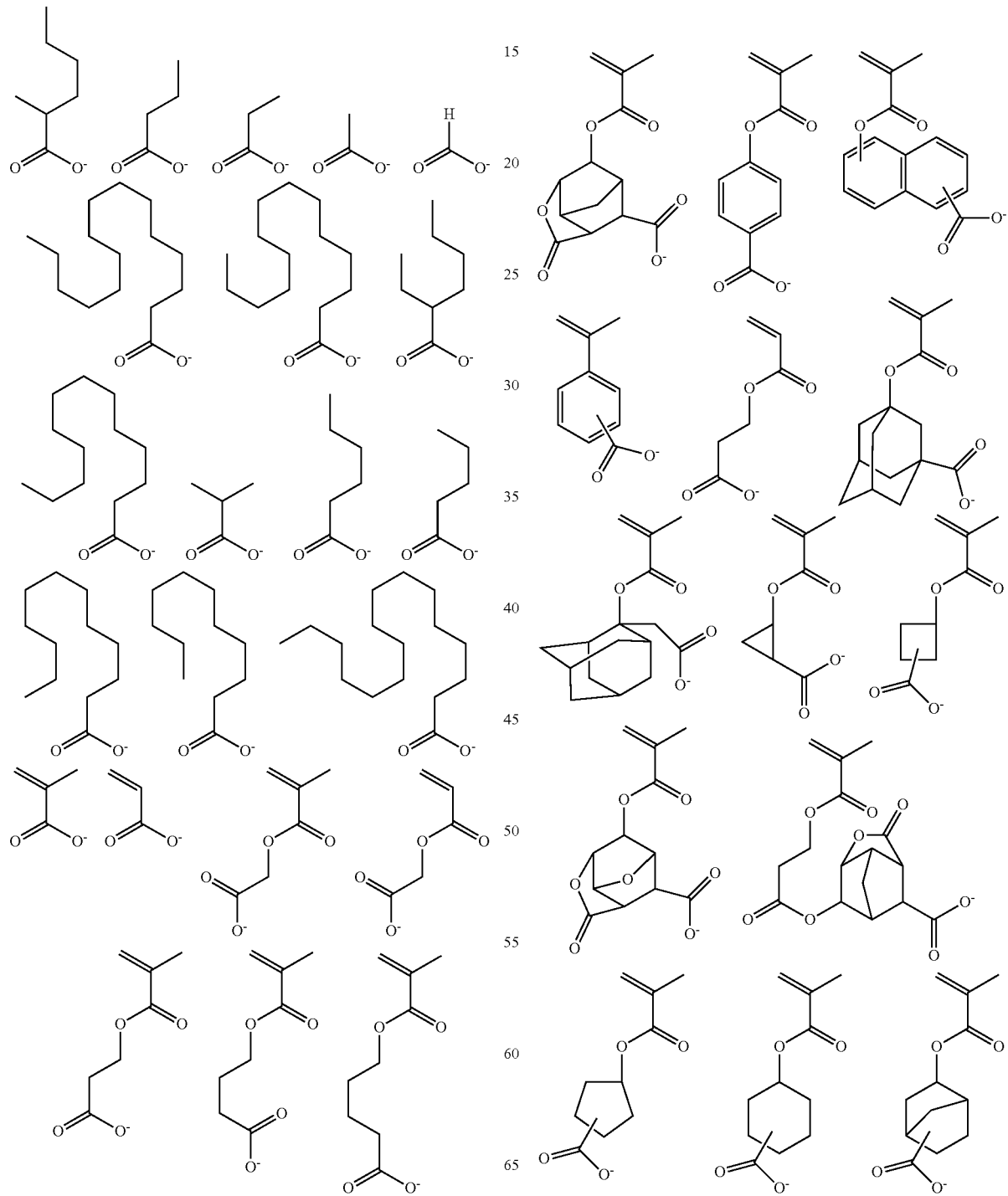

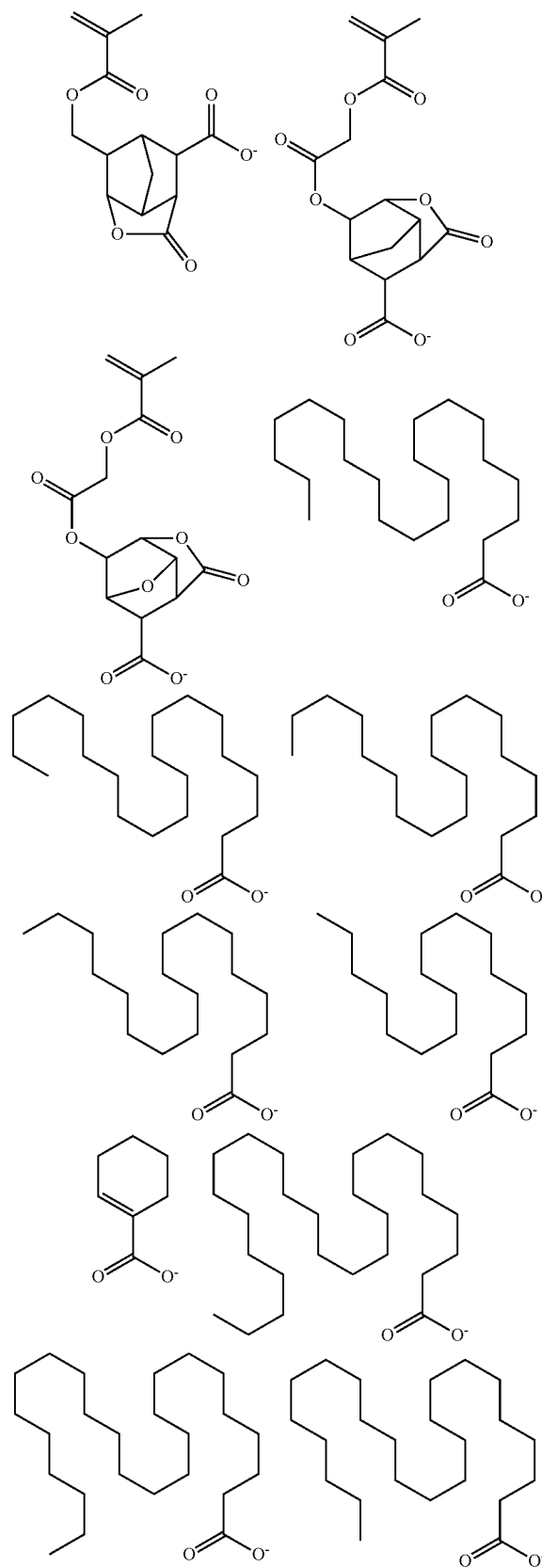
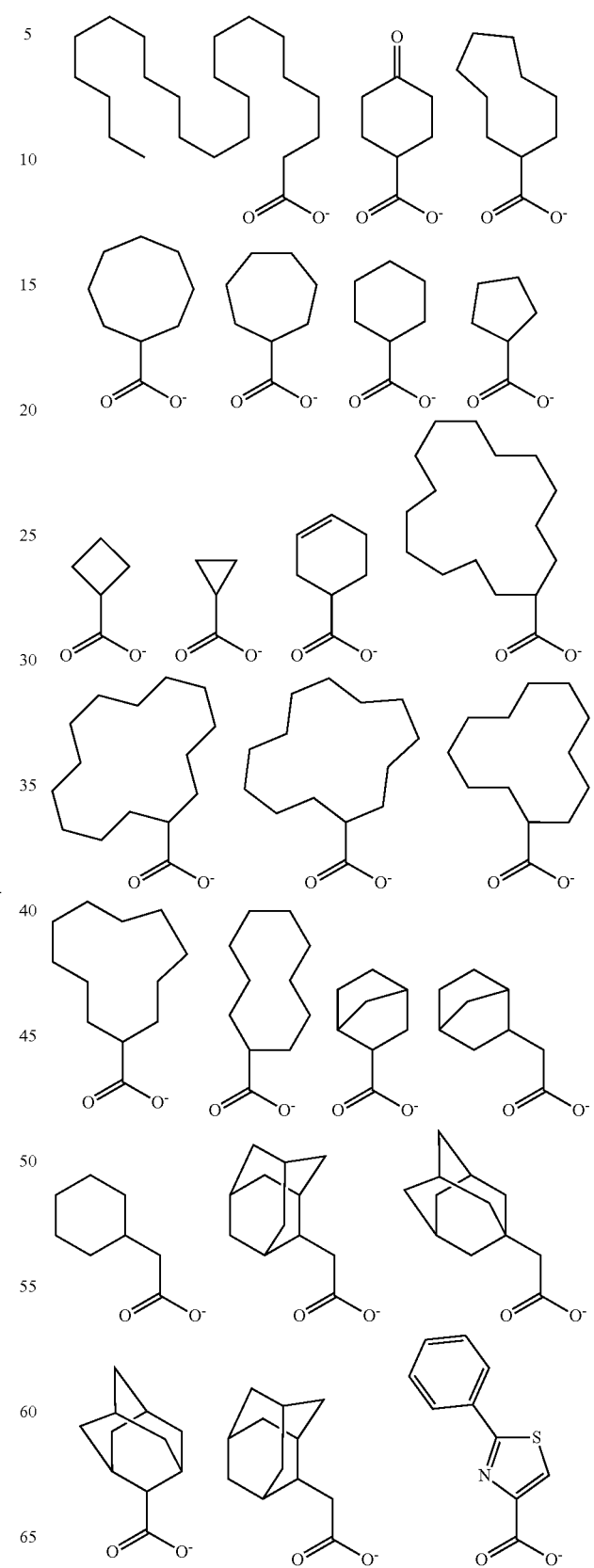

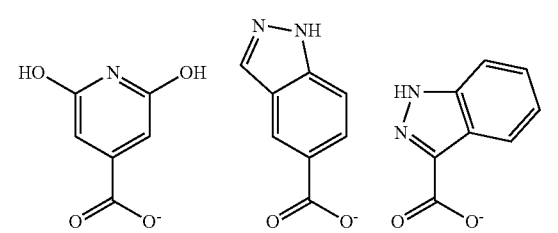
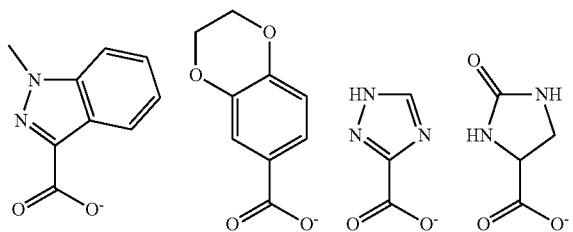
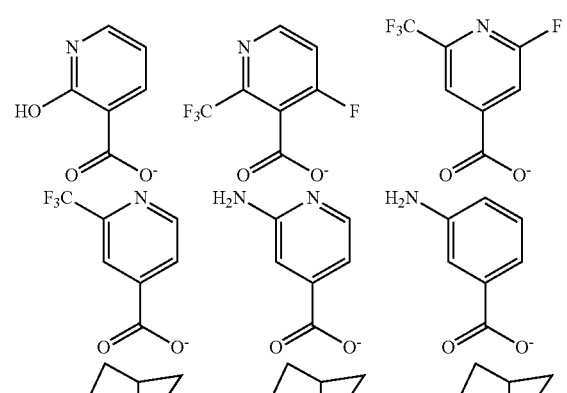
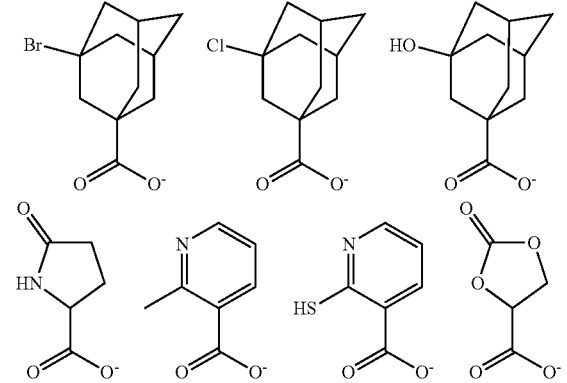
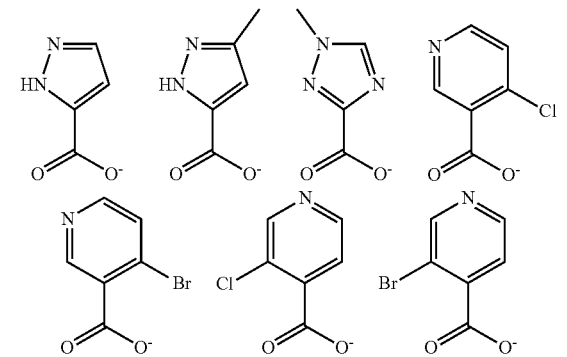
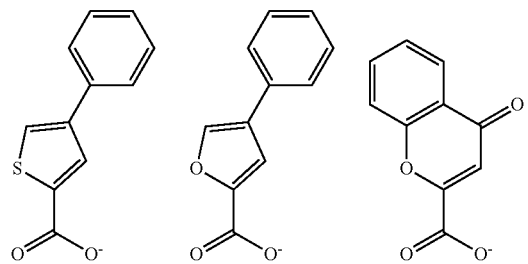
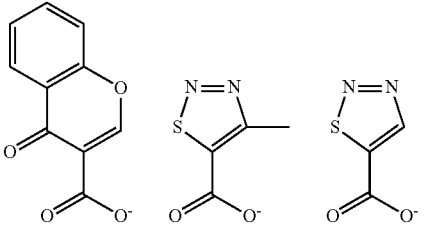
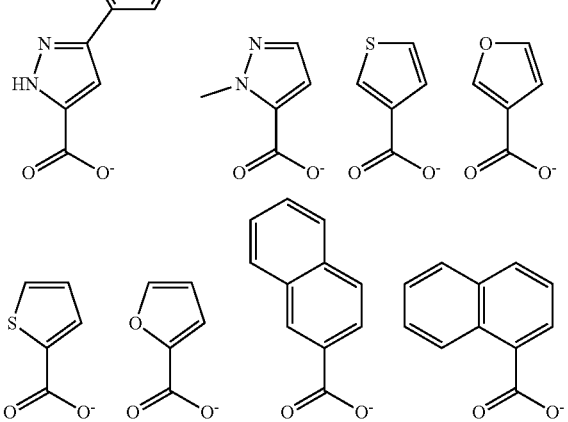
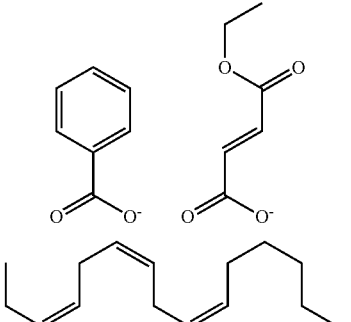
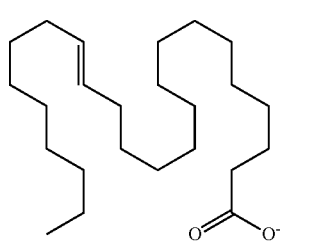

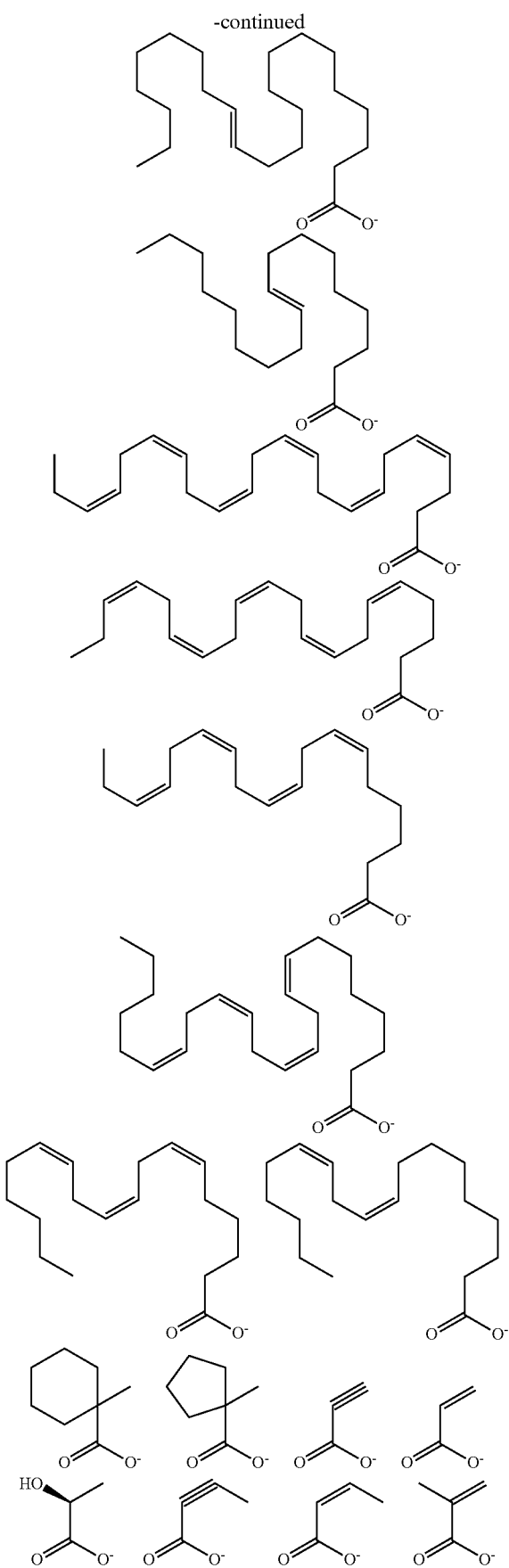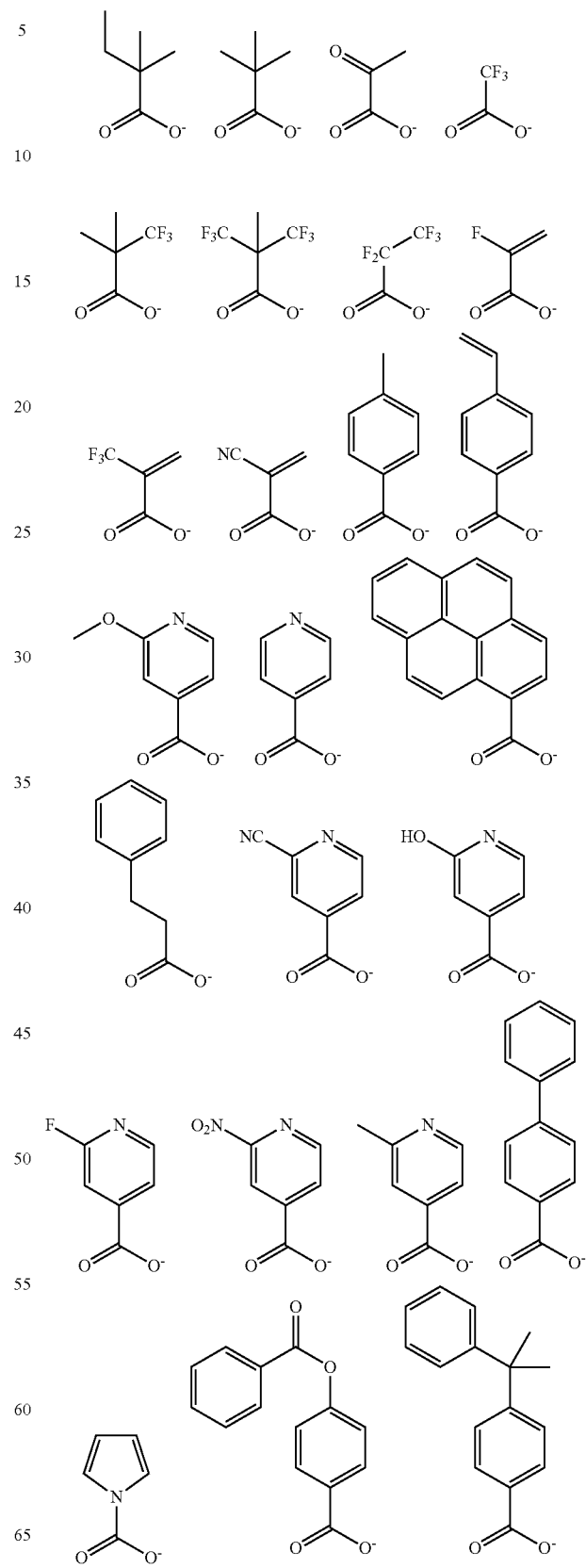

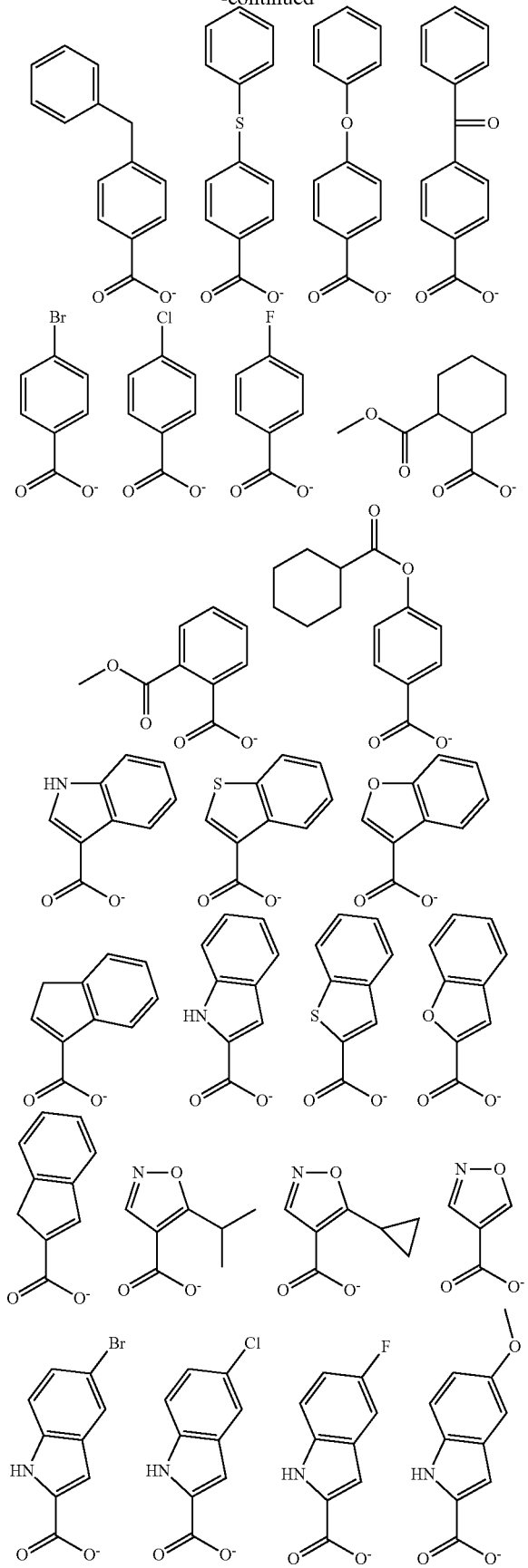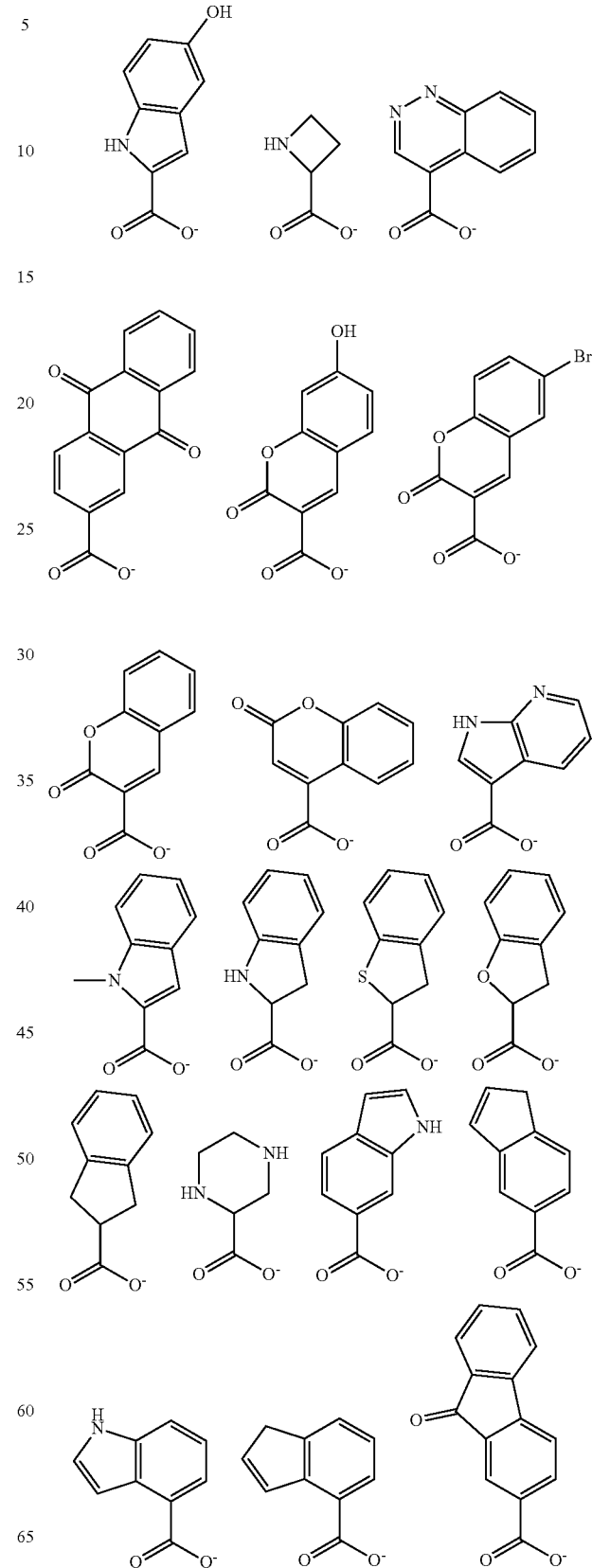

91
-continued
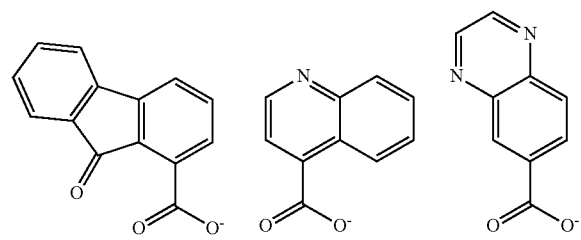
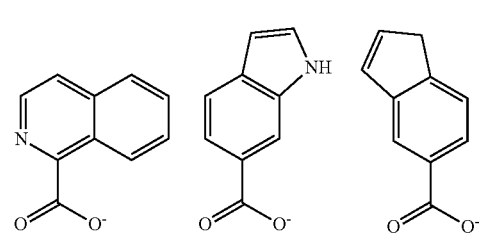
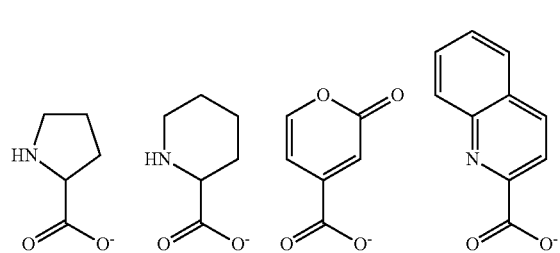
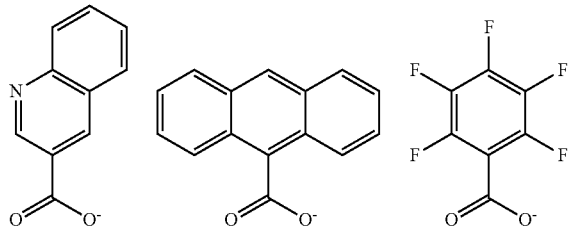
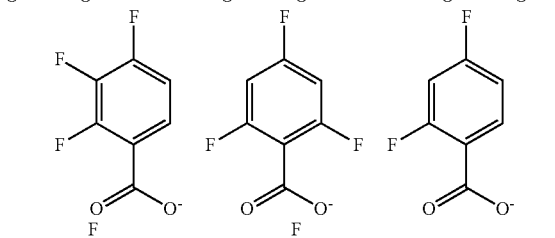
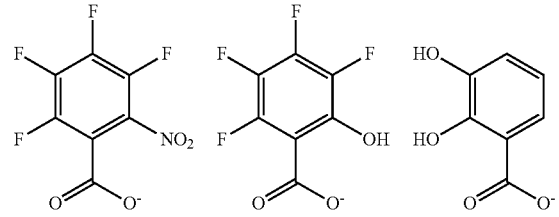
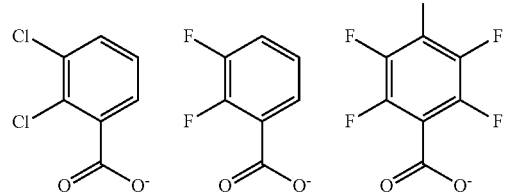
92
-continued
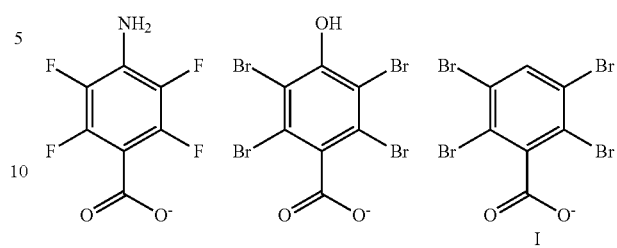
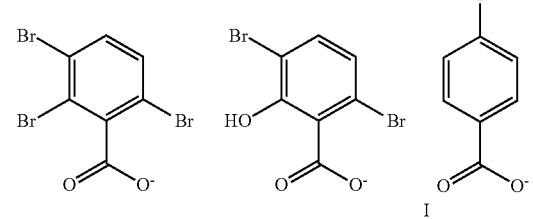
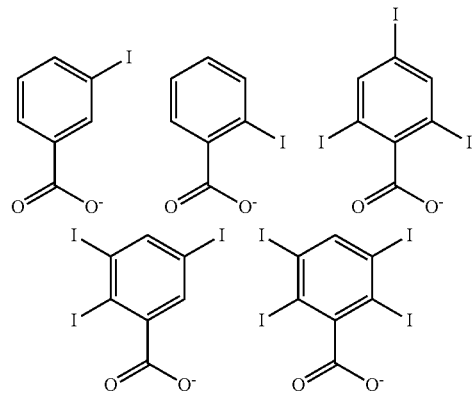
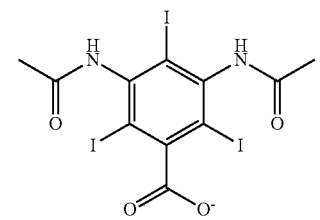
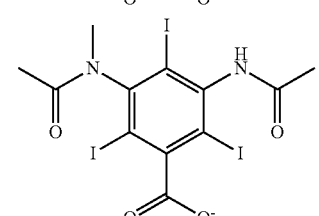
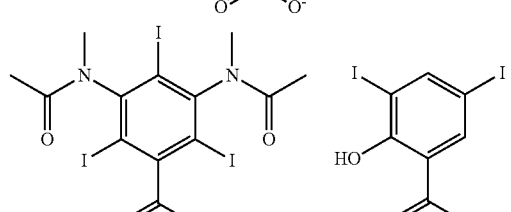
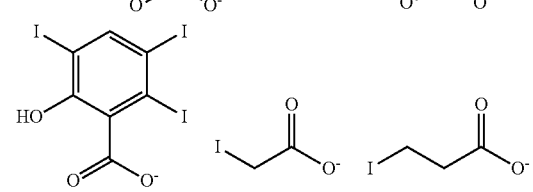

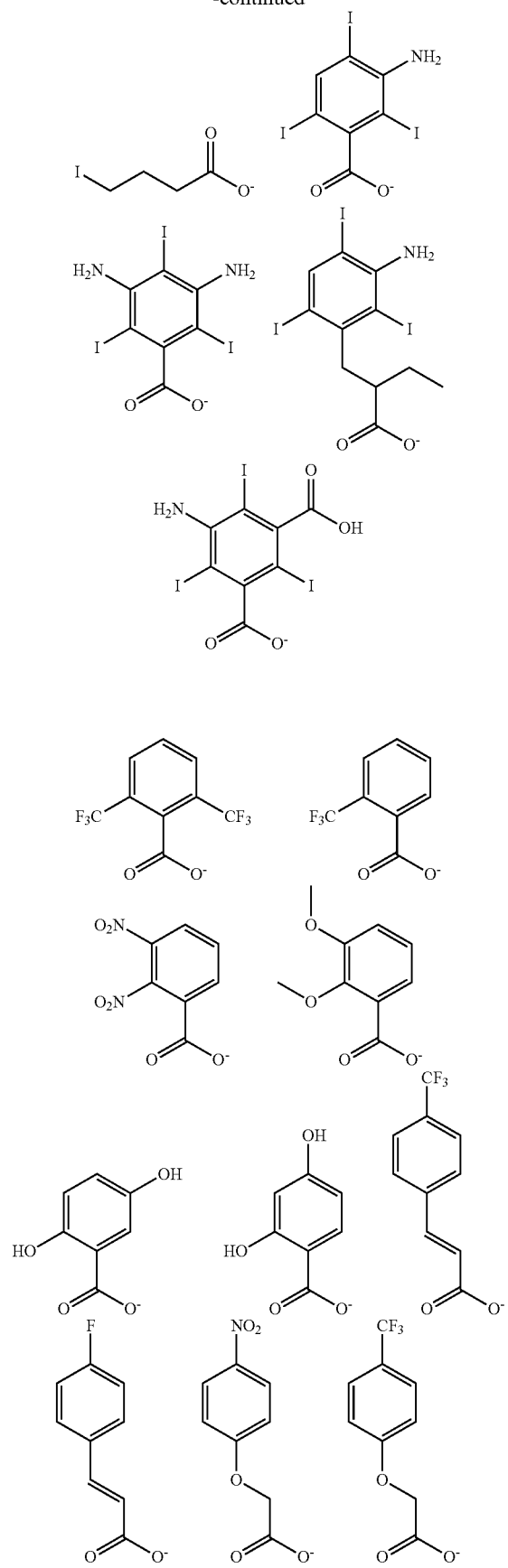
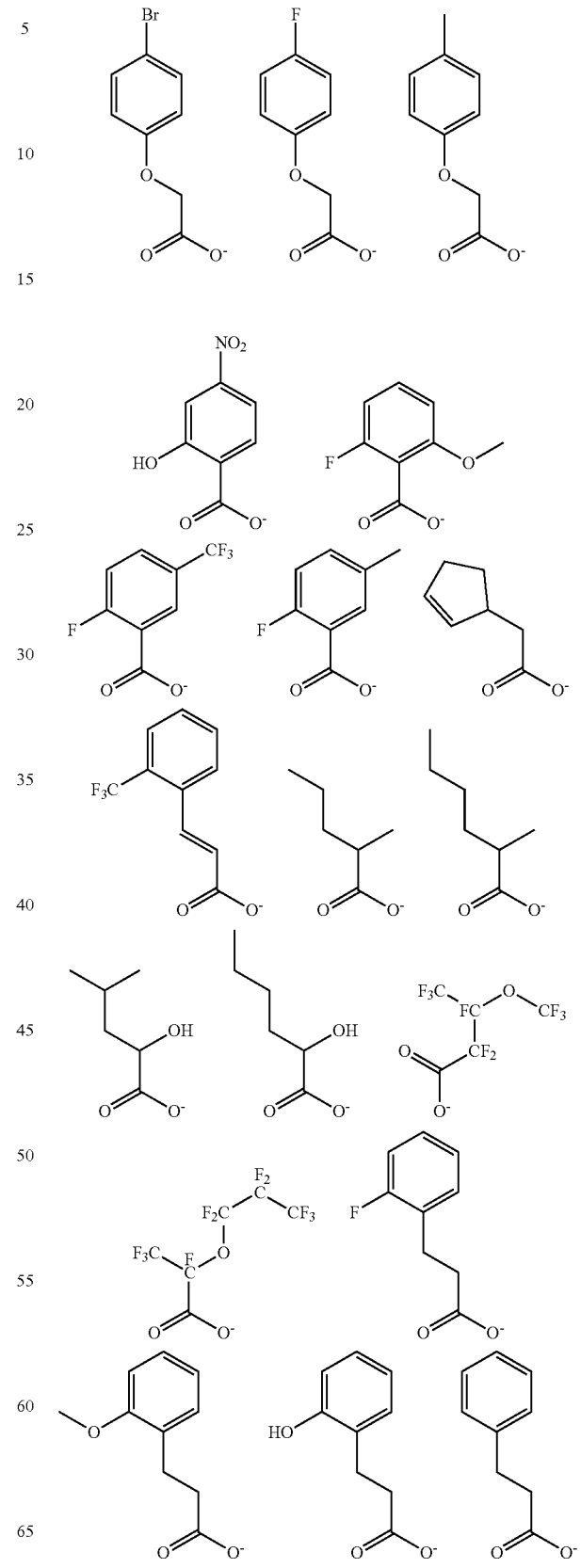

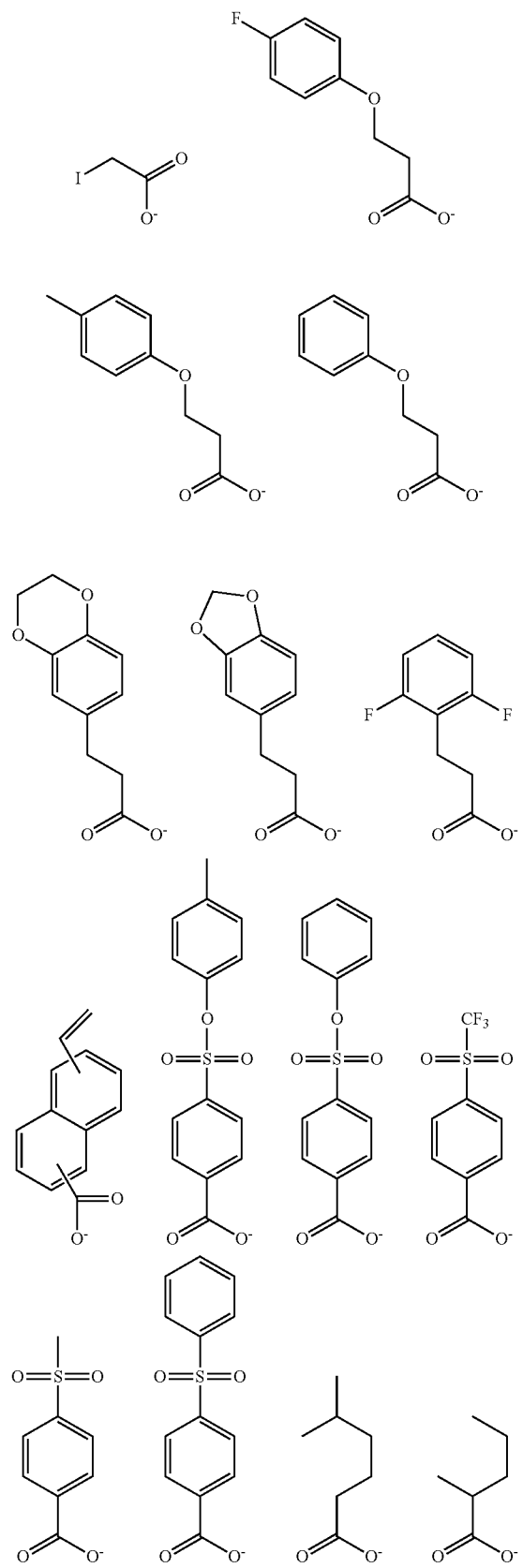
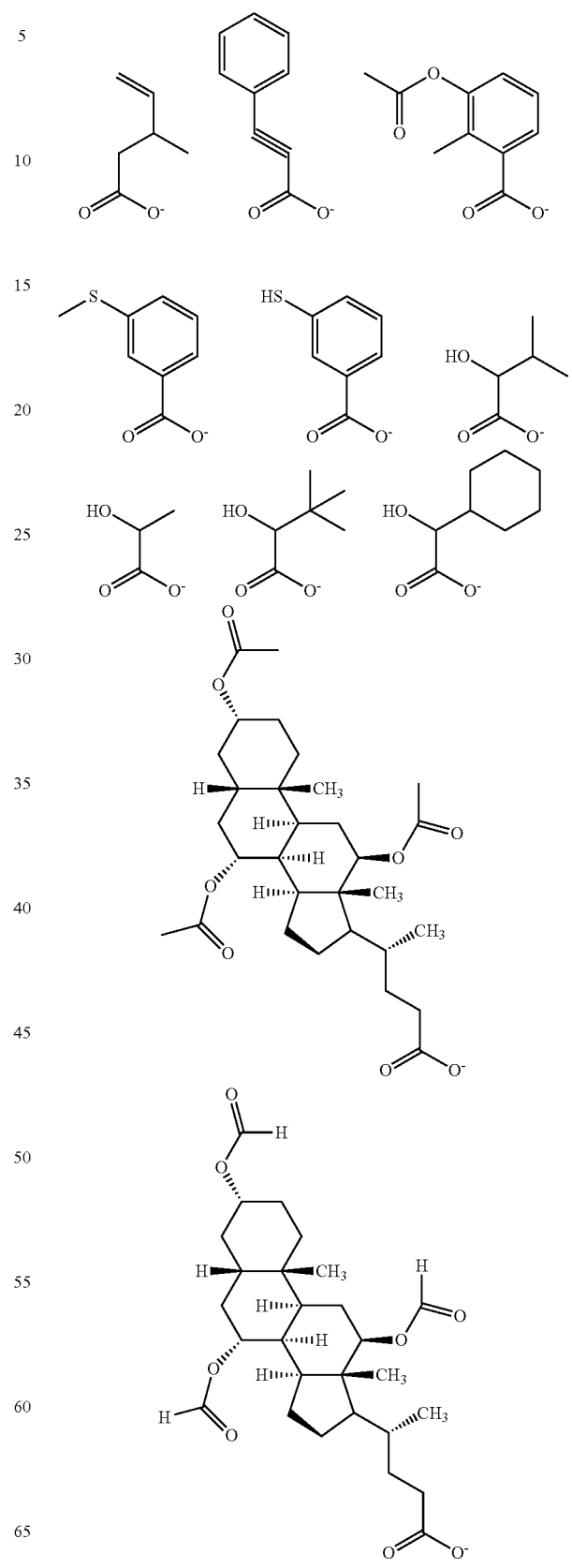

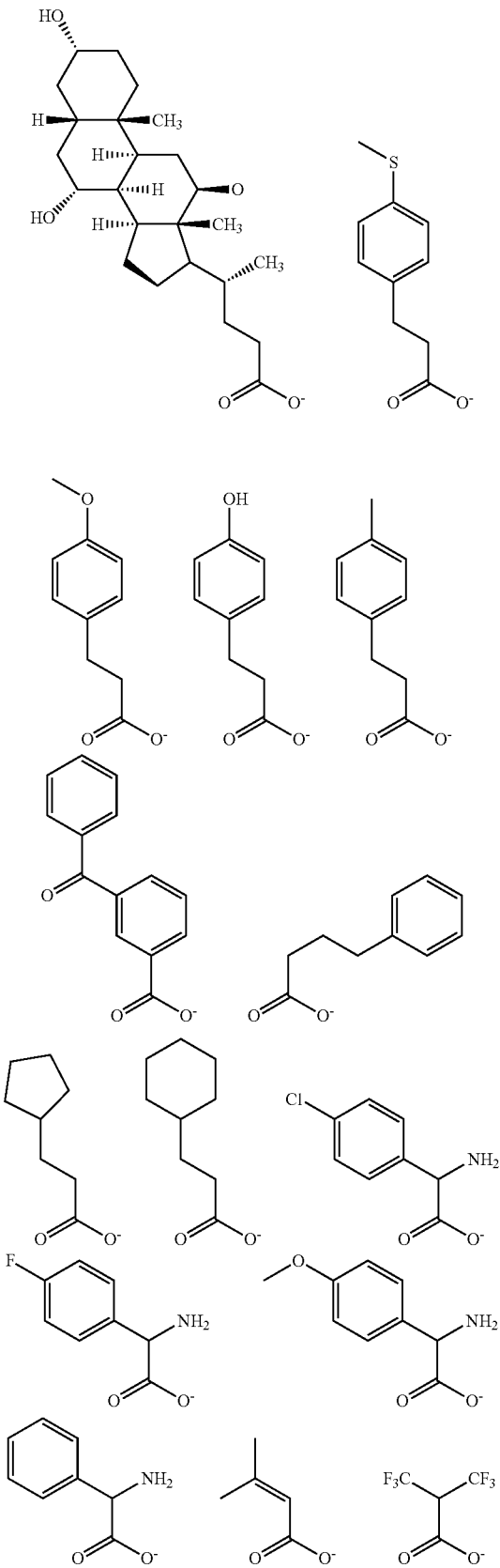
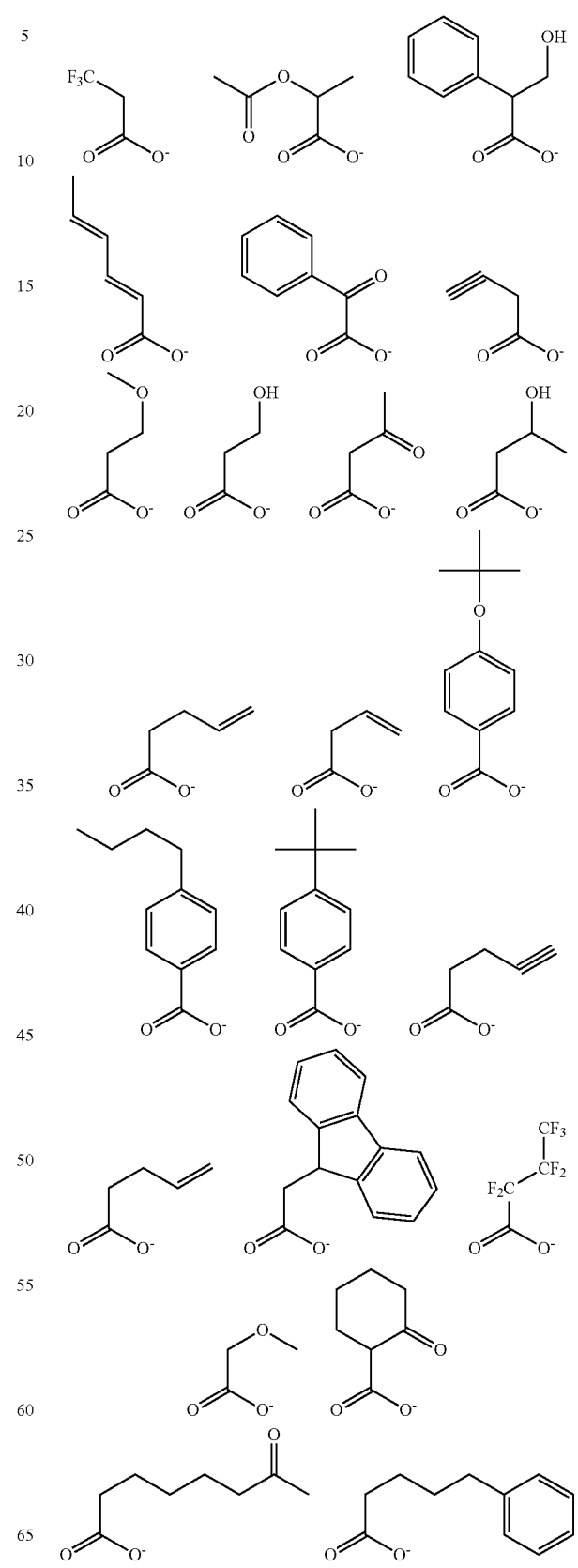

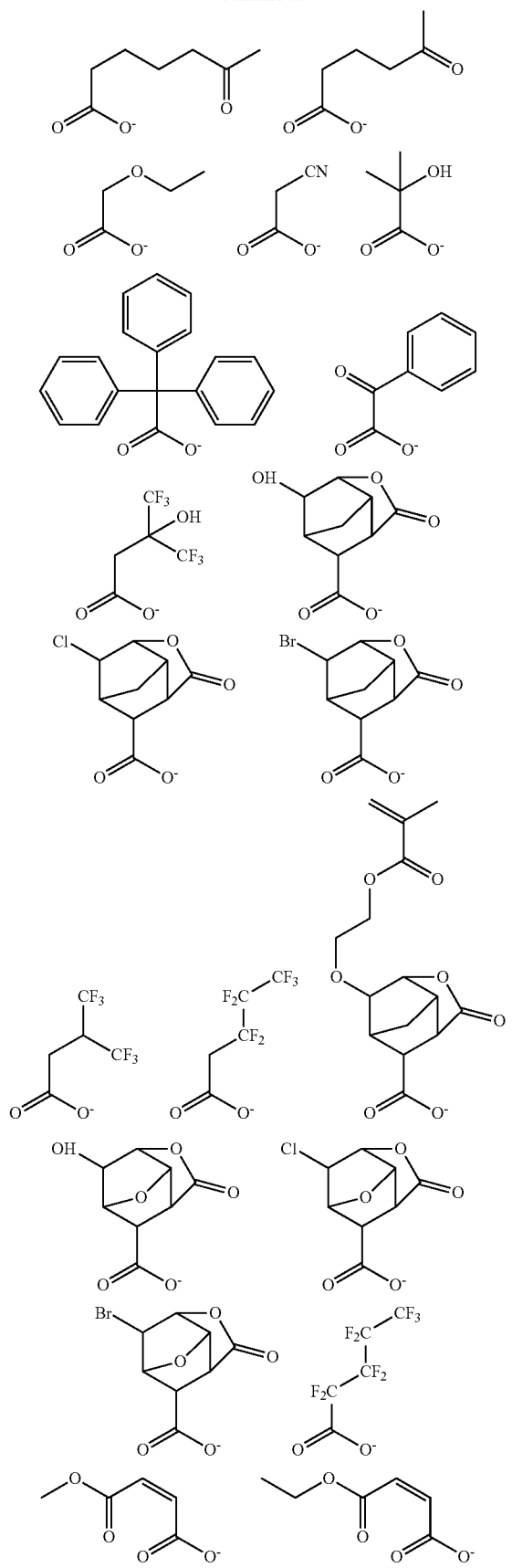
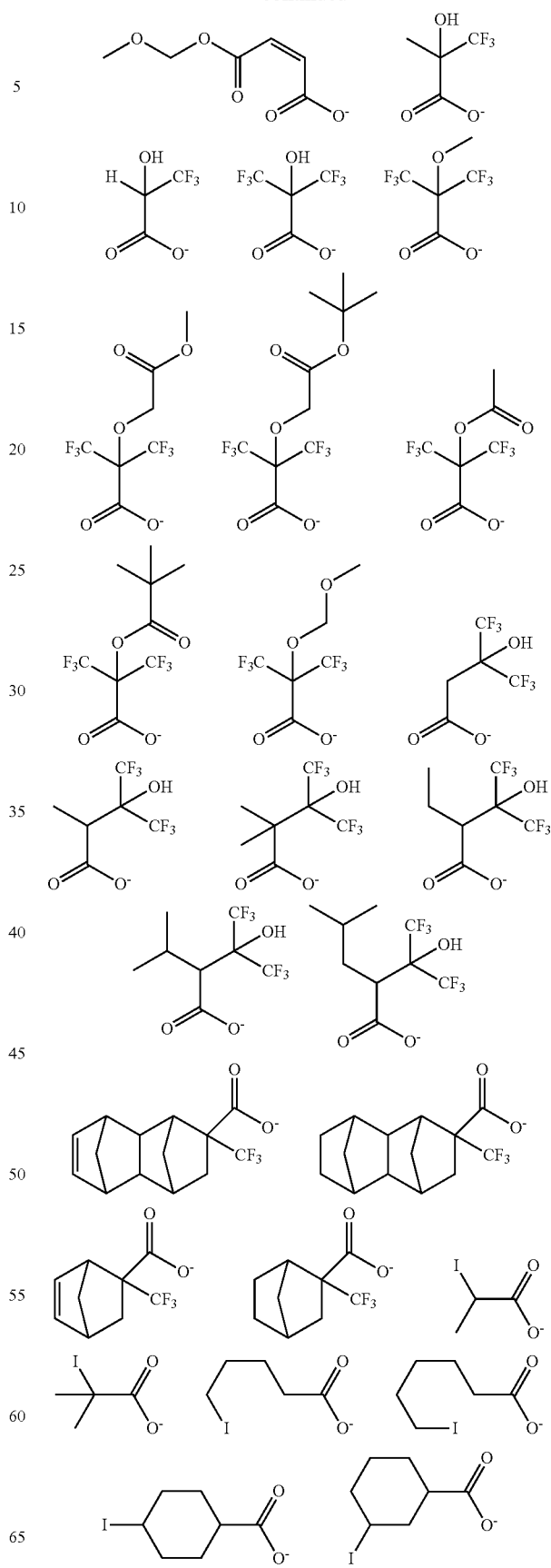

101
-continued
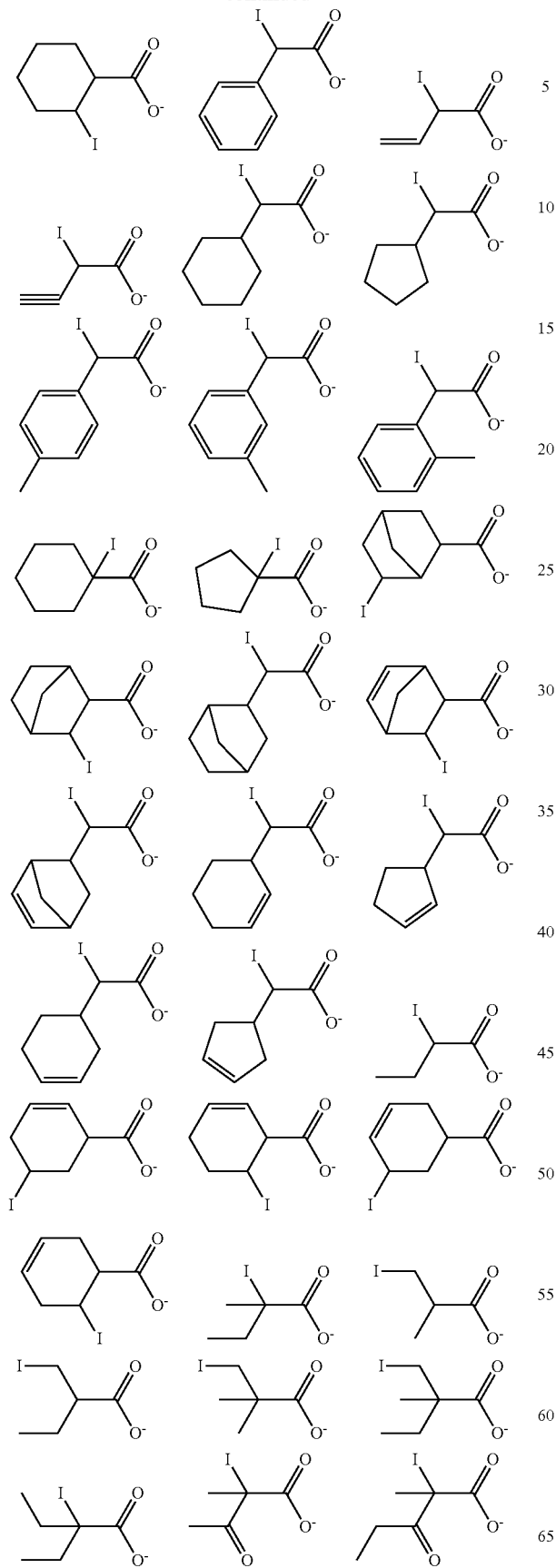
102
-continued
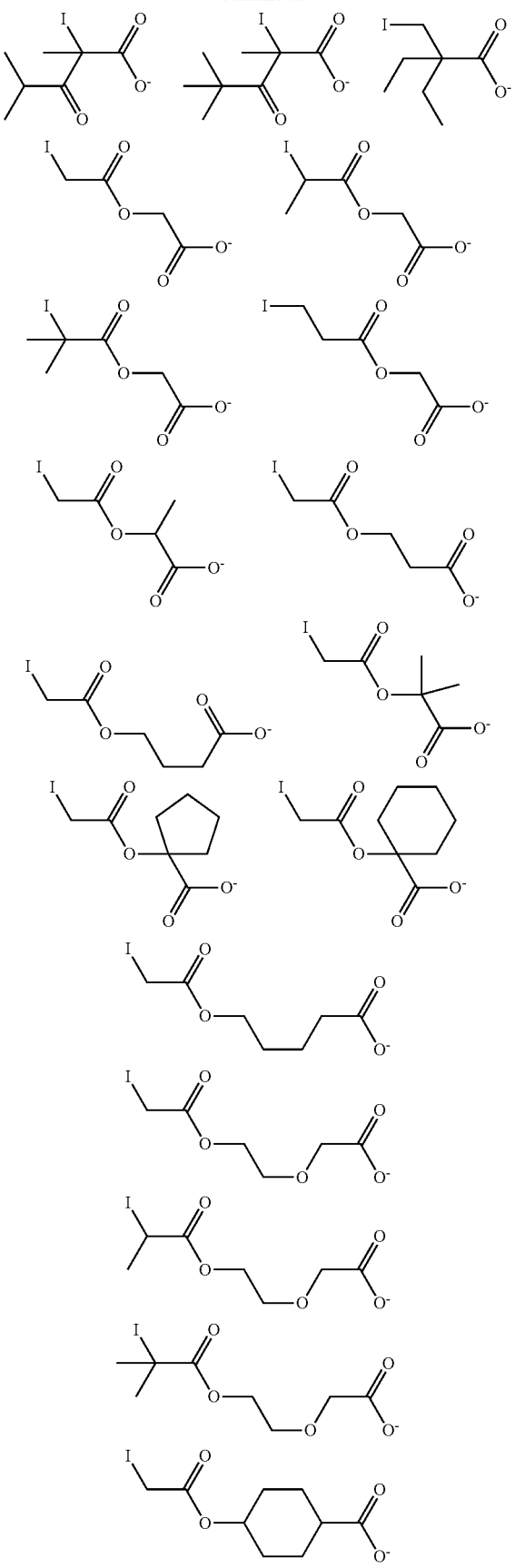

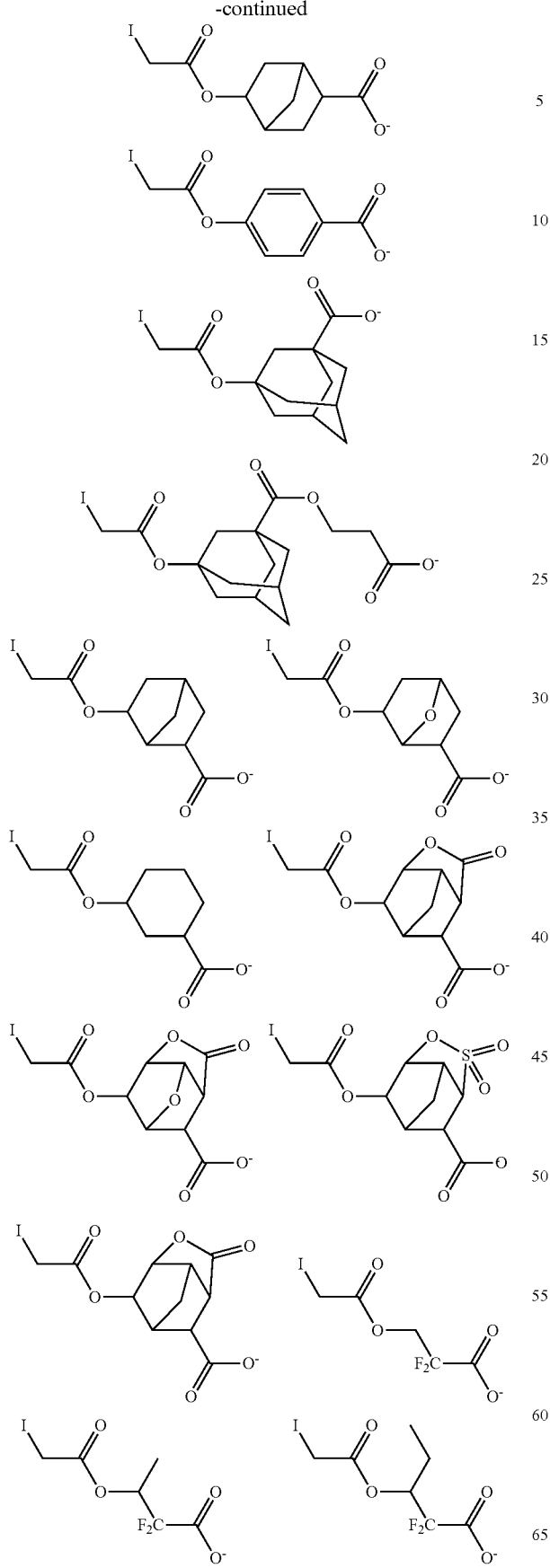
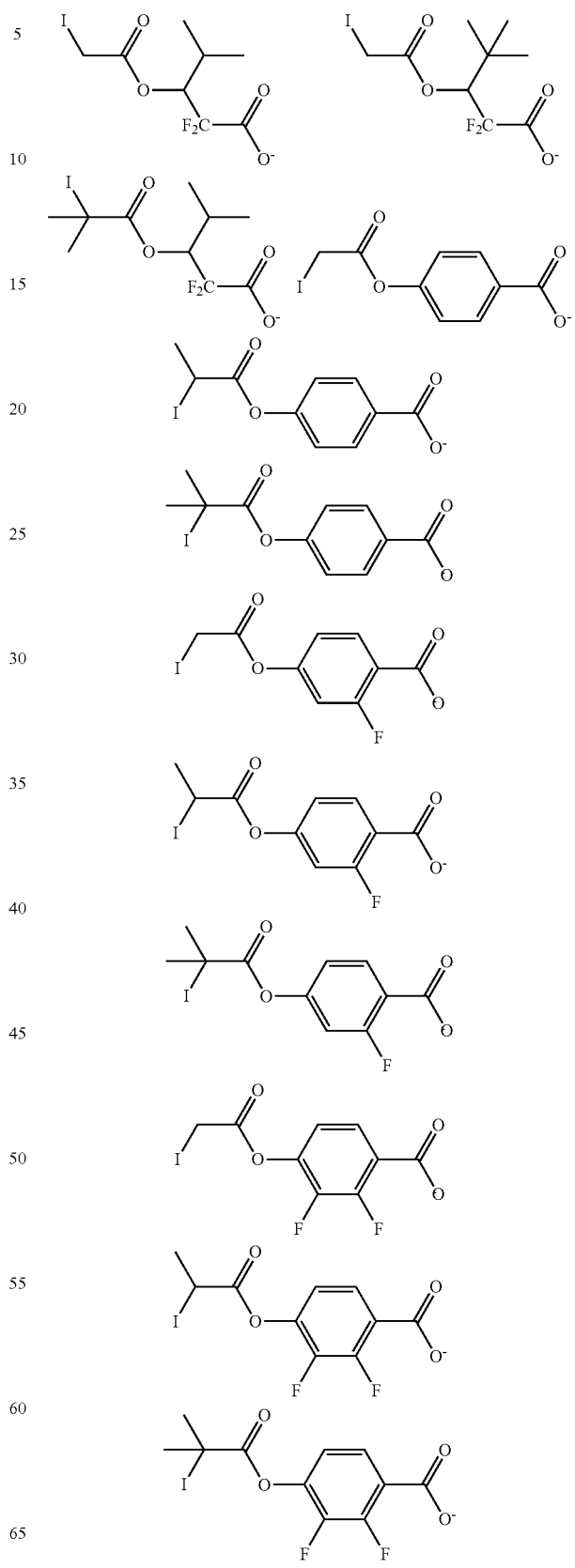

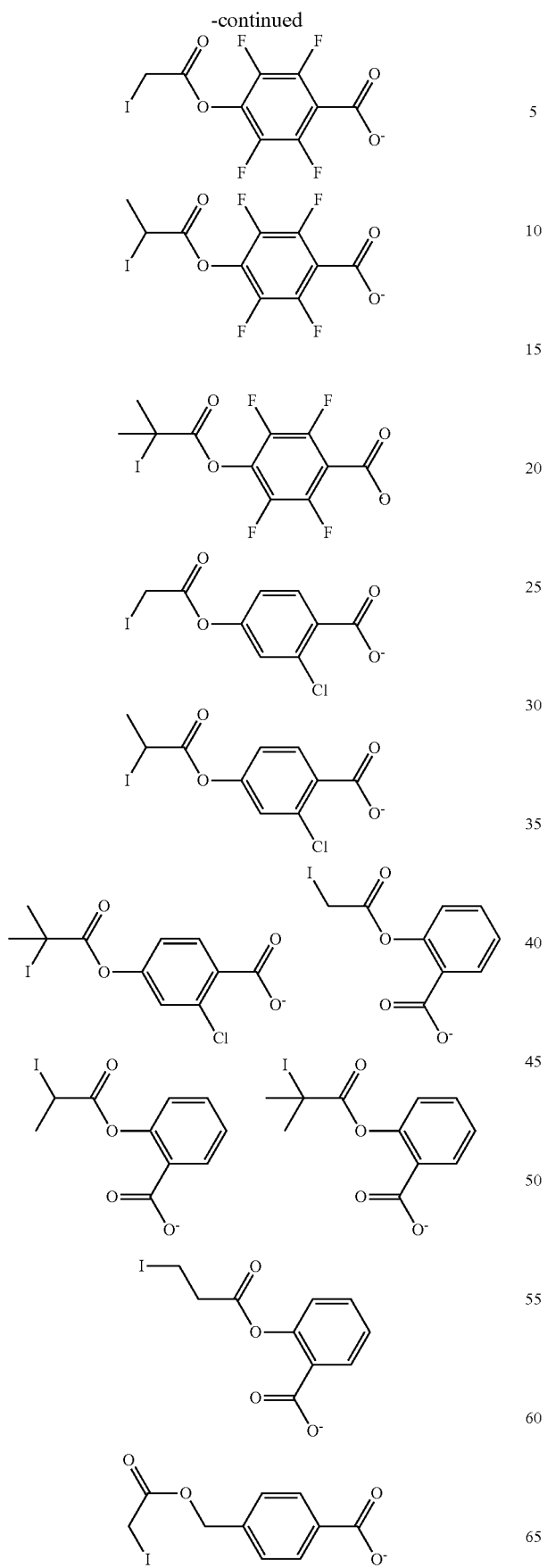
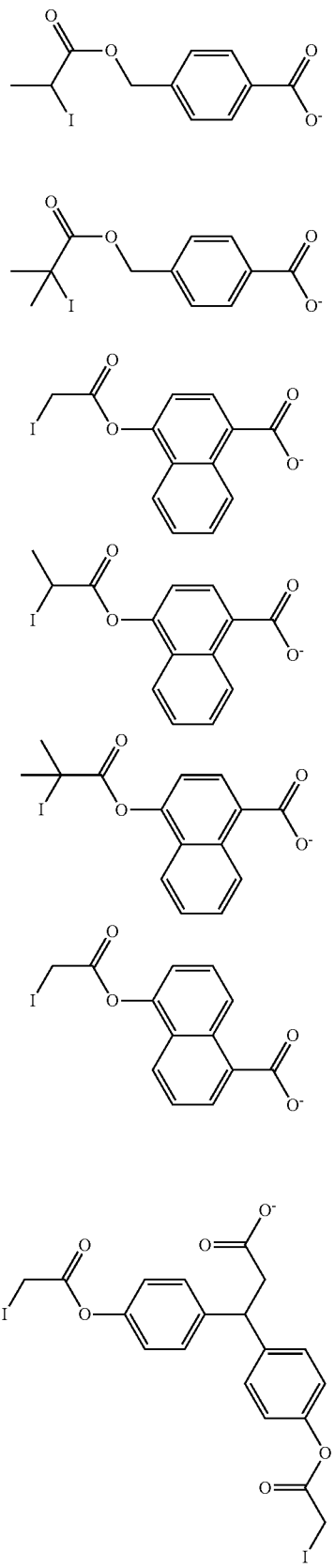

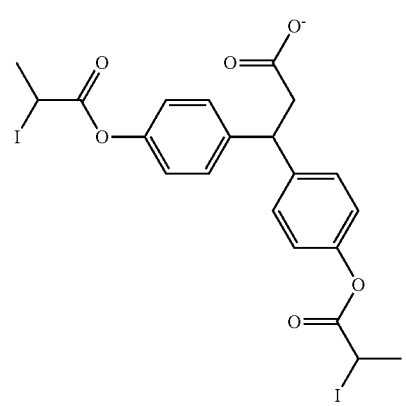
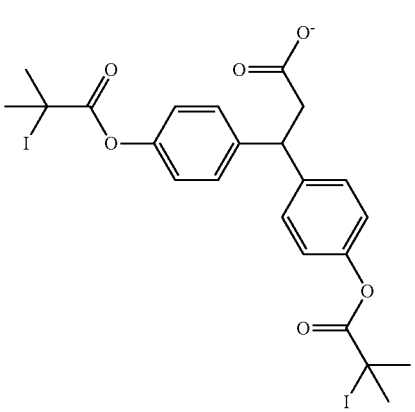
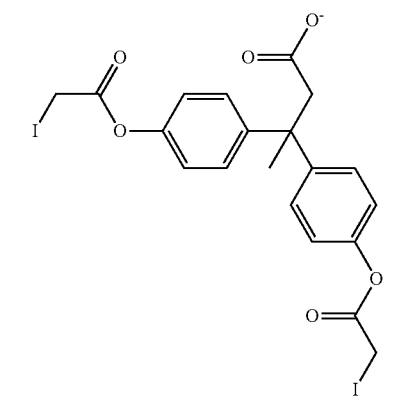
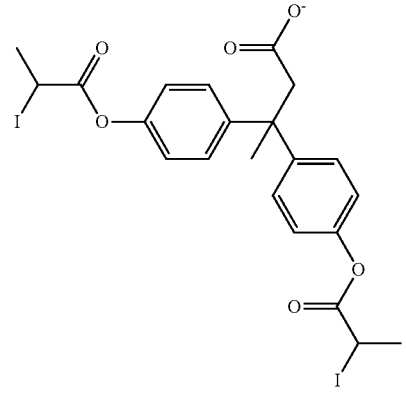
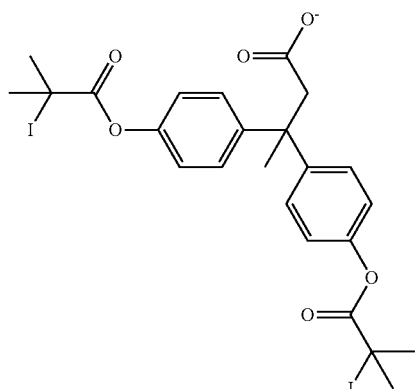
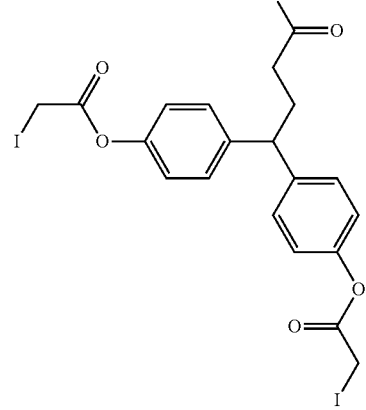
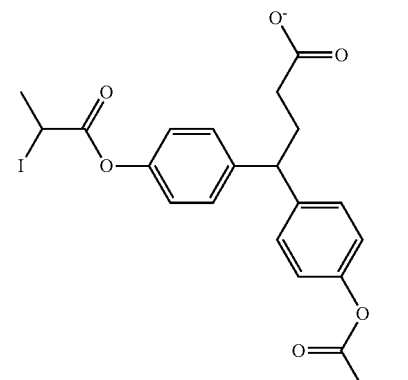
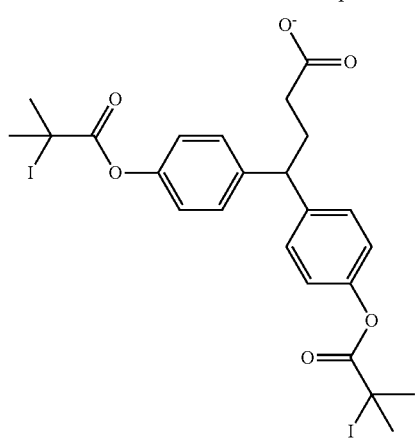

109
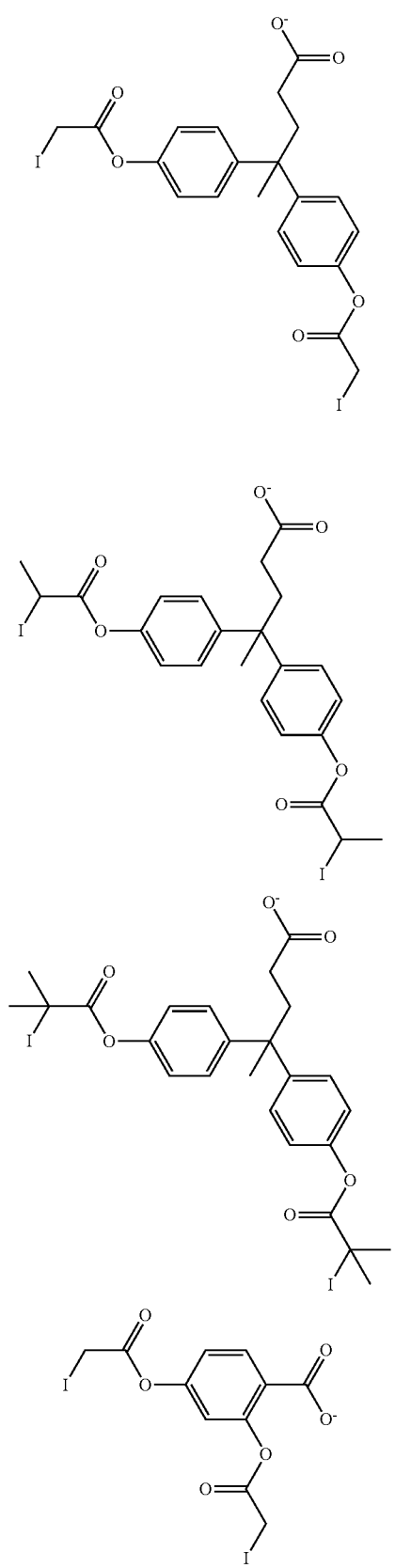
110
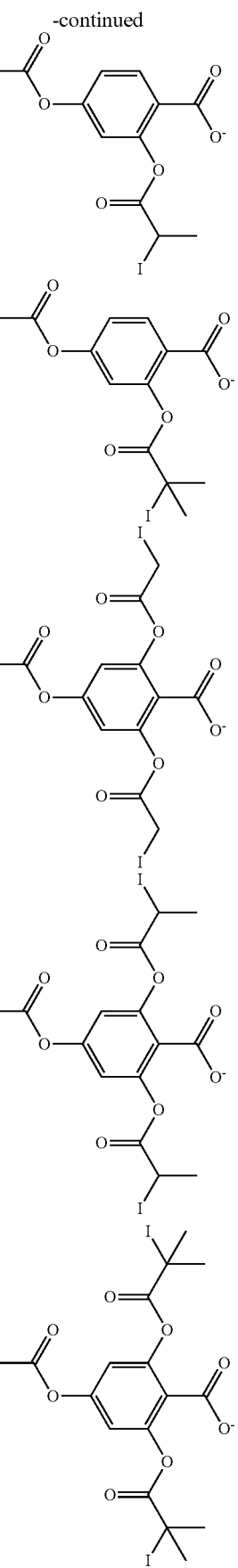

111
-continued
112
-continued
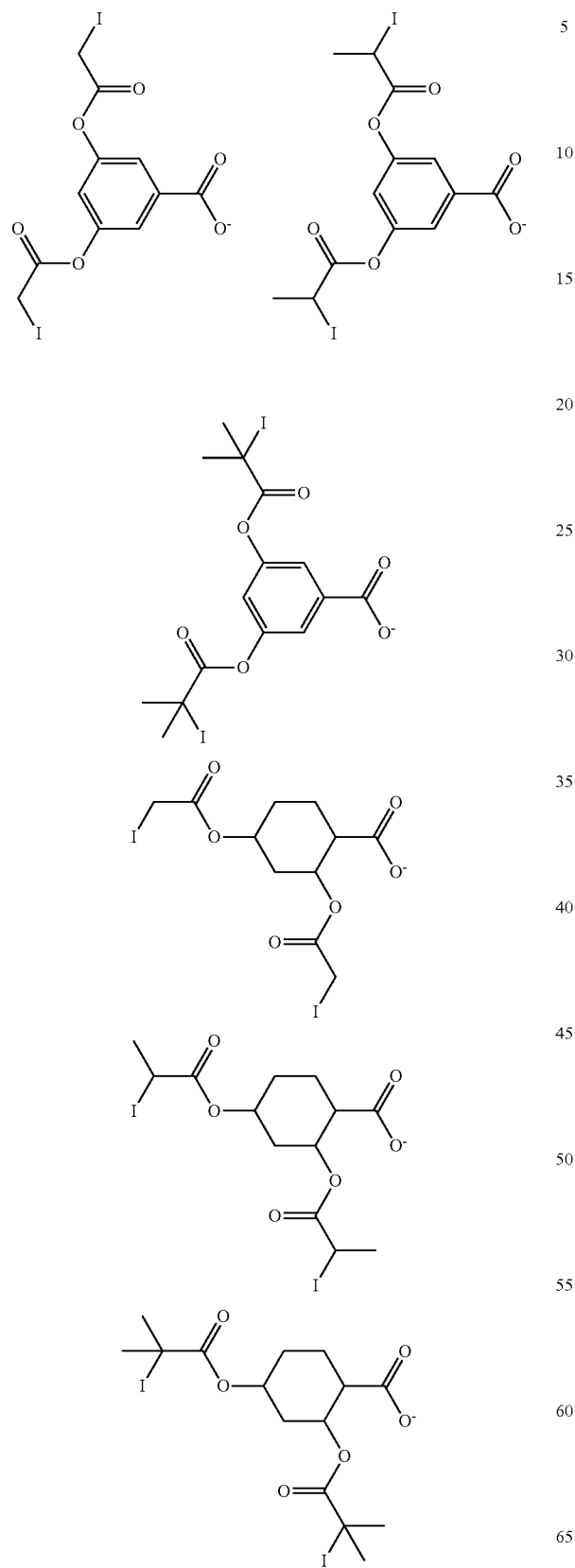
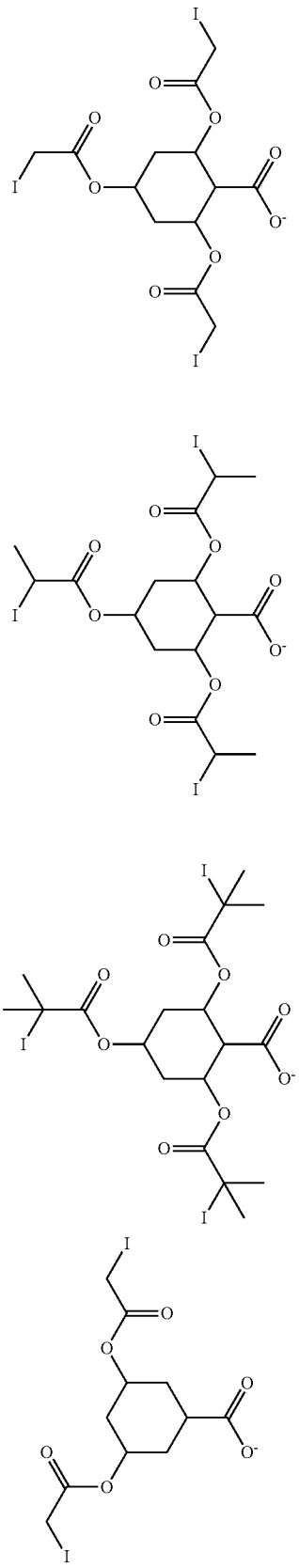

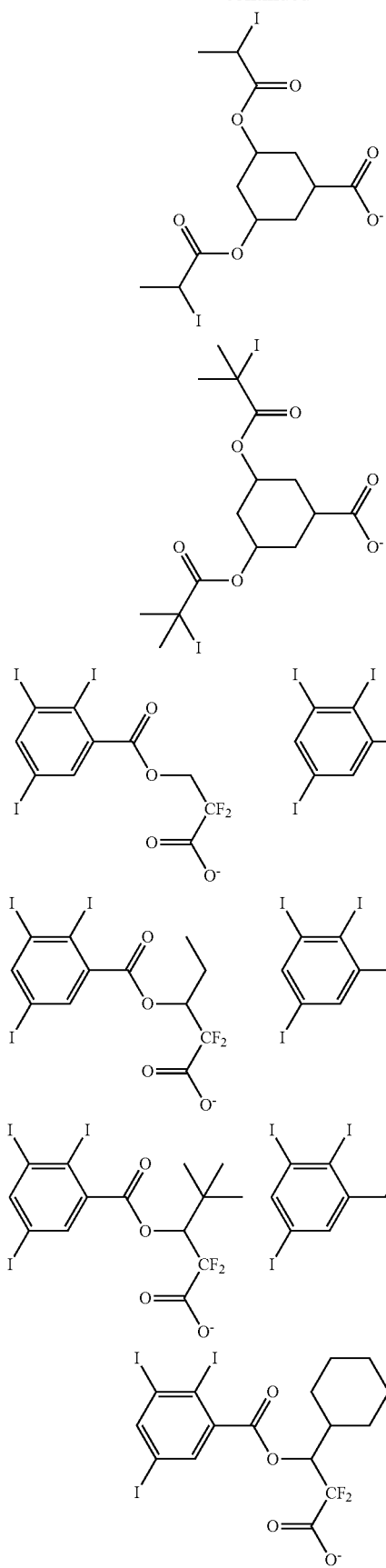

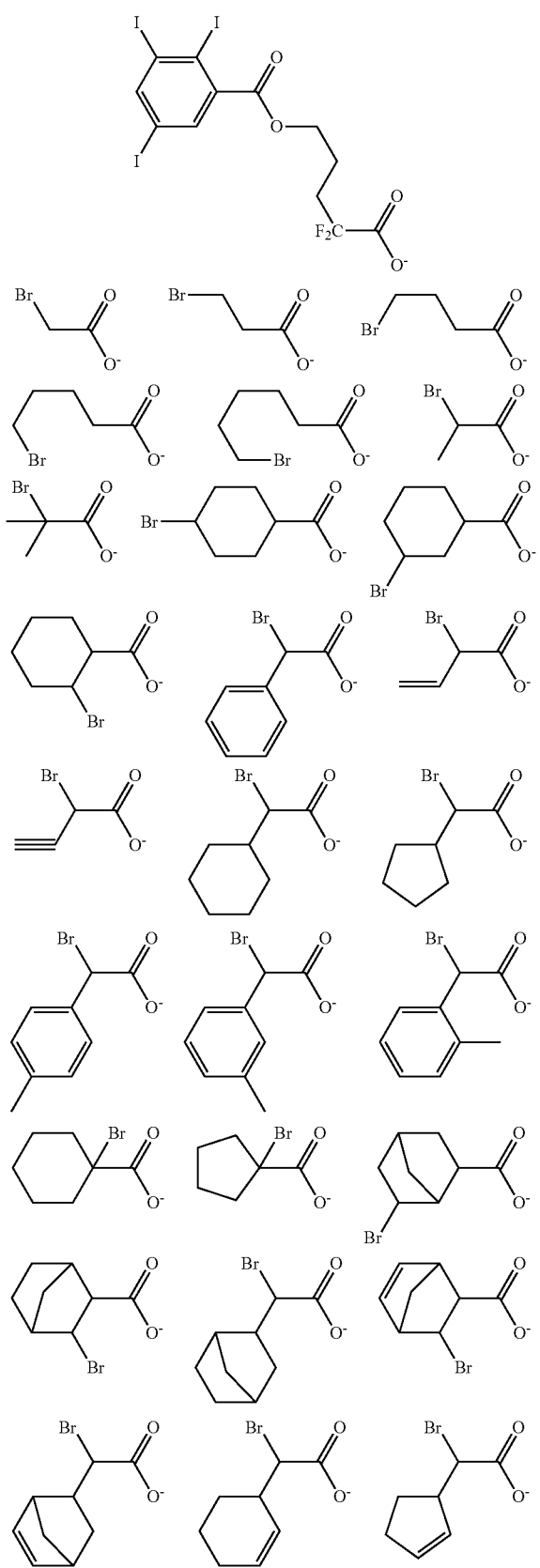
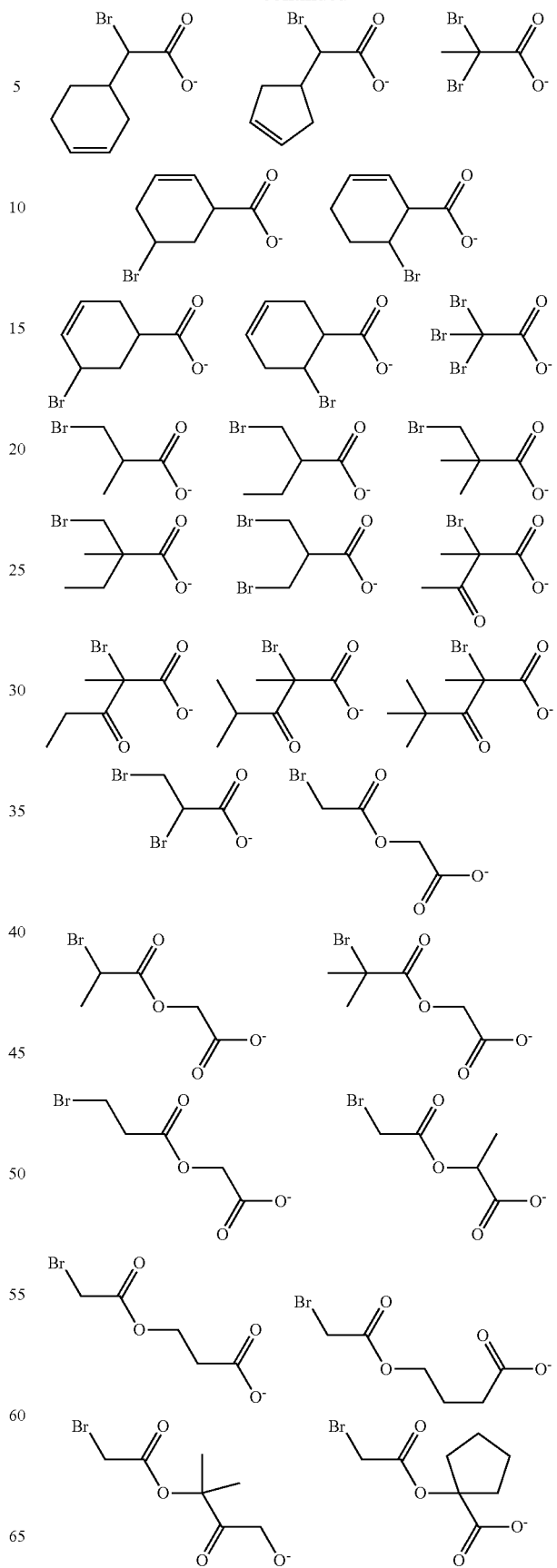

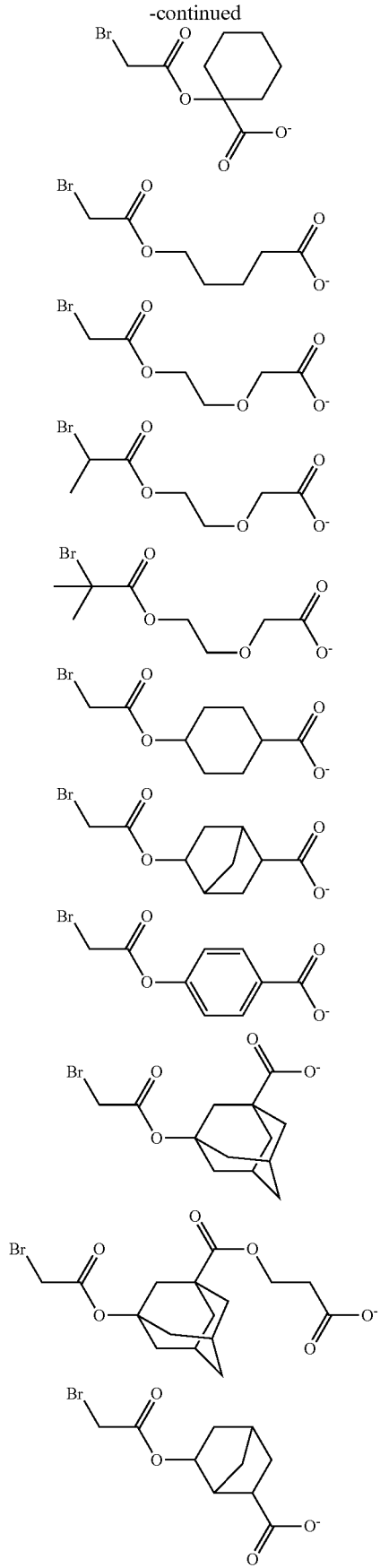
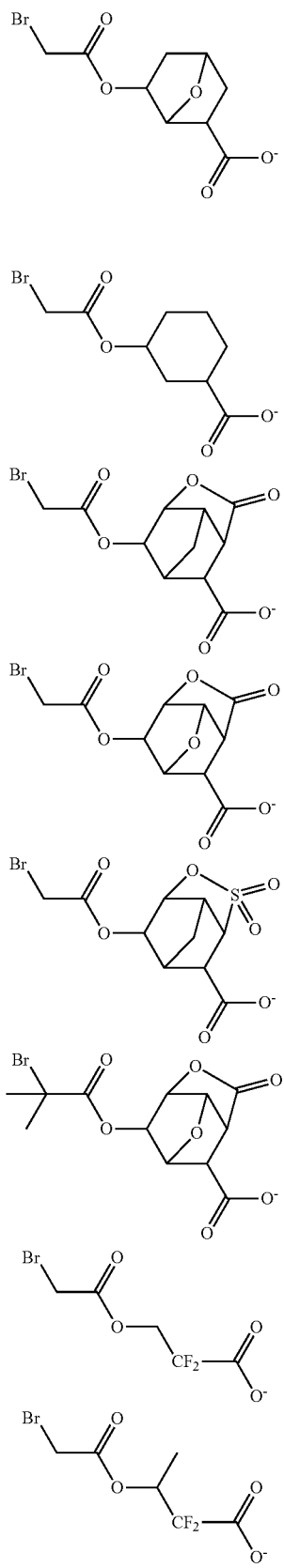

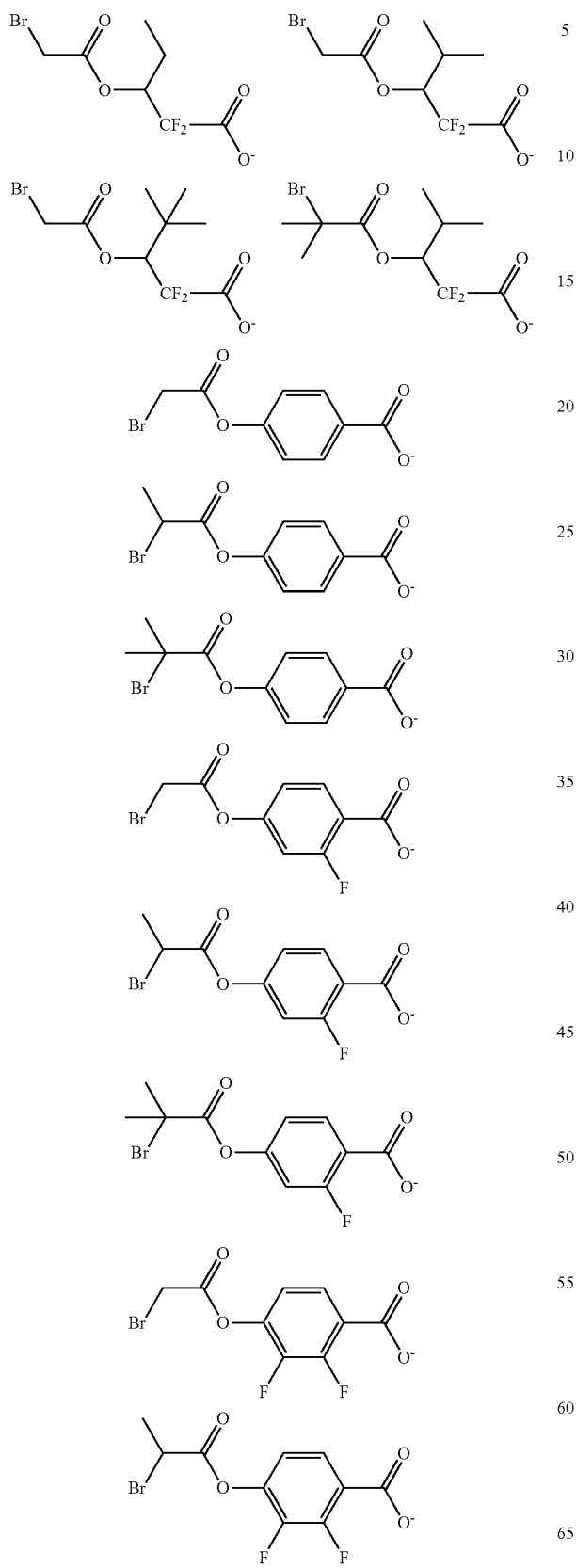
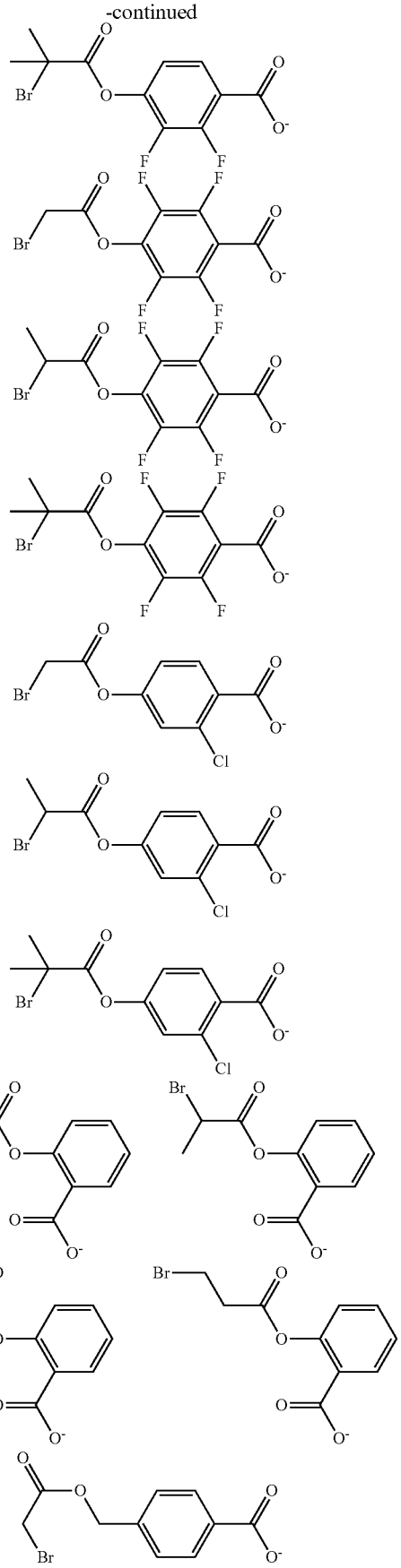

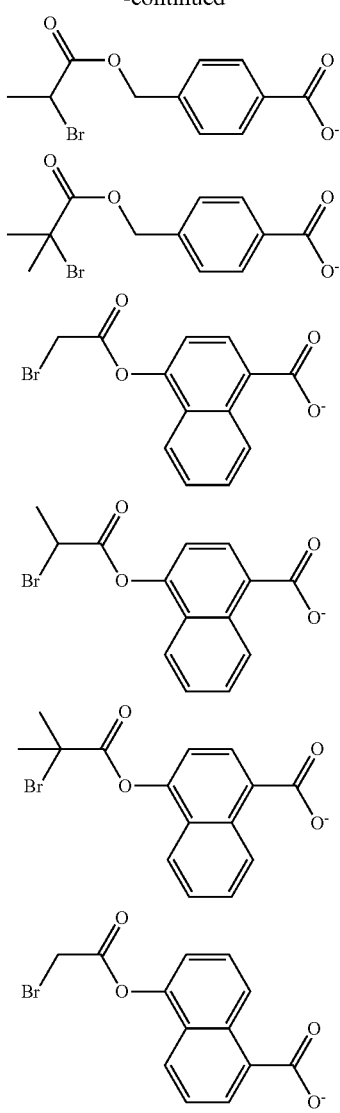
Examples of the sulfonamide anion are shown below, but not limited thereto.
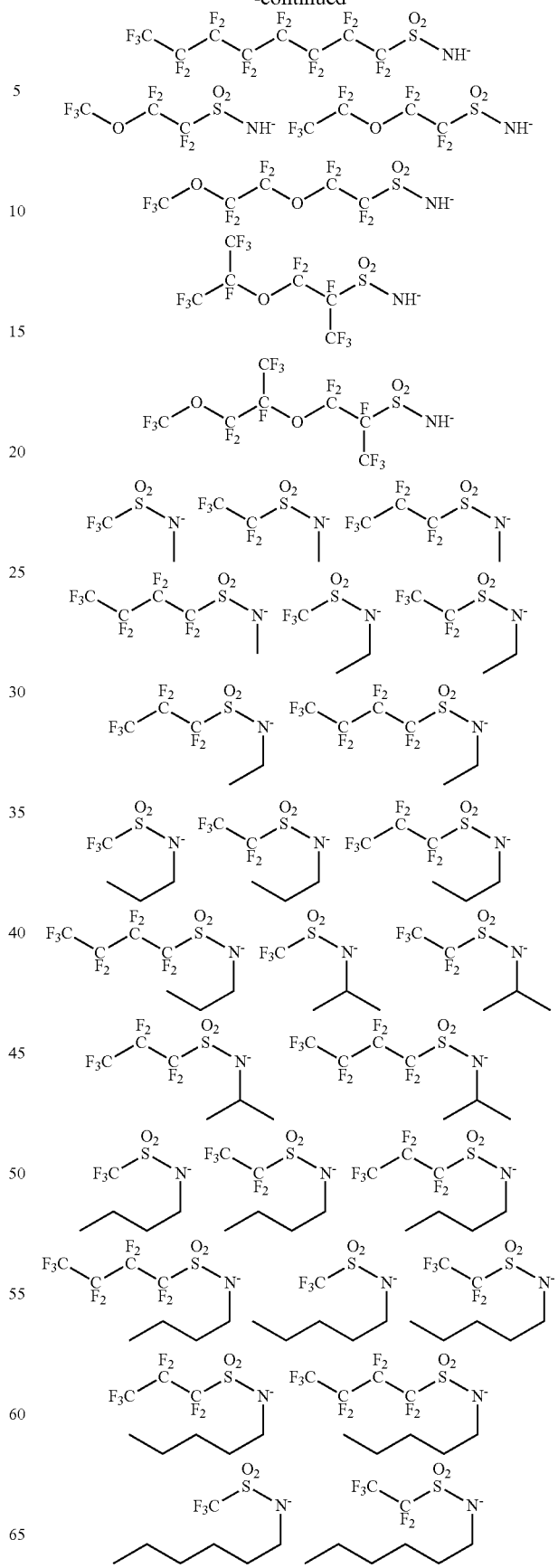

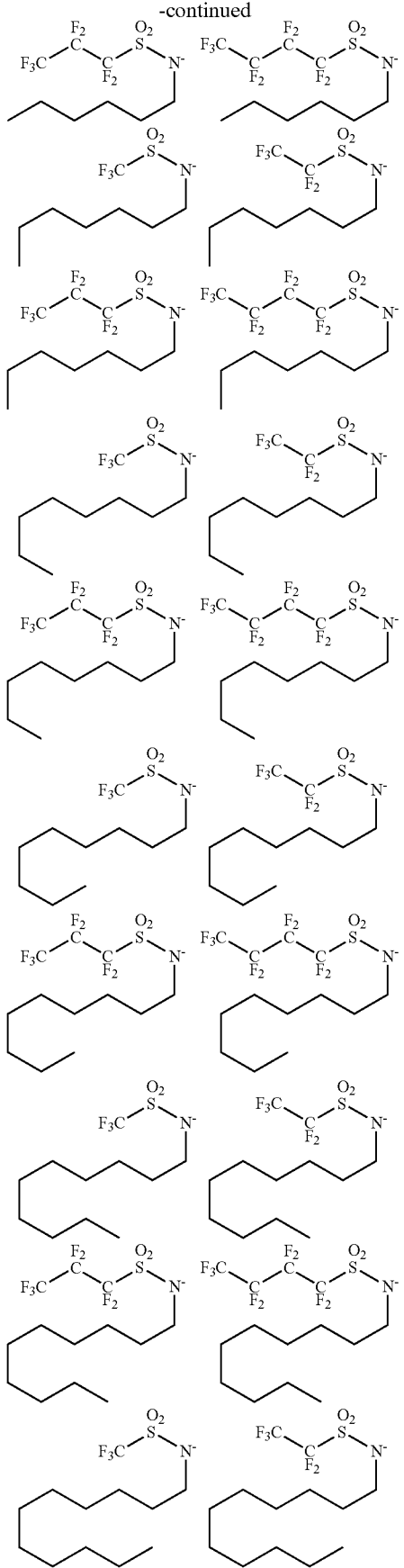
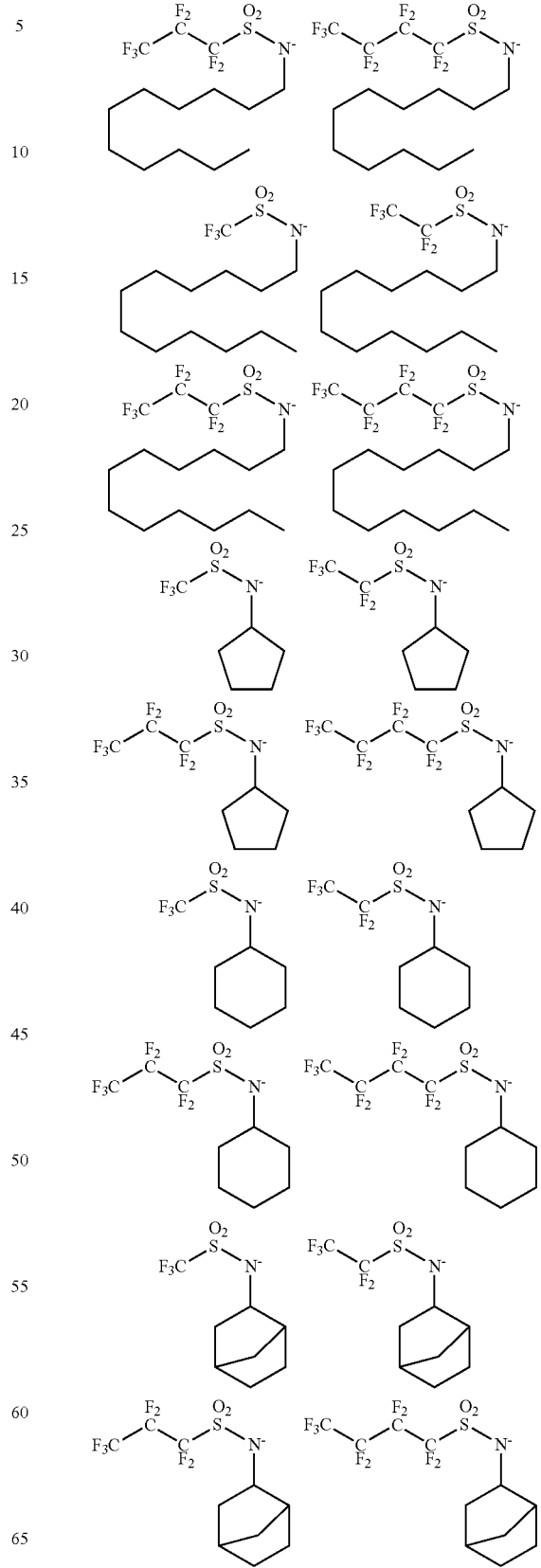

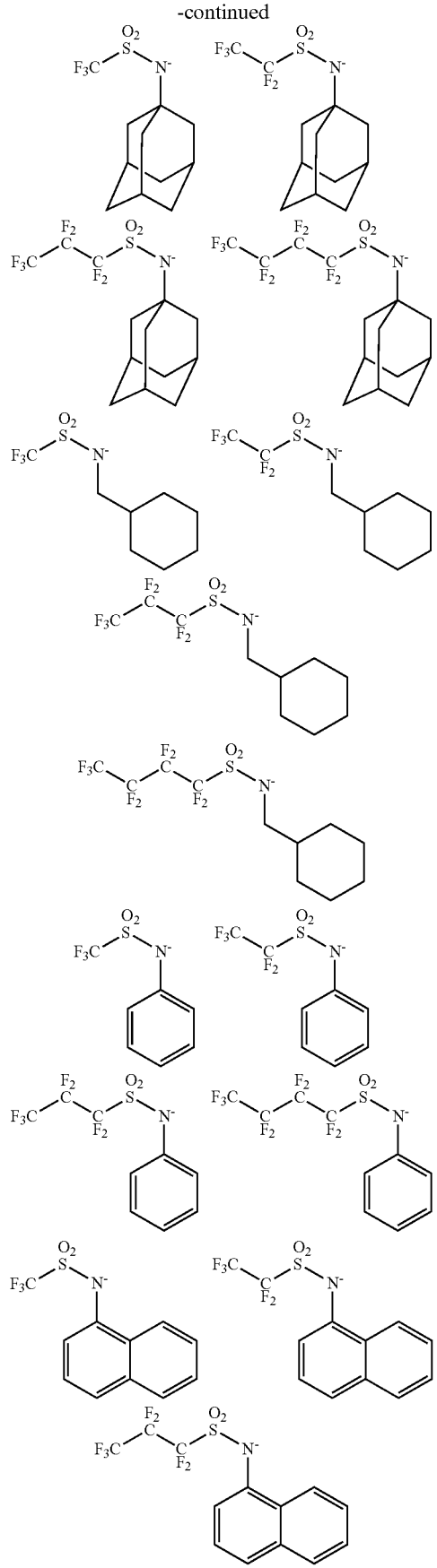
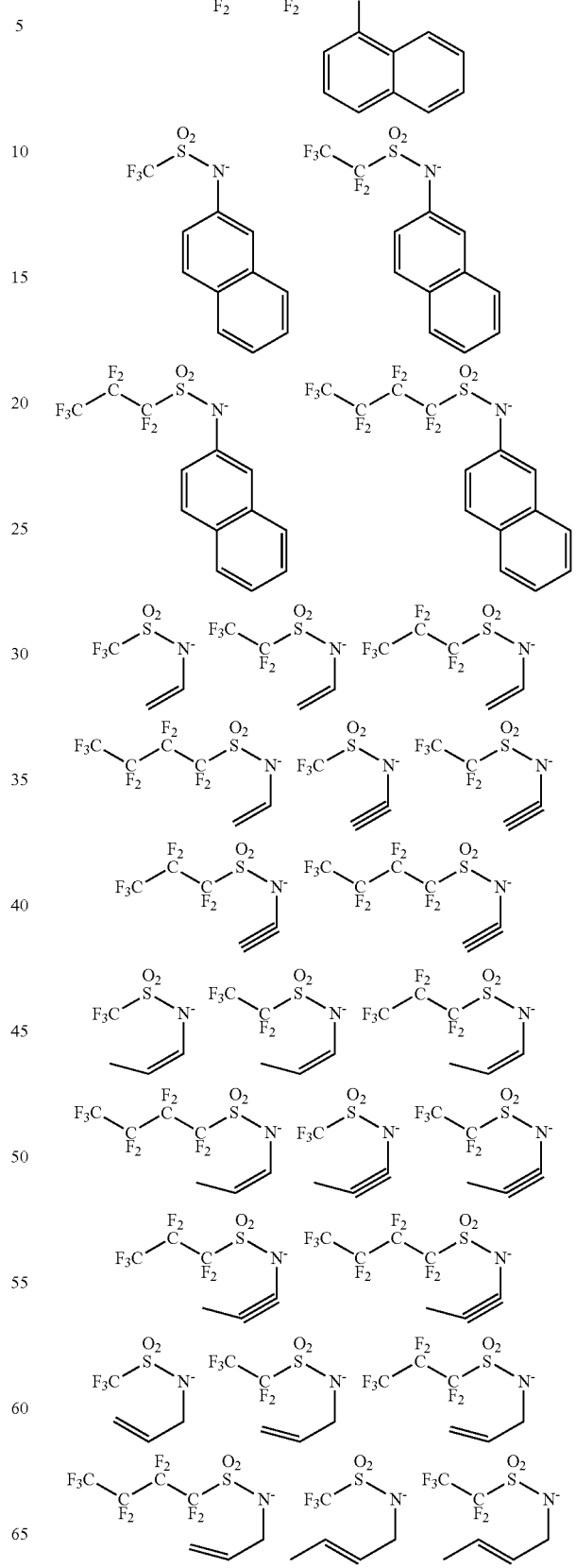

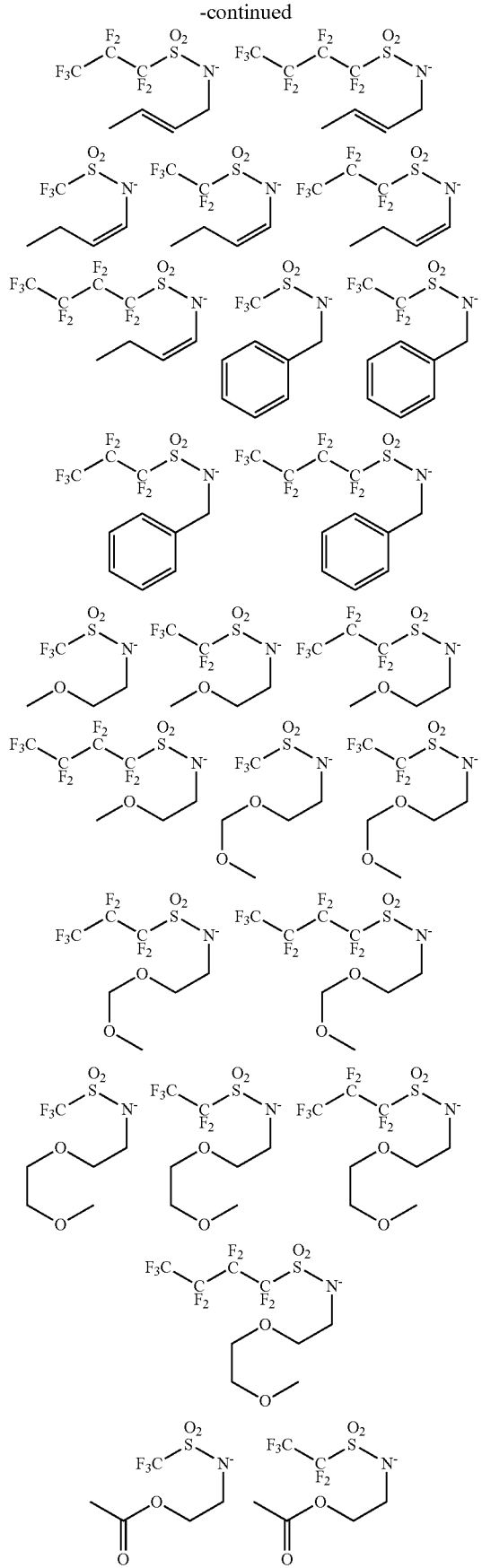
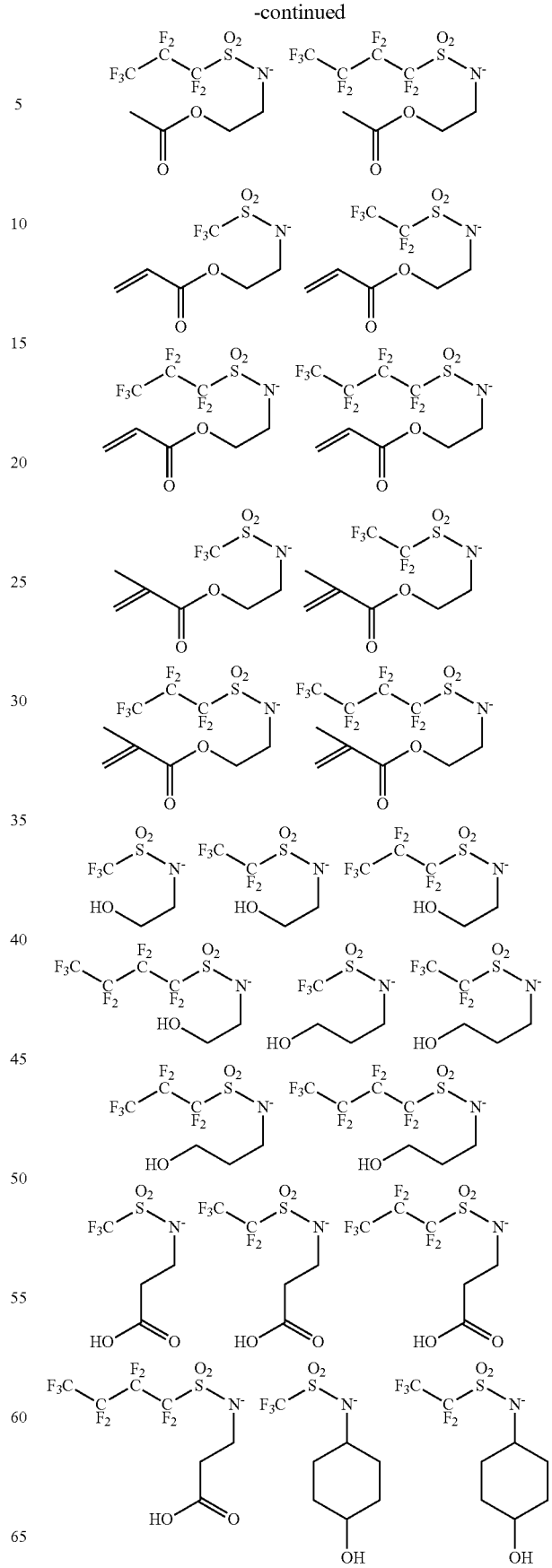

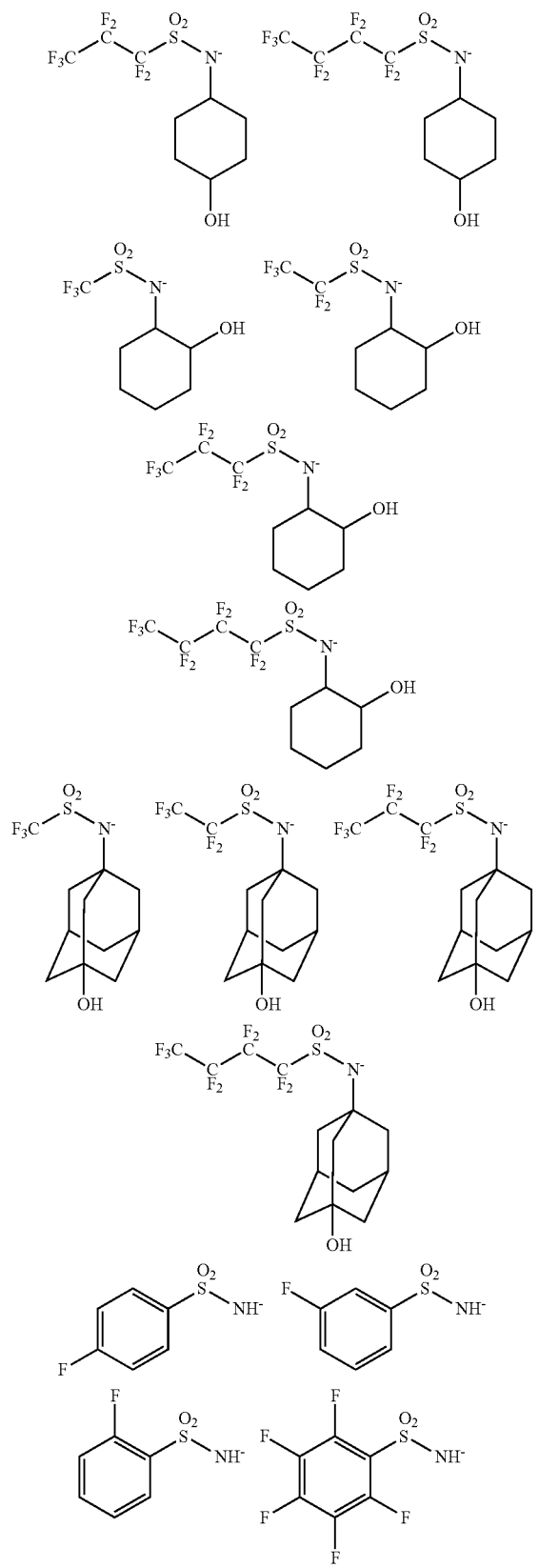

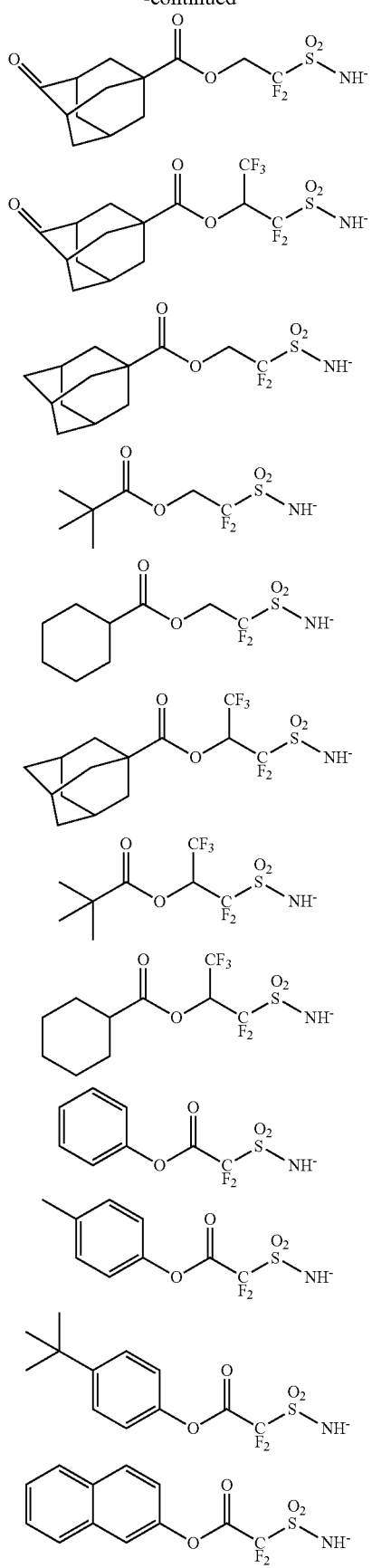
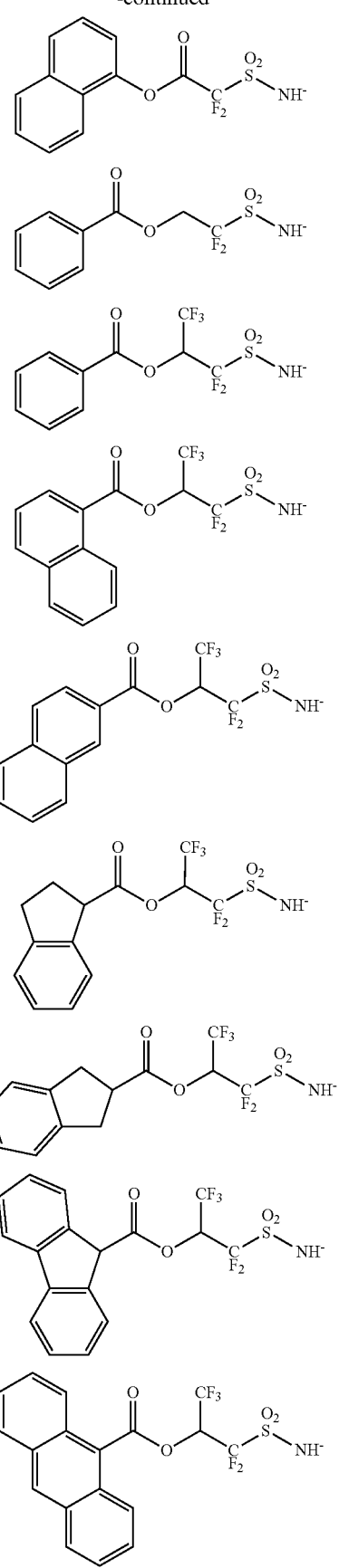

-continued
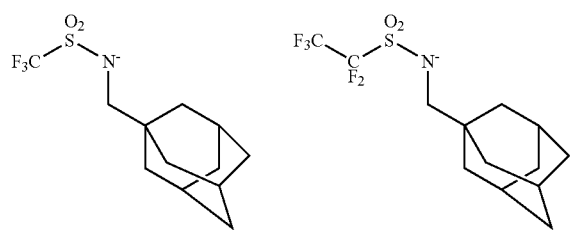
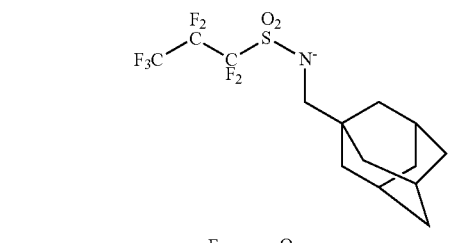
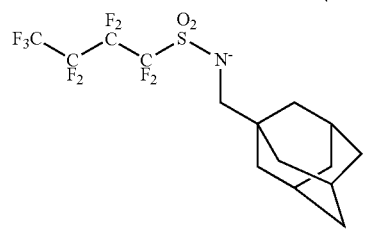
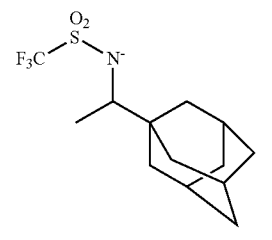
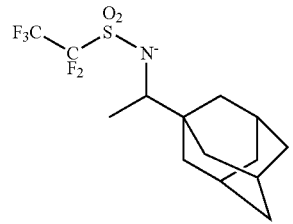
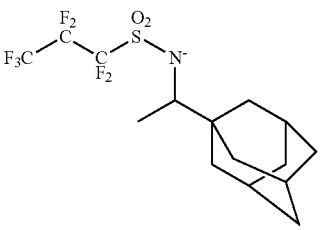
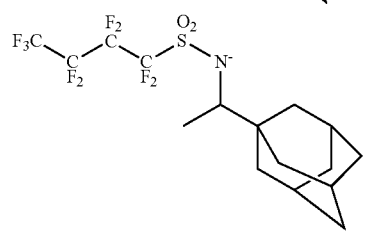
-continued
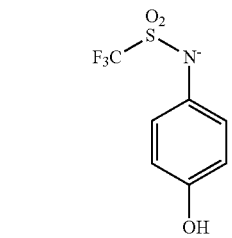
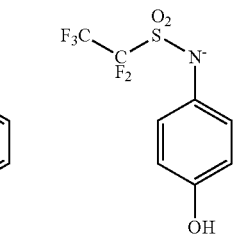
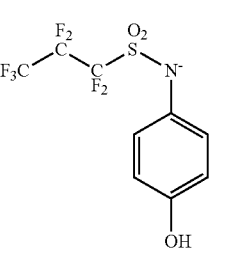
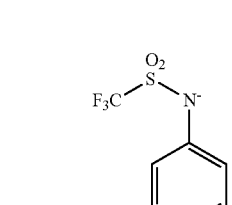
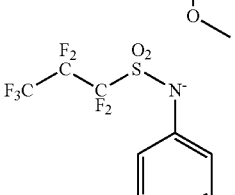
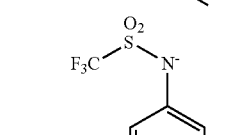
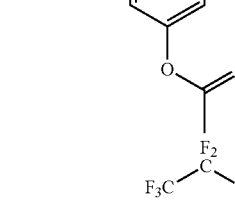

135
-continued
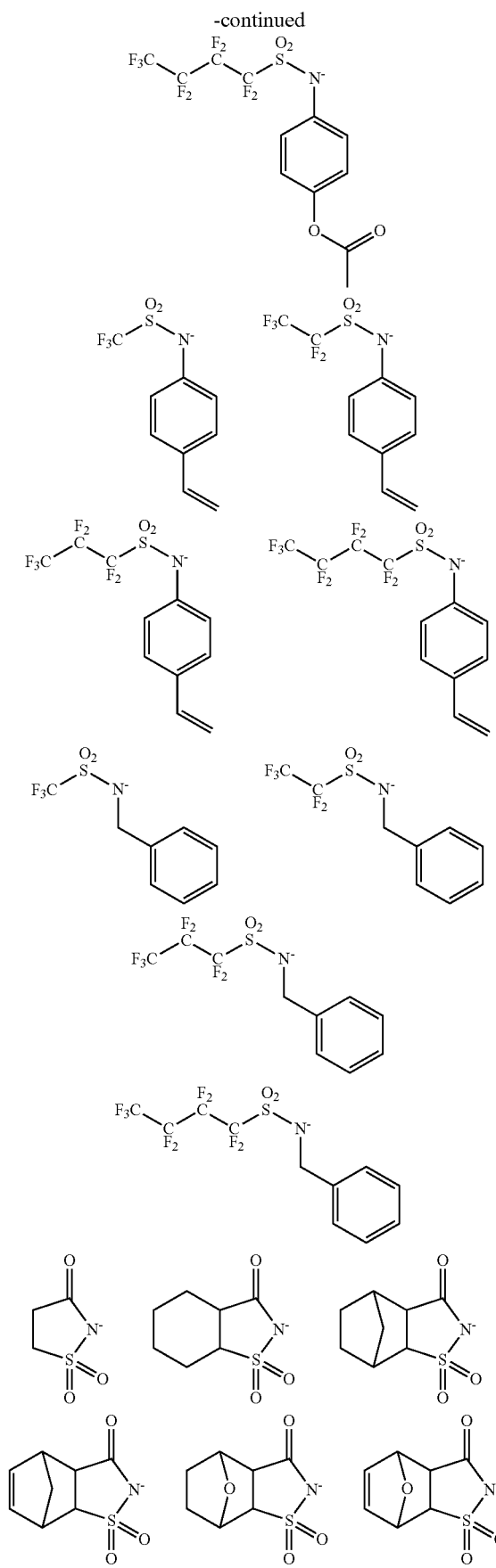
136
-continued
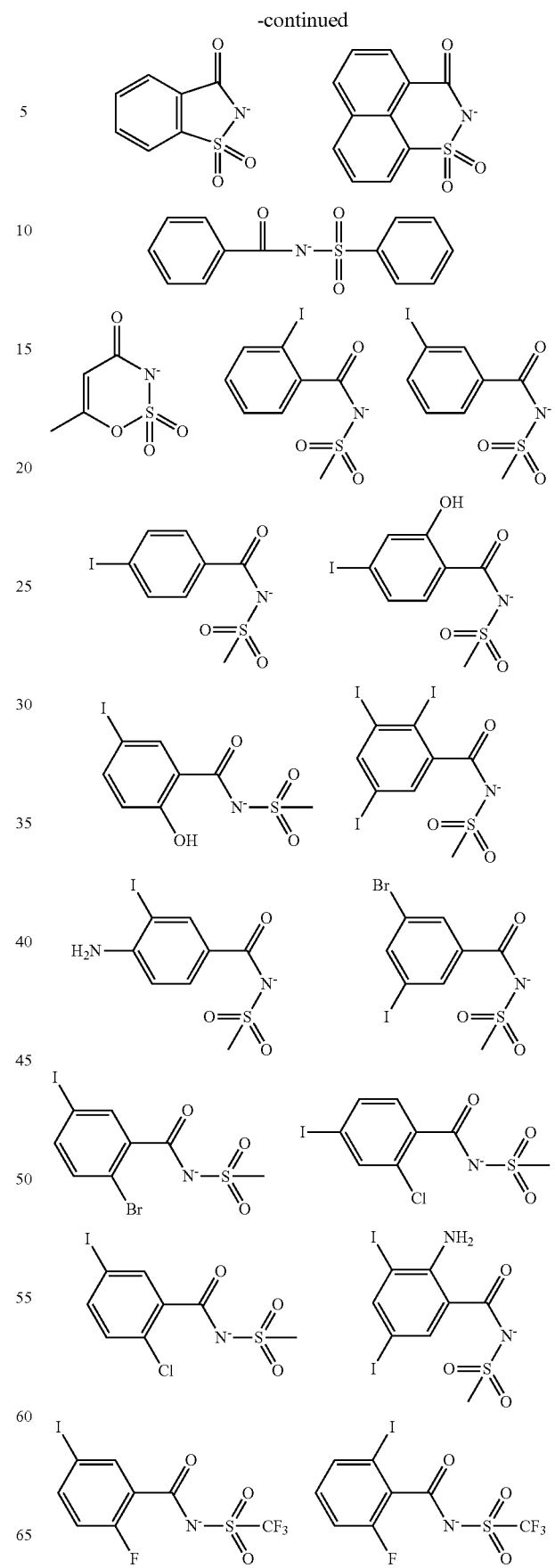

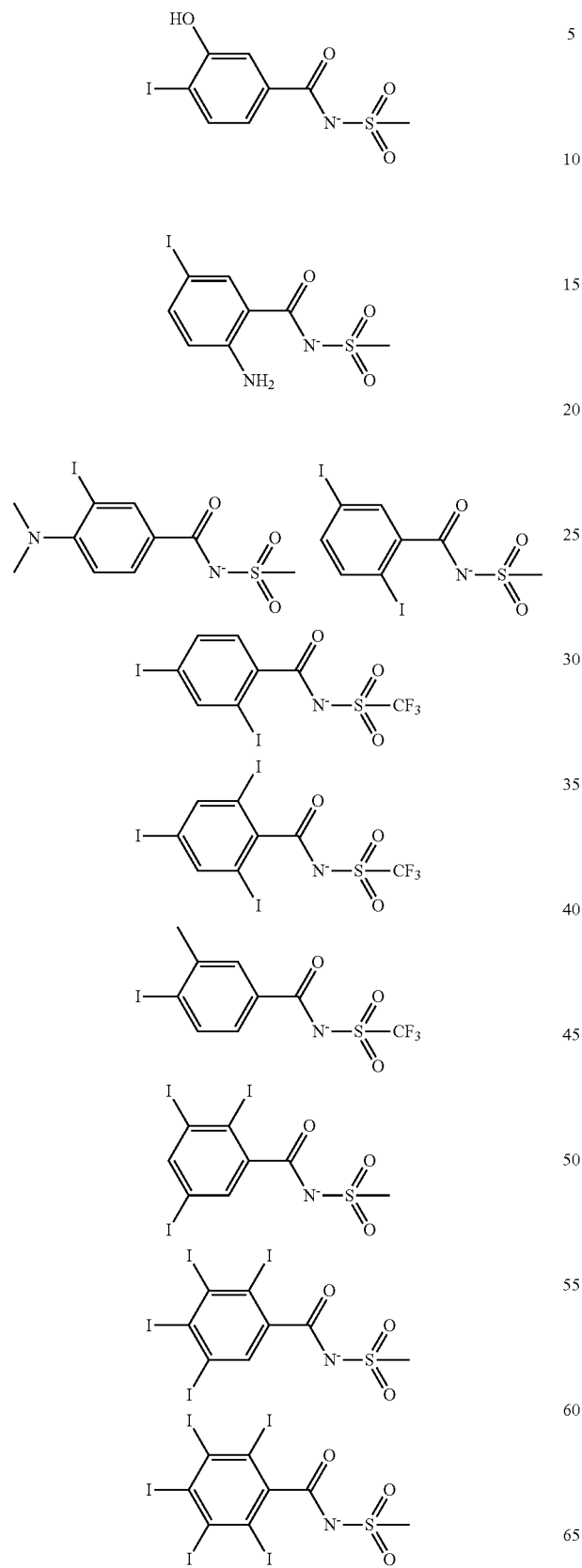
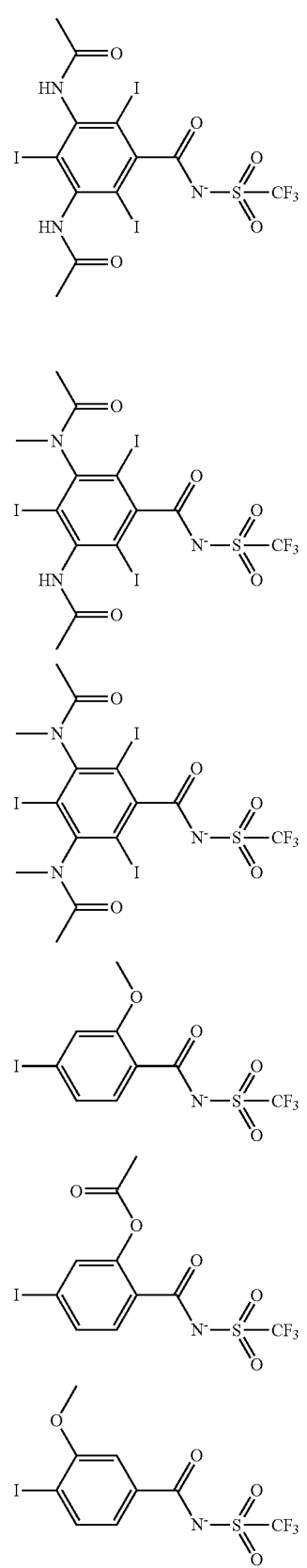

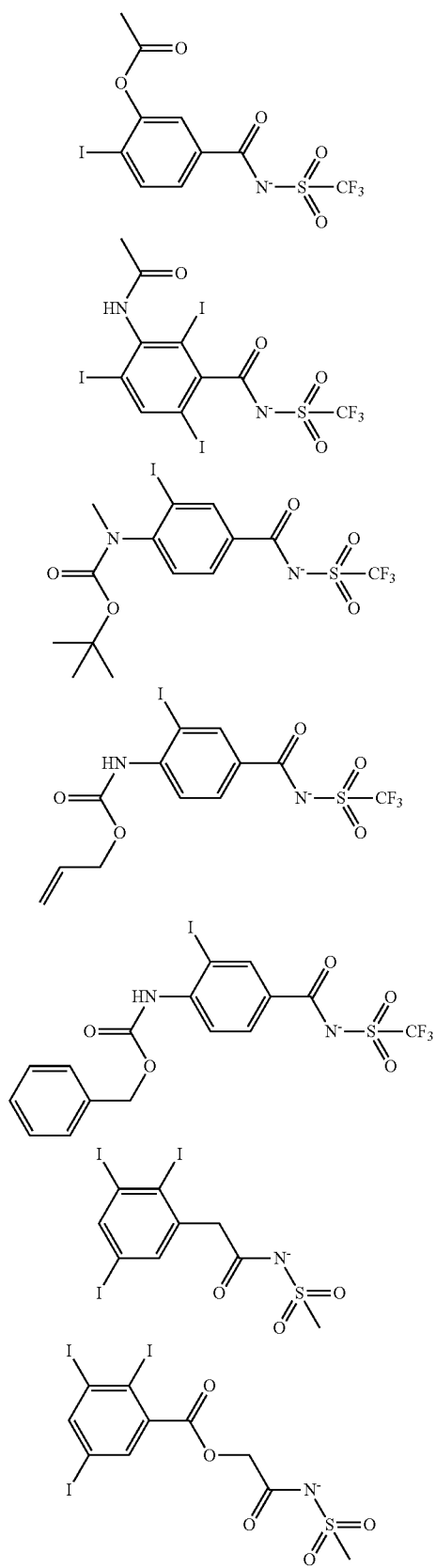
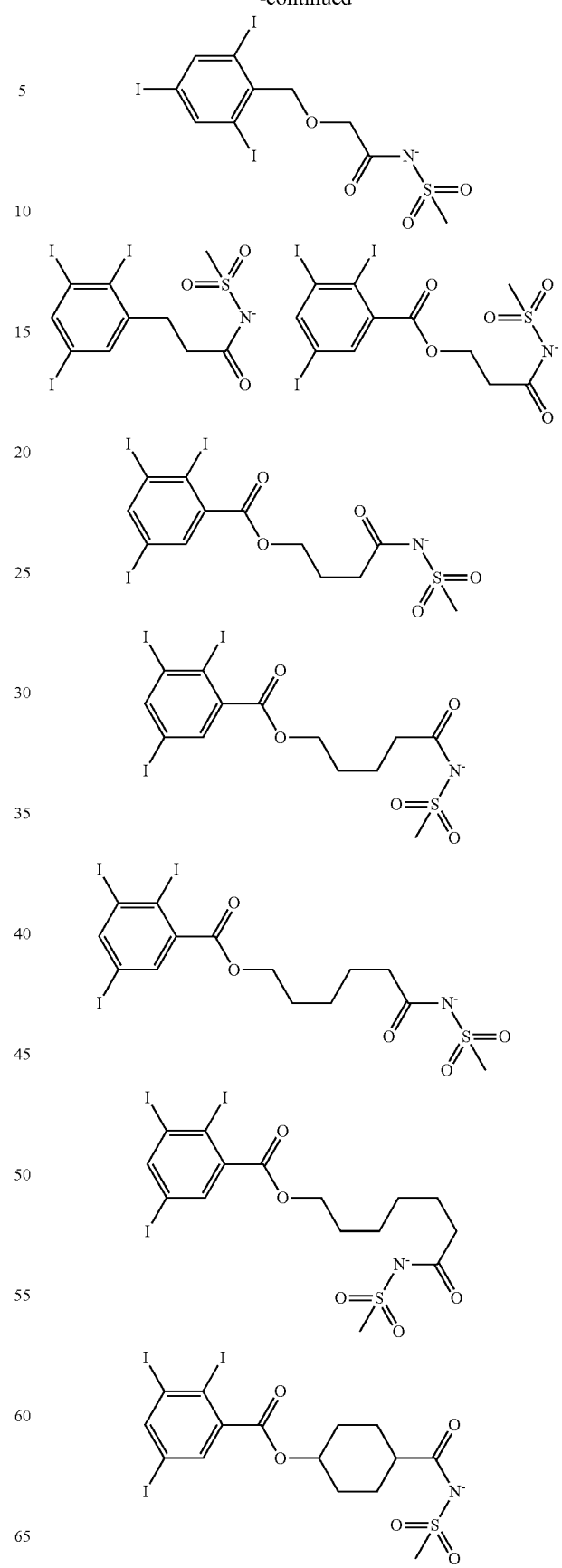

141
-continued
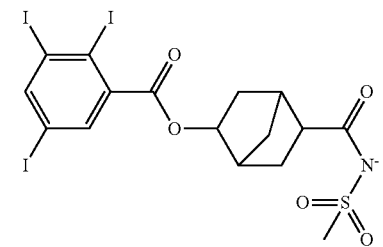
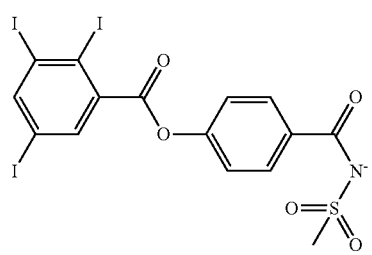
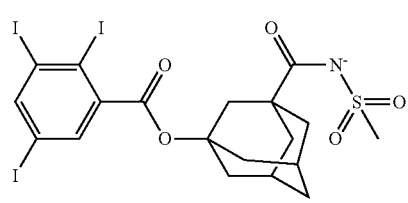
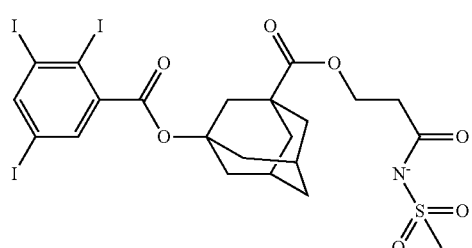
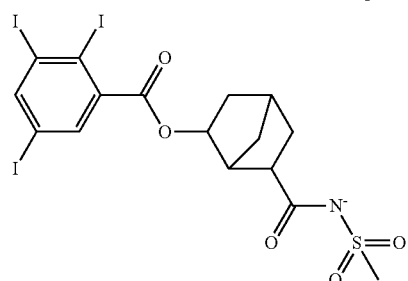
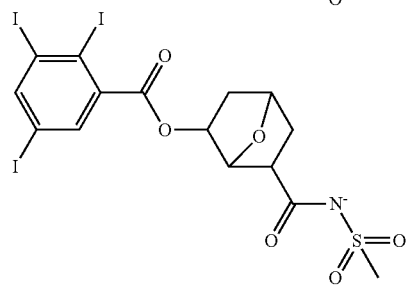
142
-continued
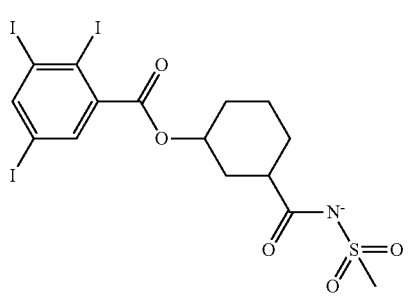
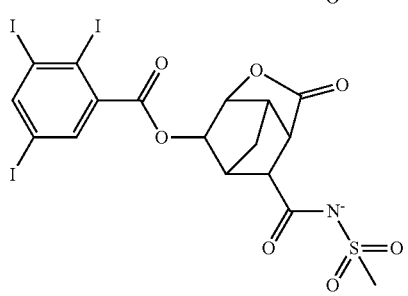
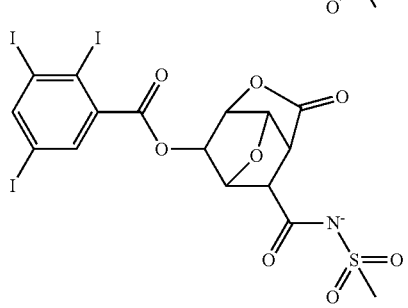
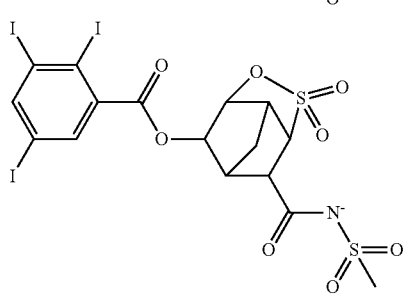
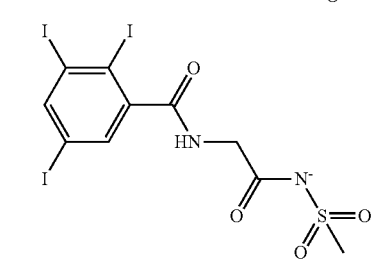
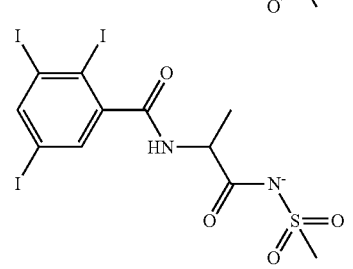

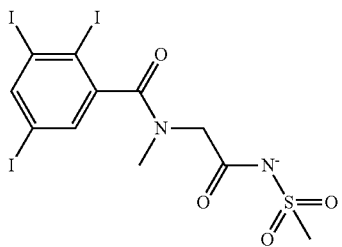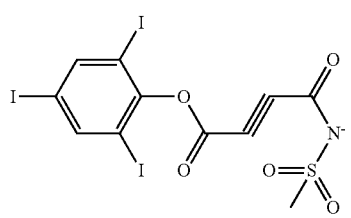

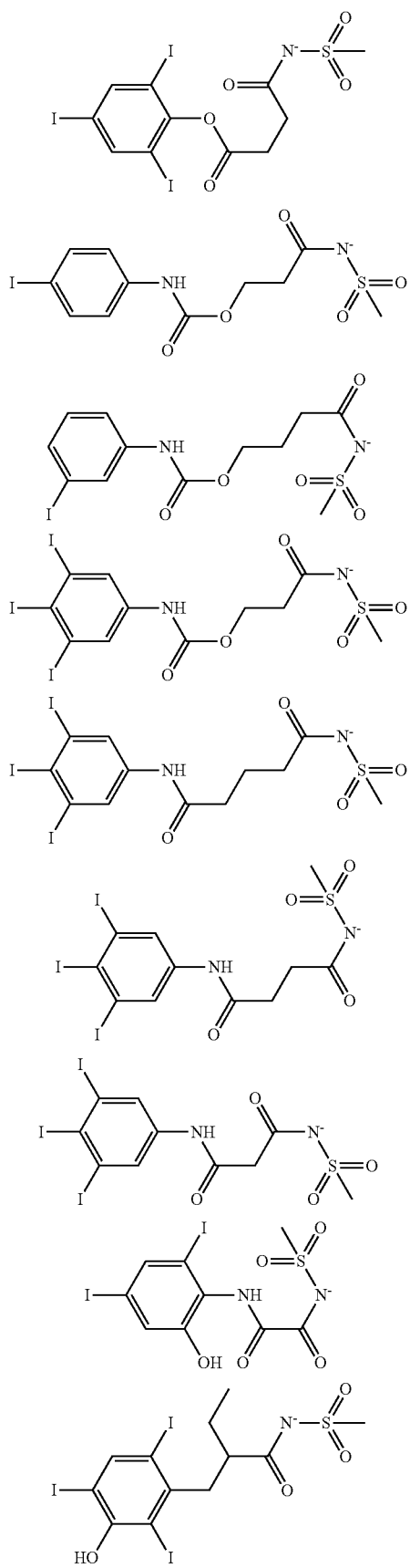
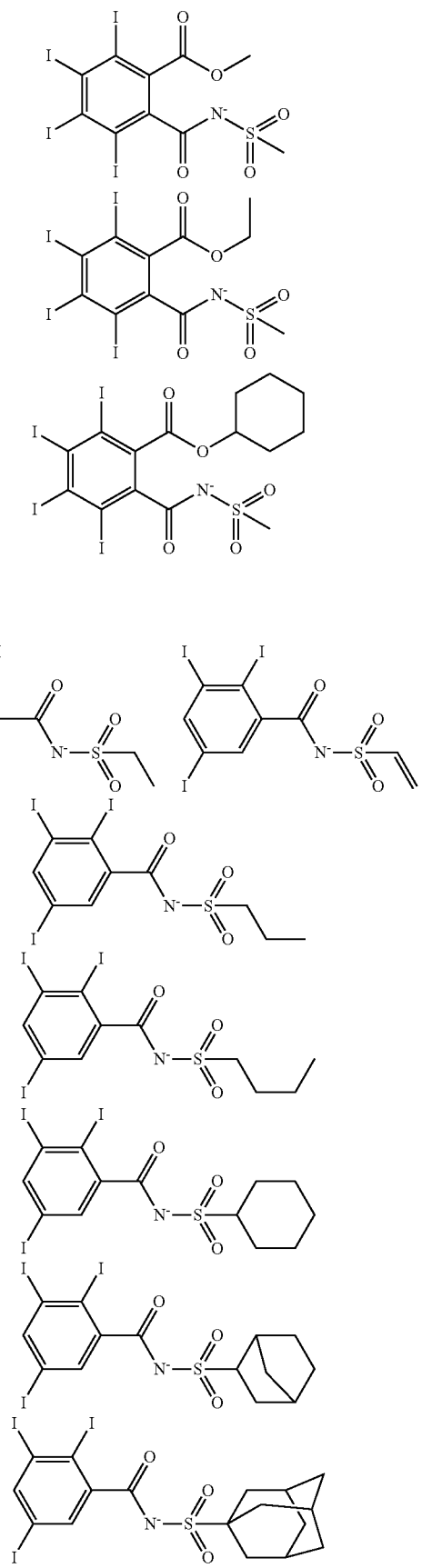

147
-continued
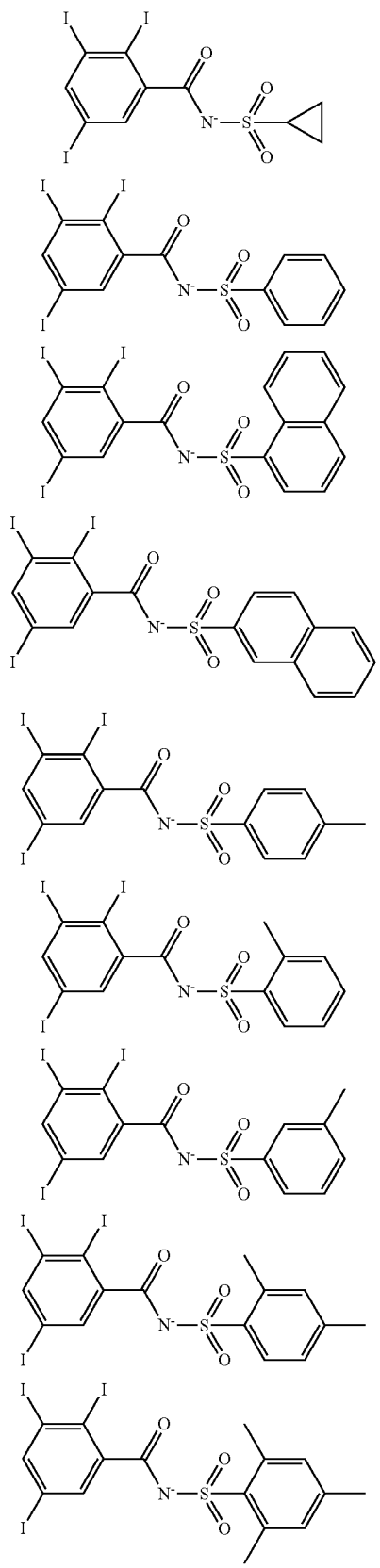
148
-continued
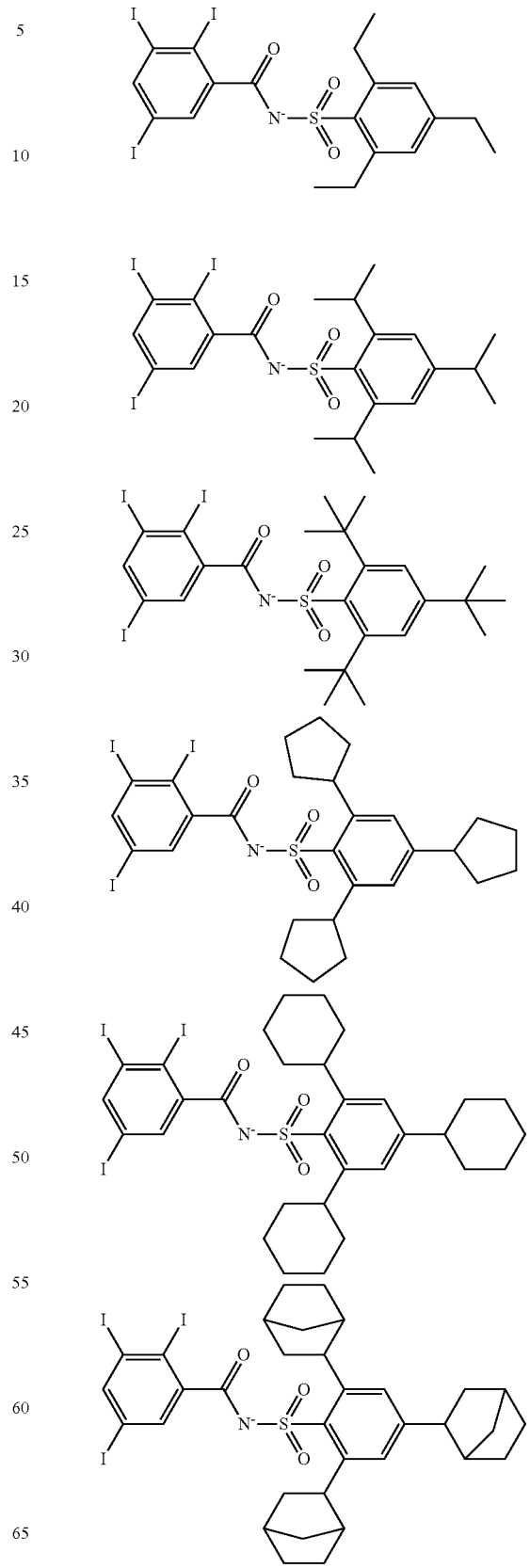

149
-continued
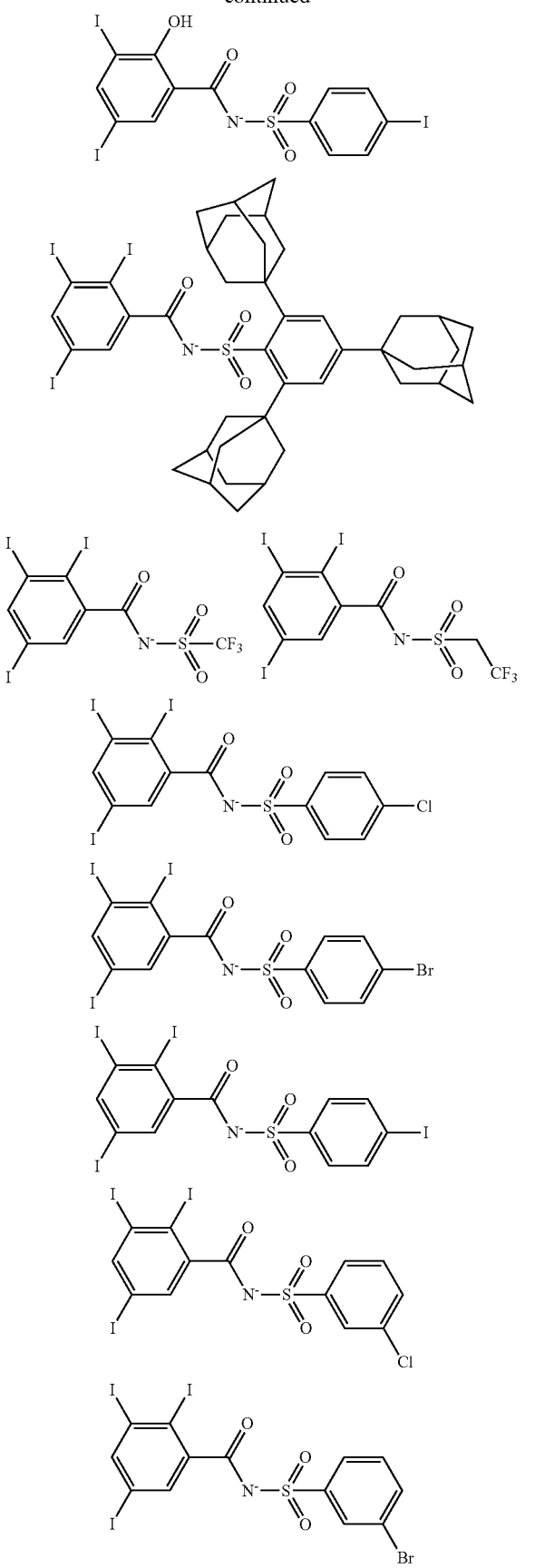
150
-continued
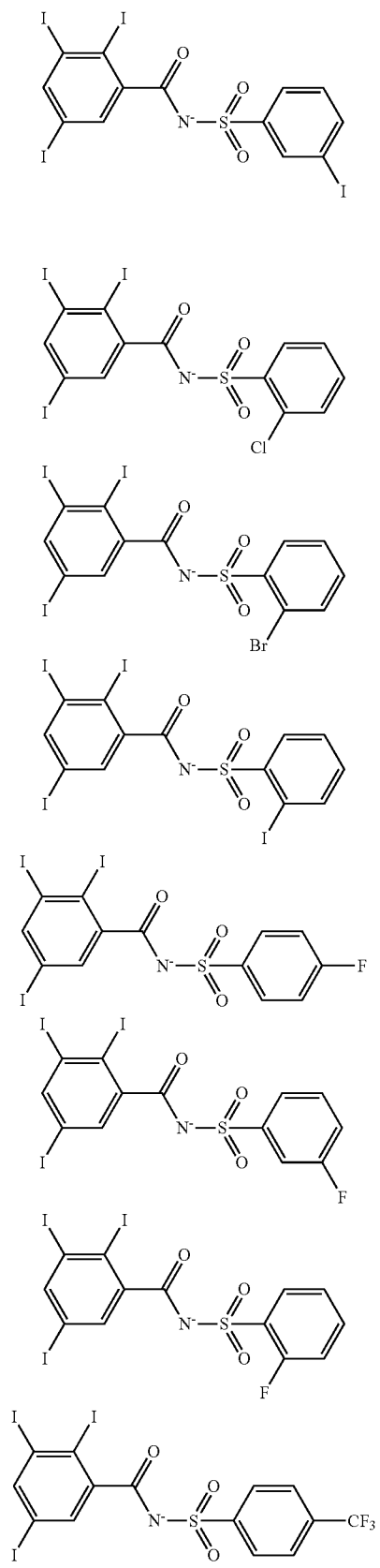

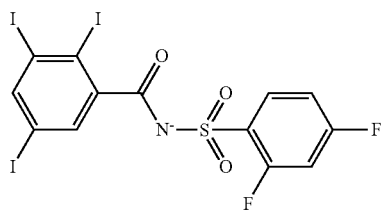
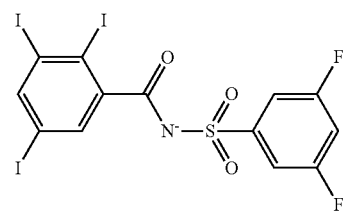
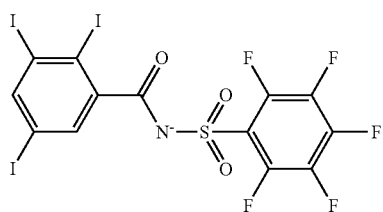
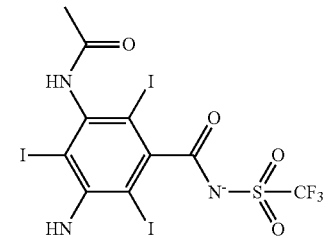
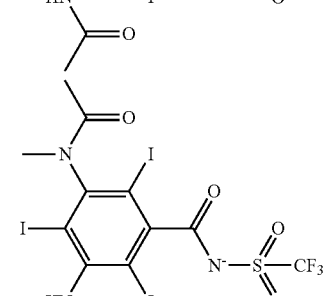
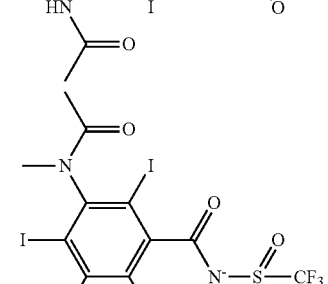
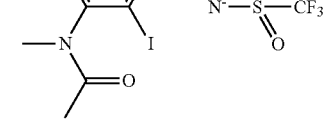
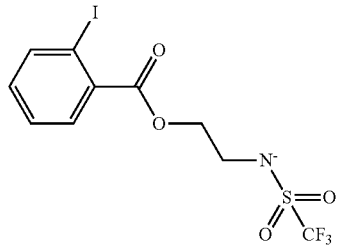
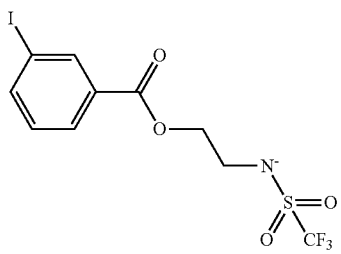
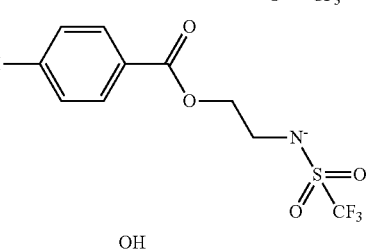
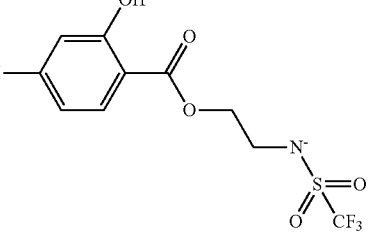
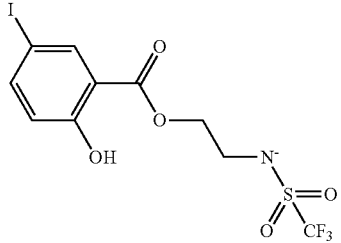
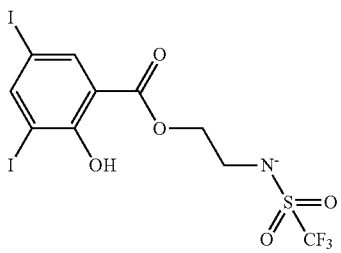
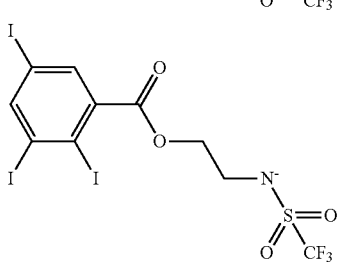

-continued
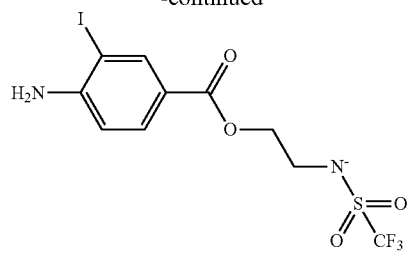
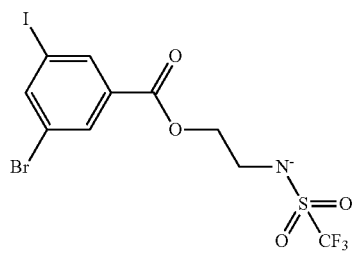
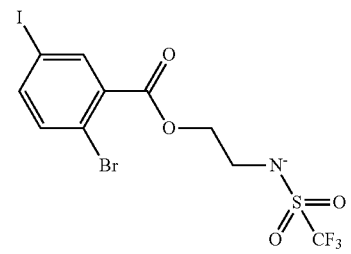
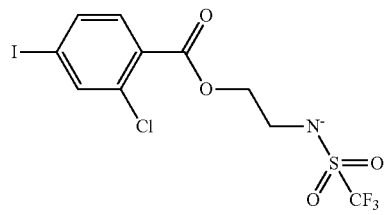
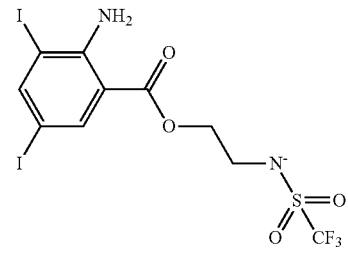
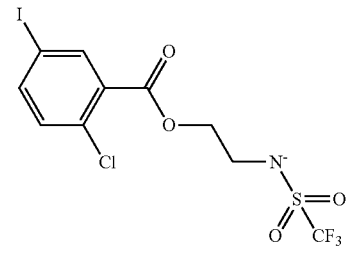
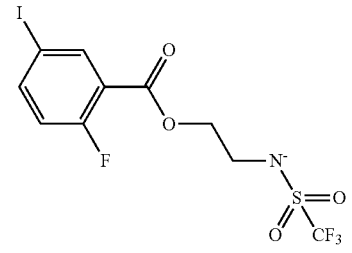
-continued
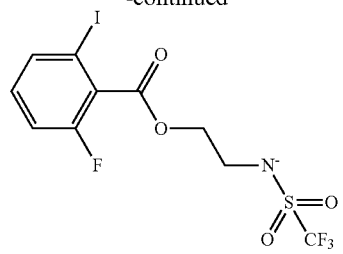
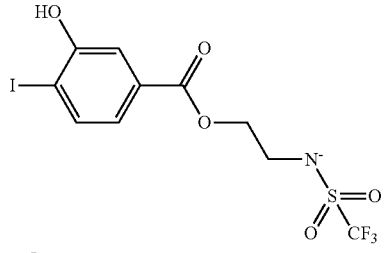
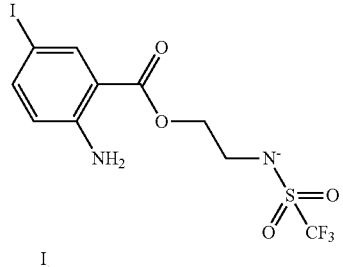
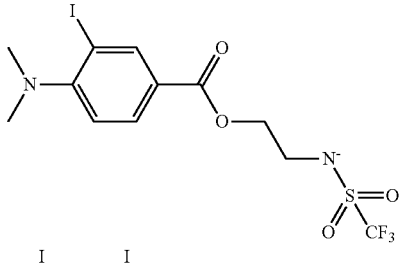
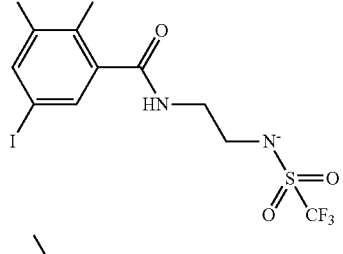
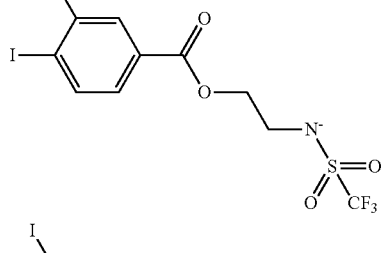
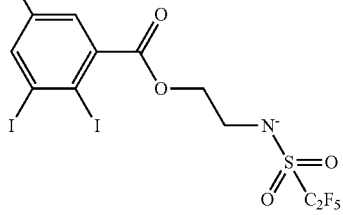

155
-continued
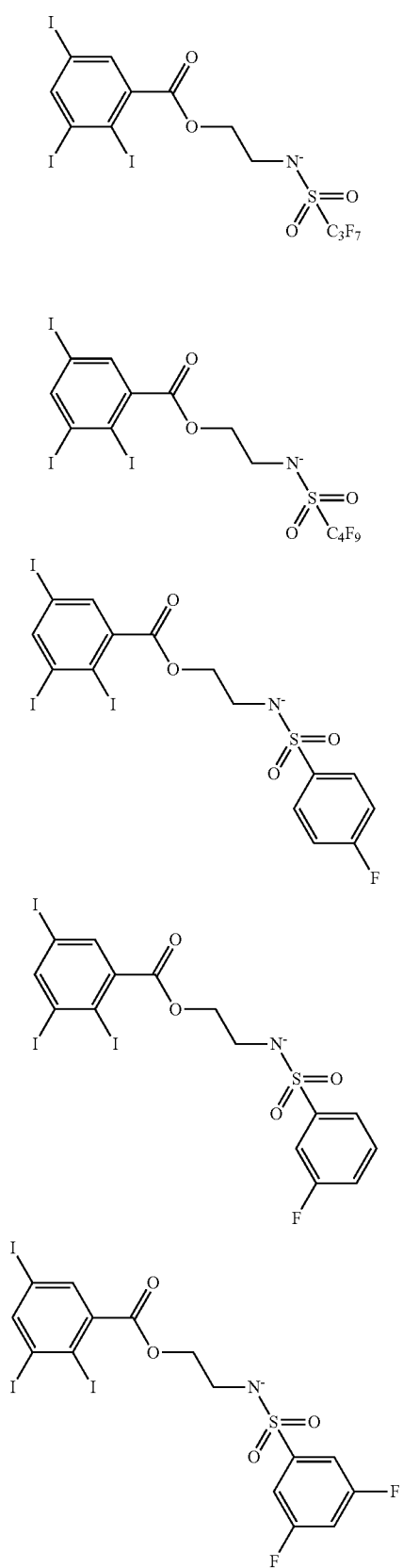
156
-continued
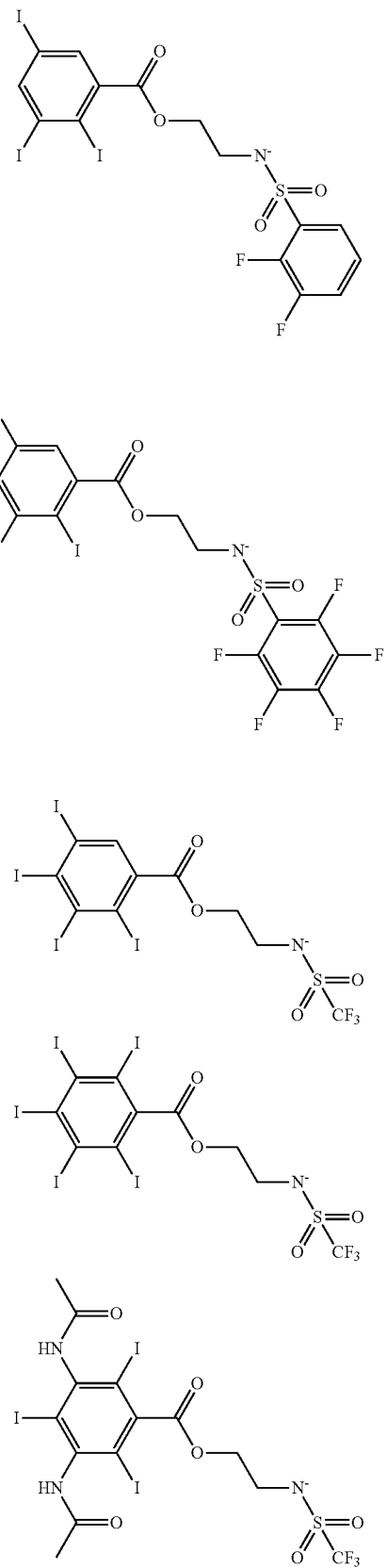

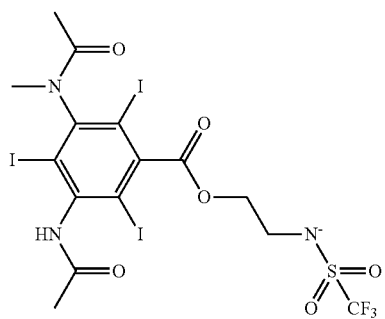
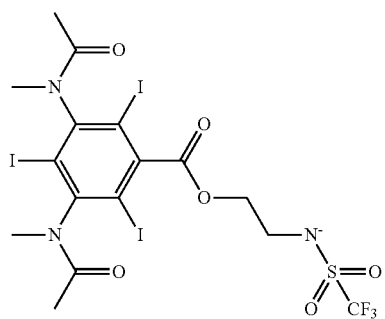
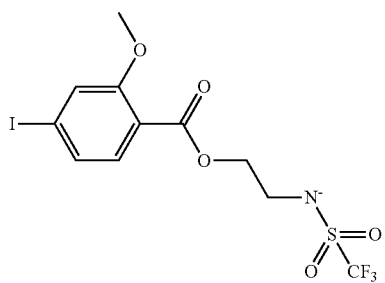
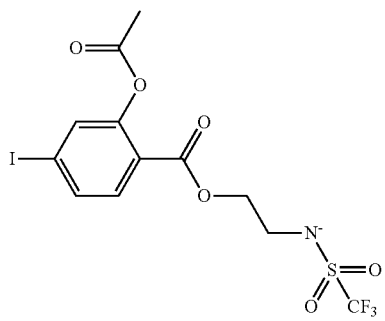
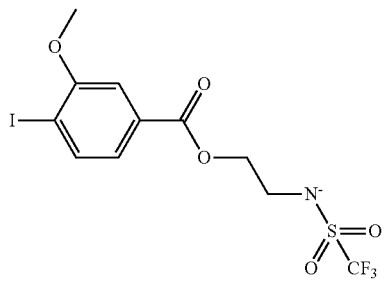
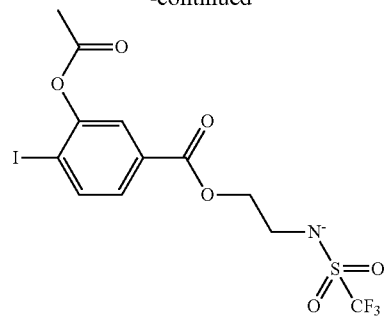
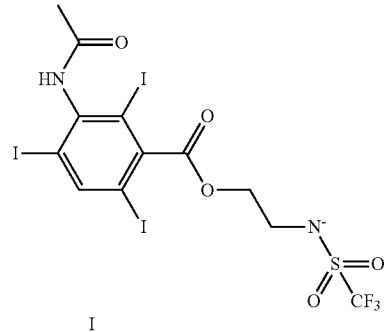
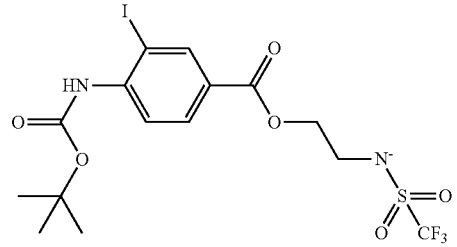
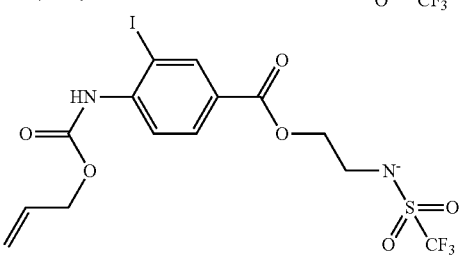
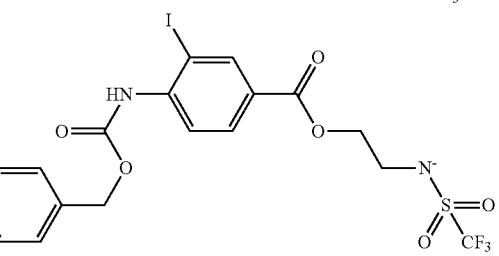
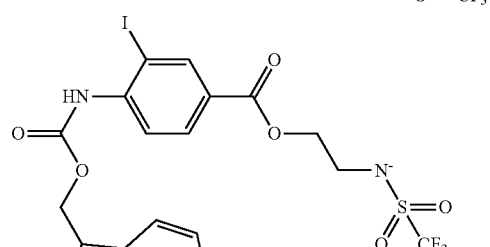

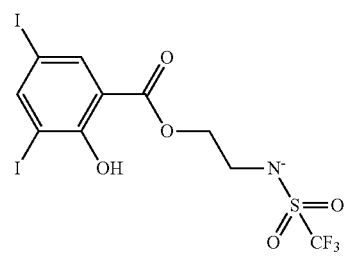
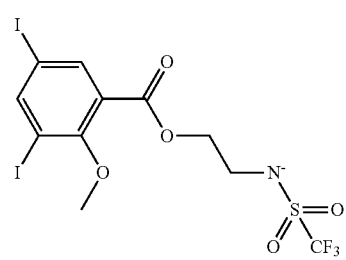
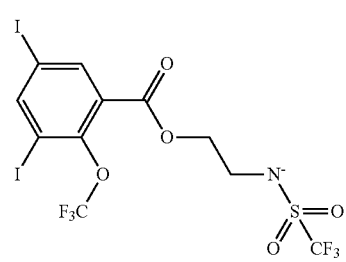
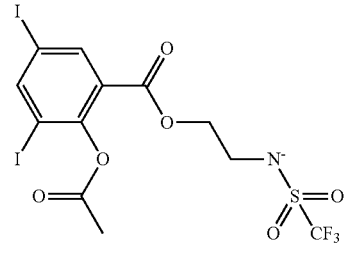
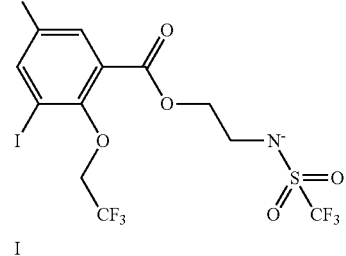
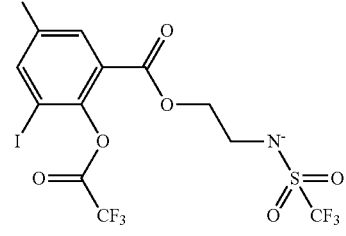
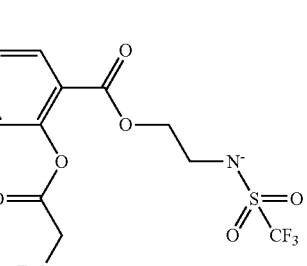
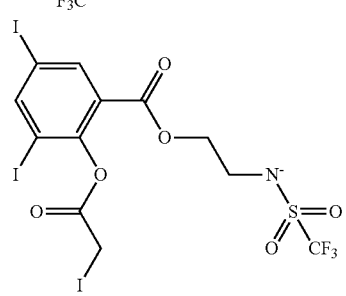
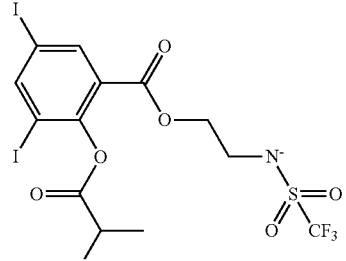
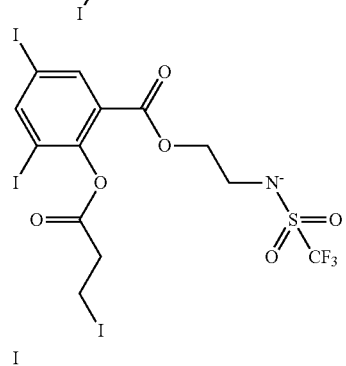
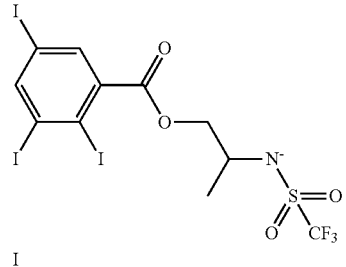
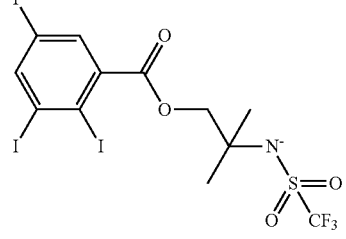

-continued
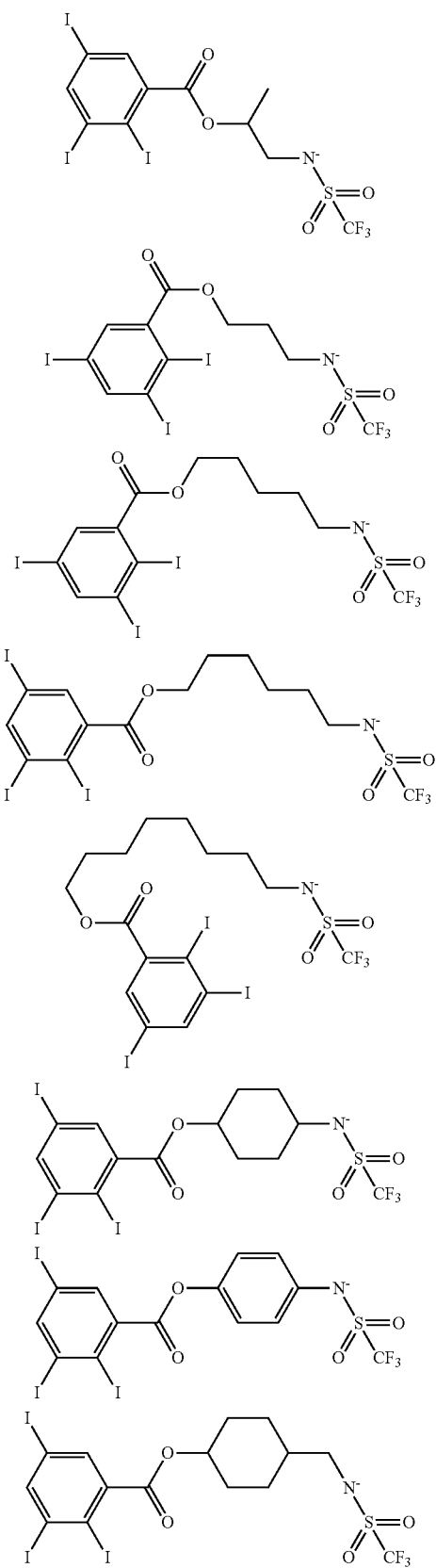
-continued
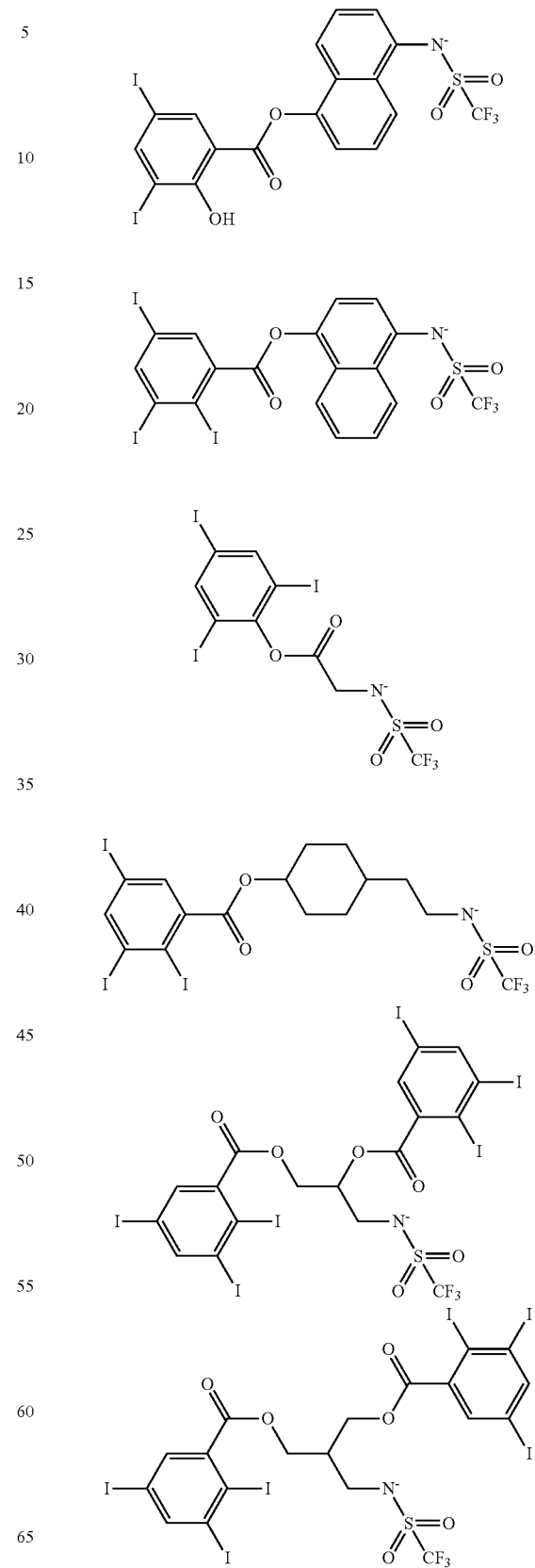

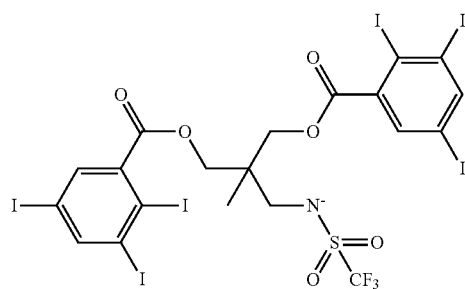
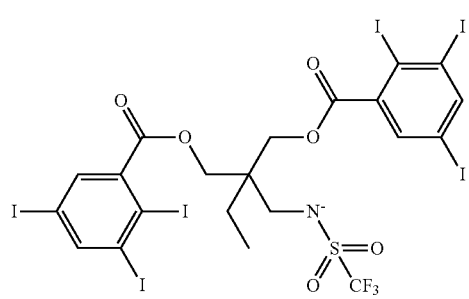
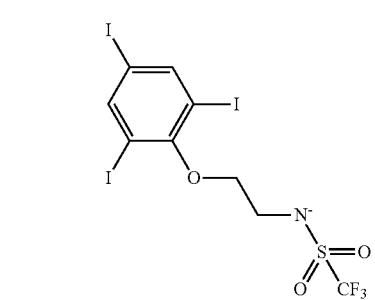
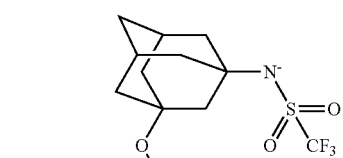
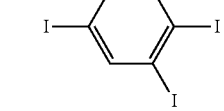
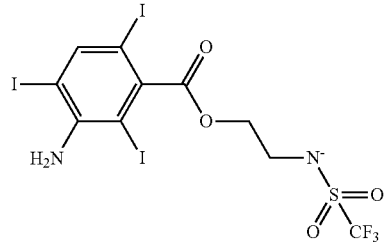
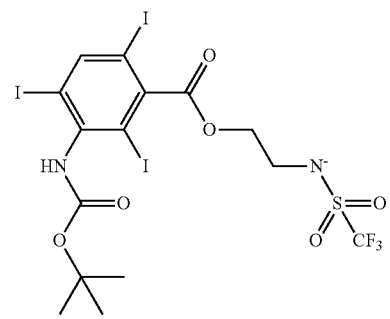
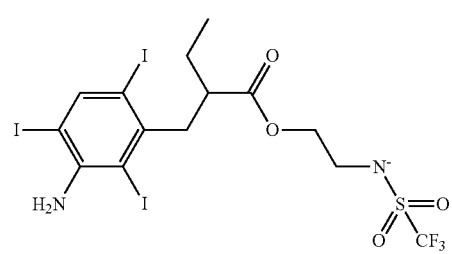
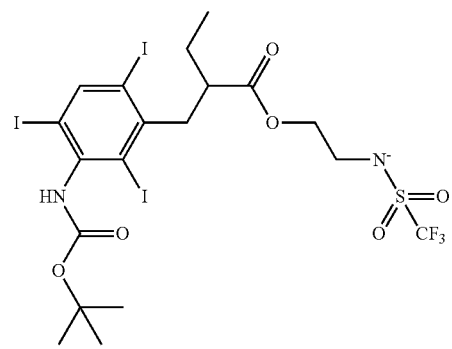
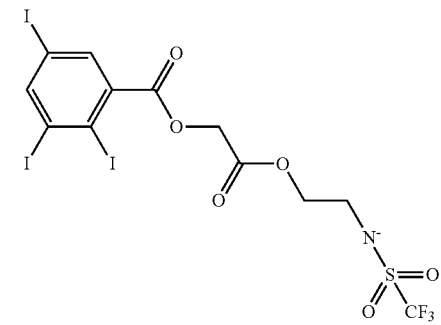
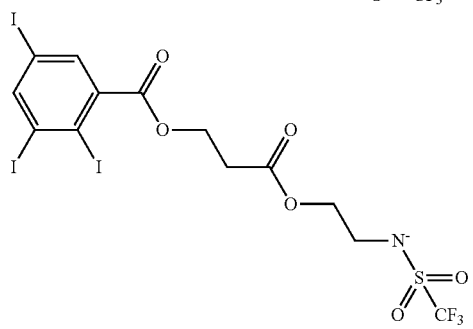

-continued
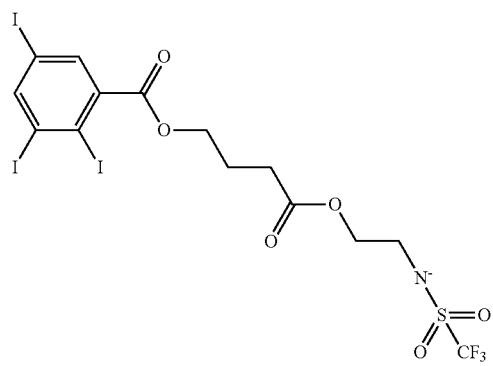
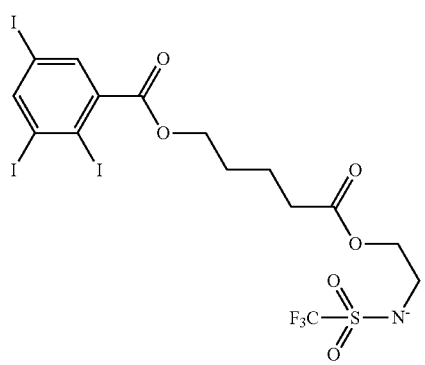
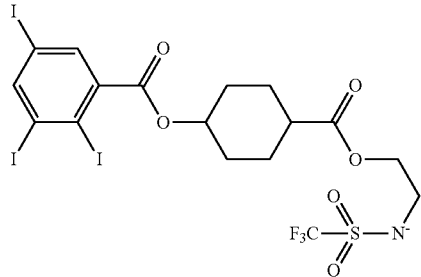
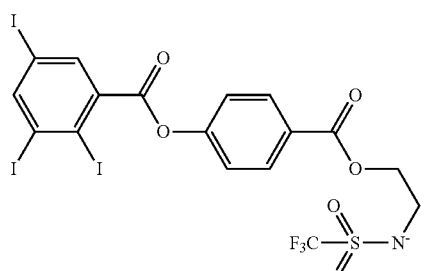
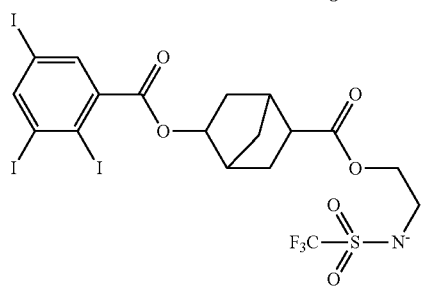
-continued
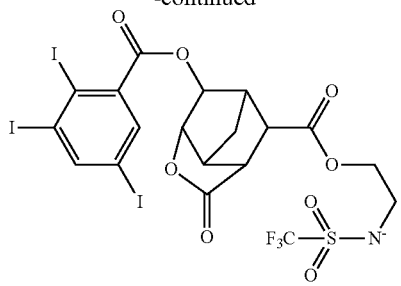
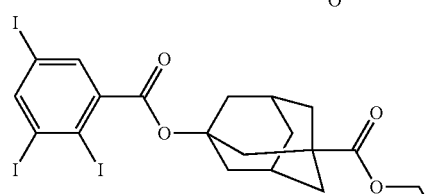
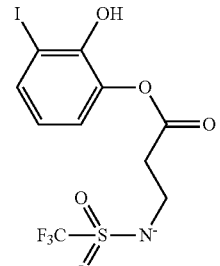
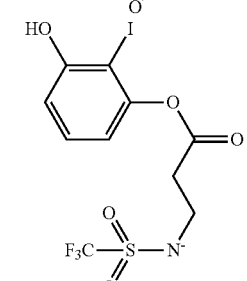
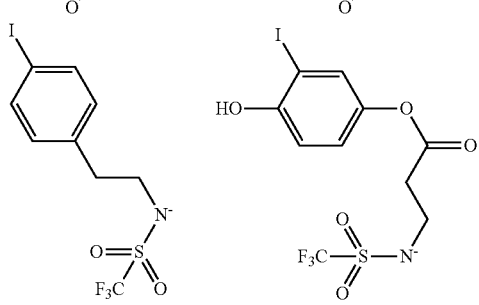
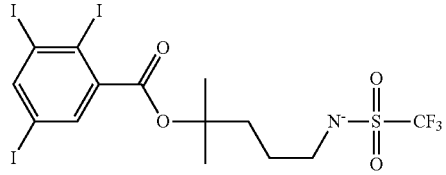
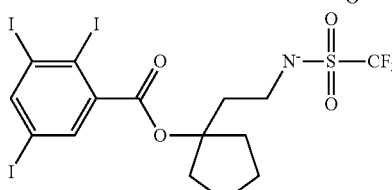
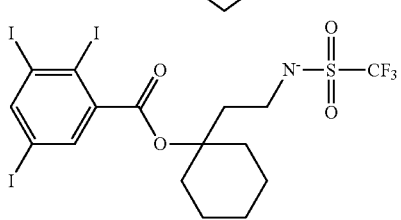

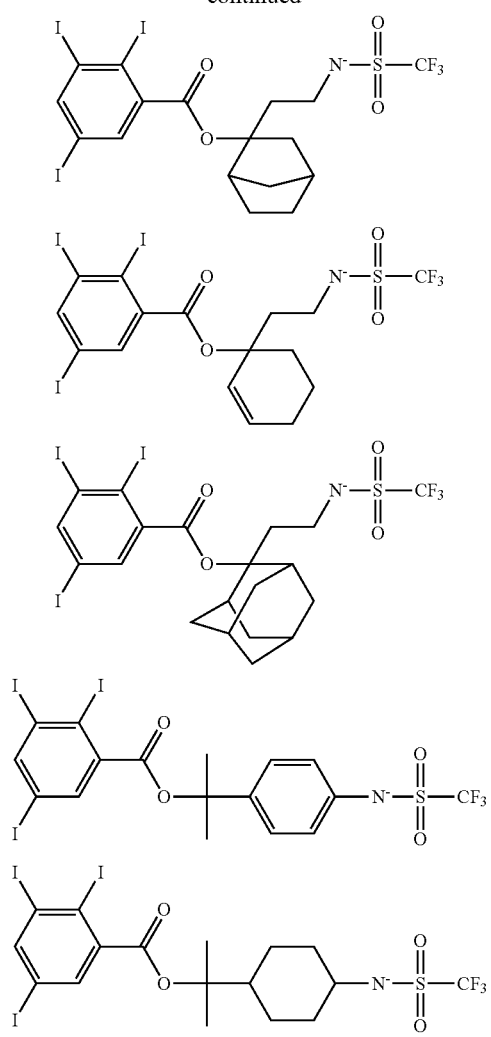
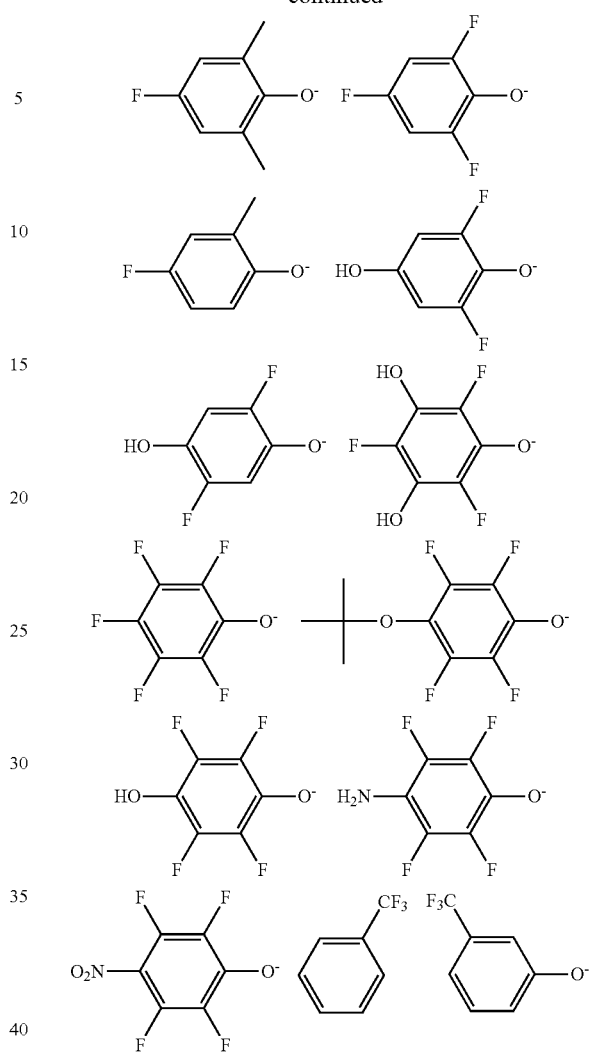
Examples of the halogenated phenoxide anion are shown below, but not limited thereto.
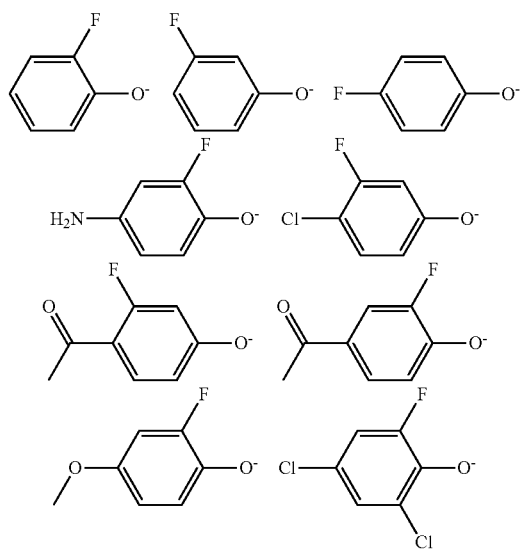
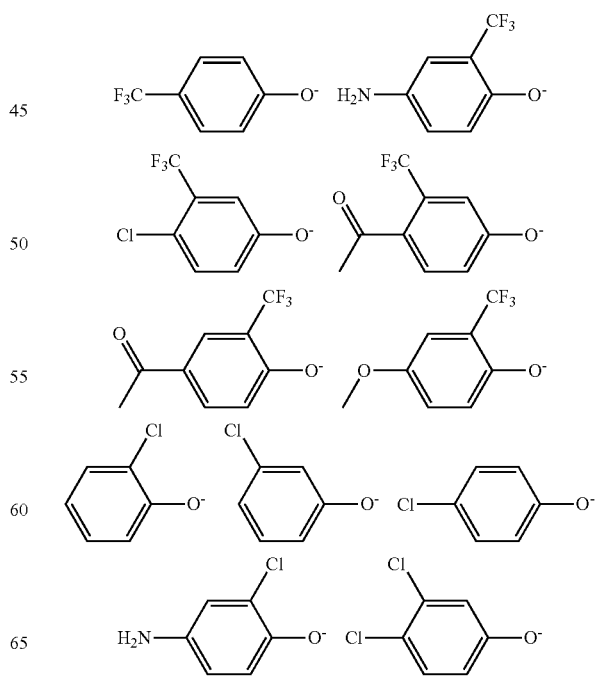

169
-continued
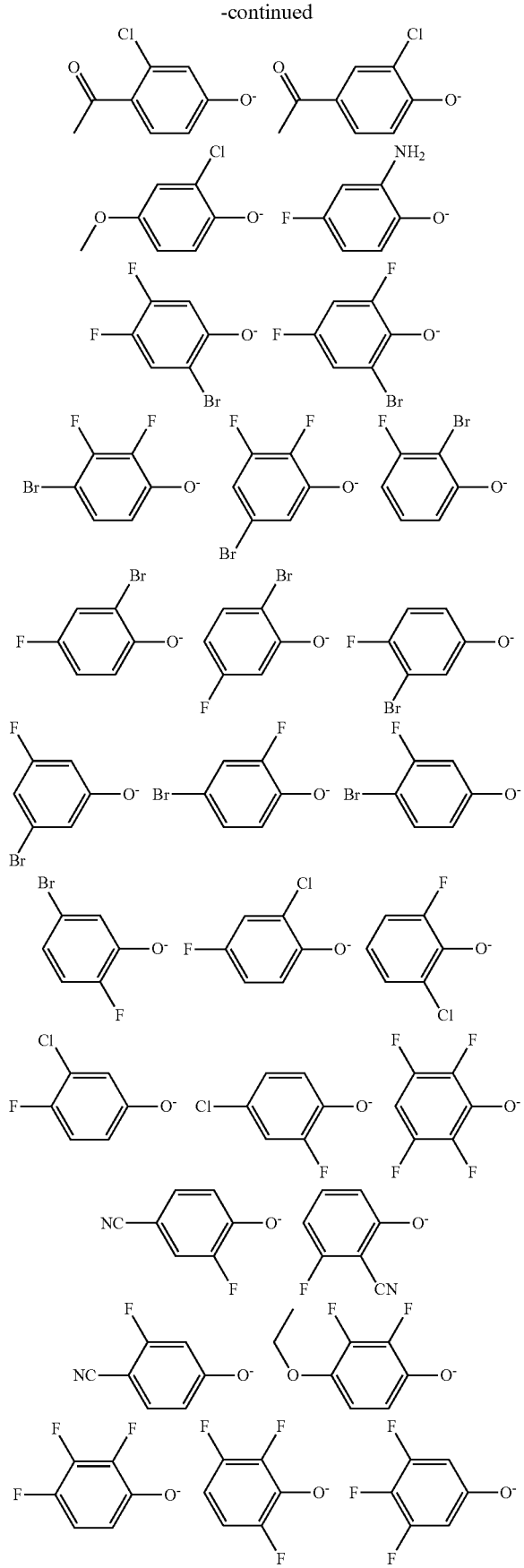
170
-continued
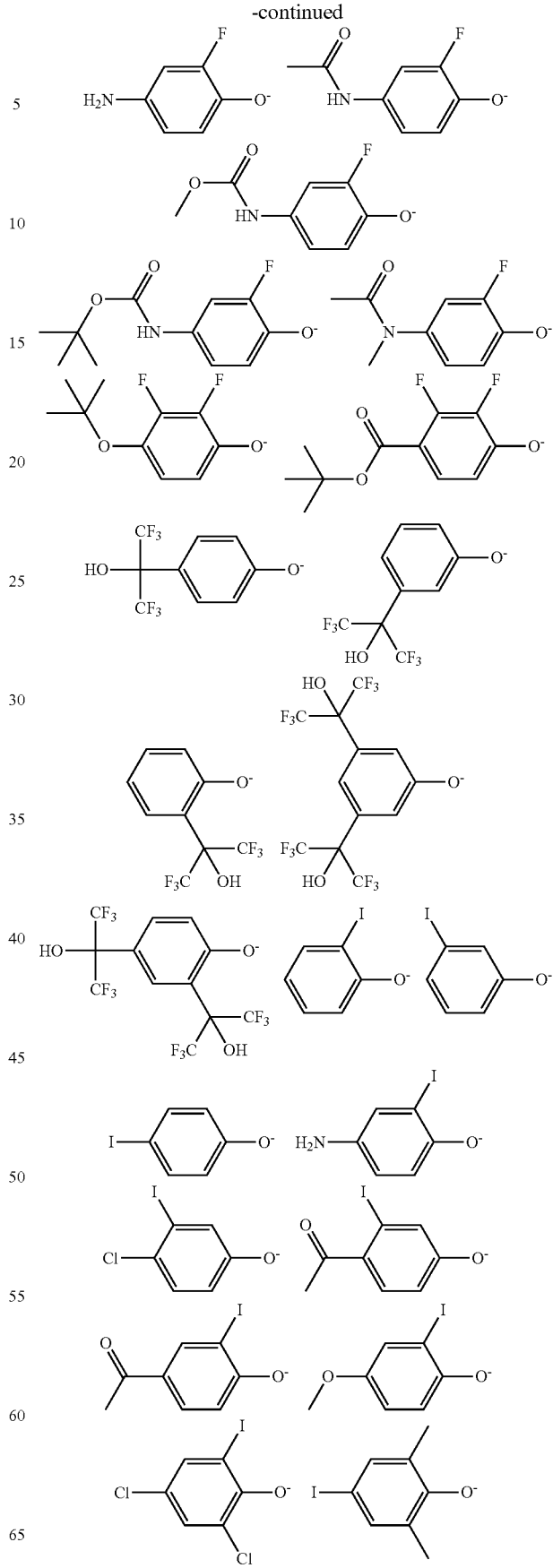

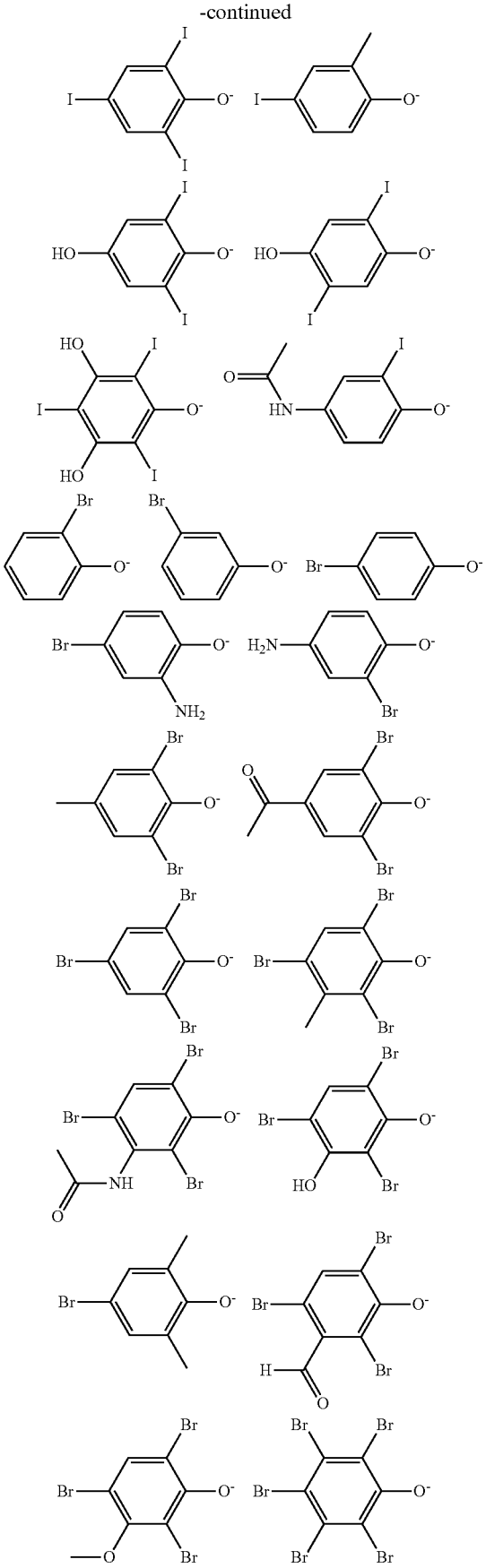

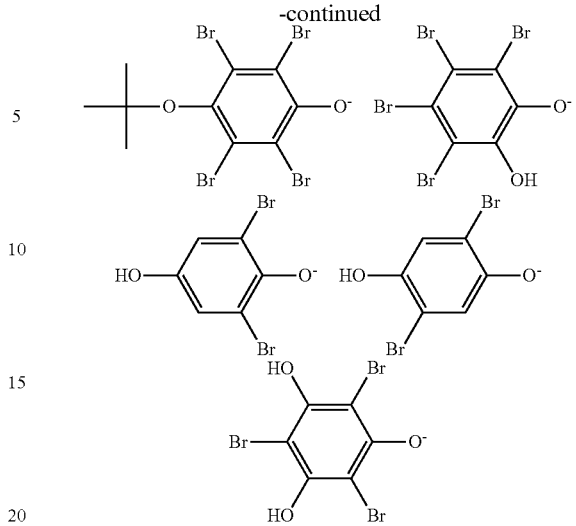

Exemplary halide anions include fluoride, chloride, bromide and iodide ions.

Of the foregoing anions, iodine or bromine-containing carboxylate anions, iodine or bromine-containing sulfonamide anions, and iodine or bromine-containing phenoxide anions are preferred because a sensitivity-enhancing effect is exerted by the generation of adequate secondary electrons due to high EUV absorption.

Of the salt compounds having formula (A), those compounds containing an iodine-containing carboxylate anion or iodine-containing phenoxide anion having the following formula (A') are preferred.

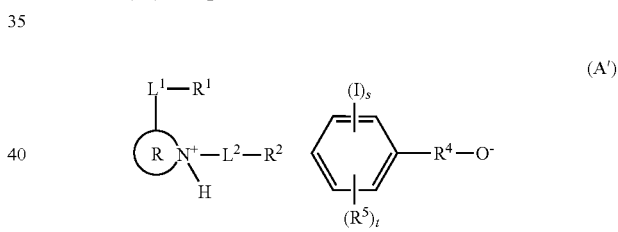

In formula (A'), R, $L^1$, $L^2$, $R^1$, and $R^2$ are as defined above. $R^4$ is a single bond or carbonyl group. $R^5$ is hydrogen, hydroxy group, optionally halogenated $C_1$-$C_6$ saturated hydrocarbyl group, optionally halogenated $C_1$-$C_6$ saturated hydrocarbyloxy group, optionally halogenated $C_2$-$C_7$ saturated hydrocarbylcarbonyloxy group, optionally halogenated $C_1$-$C_4$ saturated hydrocarbylsulfonyloxy group, fluorine, chlorine, bromine, amino group, nitro group, cyano group, —N($R^{51}$)—C(=O)—$R^{32}$, or —N($R^{51}$)—C(=O)—O—$R^{52}$. $R^{51}$ is hydrogen or a $C_1$-$C_6$ saturated hydrocarbyl group. $R^{52}$ is a $C_1$-$C_6$ saturated hydrocarbyl group or $C_2$-$C_8$ unsaturated aliphatic hydrocarbyl group. The subscript s is an integer of 1 to 5, t is an integer of 0 to 3, meeting 1≤s+t≤5. Examples of the groups represented by $R^5$, $R^{51}$, and $R^{52}$ are as exemplified above for the groups represented by $R^{c2}$, $R^{c21}$, and $R^{c22}$ in formula (Ac).

The fluorinated cyclic ammonium salt compound may be synthesized, for example, by neutralization reaction of a fluorinated cyclic amine compound of the structure that the hydrogen atom on the quaternary nitrogen atom in the cation of the fluorinated cyclic ammonium salt compound is eliminated with a carboxylic acid compound, sulfonamide compound, halogenated phenol compound, or hydrogen halide compound. The neutralization reaction is preferably carried out under the conditions that the amino group in the fluorinated cyclic amine compound and the carboxylic acid compound, sulfonamide compound, halogenated phenol compound, or hydrogen halide compound are in a stoichiometric ratio (or molar ratio) of 1:1 although either one of the compounds may be in excess. The fluorinated cyclic amine compound may be synthesized, for example, by the method of U.S. Pat. No. 7,468,236 (JP-A 2007-108451).

The fluorinated cyclic ammonium salt compound has at least three fluorine atoms on the cation side. The electric repulsion of fluorine atoms prevents the quencher from agglomerating together. This enables uniform acid diffusion on a nanometer level, leading to improvements in LWR and CDU of resist patterns after development, In the resist composition, the fluorinated cyclic ammonium salt compound is preferably present in an amount of 0.001 to 50 parts by weight, more preferably 0.01 to 40 parts by weight per 100 parts by weight of the base polymer, as viewed from sensitivity and acid diffusion suppressing effect. The fluorinated cyclic ammonium salt compound may be used alone or in admixture.

Base Polymer

Where the resist composition is of positive tone, the base polymer comprises repeat units containing an acid labile group, preferably repeat units having the formula (a1) or repeat units having the formula (a2). These units are simply referred to as repeat units (a1) and (a2).

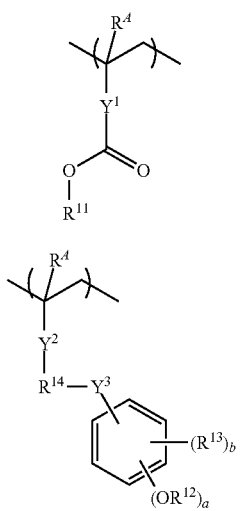

In formulae (a1) and (a2). $R^A$ is each independently hydrogen or methyl. $Y^1$ is a single bond, phenylene or naphthylene group, or $C_1$-$C_{12}$ linking group containing at least one moiety selected from ester bond and lactone ring. $Y^2$ is a single bond or ester bond. $Y^3$ is a single bond, ether bond or ester bond. $R^{11}$ and $R^{12}$ are each independently an acid labile group. When the base polymer contains both repeat units (a1) and (a2), $R^{11}$ and $R^{12}$ may be the same or different. $R^{13}$ is fluorine, trifluoromethyl, cyano or $C_1$-$C_6$ saturated hydrocarbyl group. $R^{14}$ is a single bond or a $C_1$-$C_6$ alkanediyl group in which some carbon may be replaced by an ether bond or ester bond. The subscript "a" is 1 or 2, "b" is an integer of 0 to 4, and $1 \le a+b \le 5$.

Examples of the monomer from which the repeat units (a1) are derived are shown below, but not limited thereto. $R^A$ and $R^{11}$ are as defined above.

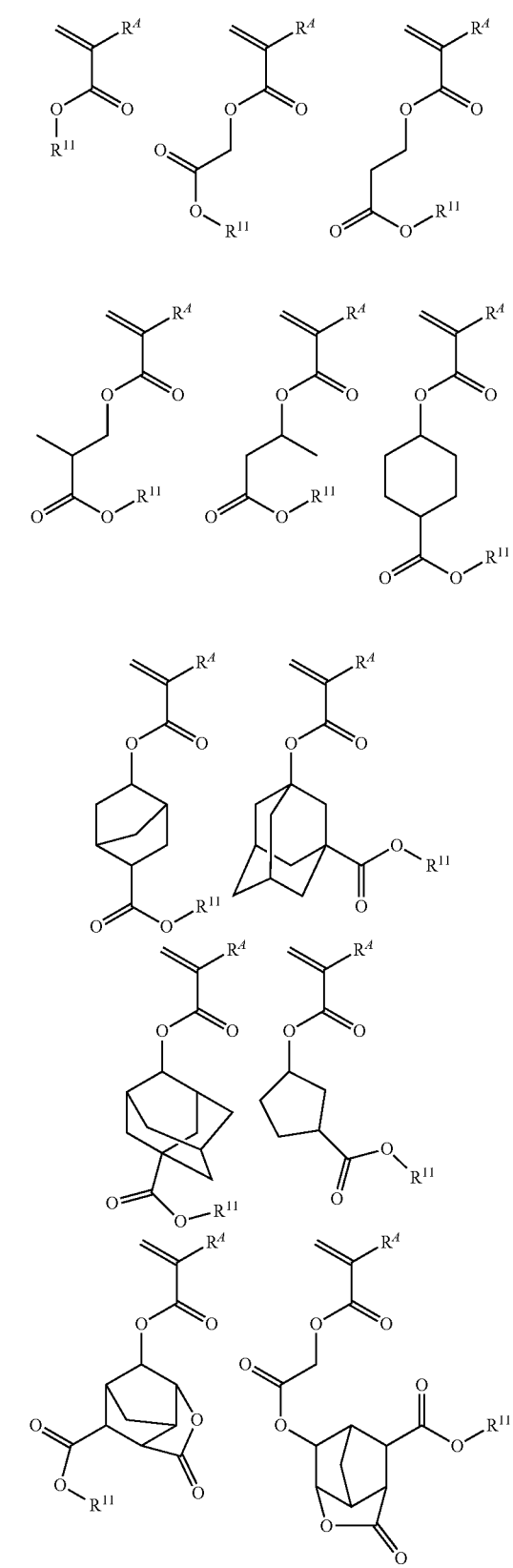

-continued

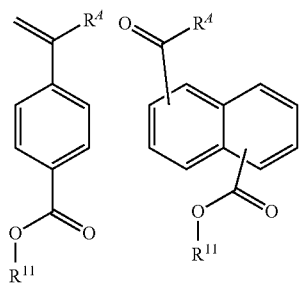

Examples of the monomer from which the repeat units (a2) are derived are shown below, but not limited thereto. $R^A$ and $R^{12}$ are as defined above.

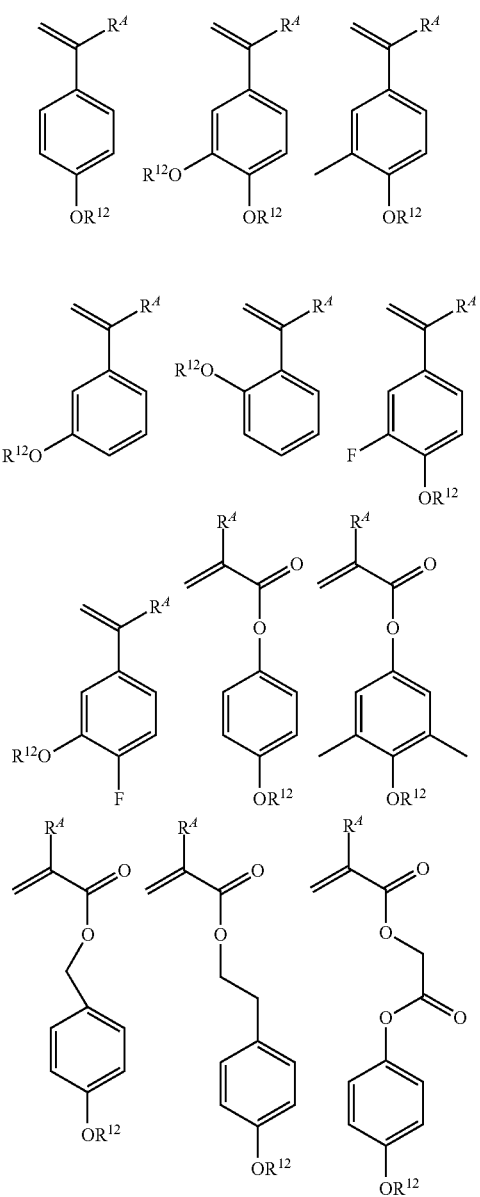

-continued

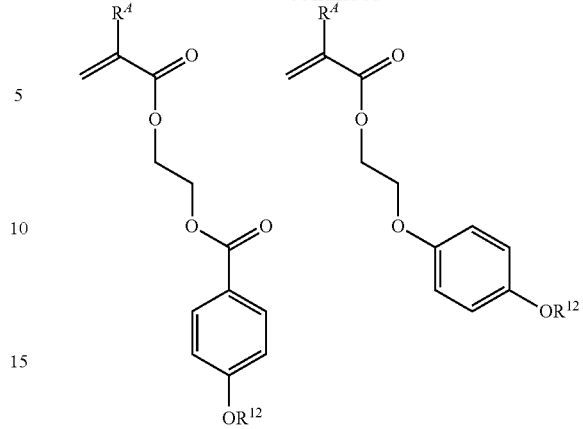

The acid labile groups represented by $R^{11}$ and $R^{12}$ in formulae (a1) and (a2) may be selected from a variety of such groups, for example, those groups described in JP-A 2013-080033 (U.S. Pat. No. 8,574,817) and JP-A 2013-083821 (U.S. Pat. No. 8,846,303).

Typical of the acid labile group are groups of the following formulae (AL-1) to (AL-3).

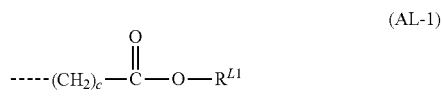  (AL-1)

  (AL-2)

  (AL-3)

In formulae (AL-1) and (AL-2), $R^{L1}$ and $R^{L2}$ are each independently a $C_1$-$C_{40}$ hydrocarbyl group which may contain a heteroatom such as oxygen, sulfur, nitrogen or fluorine. The hydrocarbyl group may be saturated or unsaturated and straight, branched or cyclic. Inter alia, $C_1$-$C_{40}$ saturated hydrocarbyl groups are preferred, and $C_1$-$C_{20}$ saturated hydrocarbyl groups are more preferred.

In formula (AL-1), c is an integer of 0 to 10, preferably 1 to 5.

In formula (AL-2), $R^{L3}$ and $R^{L4}$ are each independently hydrogen or a $C_1$-$C_{20}$ hydrocarbyl group which may contain a heteroatom such as oxygen, sulfur, nitrogen or fluorine. The hydrocarbyl group may be saturated or unsaturated and straight, branched or cyclic. Inter alia, $C_1$-$C_{20}$ saturated hydrocarbyl groups are preferred. Any two of $R^{L2}$, $R^{L3}$ and $R^{L4}$ may bond together to form a $C_3$-$C_{20}$ ring with the carbon atom or carbon and oxygen atoms to which they are attached. The ring preferably contains 4 to 16 carbon atoms and is typically alicyclic.

In formula (AL-3), $R^{L5}$, $R^{L6}$ and $R^{L7}$ are each independently a $C_1$-$C_{20}$ hydrocarbyl group which may contain a heteroatom such as oxygen, sulfur, nitrogen or fluorine. The hydrocarbyl group may be saturated or unsaturated and straight, branched or cyclic. Inter alia, $C_1$-$C_{20}$ saturated hydrocarbyl groups are preferred. Any two of $R^{L5}$, $R^{L6}$ and $R^{L7}$ may bond together to form a $C_3$-$C_{20}$ ring with the carbon atom to which they are attached. The ring preferably contains 4 to 16 carbon atoms and is typically alicyclic.

The base polymer may further comprise repeat units (b) having a phenolic hydroxy group as an adhesive group. Examples of suitable monomers from which repeat units (b) are derived are given below, but not limited thereto. Herein $R^A$ is as defined above.

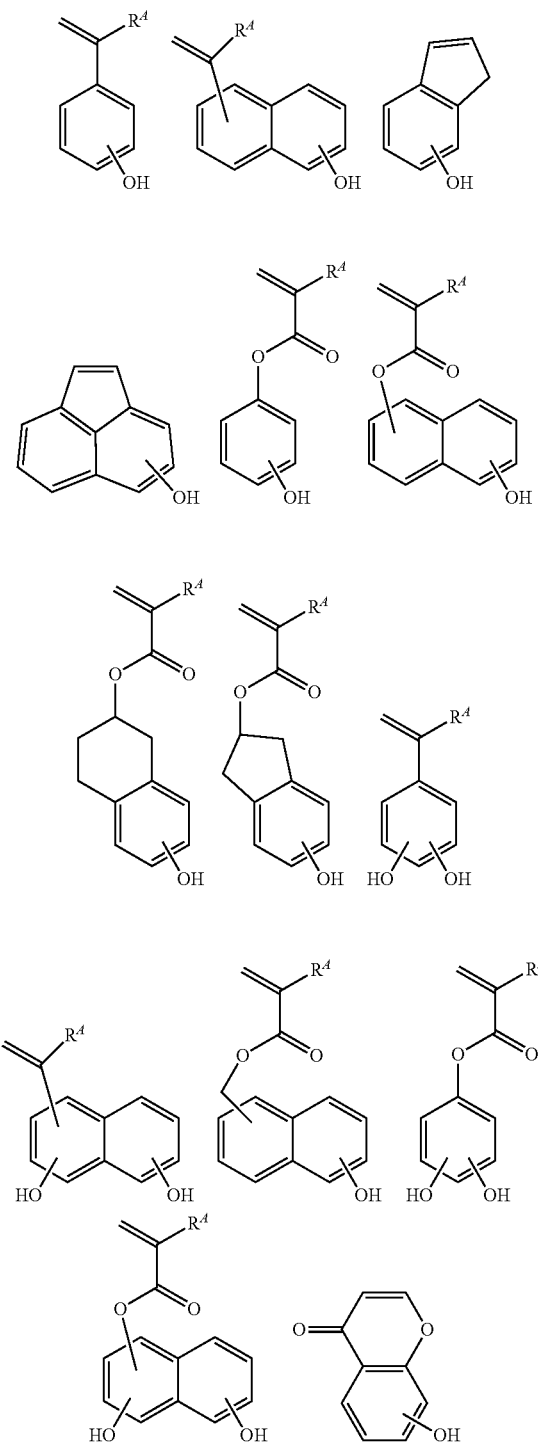

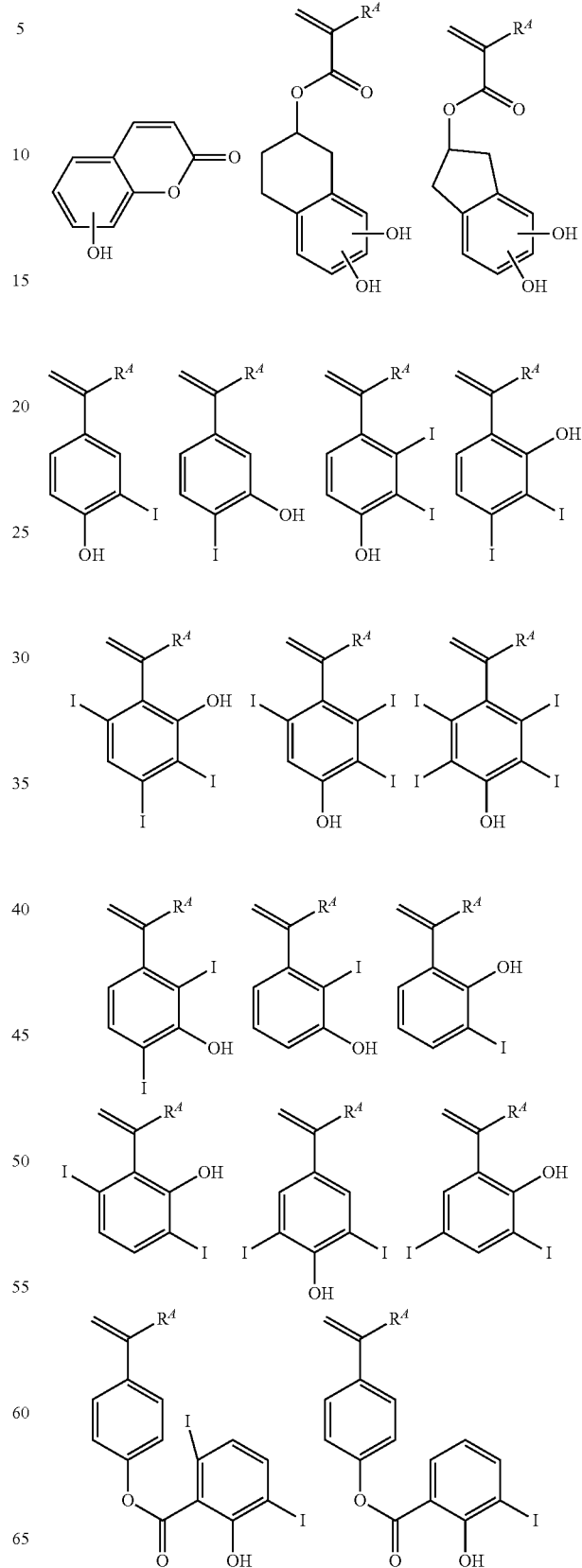

-continued

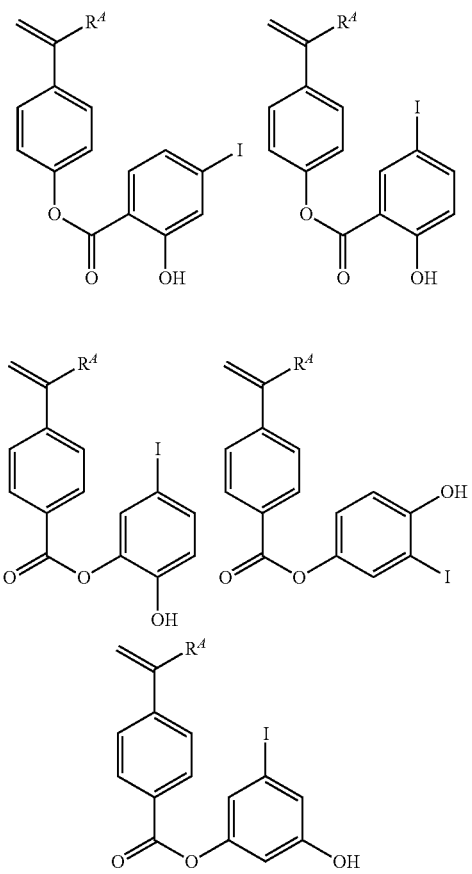

Further, repeat units (c) having another adhesive group selected from hydroxy group (other than the foregoing phenolic hydroxy), lactone ring, sultone ring, ether bond, ester bond, sulfonate bond, carbonyl group, sulfonyl group, cyano group, and carboxy group may also be incorporated in the base polymer. Examples of suitable monomers from which repeat units (c) are derived are given below, but not limited thereto. Herein $R^A$ is as defined above.

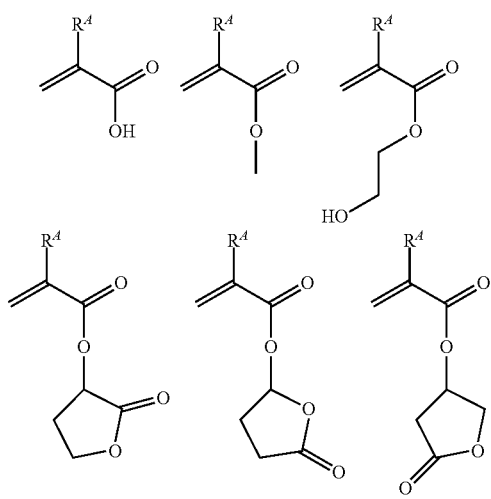

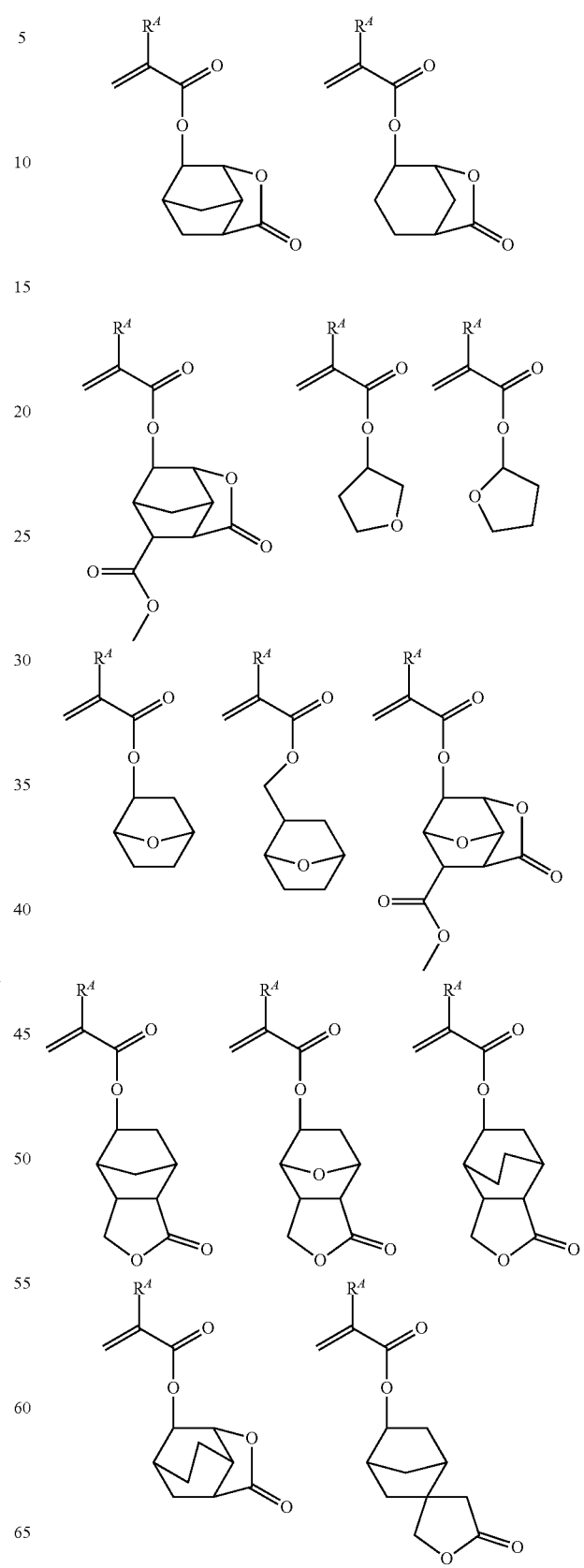

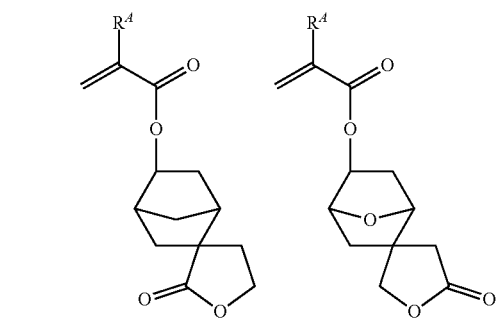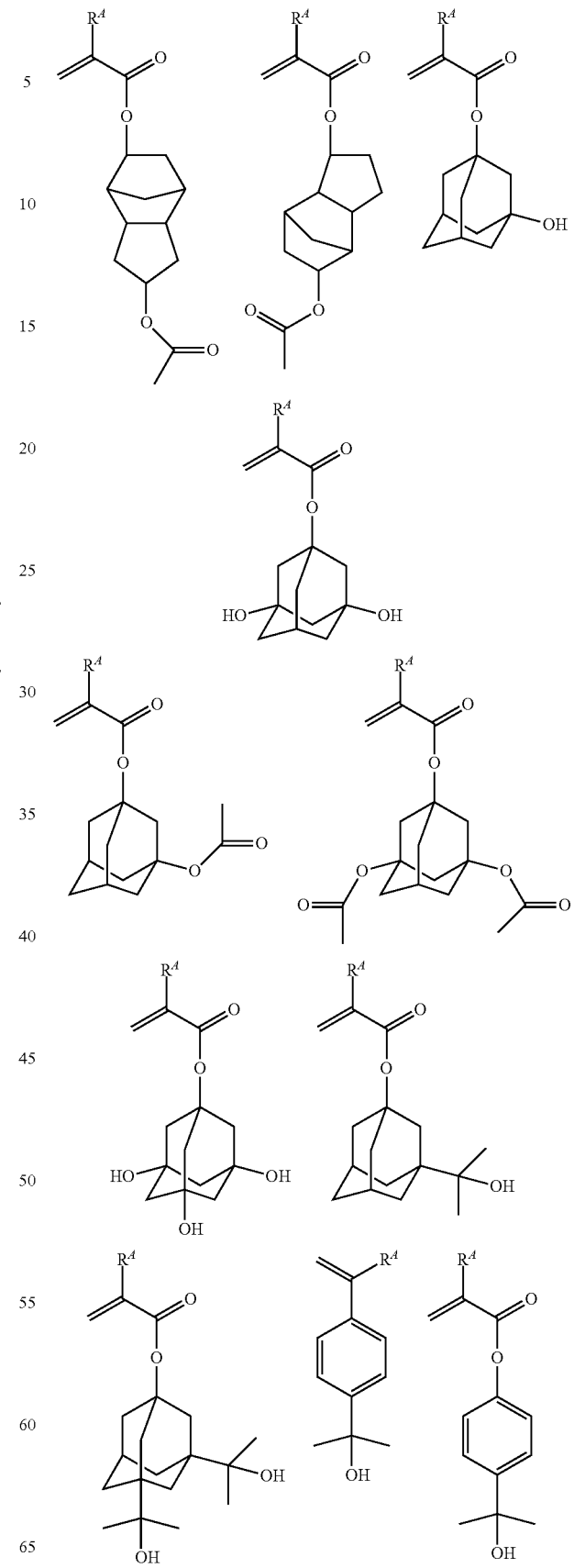

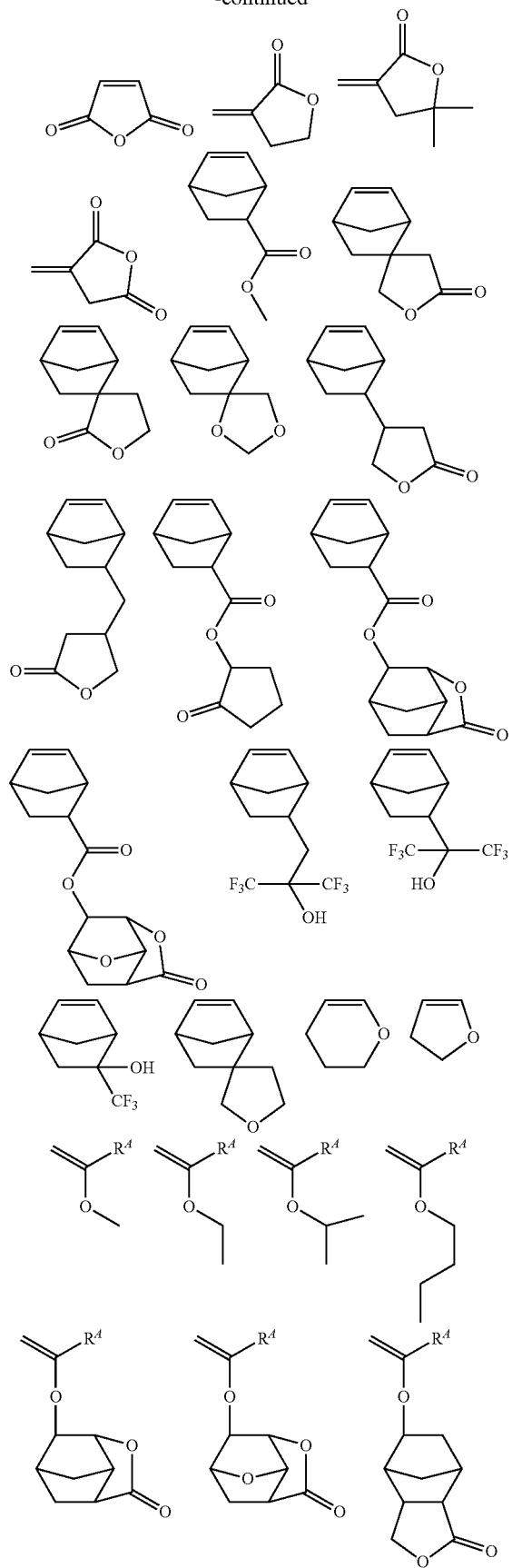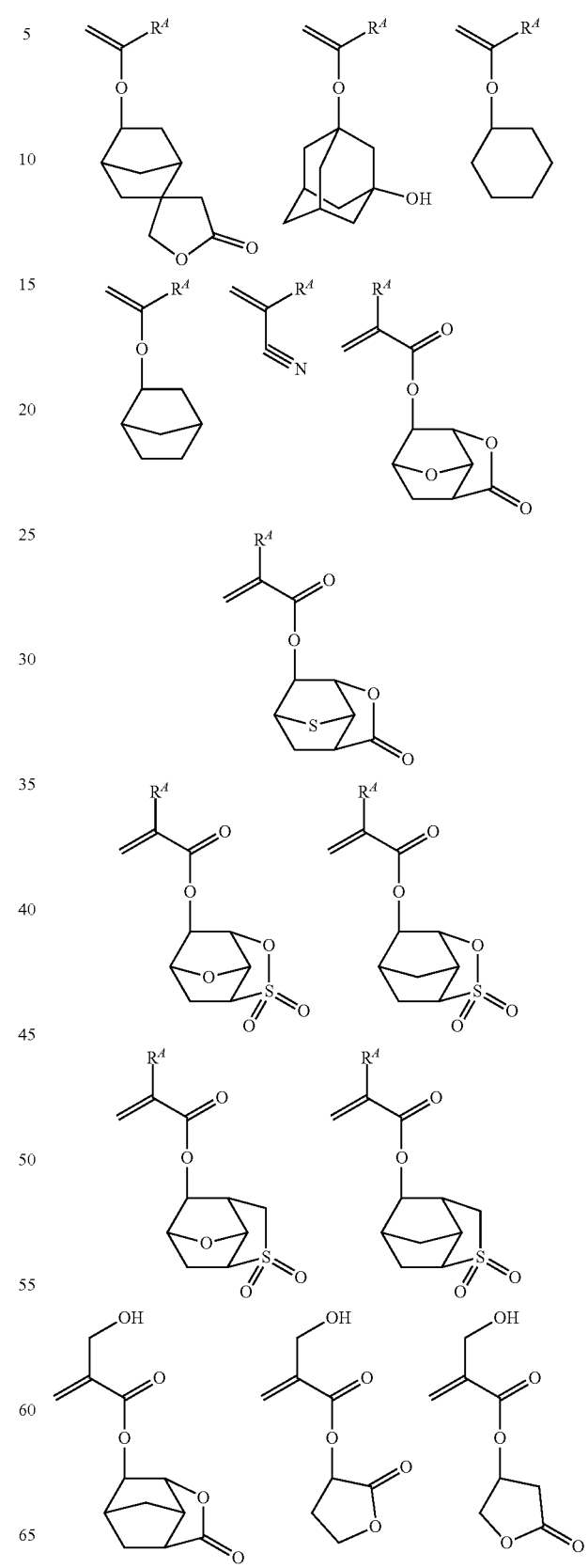

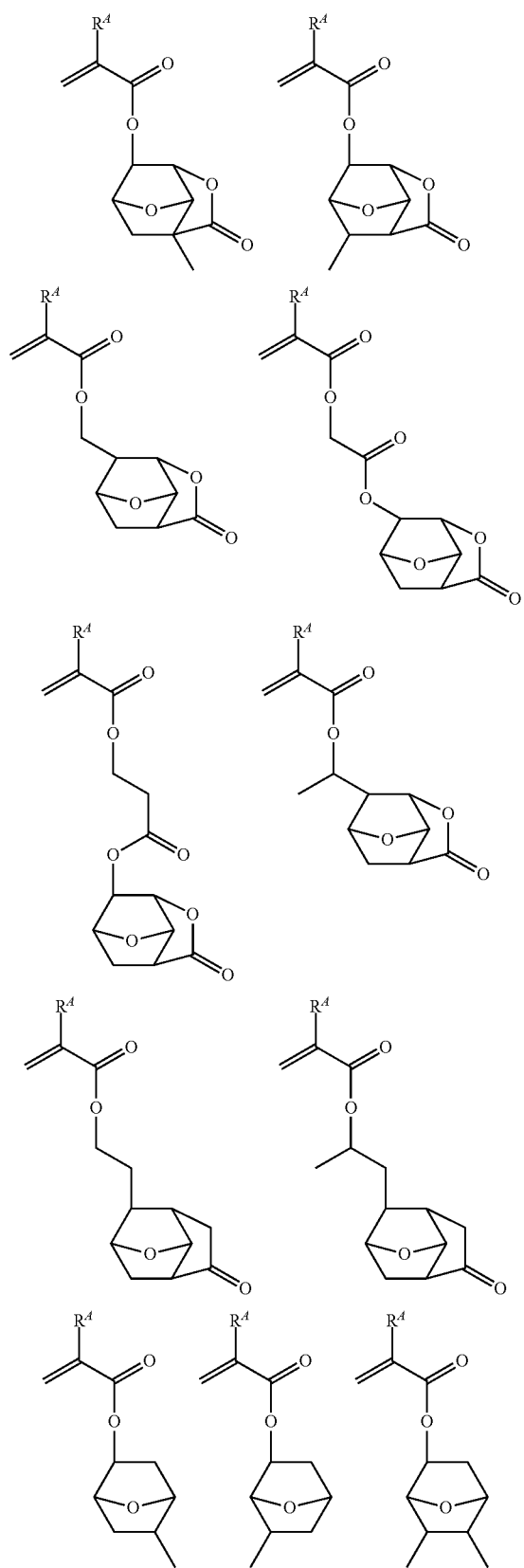
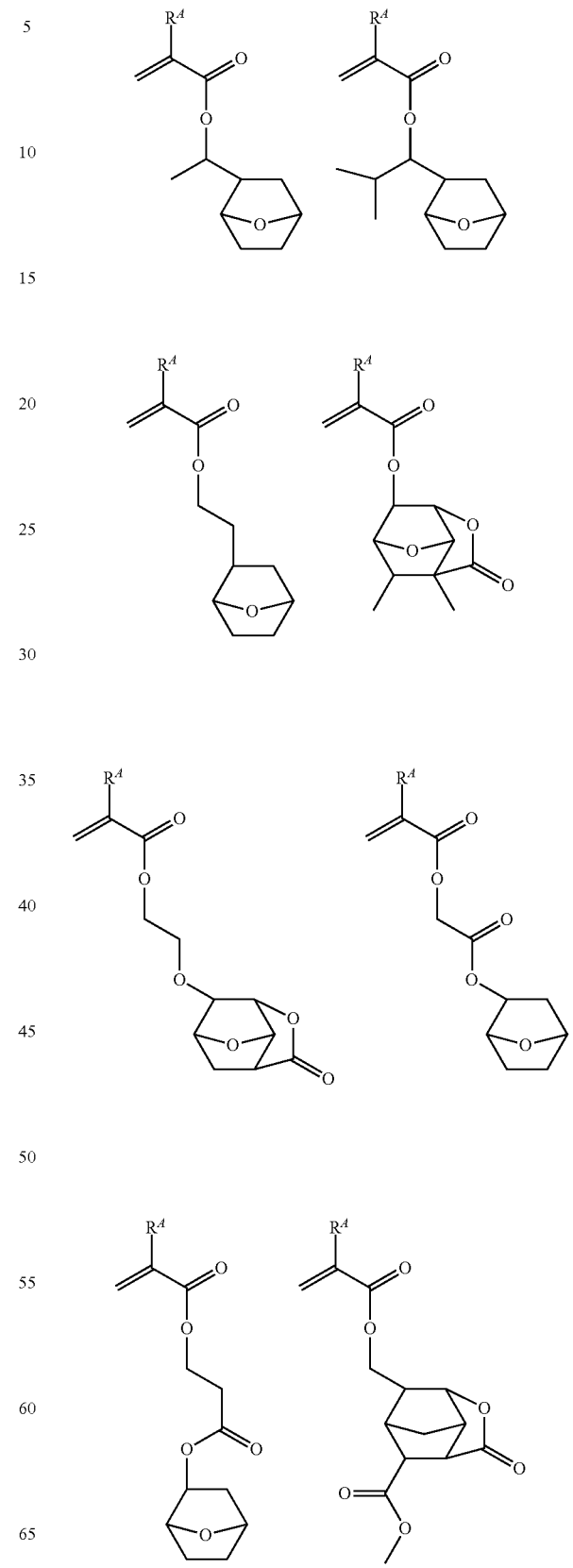

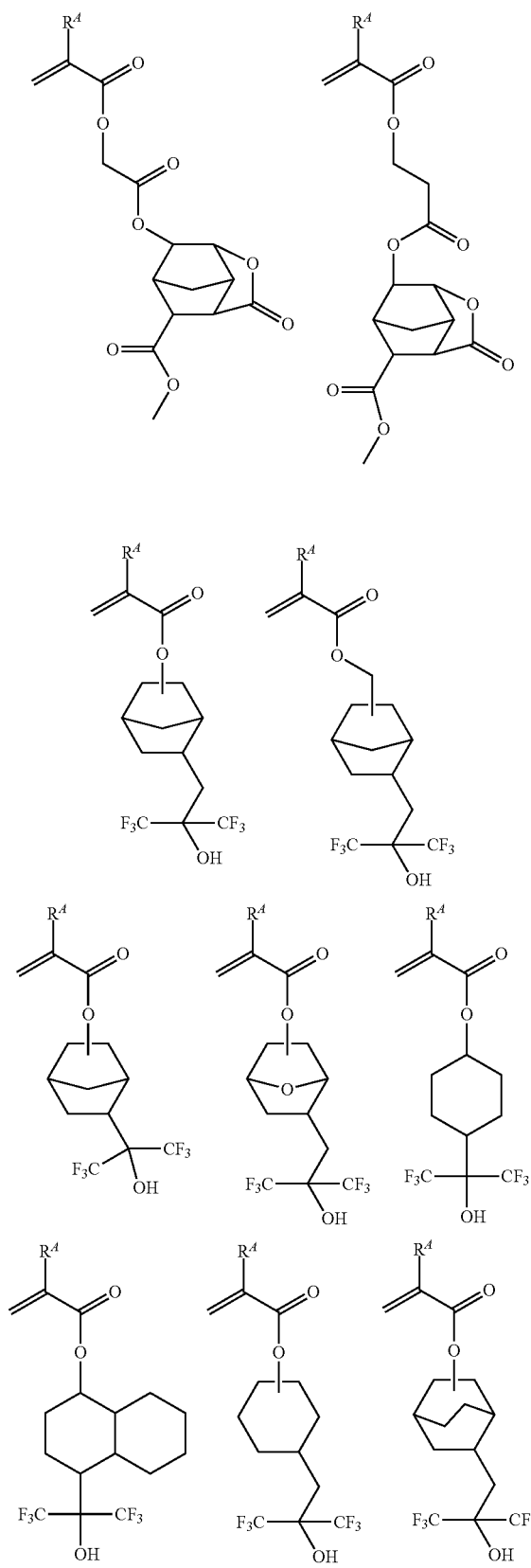
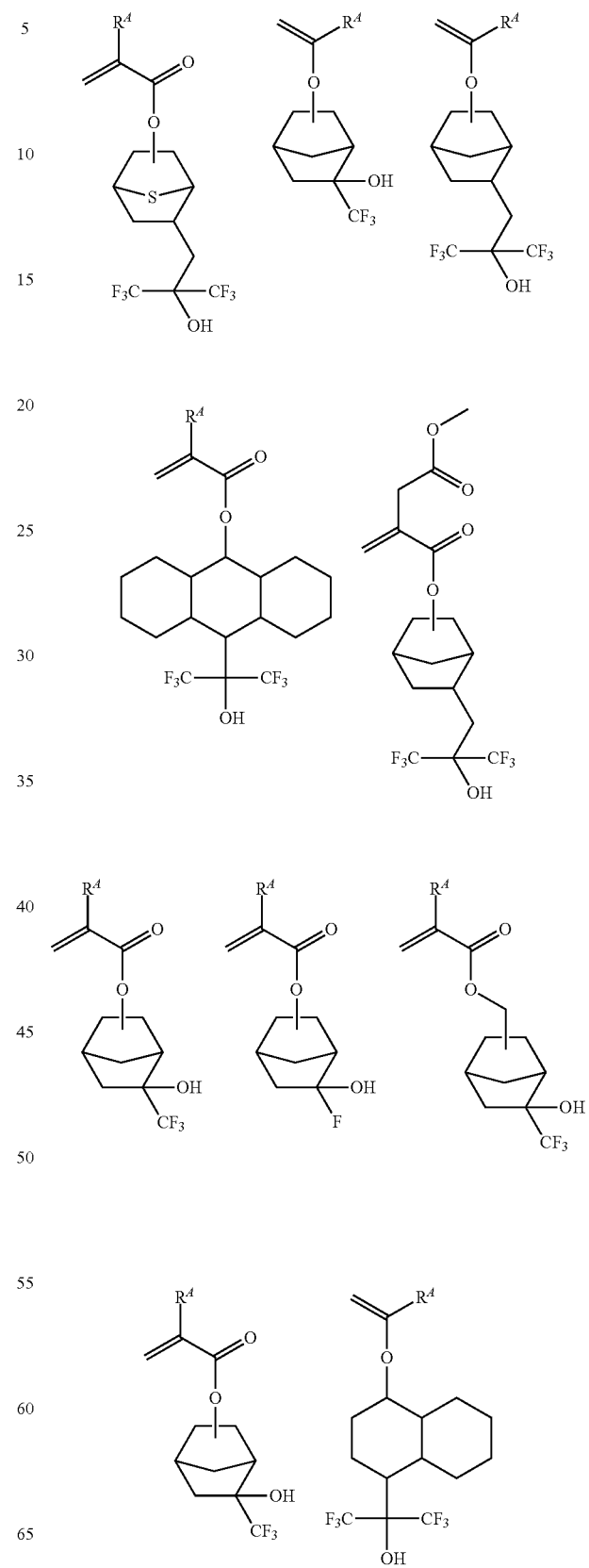

189
-continued
190
-continued
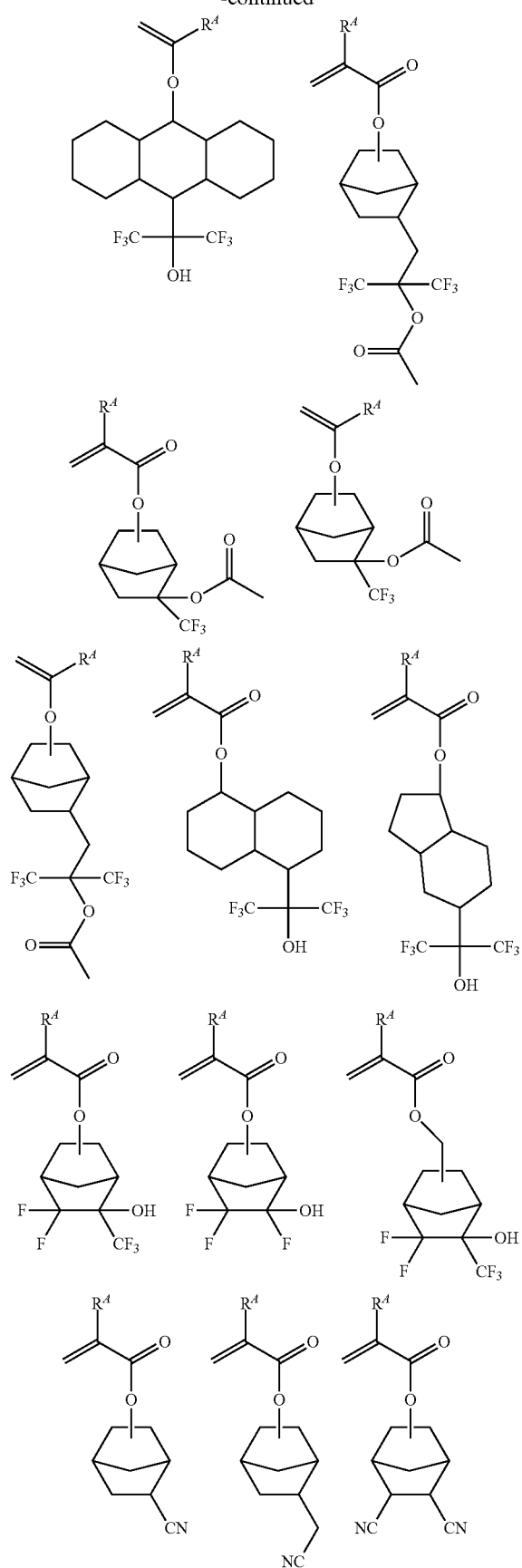
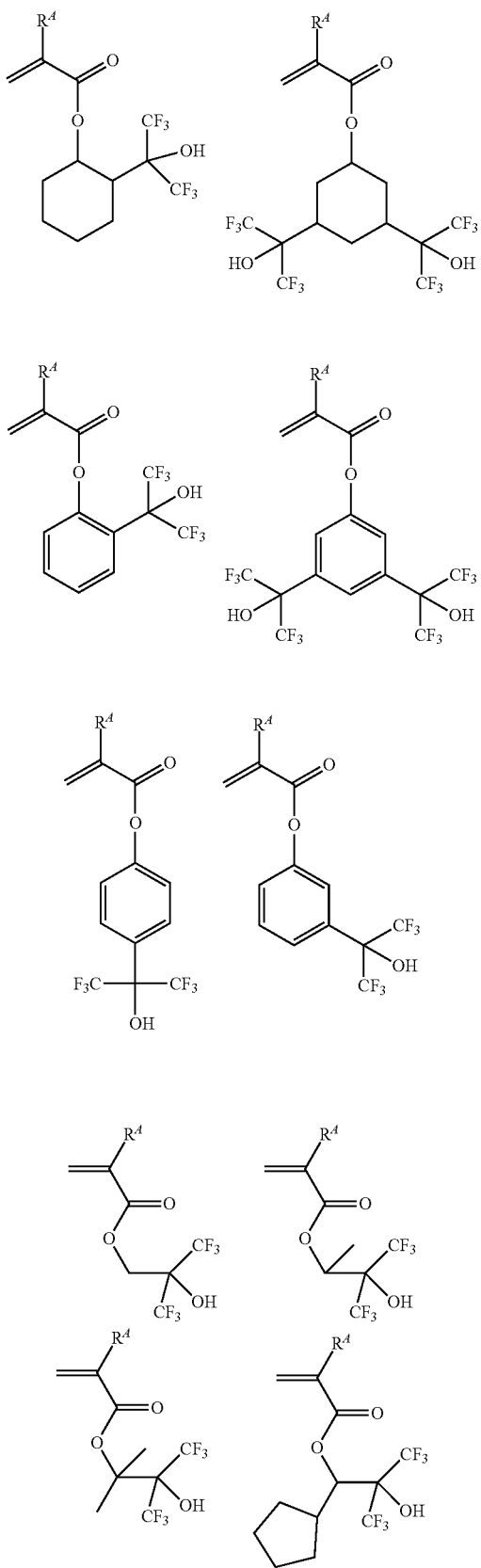

191
-continued
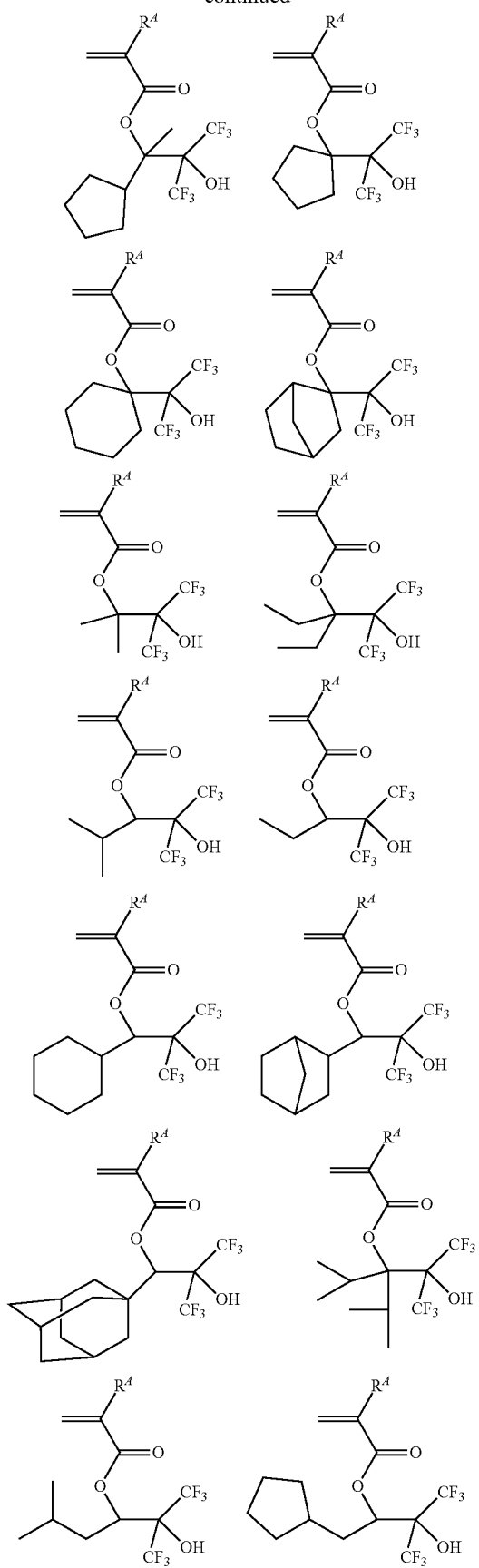
192
-continued
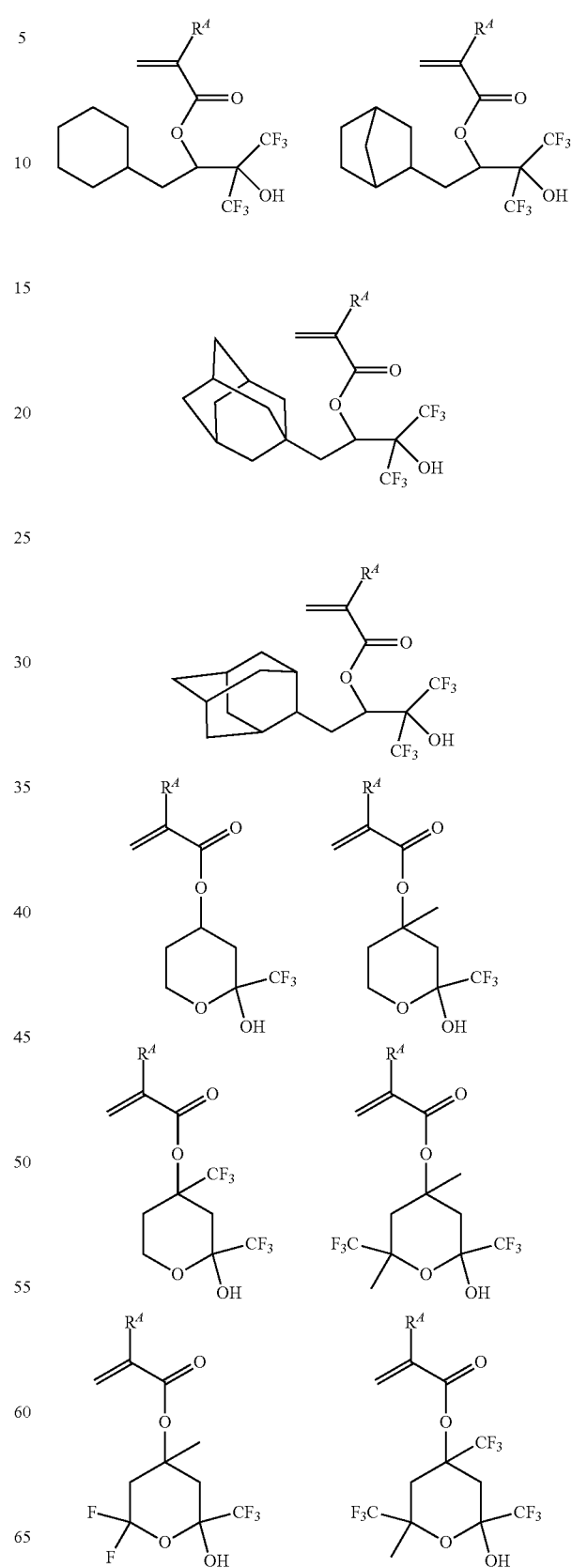

-continued
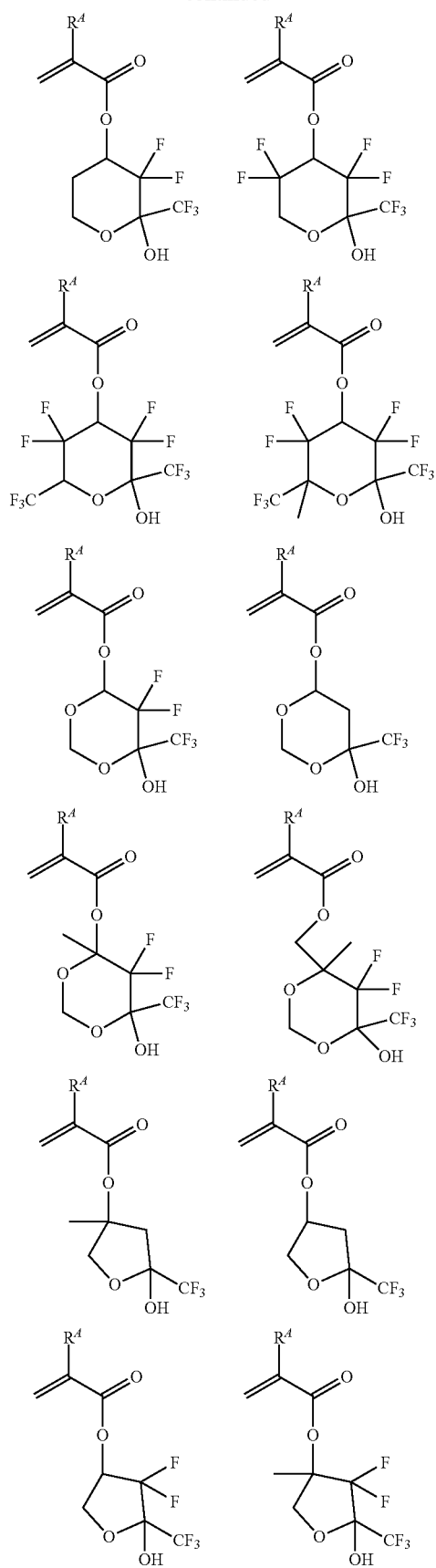
-continued
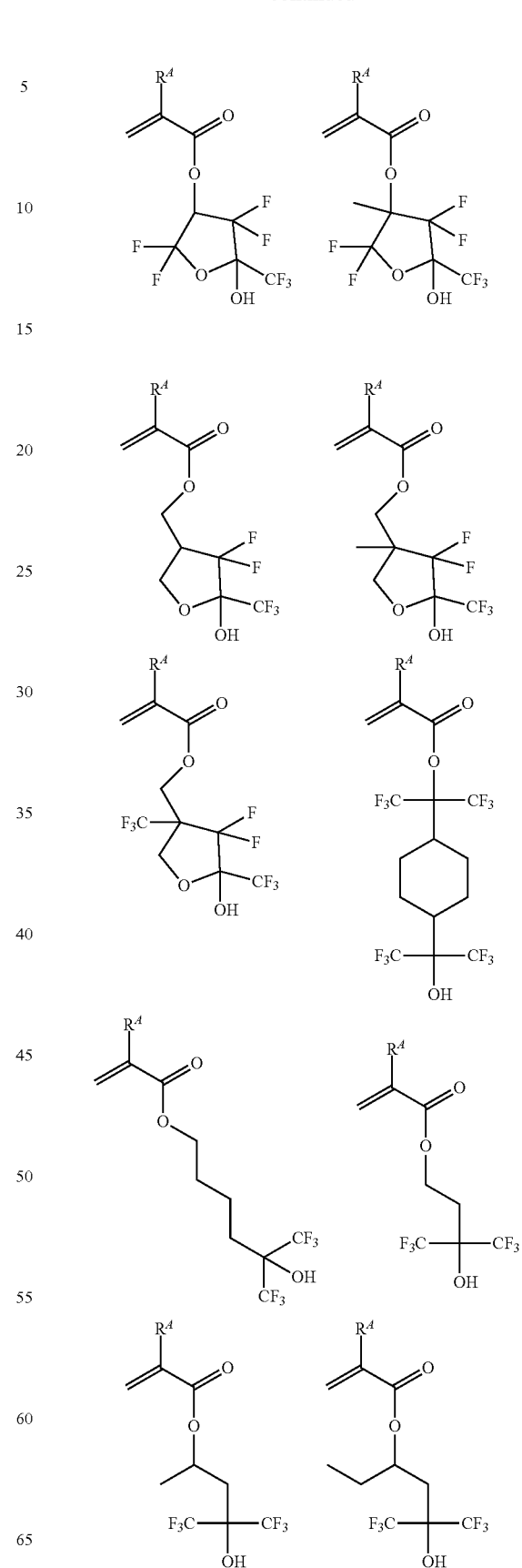

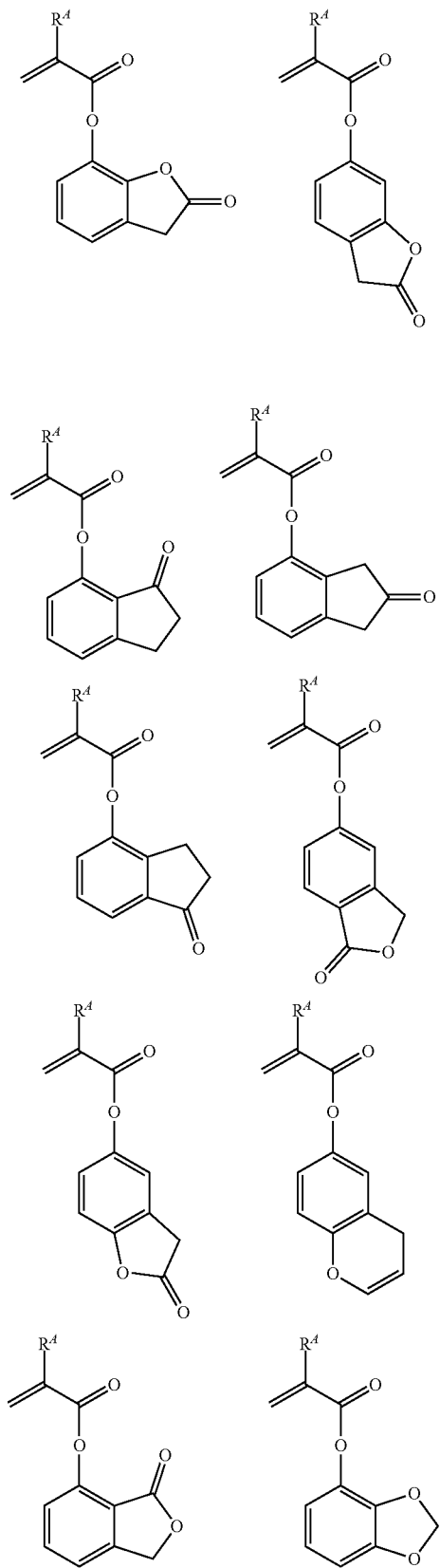
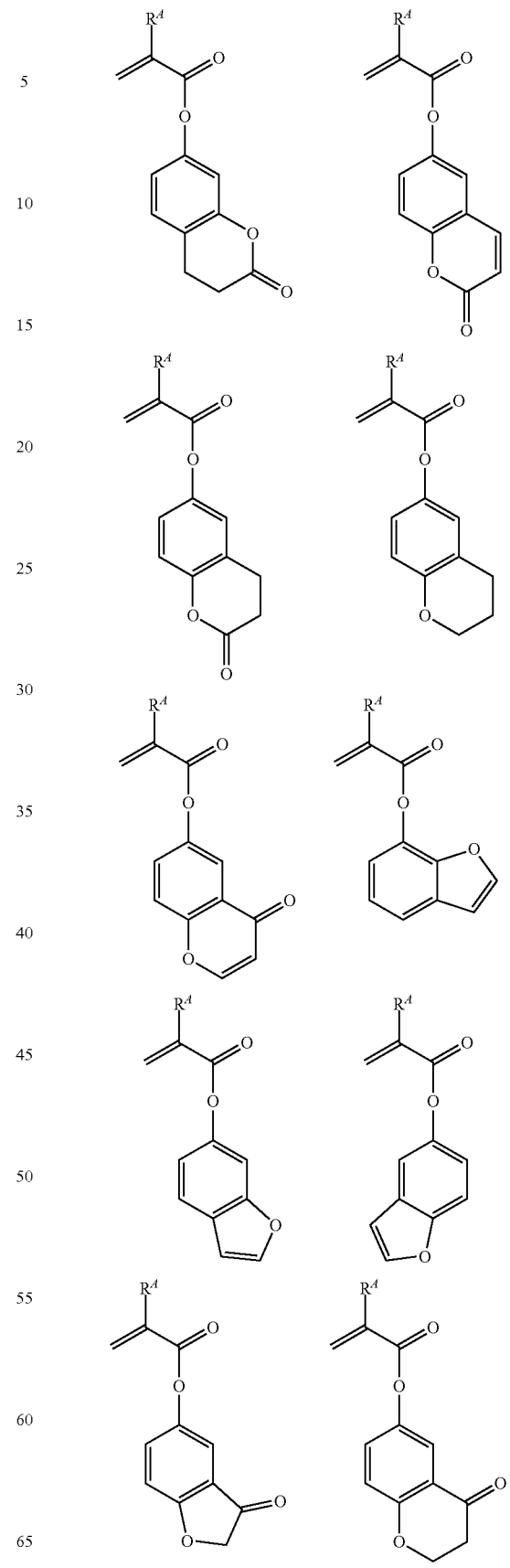

197
-continued
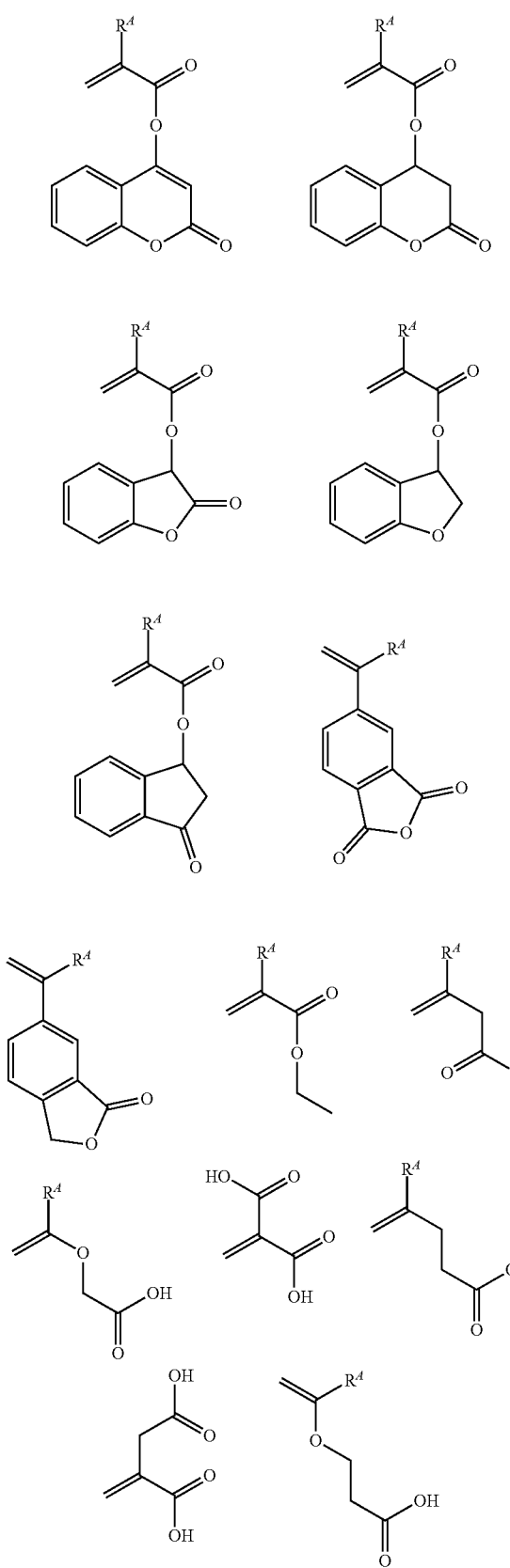
198
-continued
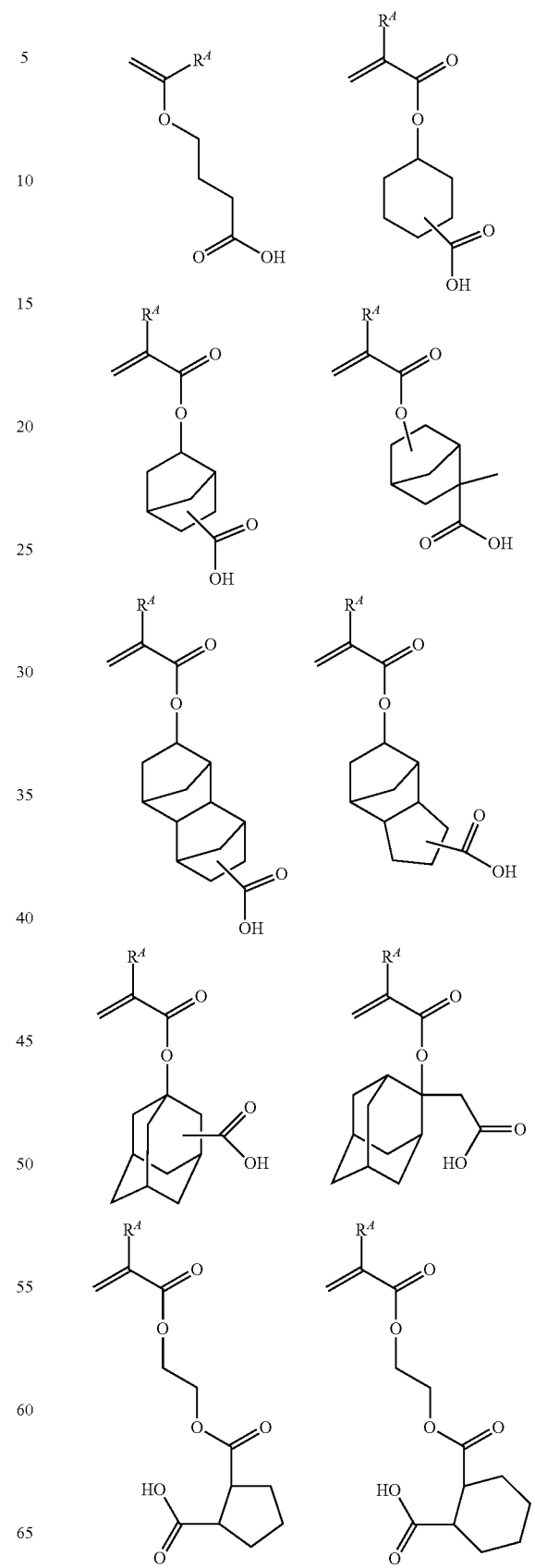

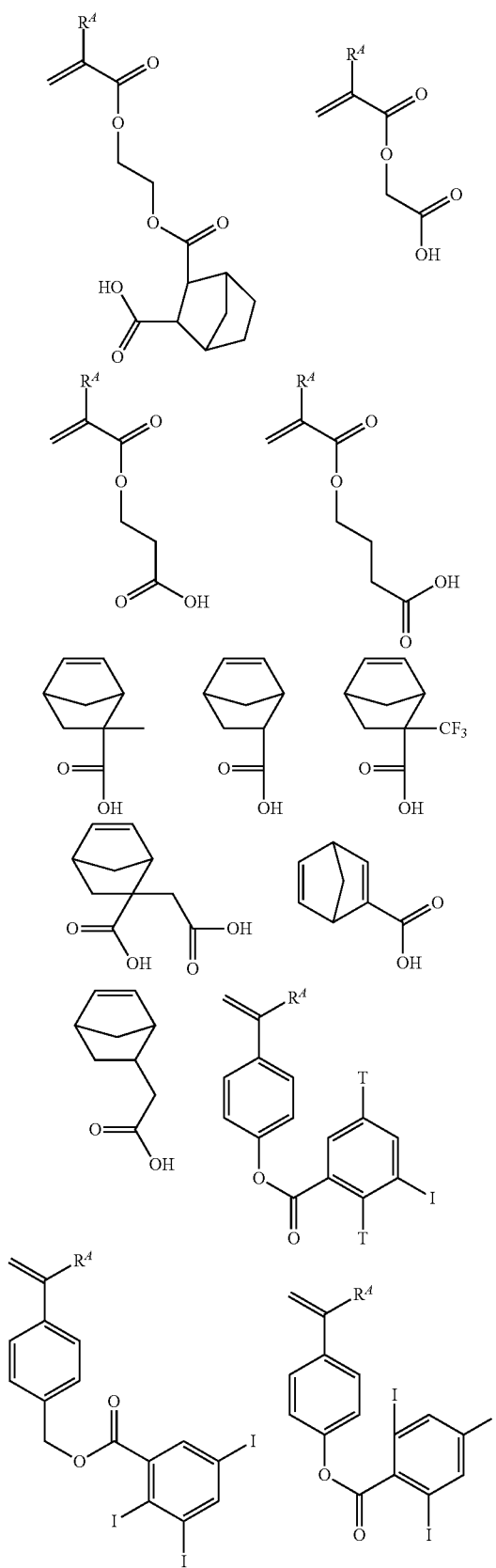
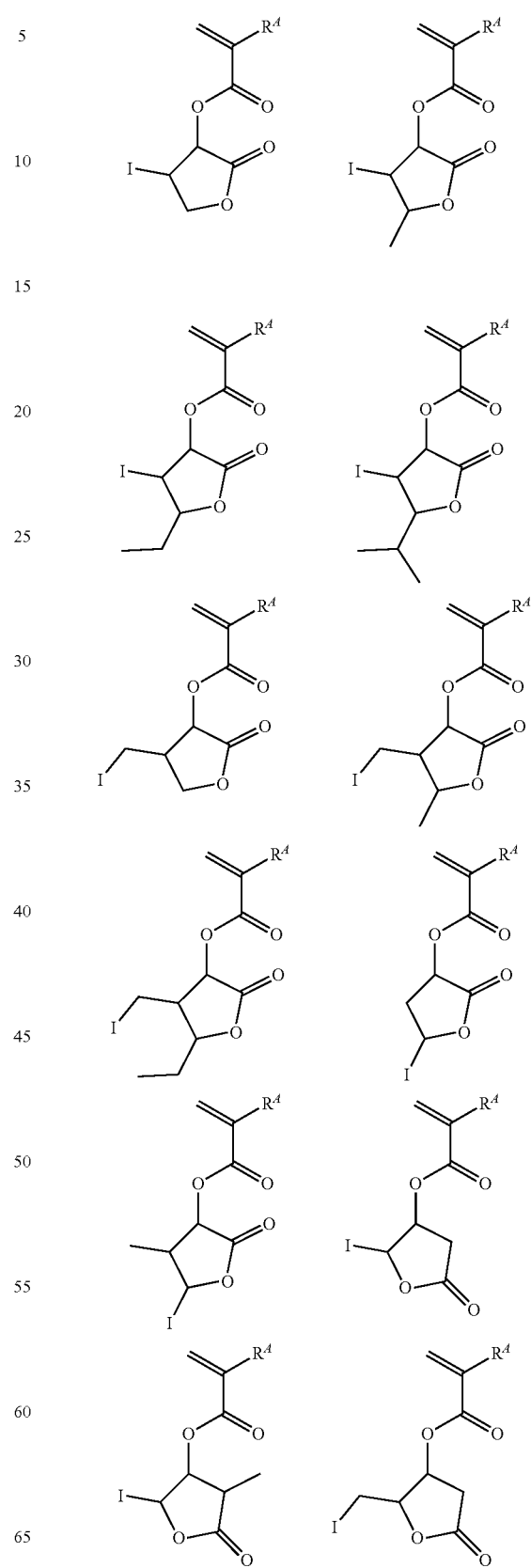

-continued

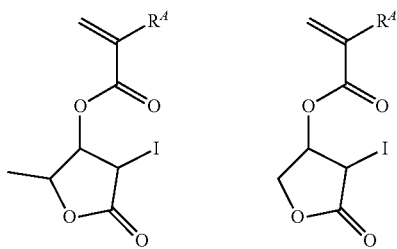

In another preferred embodiment, the base polymer may further comprise repeat units (d) derived from indene, benzofuran, benzothiophene, acenaphthylene, chromone, coumarin, and norbornadiene, or derivatives thereof. Suitable monomers are exemplified below.

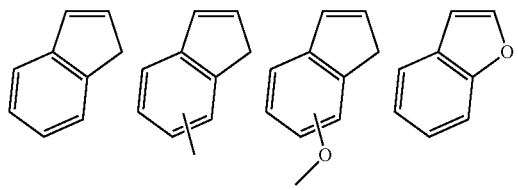

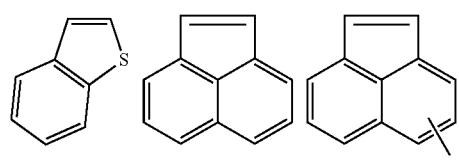

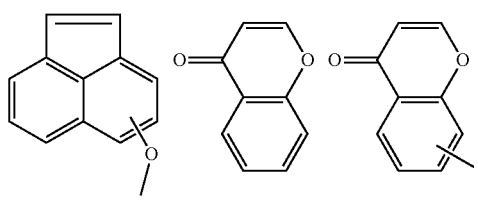

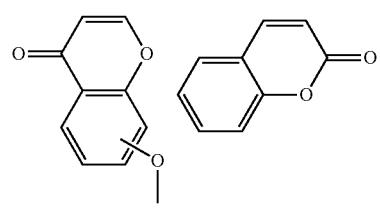

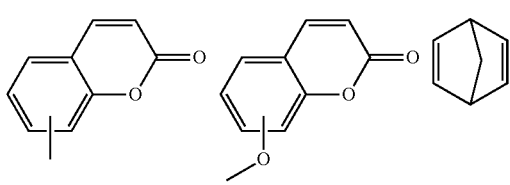

-continued

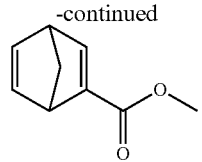

Furthermore, repeat units (e) may be incorporated in the base polymer, which are derived from styrene, vinylnaphthalene, vinylanthracene, vinylpyrene, methyleneindeno, vinylpyridine, or vinylcarbazole.

In a further embodiment, repeat units (f) derived from an onium salt having a polymerizable unsaturated bond may be incorporated in the base polymer. Specifically, the base polymer may comprise repeat units of at least one type selected from repeat units having formulae (f1), (f2) and (f). These units are simply referred to as repeat units (f1), (f2) and (f3), which may be used alone or in combination of two or more types.

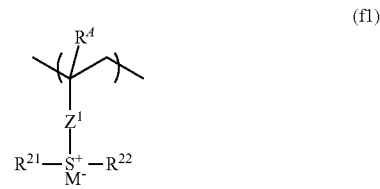
(f1)

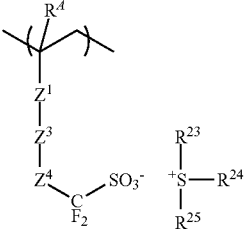
(f2)

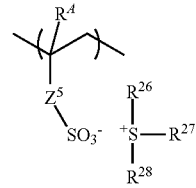
(f3)

In formulae (f1) to (f3), $R^A$ is each independently hydrogen or methyl. $Z^1$ is a single bond, a $C_1$-$C_6$ aliphatic hydrocarbylene group, phenylene group, naphthylene group, or $C_7$-$C_{18}$ group obtained by combining the foregoing, or —O—$Z^{11}$—, —C(=O)—O—$Z^{11}$— or —C(=O)—NH—$Z^{11}$—, wherein $Z^{11}$ is a $C_1$-$C_6$ aliphatic hydrocarbylene group, phenylene group, naphthylene group, or $C_7$-$C_{18}$ group obtained by combining the foregoing, which may contain a carbonyl moiety, ester bond, ether bond or hydroxy moiety. $Z^2$ is a single bond or ester bond. $Z^3$ is a single bond, —$Z^{31}$—C(=O)—O—, —$Z^{31}$—O— or —$Z^{31}$—O—C(=O)—, wherein $Z^{31}$ is a $C_1$-$C_{12}$ hydrocarbylene group, phenylene group, or $C_7$-$C_{18}$ group obtained by combining the foregoing, which may contain a carbonyl moiety, ester bond, ether bond, iodine or bromine. $Z^4$ is a methylene, 2,2,2-trifluoro-1,1-ethanediyl or carbonyl group. $Z^5$ is a single bond, methylene, ethylene, phenylene, fluorinated phenylene, trifluoromethyl-substituted phenylene group, —O—$Z^{51}$—, —C(=O)—O—$Z^{51}$—, or —C(=O)—NH—

$Z^{51}$—, wherein $Z^{51}$ is a $C_1$-$C_6$ aliphatic hydrocarbylene group, phenylene group, fluorinated phenylene group, or trifluoromethyl-substituted phenylene group, which may contain a carbonyl moiety, ester bond, ether bond or hydroxy moiety.

In formulae (f1) to (f3), $R^{21}$ to $R^{28}$ are each independently halogen or a $C_1$-$C_{20}$ hydrocarbyl group which may contain a heteroatom. The hydrocarbyl group may be saturated or unsaturated and straight, branched or cyclic. Examples thereof are as will be exemplified later for $R^{101}$ to $R^{105}$ in formulae (1-1) and (1-2). In these groups, some or all of the hydrogen atoms may be substituted by a moiety containing a heteroatom such as oxygen, sulfur, nitrogen or halogen and some carbon may be replaced by a moiety containing a heteroatom such as oxygen, sulfur or nitrogen, so that the group may contain a hydroxy moiety, fluorine, chlorine, bromine, iodine, cyano moiety, nitro moiety, carbonyl moiety, ether bond, ester bond, sulfonate bond, carbonate bond, lactone ring, sultone ring, carboxylic anhydride, or haloalkyl moiety. A pair of $R^{23}$ and $R^{24}$, or $R^{26}$ and $R^{27}$ may bond together to form a ring with the sulfur atom to which they are attached. Examples of the ring are as will be exemplified later for the ring that $R^{101}$ and $R^{102}$ in formula (1-1), taken together, form with the sulfur atom to which they are attached.

In formula (f1), M⁻ is a non-nucleophilic counter ion. Examples of the non-nucleophilic counter ion include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imide ions such as bis(trifluoromethylsulfonyl)imide, bis(perfluoroethylsulfonyl)imide and bis(perfluorobutylsulfonyl)imide: methide ions such as tris(trifluoromethylsulfonyl)methide and tris(perfluoroethylsulfonyl)methide.

Also included are sulfonate ions having fluorine substituted at α-position as represented by the formula (f1-1) and sulfonate ions having fluorine substituted at α-position and trifluoromethyl at β-position as represented by the formula (f1-2).

  (f1-1)

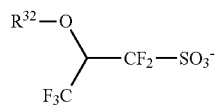  (f1-2)

In formula (f1-1), $R^{31}$ is hydrogen, or a $C_1$-$C_{20}$ hydrocarbyl group which may contain an ether bond, ester bond, carbonyl moiety, lactone ring, or fluorine atom. The hydrocarbyl group may be saturated or unsaturated and straight, branched or cyclic. Examples of the hydrocarbyl group are as will be exemplified later for $R^{111}$ in formula (1A').

In formula (f1-2), $R^{32}$ is hydrogen, or a $C_1$-$C_{30}$ hydrocarbyl group or $C_2$-$C_{30}$ hydrocarbylcarbonyl group, which may contain an ether bond, ester bond, carbonyl moiety or lactone ring. The hydrocarbyl group and hydrocarbyl moiety in the hydrocarbylcarbonyl group may be saturated or unsaturated and straight, branched or cyclic. Examples of the hydrocarbyl group are as will be exemplified later for $R^{111}$ in formula (1A').

Examples of the cation in the monomer from which repeat unit (f1) is derived are shown below, but not limited thereto. $R^A$ is as defined above.

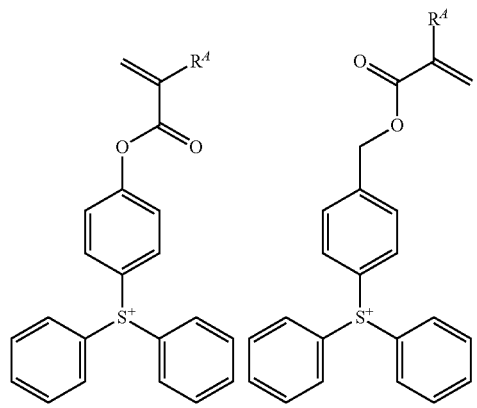

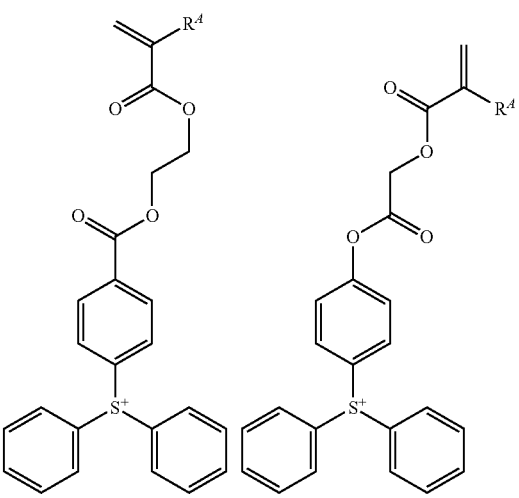

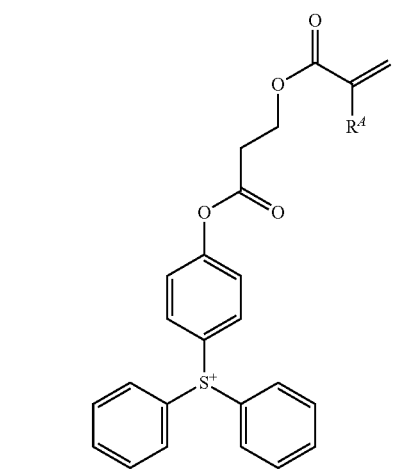

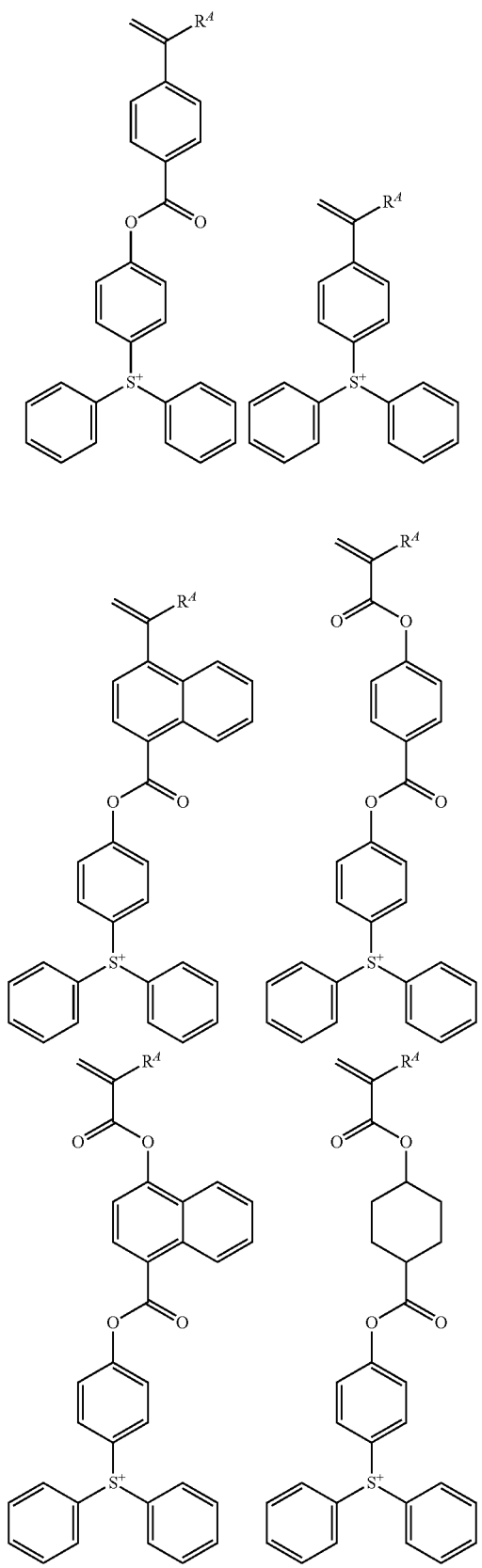
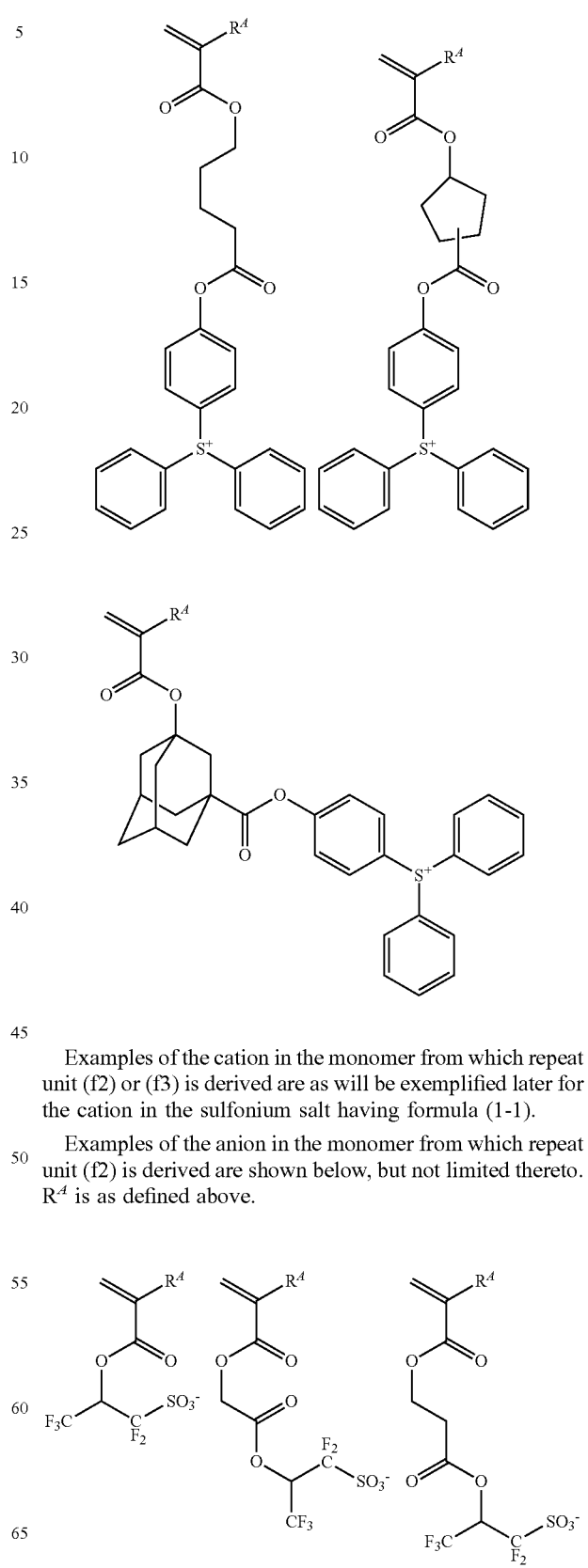
Examples of the cation in the monomer from which repeat unit (f2) or (f3) is derived are as will be exemplified later for the cation in the sulfonium salt having formula (1-1).
Examples of the anion in the monomer from which repeat unit (f2) is derived are shown below, but not limited thereto. $R^A$ is as defined above.

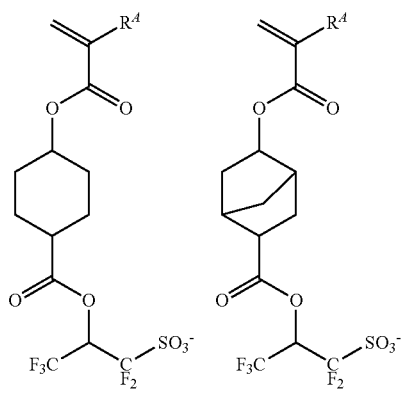
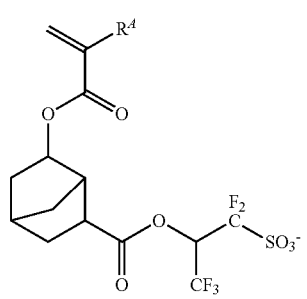
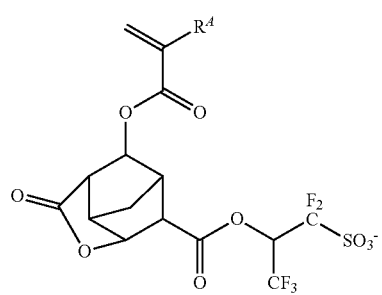
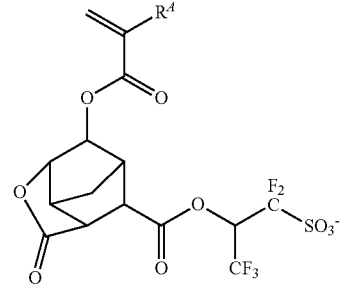
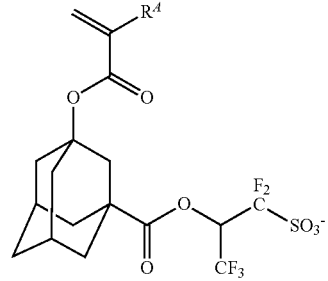
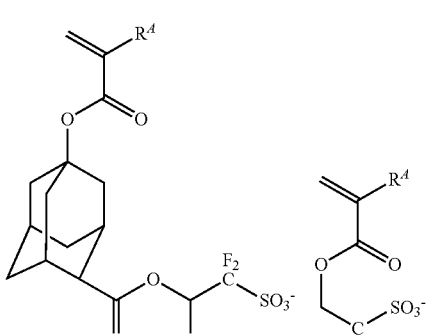
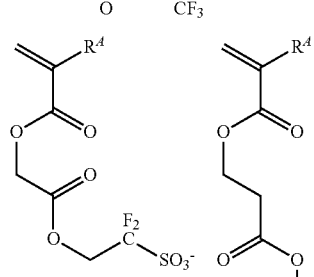
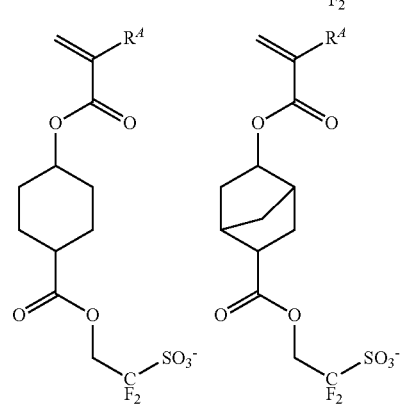
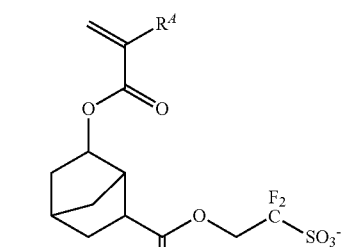
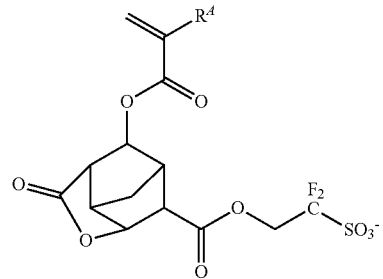

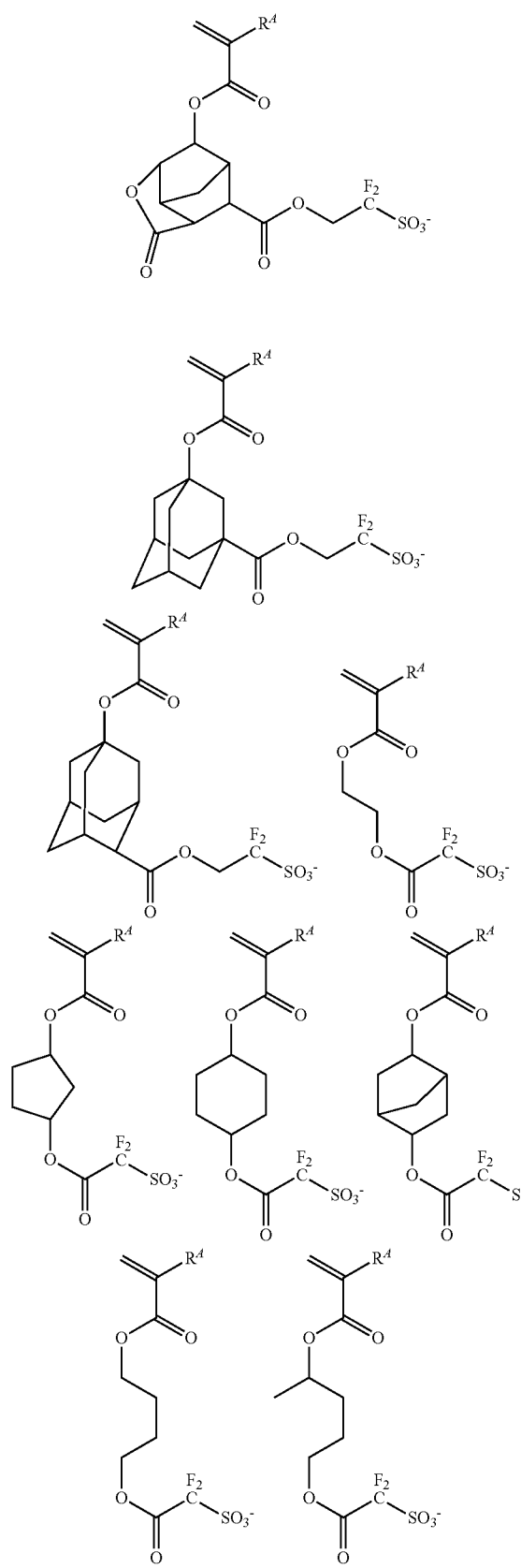
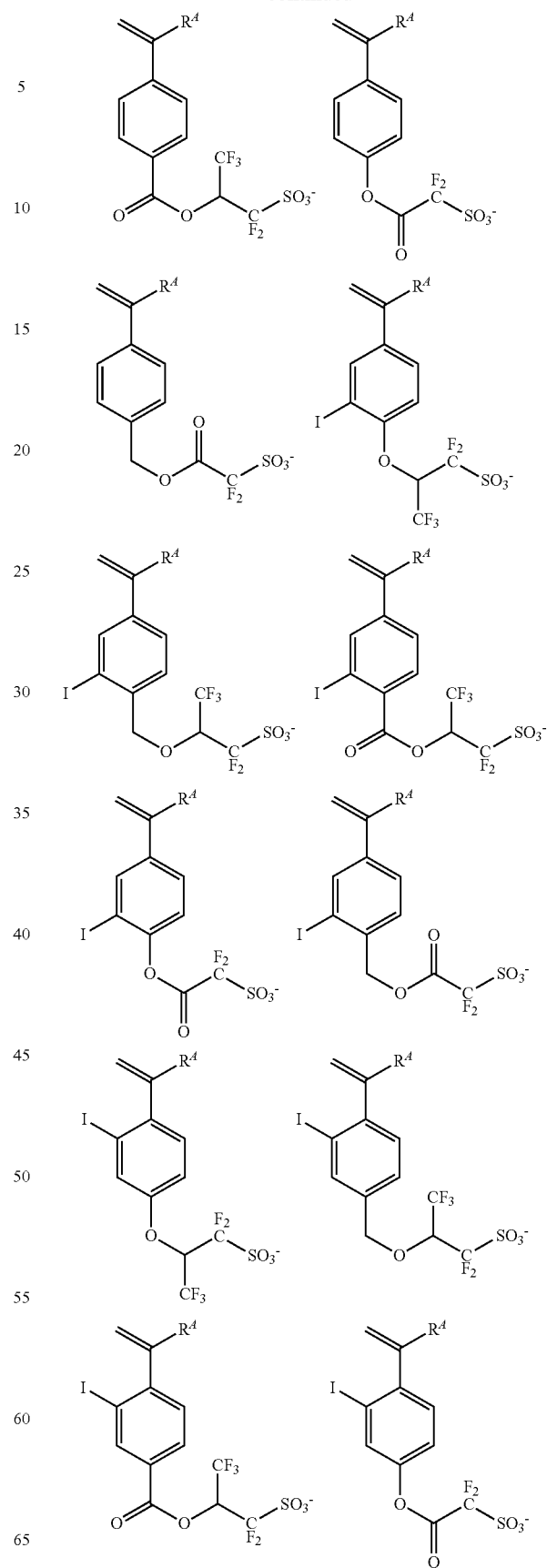

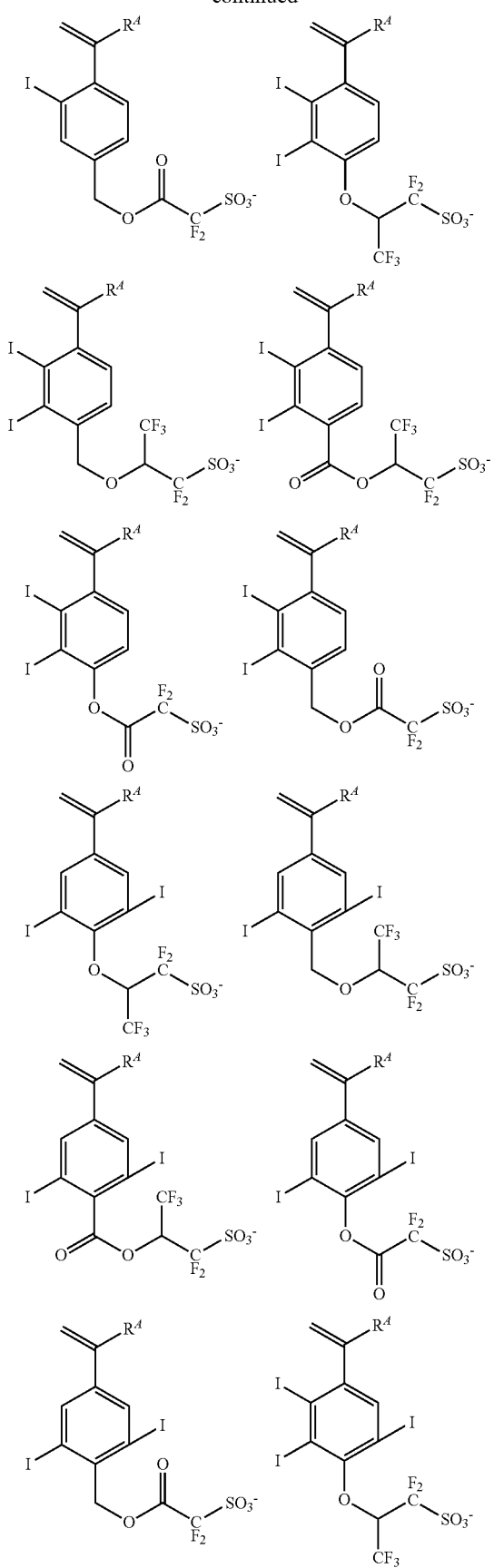
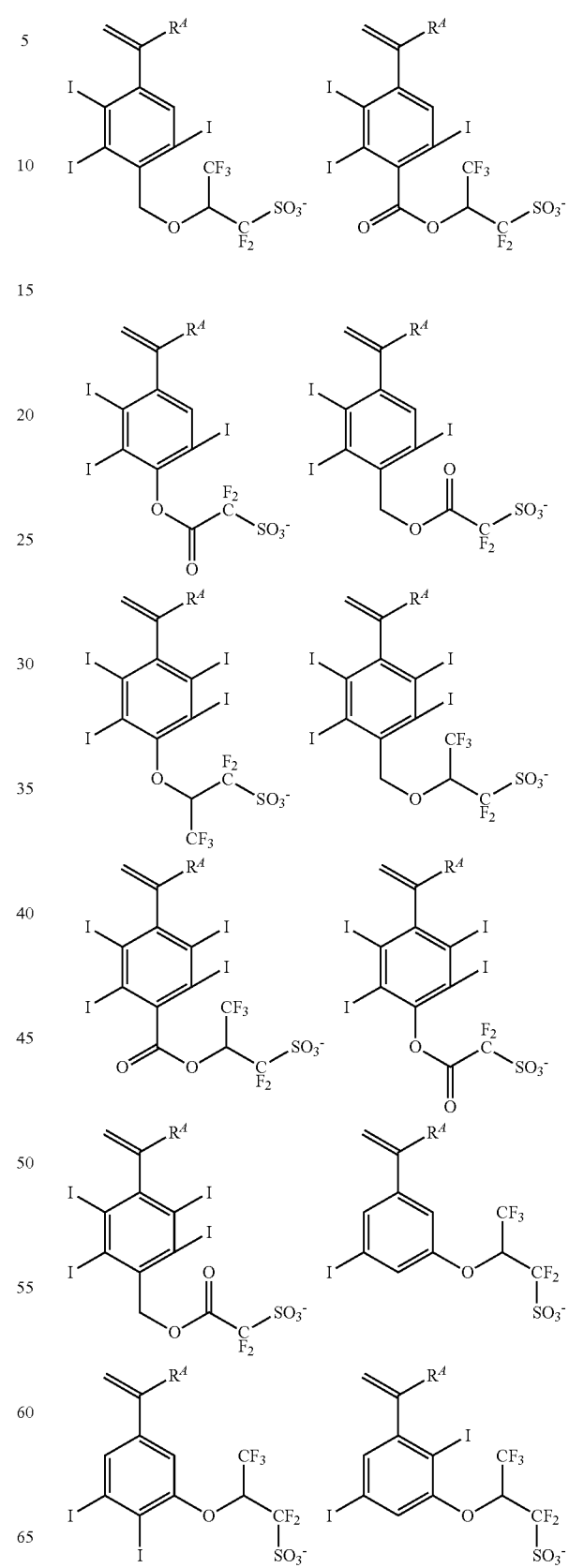

213
-continued
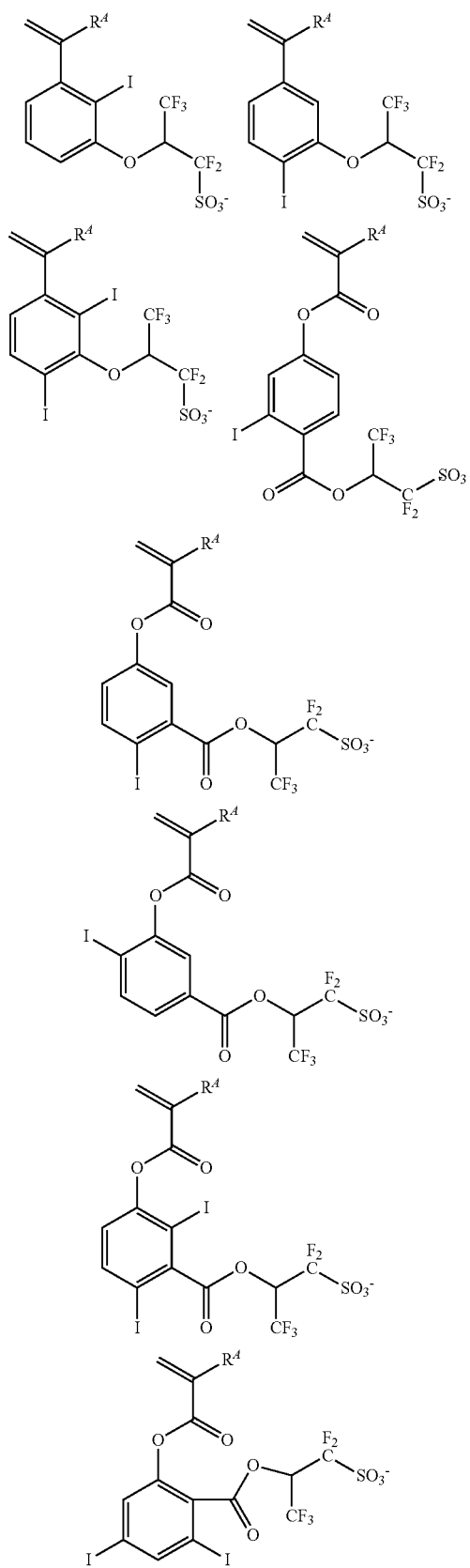
214
-continued
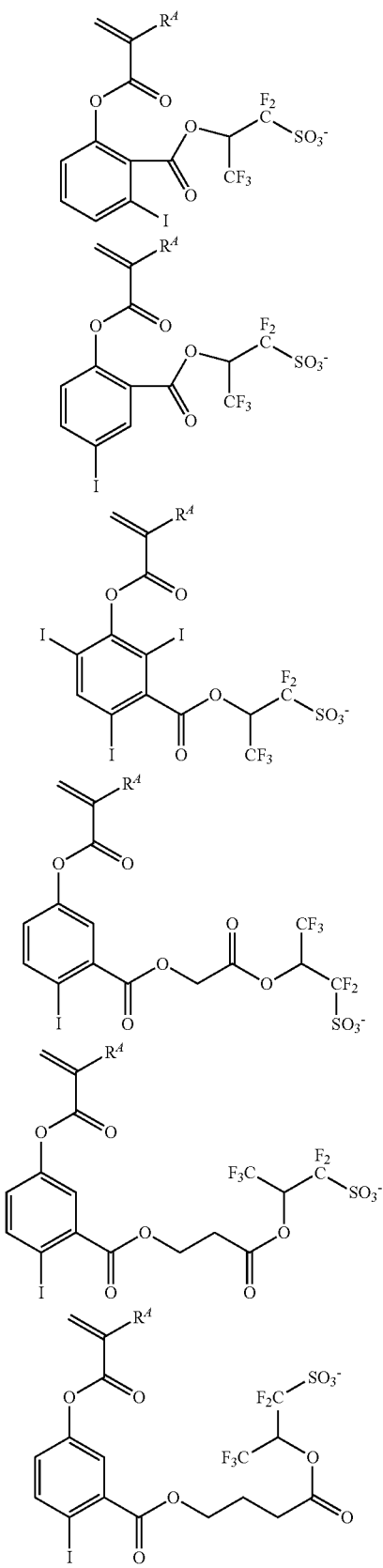

215
-continued
216
-continued
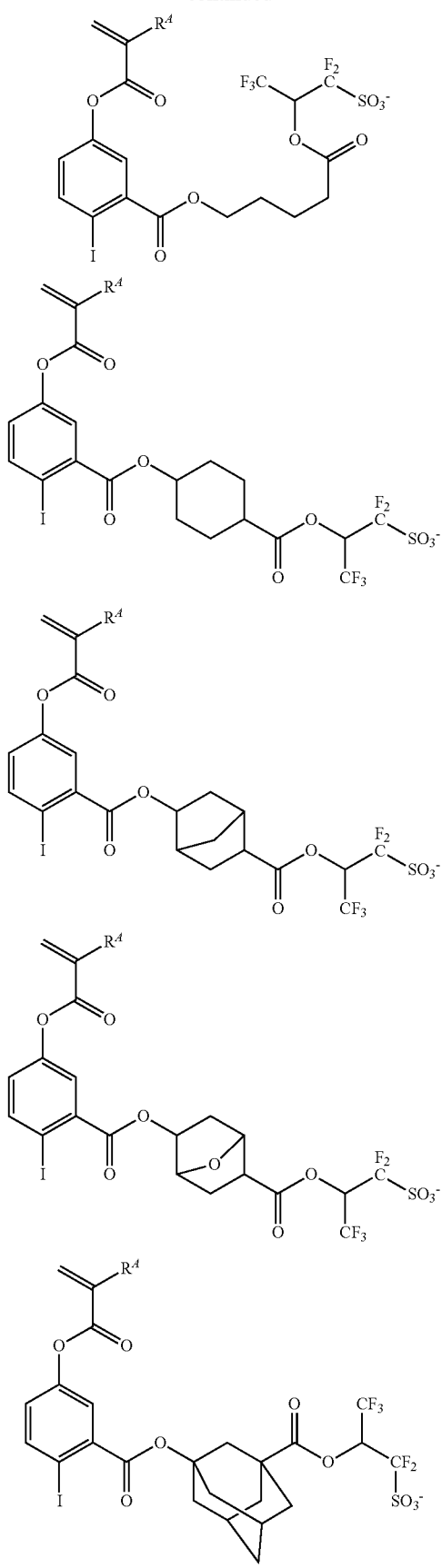
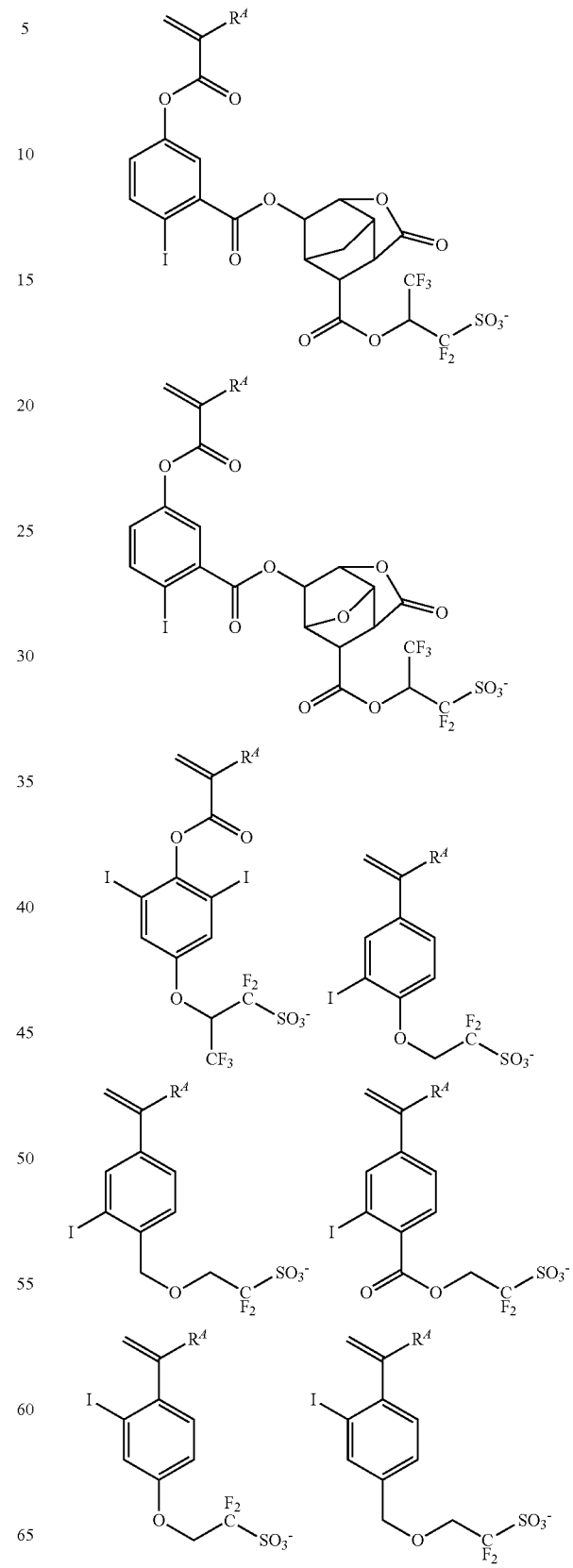

217
-continued
218
-continued
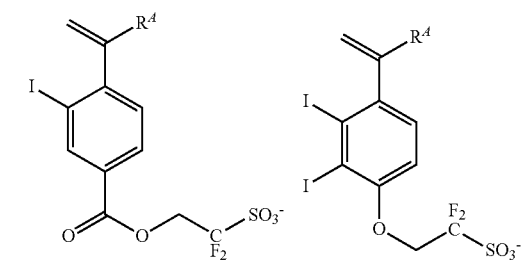
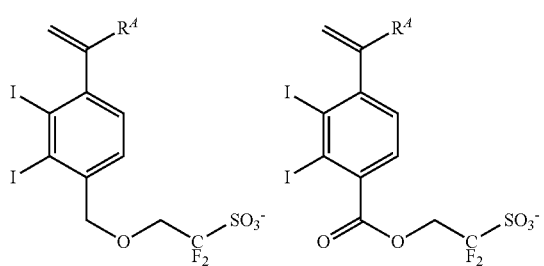
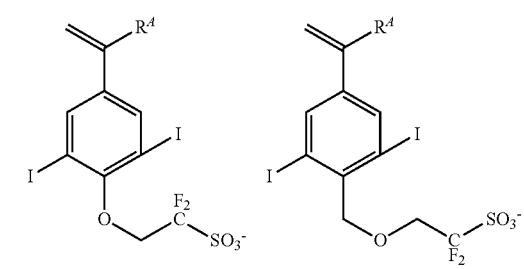
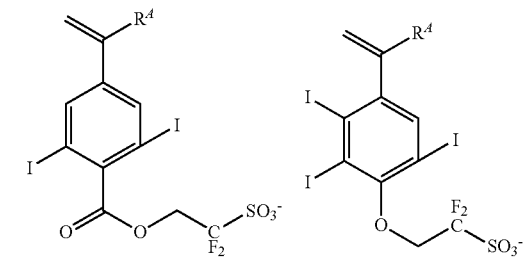
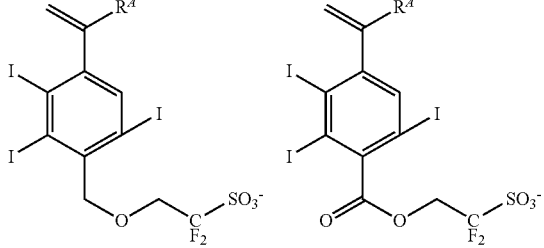
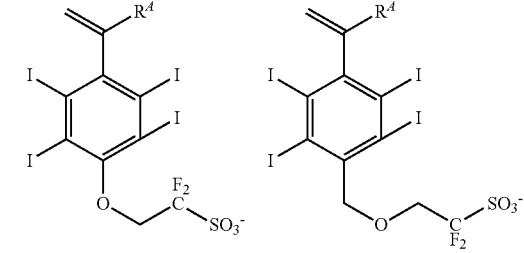
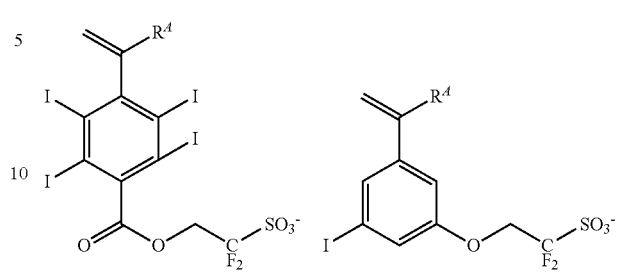
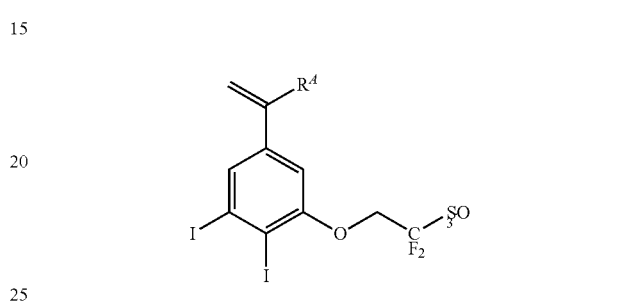
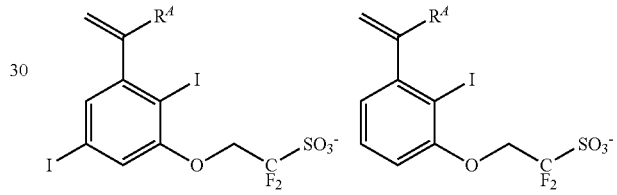
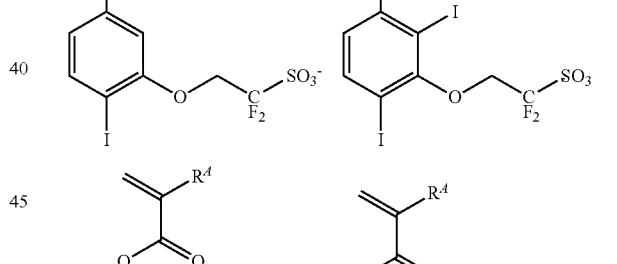
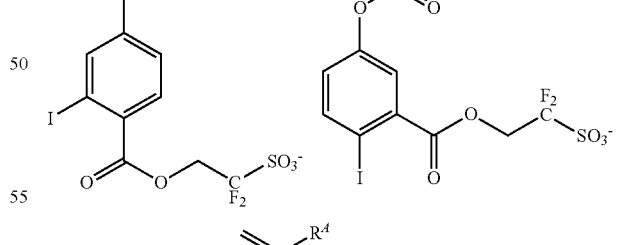
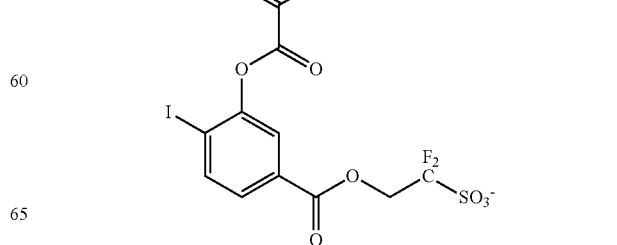

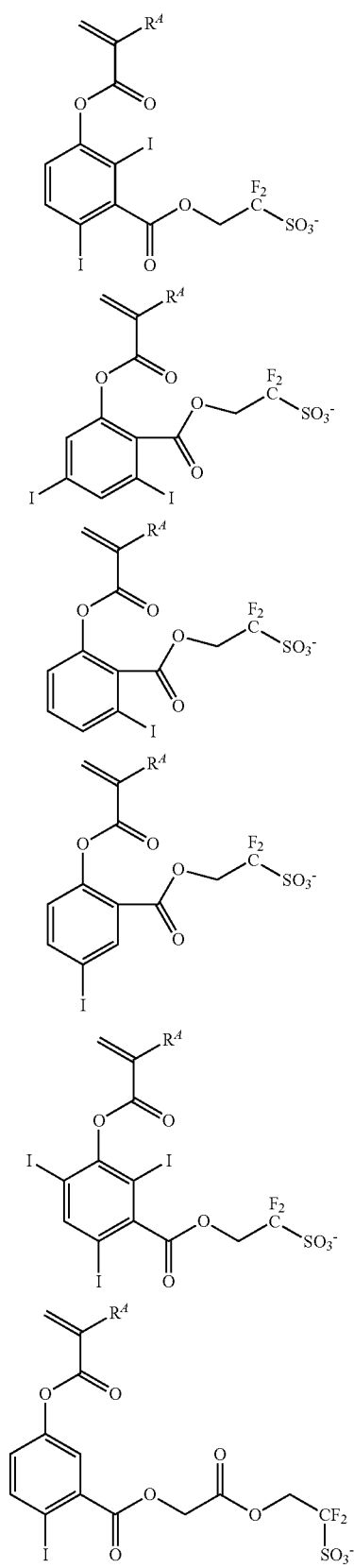
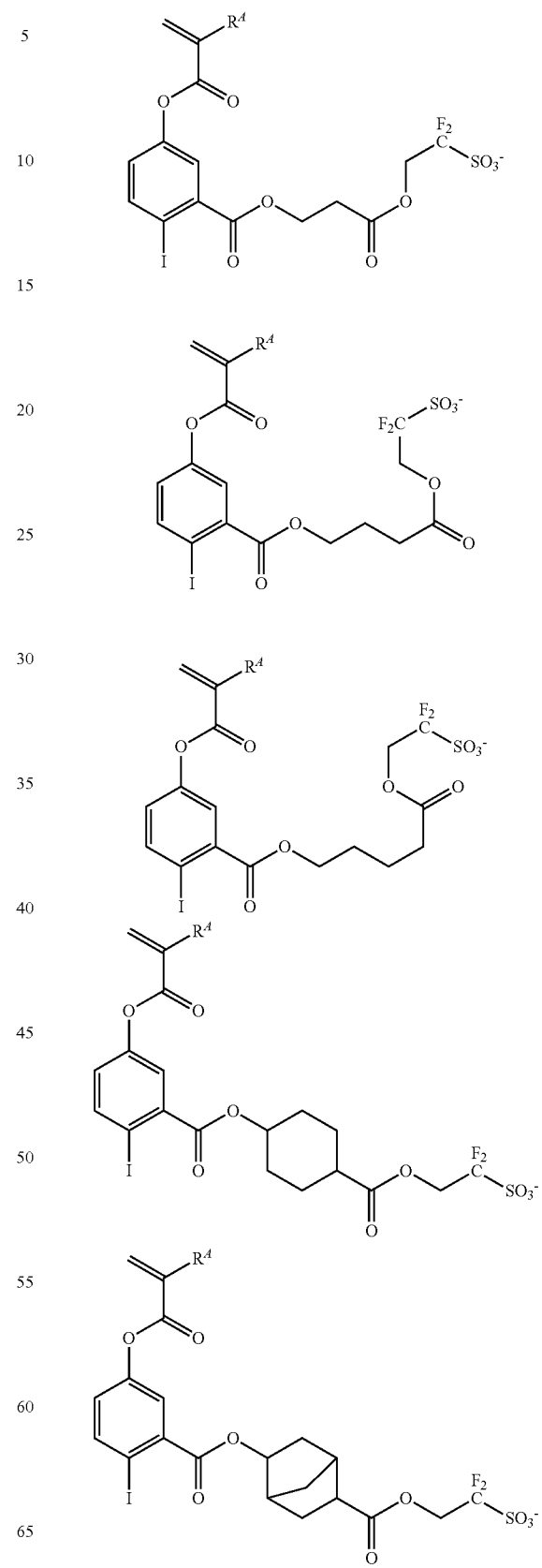

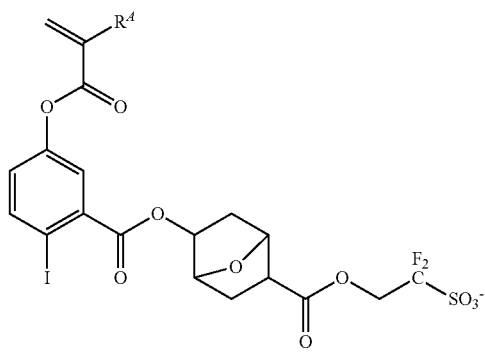
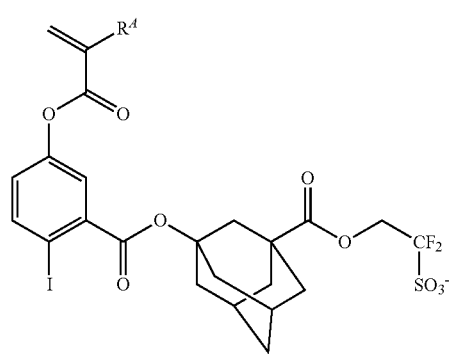
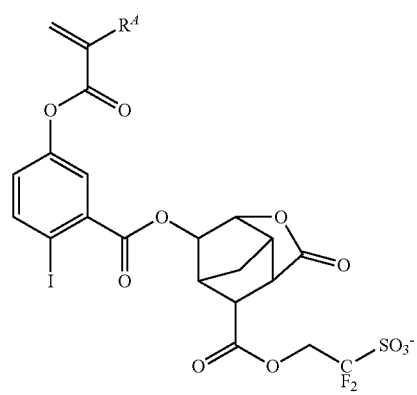
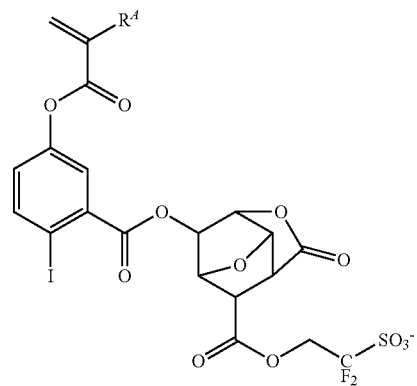
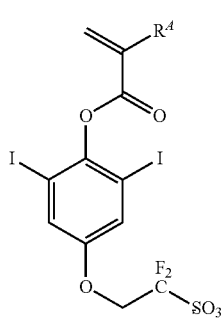
Examples of the anion in the monomer from which repeat unit (f3) is derived are shown below, but not limited thereto. $R^A$ is as defined above.
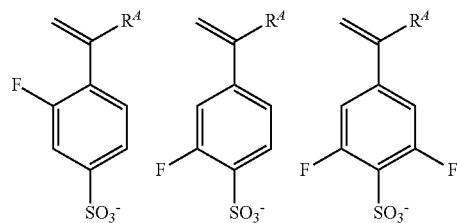
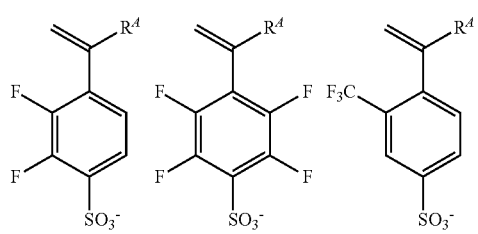
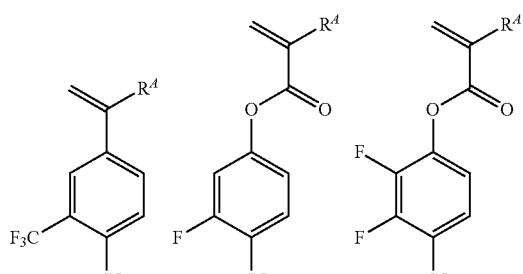
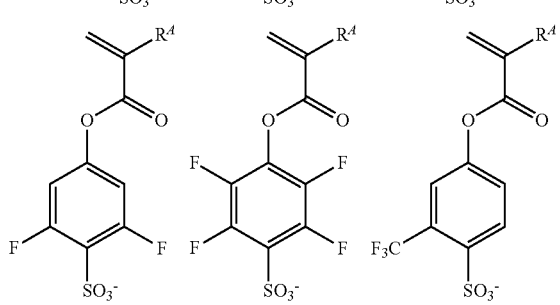

-continued

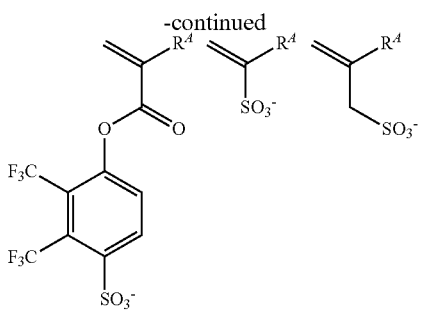

The attachment of an acid generator to the polymer main chain is effective in restraining acid diffusion, thereby preventing a reduction of resolution due to blur by acid diffusion. Also, LWR or CDU is improved since the acid generator is uniformly distributed. Where a base polymer containing repeat units (f), i.e., polymer-bound acid generator is used, the blending of an acid generator of addition type (to be described later) may be omitted.

The base polymer for formulating the positive resist composition comprises repeat units (a1) or (a2) having an acid labile group as essential component and additional repeat units (b), (c), (d), (e), and (f) as optional components. A fraction of units (a1), (a2), (b), (c), (d), (e), and (f) is; preferably $0 \le a1 < 1.0$, $0 \le a2 < 1.0$, $0 < a1+a2 < 1.0$, $0 \le b \le 0.9$, $0 \le c \le 0.9$, $0 \le d \le 0.8$, $0 \le e \le 0.8$, and $0 \le f \le 0.5$; more preferably $0 \le a1 \le 0.9$, $0 \le a2 \le 0.9$, $0.1 \le a1+a2 \le 0.9$, $0 \le b \le 0.8$, $0 \le c \le 0.8$, $0 \le d \le 0.7$, $0 \le e \le 0.7$, and $0 \le f \le 0.4$; and even more preferably $0 \le a1 \le 0.8$, $0 \le a2 \le 0.8$, $0.1 \le a1+a2 \le 0.8$, $0 \le b \le 0.75$, $0 \le c \le 0.75$, $0 \le d \le 0.6$, $0 \le e \le 0.6$, and $0 \le f \le 0.3$. Notably, $f=f1+f2+f3$, meaning that unit (f) is at least one of units (f1) to (f3), and $a1+a2+b+c+d+e+f=1.0$.

For the base polymer for formulating the negative resist composition, an acid labile group is not necessarily essential. The base polymer comprises repeat units (b), and optionally repeat units (e), (d), (e), and/or (f). A fraction of these units is; preferably $0 < b \le 1.0$, $0 \le c \le 0.9$, $0 \le d \le 0.8$, $0 \le e \le 0.8$, and $0 \le f \le 0.5$; more preferably $0.2 \le b \le 1.0$, $0 \le c \le 0.8$, $0 \le d \le 0.7$, $0 \le e \le 0.7$, and $0 \le f \le 0.4$; and even more preferably $0.3 \le b \le 1.0$, $0 \le c \le 0.75$, $0 \le d \le 0.6$, $0 \le e \le 0.6$, mid $0 \le f \le 0.3$. Notably, $f=f1+f2+f3$, meaning that unit (f) is at least one of units (f1) to (13), and $b+c+d+e+f=1.0$.

The base polymer may be synthesized by any desired methods, for example, by dissolving one or more monomers selected from the monomers corresponding to the foregoing repeat units in an organic solvent, adding a radical polymerization initiator thereto, and heating for polymerization. Examples of the organic solvent which can be used for polymerization include toluene, benzene, tetrahydrofuran (THF), diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably, the reaction temperature is 50 to 80° C. and the reaction time is 2 to 100 hours, more preferably 5 to 20 hours.

Where a monomer having a hydroxy group is copolymerized, the hydroxy group may be replaced by an acetal group susceptible to deprotection with acid, typically ethoxyethoxy, prior to polymerization, and the polymerization be followed by deprotection with weak acid and water. Alternatively, the hydroxy group may be replaced by an acetyl, formyl, pivaloyl or similar group prior to polymerization, and the polymerization be followed by alkaline hydrolysis.

When hydroxystyrene or hydroxyvinylnaphthalene is copolymerized, an alternative method is possible. Specifically, acetoxystyrene or acetoxyvinylnaphthalene is used instead of hydroxystyrene or hydroxyvinynaphthalene, and after polymerization, the acetoxy group is deprotected by alkaline hydrolysis, for thereby converting the polymer product to hydroxystyrene or hydroxyvinylnaphthalene. For alkaline hydrolysis, a base such as aqueous ammonia or triethylamine may be used. Preferably the reaction temperature is −20° C. to 100° C., more preferably 0° C. to 60° C., and the reaction time is 0.2 to 100 hours, more preferably 0.5 to 20 hours.

The base polymer should preferably have a weight average molecular weight (Mw) in the range of 1,000 to 500,000, and more preferably 2,000 to 30,000, as measured by GPC versus polystyrene standards using tetrahydrofuran (THF) solvent. A Mw in the range ensures that the resist film is heat resistant and fully soluble in alkaline developer.

If a base polymer has a wide molecular weight distribution or dispersity (Mw/Mn), which indicates the presence of lower and higher molecular weight polymer fractions, there is a possibility that foreign matter is left on the pattern or the pattern profile is degraded. The influences of Mw and Mw/Mn become stronger as the pattern rule becomes finer. Therefore, the base polymer should preferably have a narrow dispersity (Mw/Mn) of 1.0 to 2.0, especially 1.0 to 1.5, in order to provide a resist composition suitable for micropatterning to a small feature size.

It is understood that a blend of two or more polymers which differ in compositional ratio, Mw or Mw/Mn is acceptable.

Acid Generator

The resist composition may comprise an acid generator capable of generating a strong acid (referred to as acid generator of addition type, hereinafter). As used herein, the term "strong acid" refers to a compound having a sufficient acidity to induce deprotection reaction of an acid labile group on the base polymer in the case of a chemically amplified positive resist composition, or a compound having a sufficient acidity to induce acid-catalyzed polarity switch reaction or crosslinking reaction in the case of a chemically amplified negative resist composition. The inclusion of such an acid generator ensures that the fluorinated cyclic ammonium salt compound functions as a quencher and the inventive resist composition functions as a chemically amplified positive or negative resist composition.

The acid generator is typically a compound (PAG) capable of generating an acid upon exposure to actinic ray or radiation. Although the PAG used herein may be any compound capable of generating an acid upon exposure to high-energy radiation, those compounds capable of generating sulfonic acid, imide acid (imidic acid) or methide acid are preferred. Suitable PAGs include sulfonium salts, iodonium salts, sulfonyldiazomethane, N-sulfonyloxyimide, and oxime-O-sulfonate acid generators. Exemplary PAGs are described in JP-A 2008-111103, paragraphs [0122]-[0142] (U.S. Pat. No. 7,537,880).

As the PAG used herein, sulfonium salts having the formula (1-1) and iodonium salts having the formula (1-2) are also preferred.

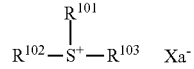

(1-1)

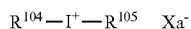
(1-2)

In formulae (1-1) and (1-2). $R^{101}$ to $R^{105}$ are each independently halogen or a $C_1$-$C_{20}$ hydrocarbyl group which may contain a heteroatom.

Suitable halogen atoms include fluorine, chlorine, bromine and iodine.

The $C_1$-$C_{20}$ hydrocarbyl group represented by $R^{101}$ to $R^{105}$ may be saturated or unsaturated and straight, branched or cyclic. Examples thereof include $C_1$-$C_{20}$ alkyl groups such as methyl, ethyl, n-propyl, isopropyl, n-butyl, isobutyl, sec-butyl, tert-butyl, n-pentyl, n-hexyl, n-octyl, n-nonyl, n-decyl, undecyl, dodecyl, tridecyl, tetradecyl, pentadecyl, heptadecyl, octadecyl, nonadecyl and icosyl: $C_3$-$C_{20}$ cyclic saturated hydrocarbyl groups such as cyclopropyl, cyclopentyl, cyclohexyl, cyclopropylmethyl, 4-methylcyclohexyl, cyclohexylmethyl, norbornyl and adamantyl; $C_2$-$C_{20}$ alkenyl groups such as vinyl, propenyl, butenyl and hexenyl; $C_2$-$C_{20}$ alkynyl groups such as ethynyl, propynyl and butynyl; $C_3$-$C_{20}$ cyclic unsaturated aliphatic hydrocarbyl groups such as cyclohexenyl and norbornenyl; $C_6$-$C_{20}$ aryl groups such as phenyl, methylphenyl, ethylphenyl, n-propylphenyl, isopropylphenyl, n-butylphenyl, isobutylphenyl, sec-butylphenyl, tert-butylphenyl, naphthyl, methylnaphthyl, ethylnaphthyl, n-propyhnaphthyl, isopropylnaphthyl, n-butylnaphthyl, isobutylnaphthyl, sec-butyluaphthyl and tert-butylnaphthyl: $C_7$-$C_{20}$ aralkyl groups such as benzyl and phenethyl: and combinations thereof.

Also included are substituted forms of the foregoing groups in which some or all of the hydrogen atoms are substituted by a moiety containing a heteroatom such as oxygen, sulfur, nitrogen or halogen, or some carbon is replaced by a moiety containing a heteroatom such as oxygen, sulfur or nitrogen, so that the group may contain a hydroxy moiety, fluorine, chlorine, bromine, iodine, cyano moiety, nitro moiety, carbonyl moiety, ether bond, ester bond, sulfonic acid ester bond, carbonate bond, lactone ring, sultone ring, carboxylic anhydride or haloalkyl moiety.

A pair of $R^{101}$ and $R^{102}$ may bond together to form a ring with the sulfur atom to which they are attached. Preferred are those rings of the structure shown below.

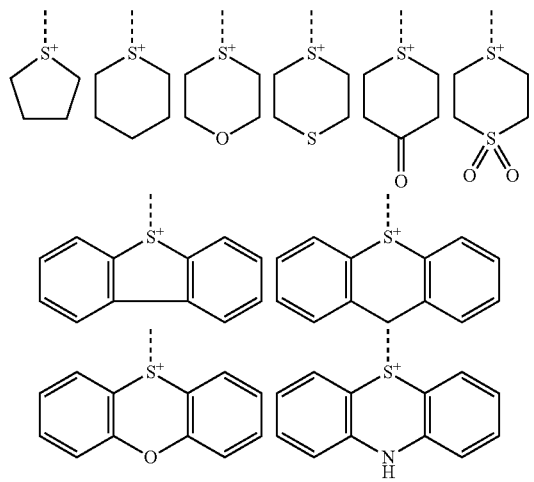

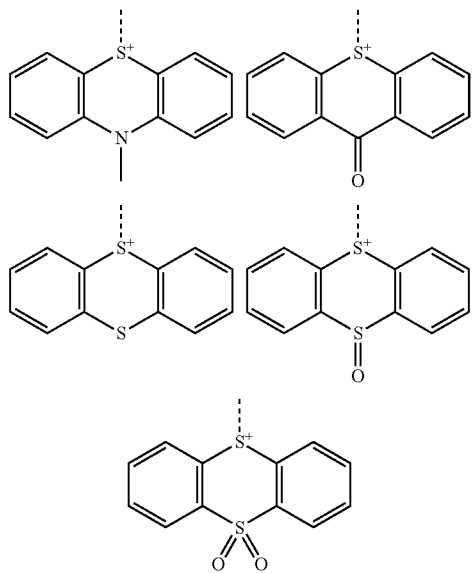

Herein, the broken line denotes a point of attachment to $R^{103}$

Examples of the cation in the sulfonium salt having formula (1-1) are shown below, but not limited thereto.

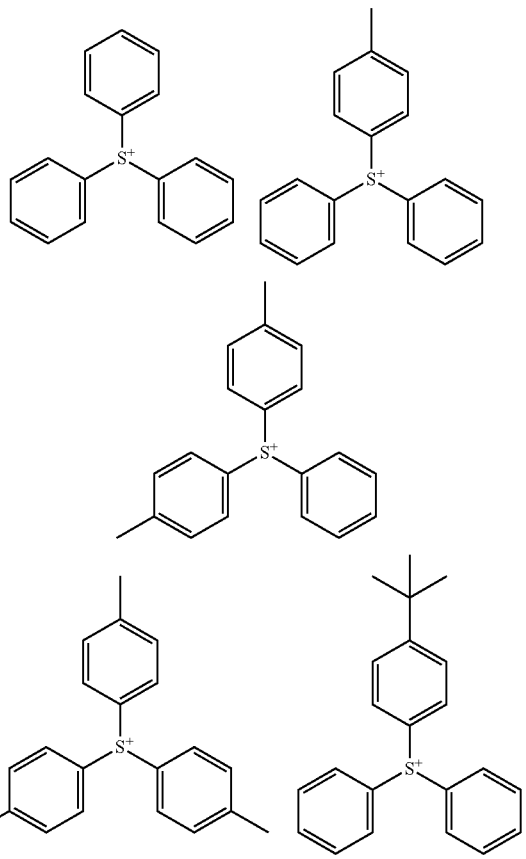

227
-continued
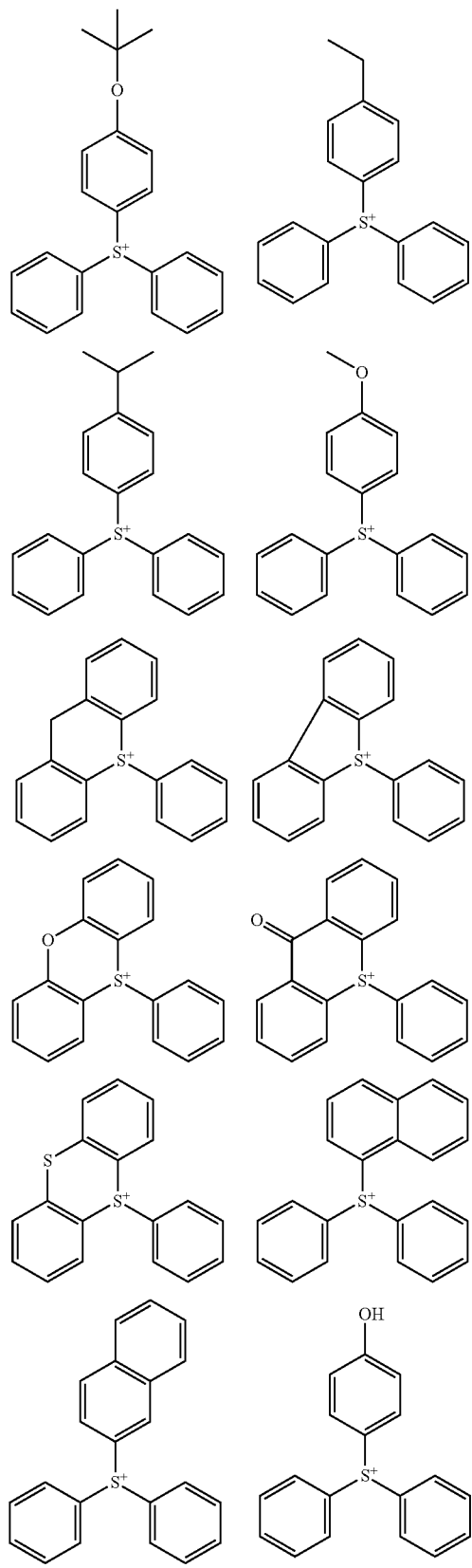
228
-continued
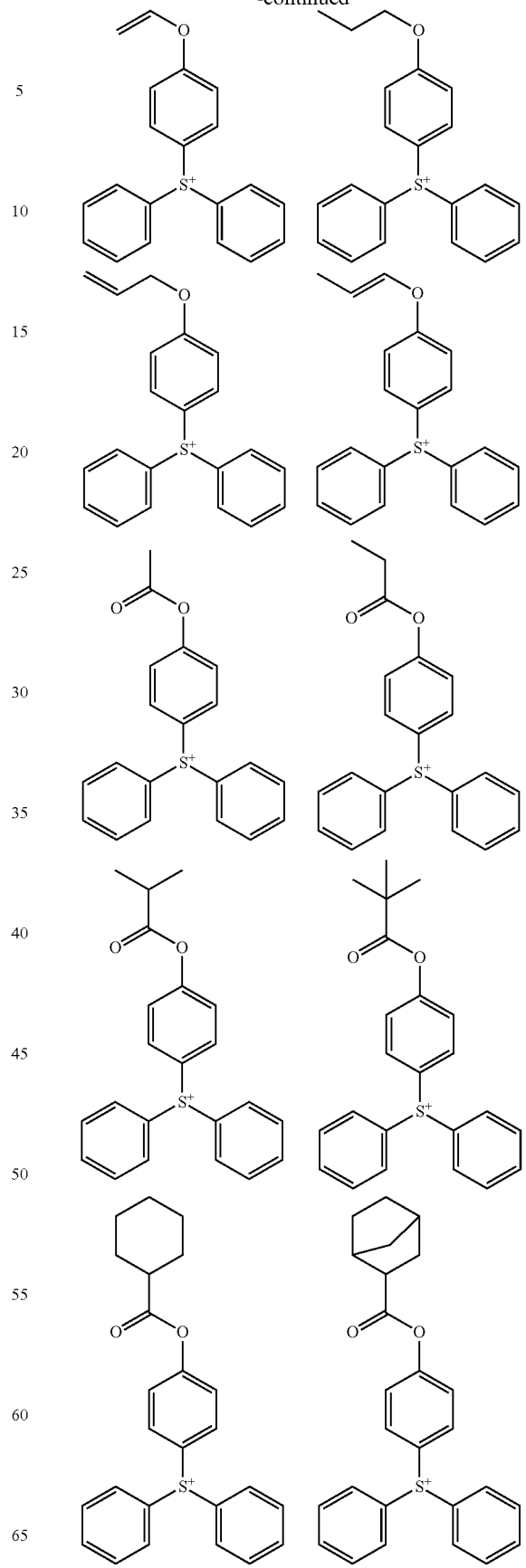

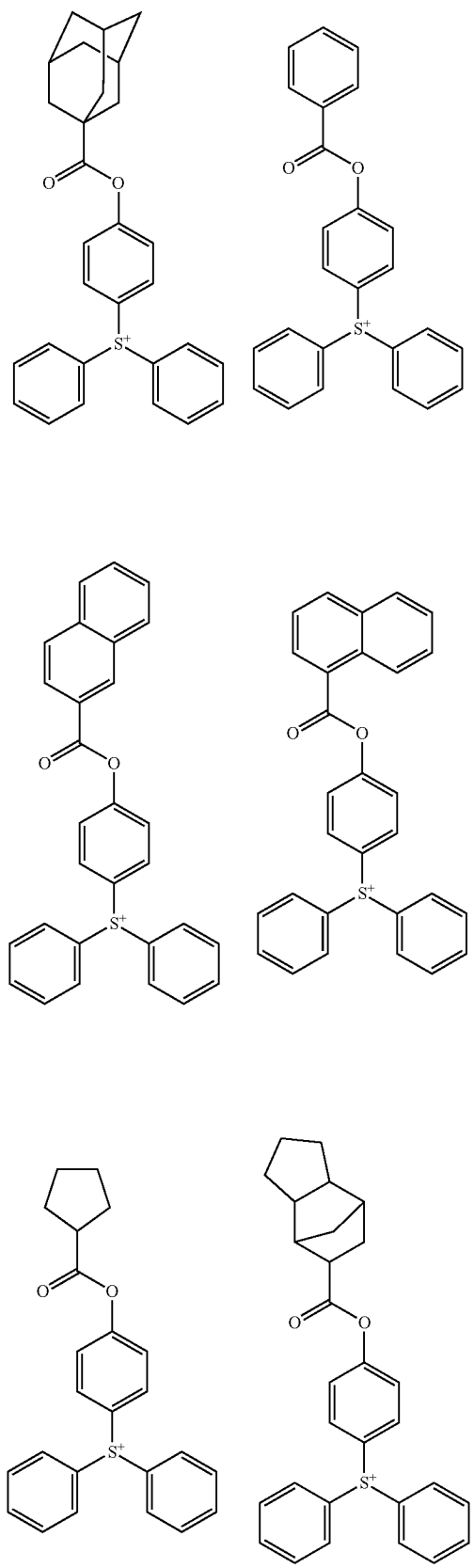

231
-continued
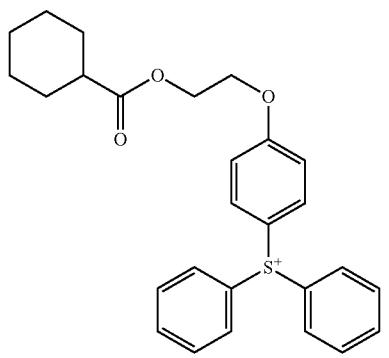
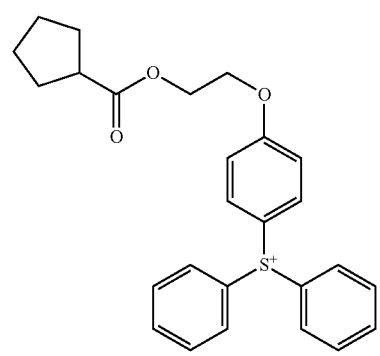
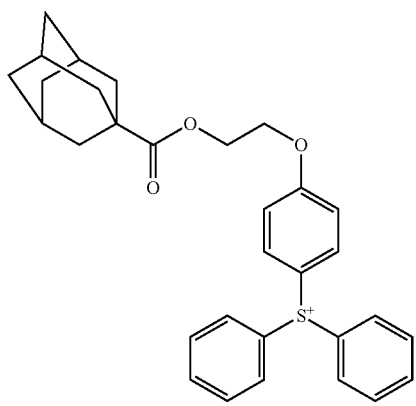
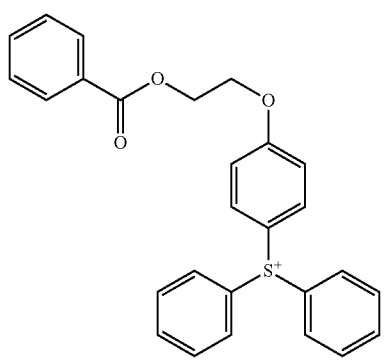
232
-continued
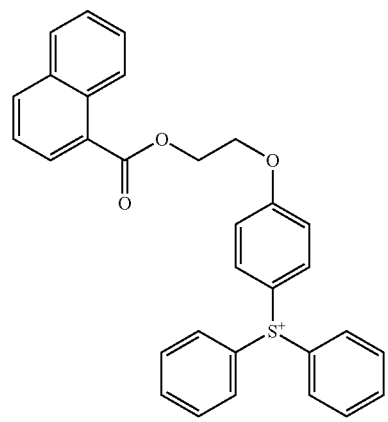
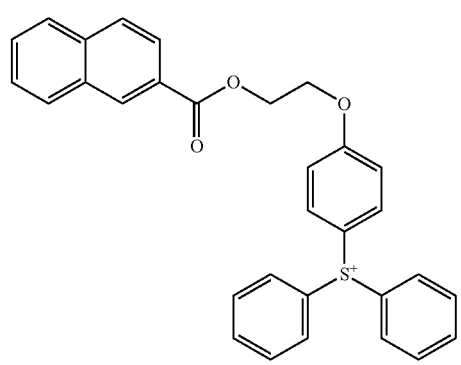
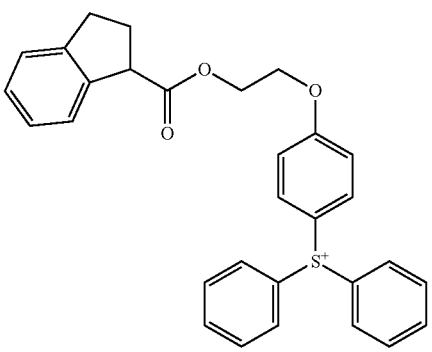
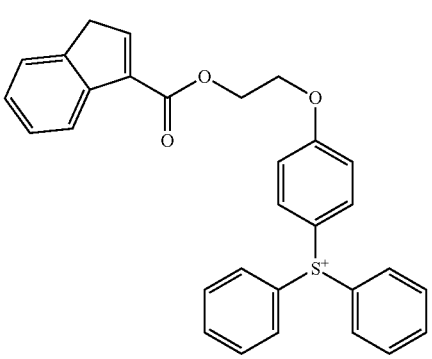

233
-continued
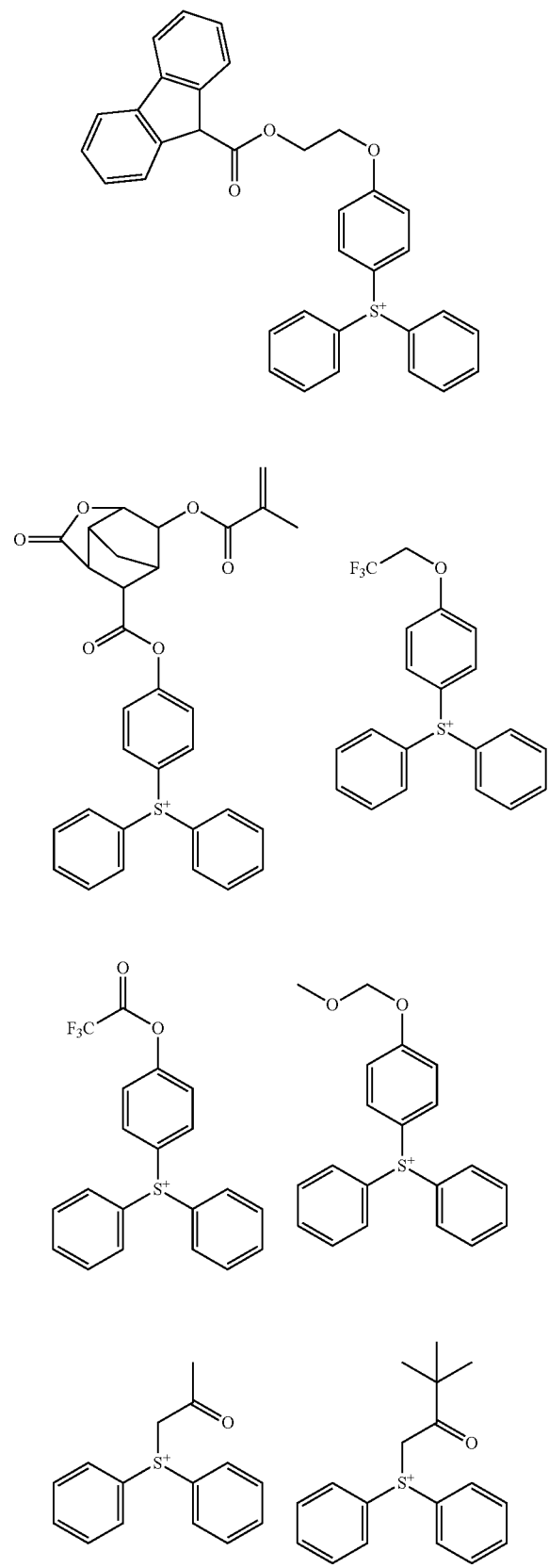
234
-continued
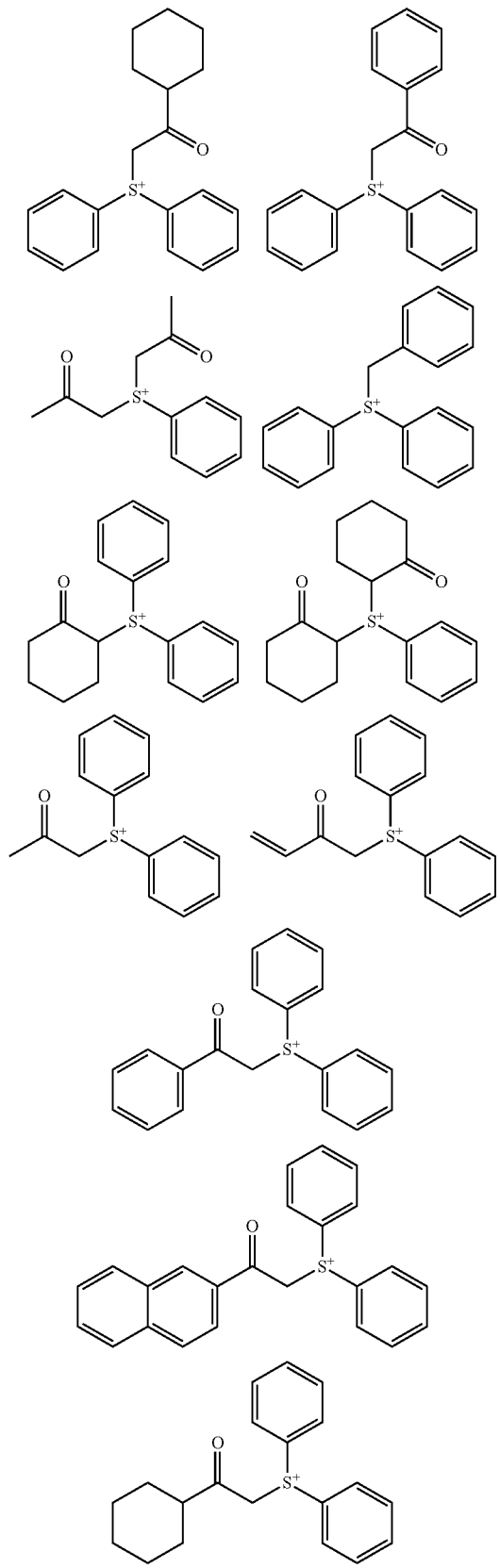

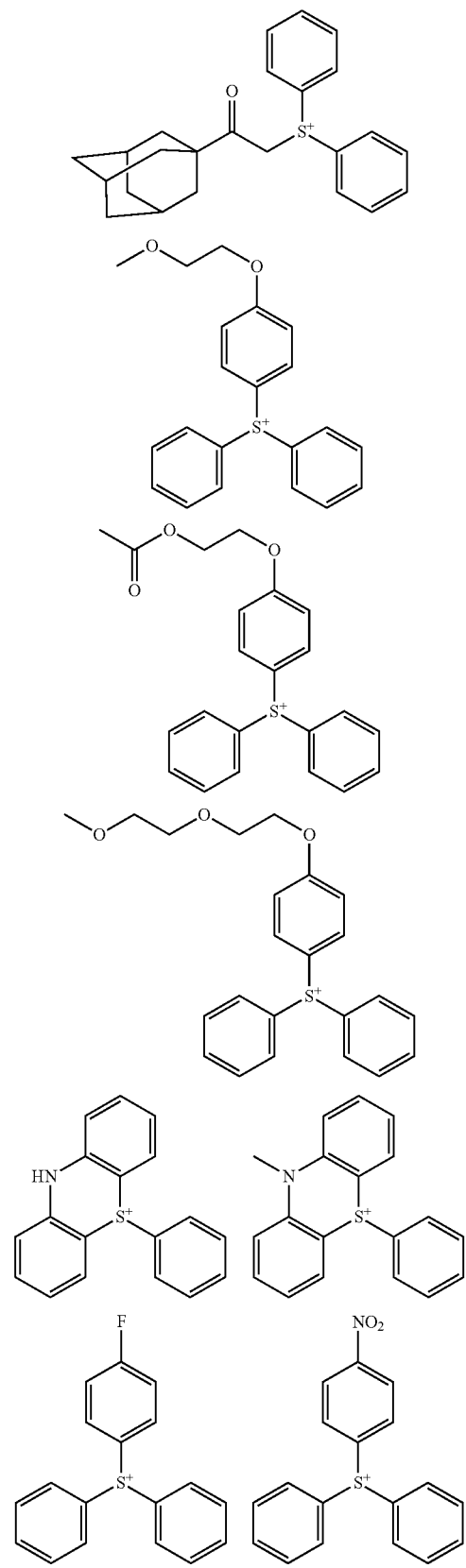
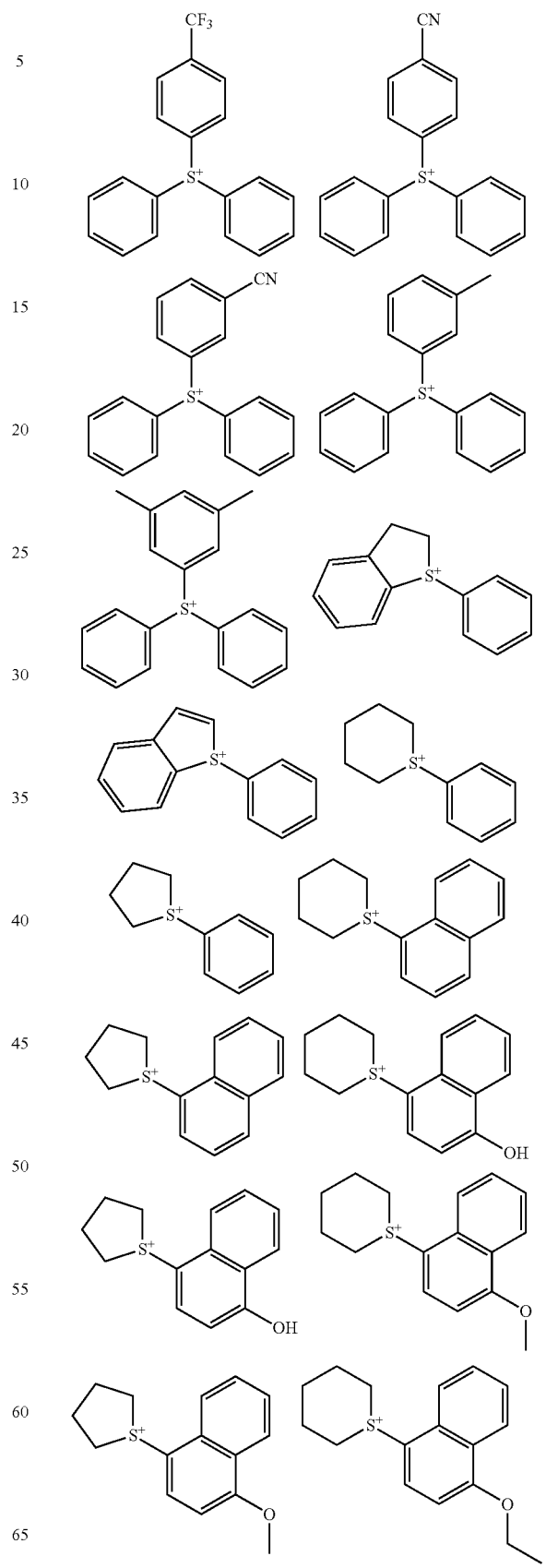

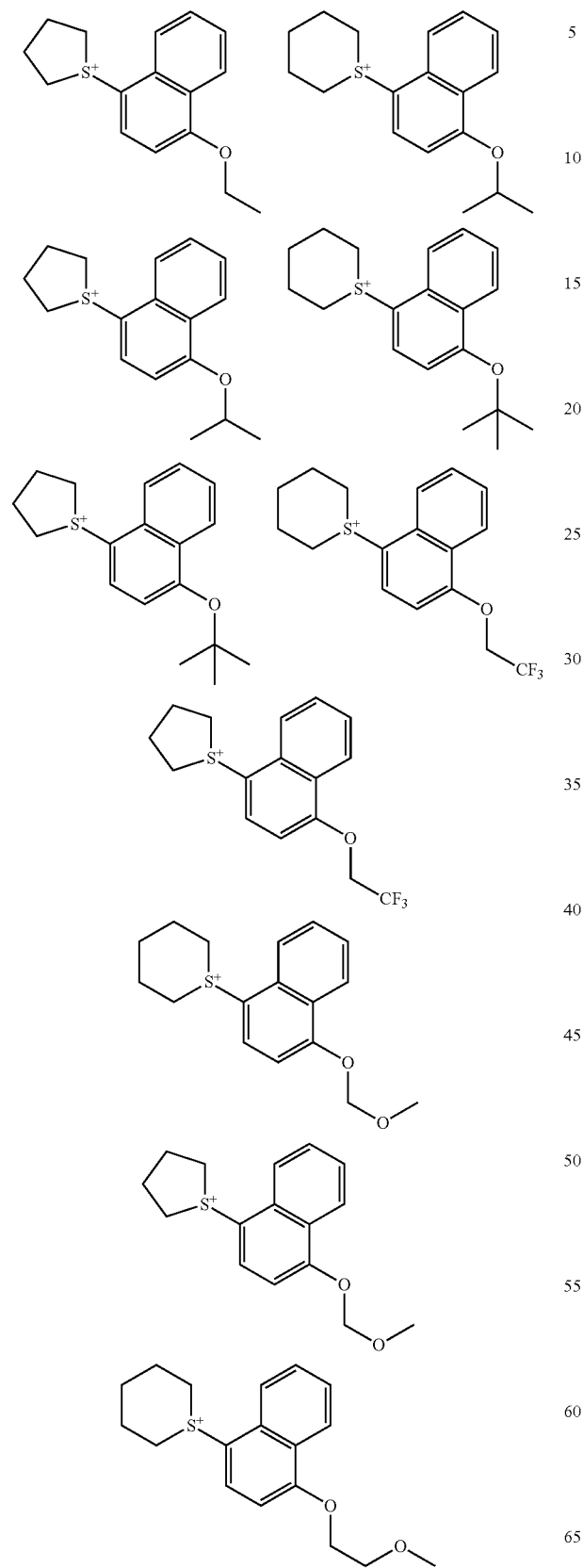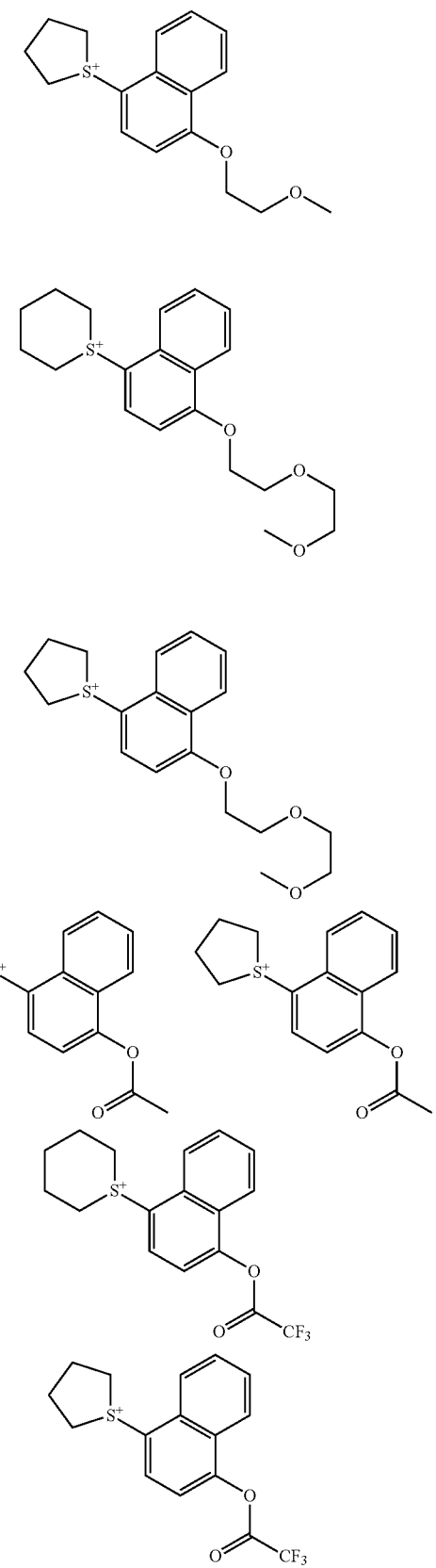

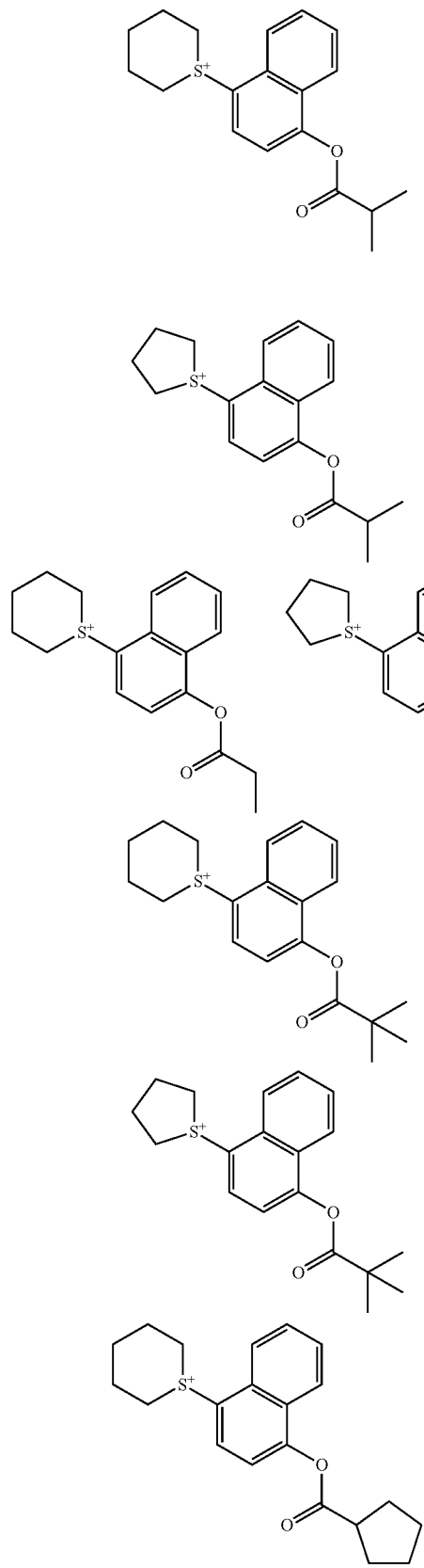
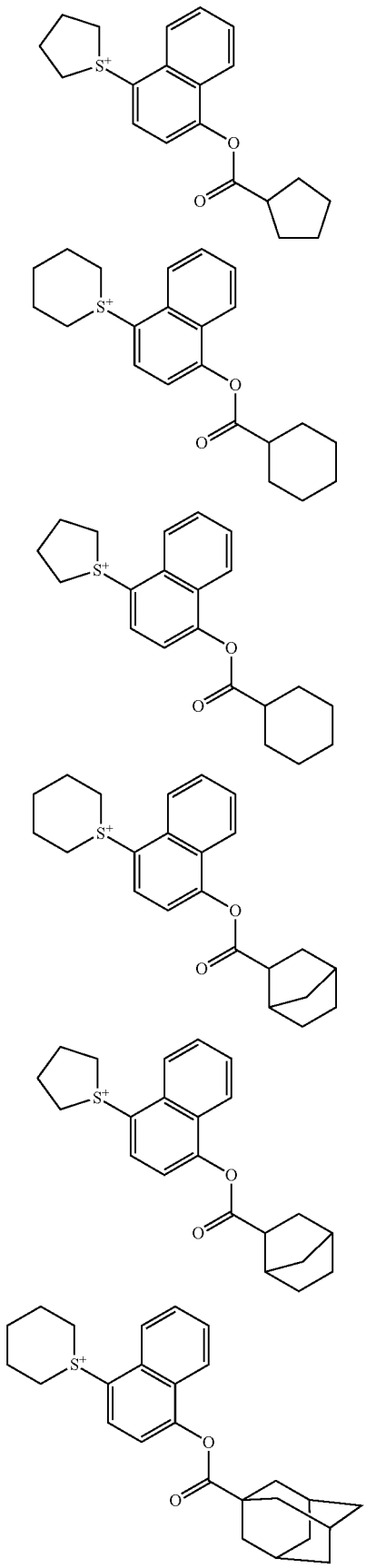

-continued
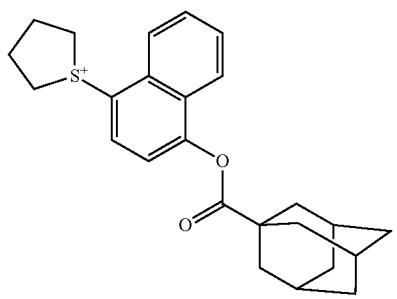
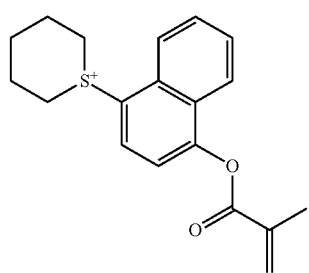
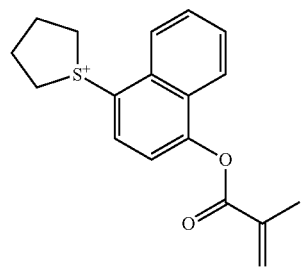
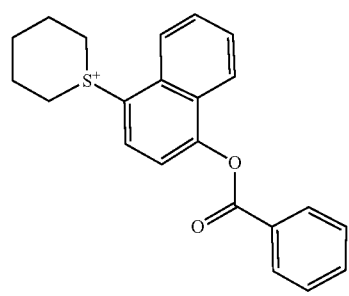
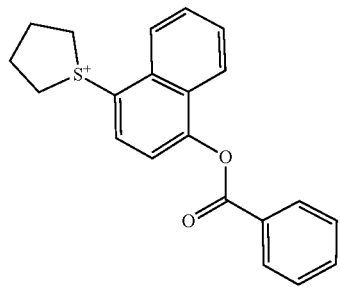
-continued
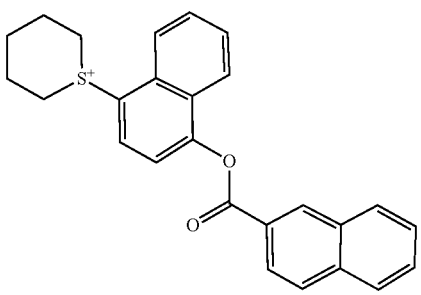
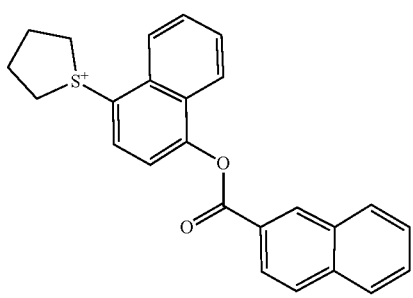
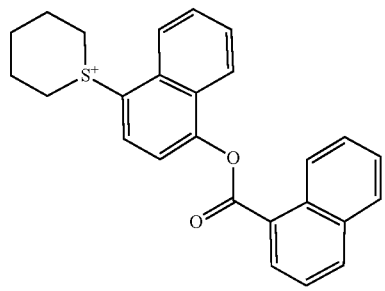
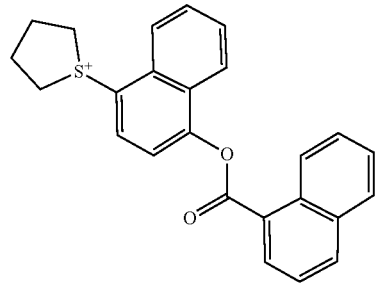
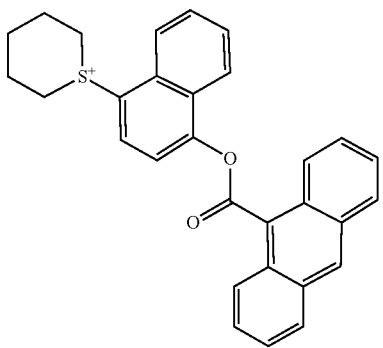

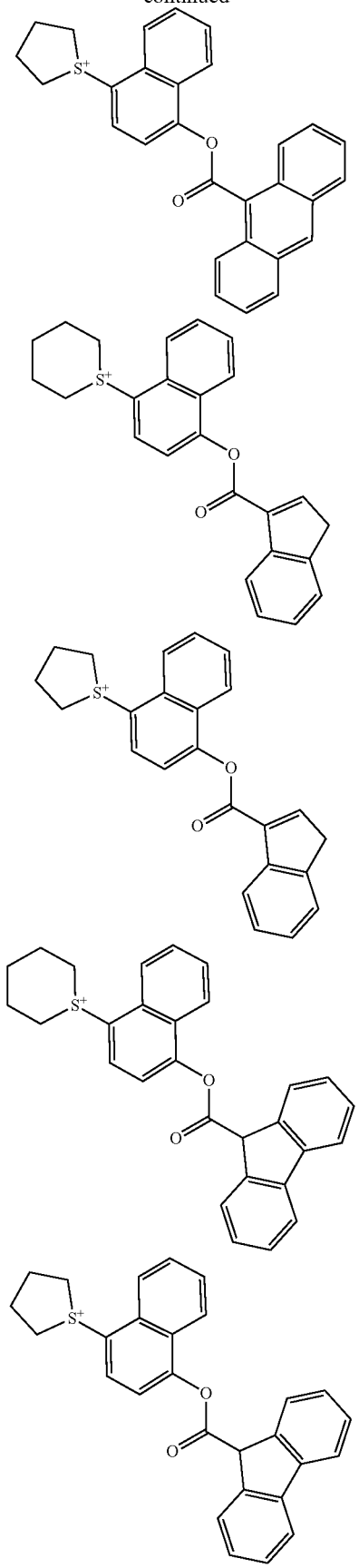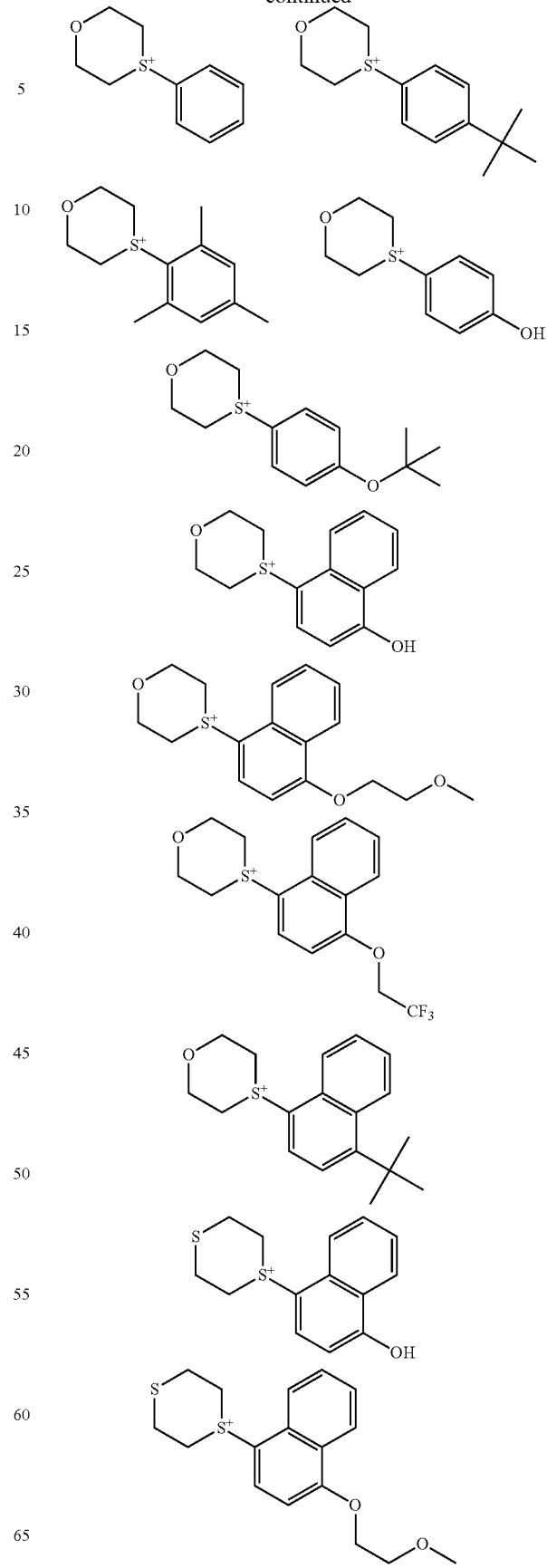

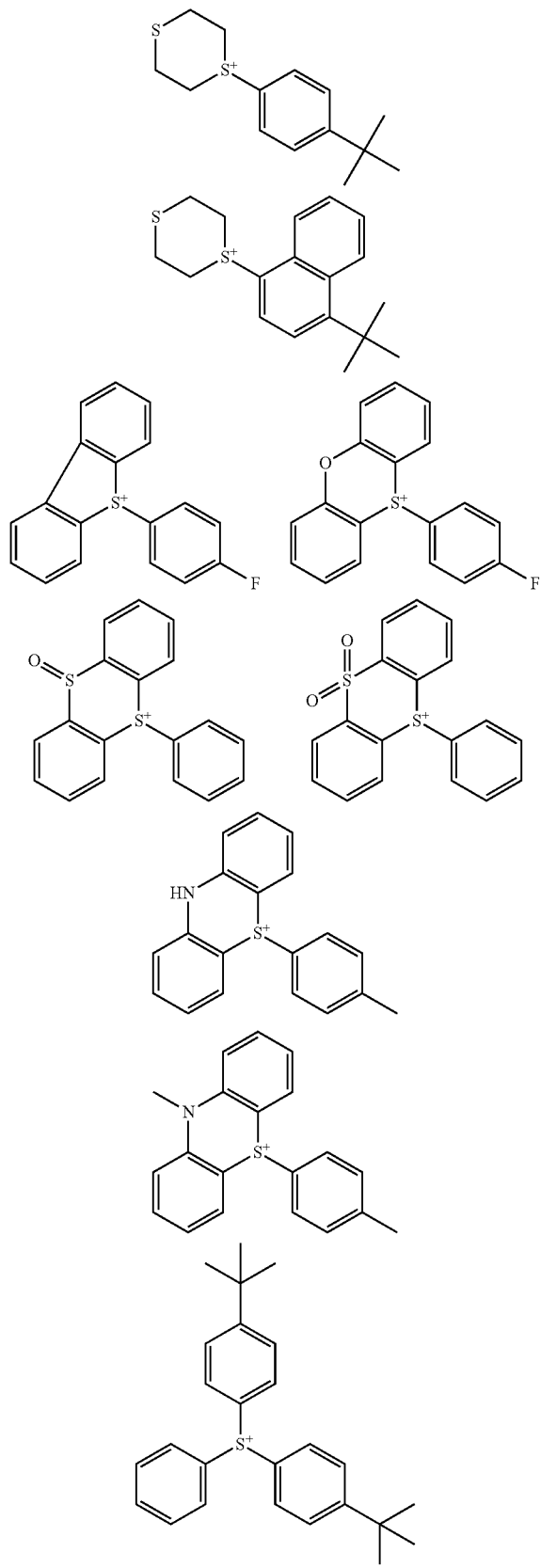
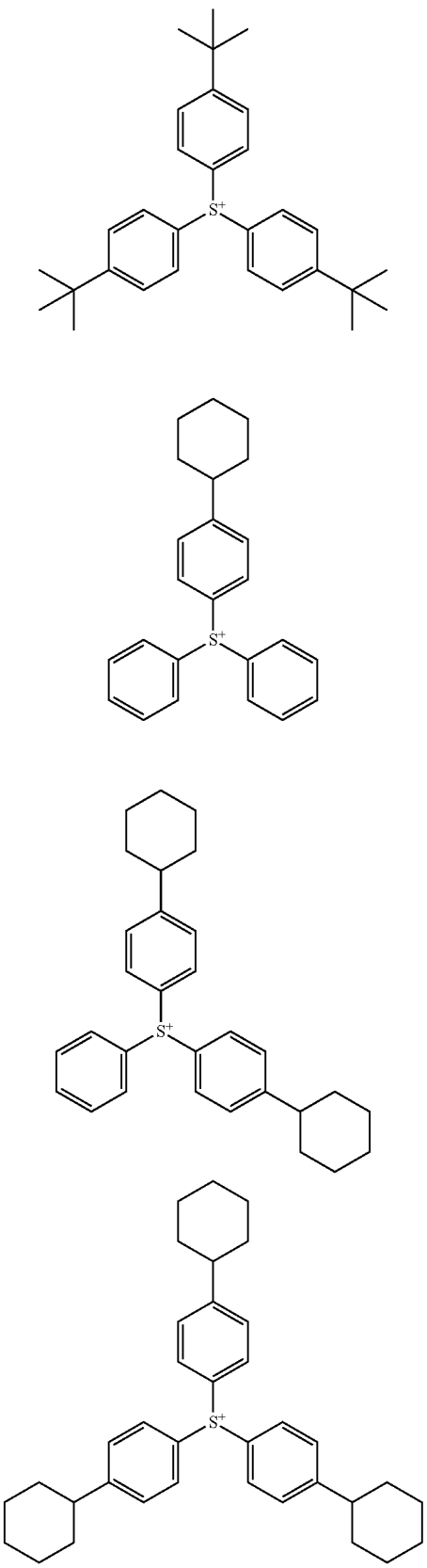

247
-continued
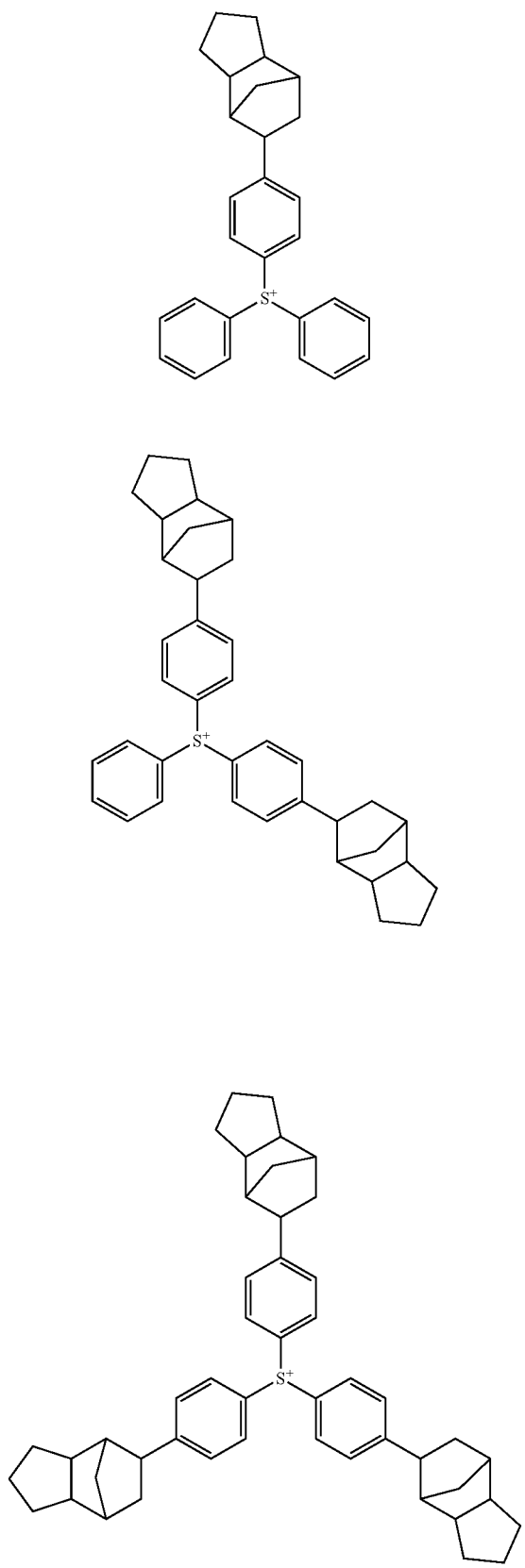
248
-continued
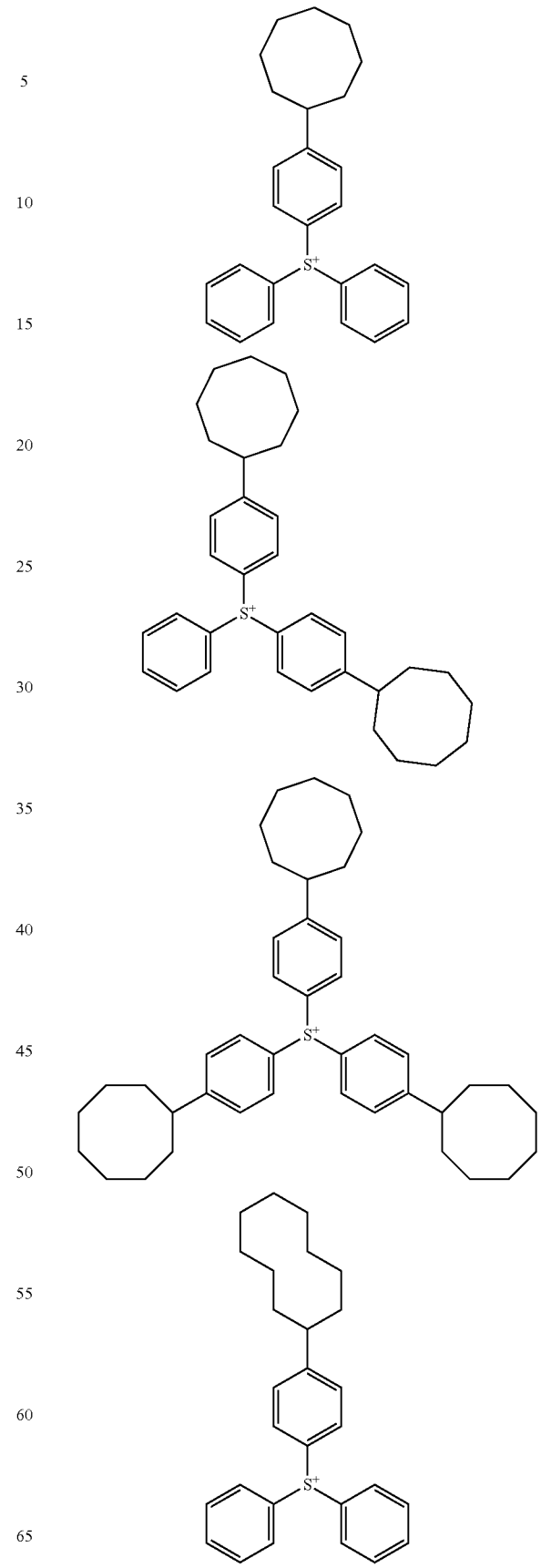

249
-continued
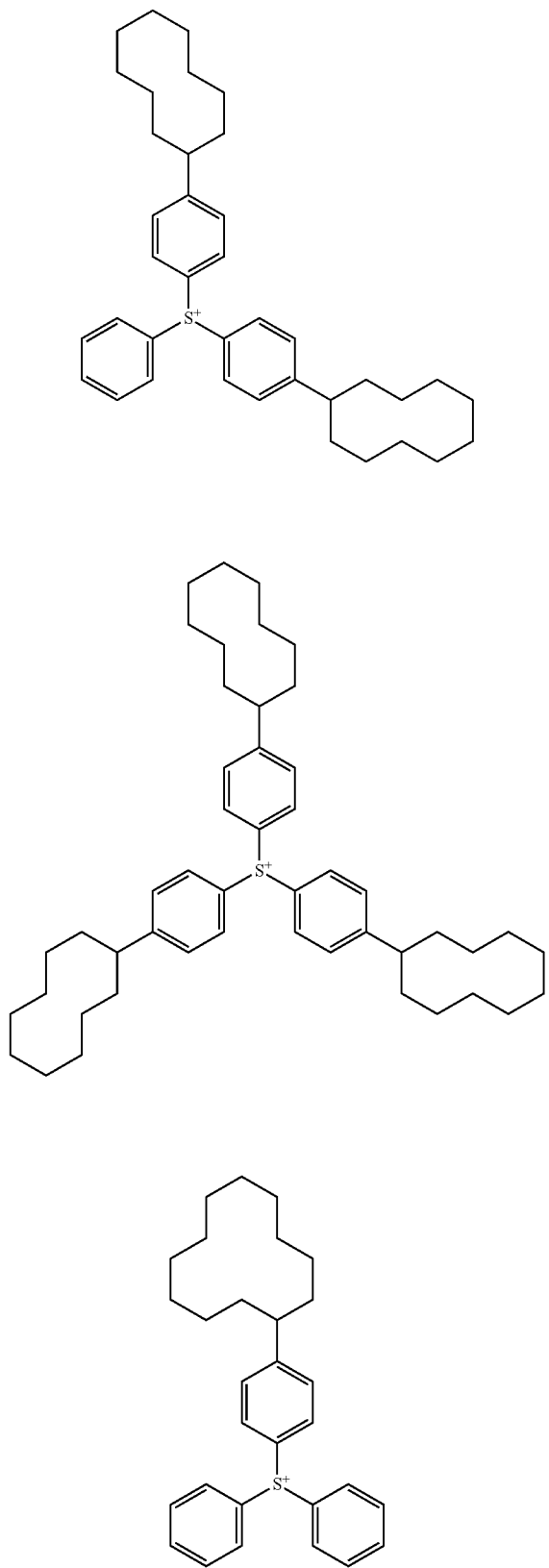
250
-continued
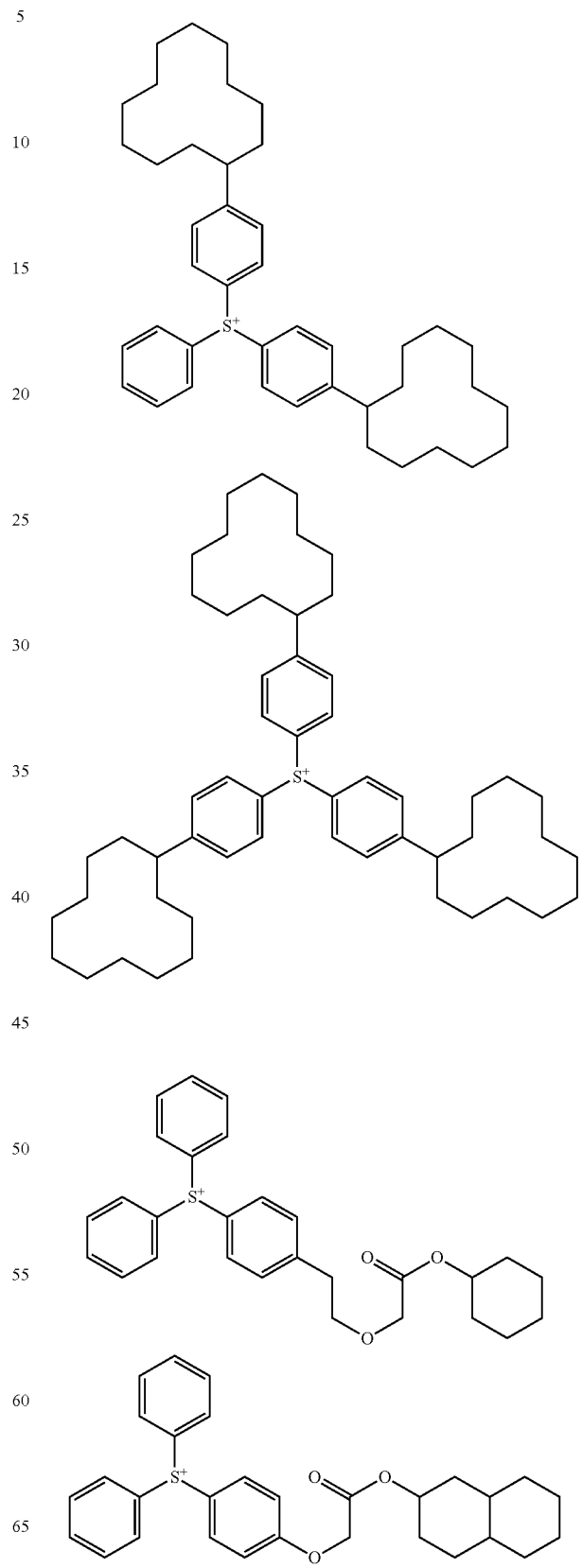

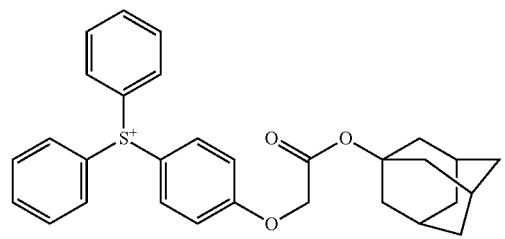
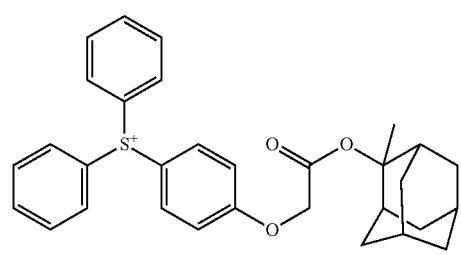
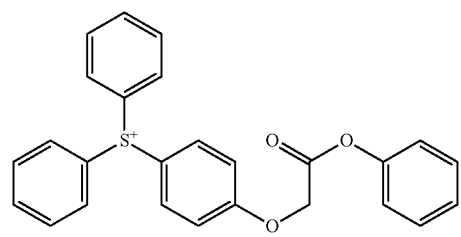
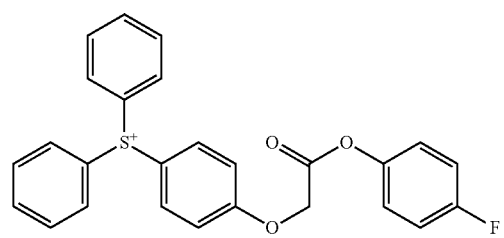
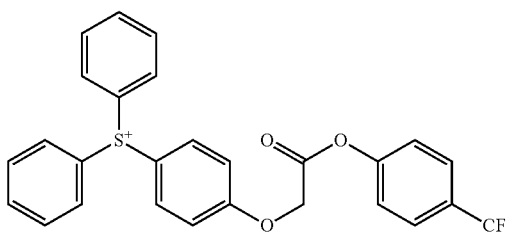
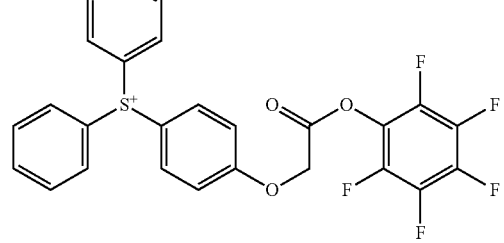
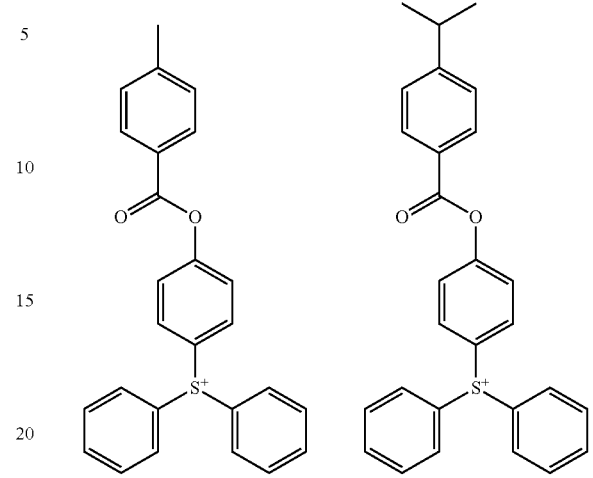
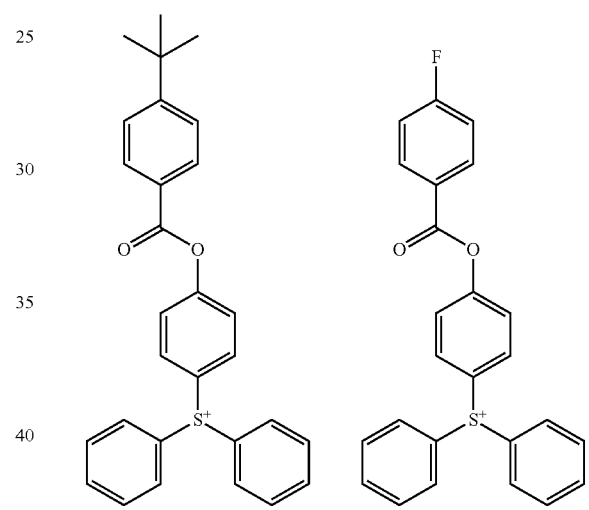
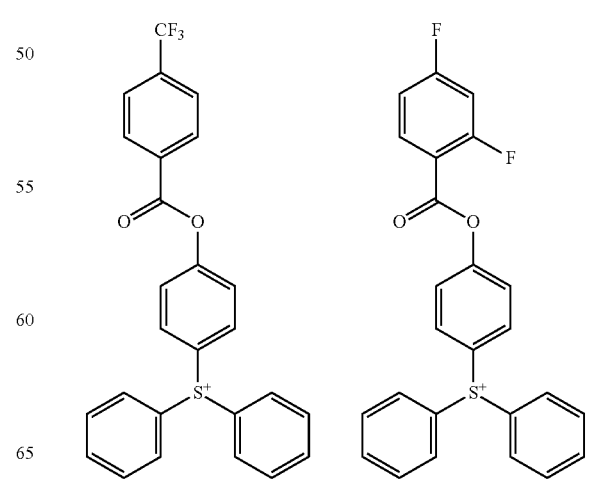

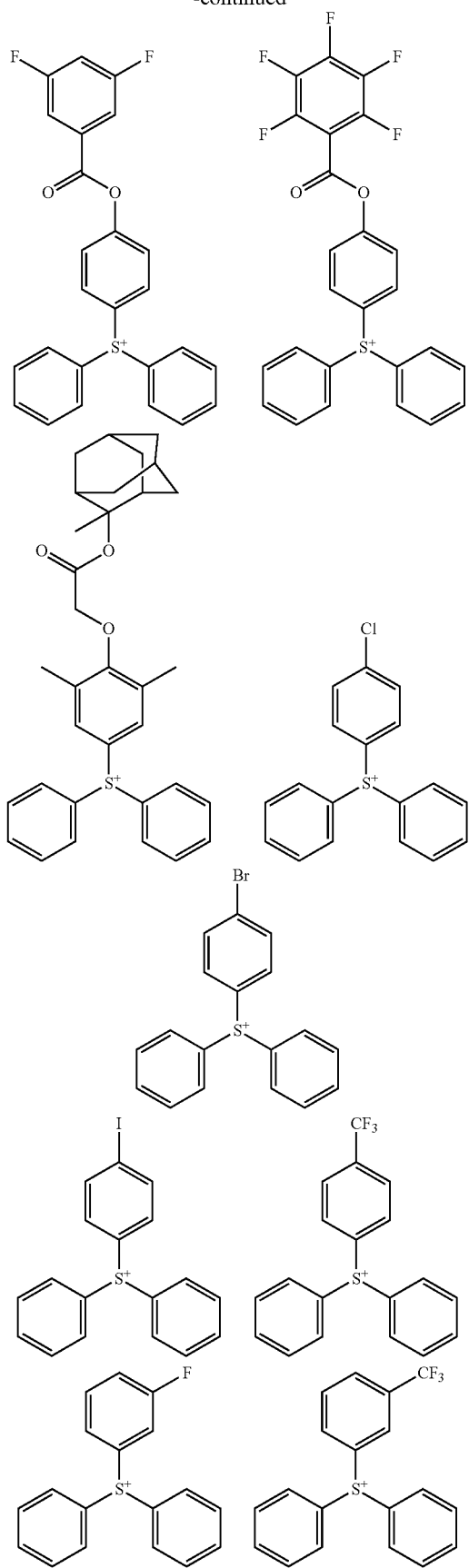
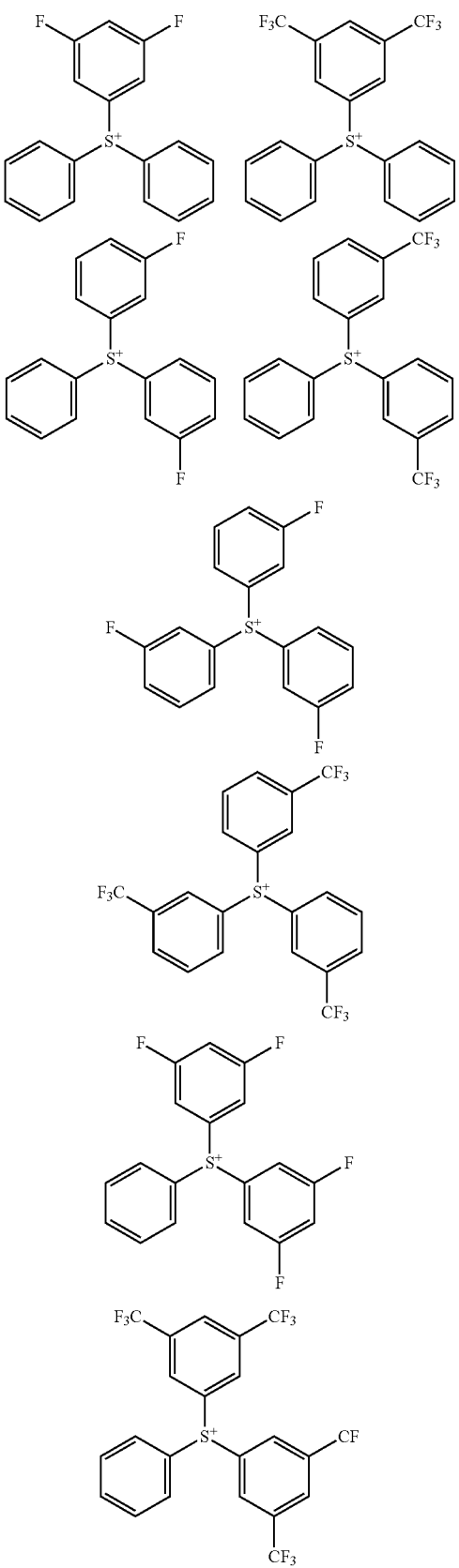

-continued
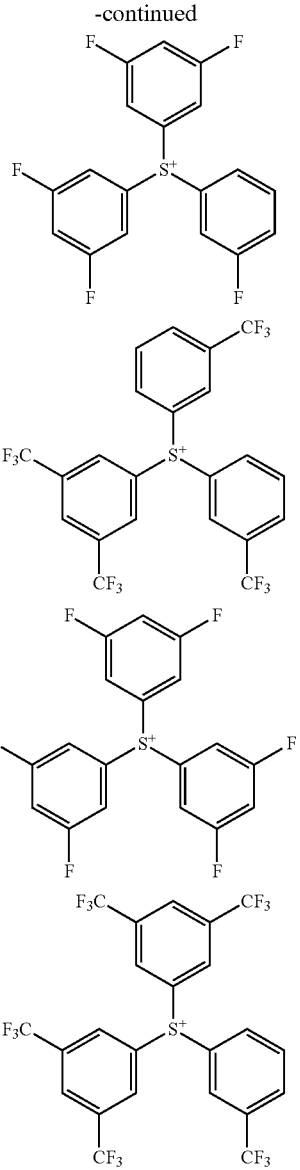
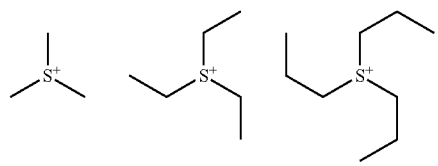
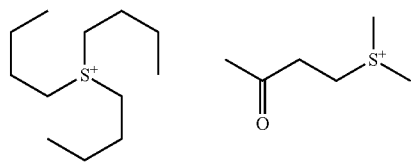
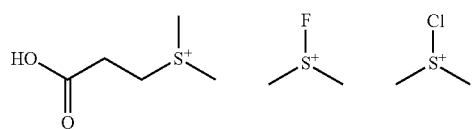
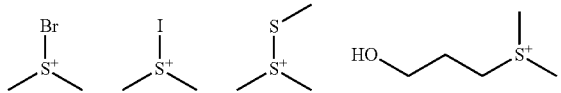
-continued
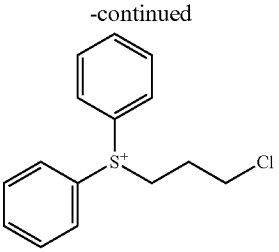
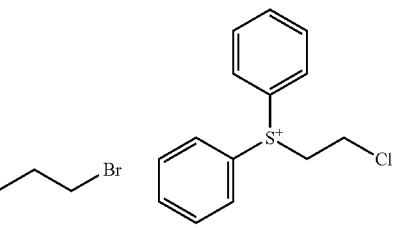
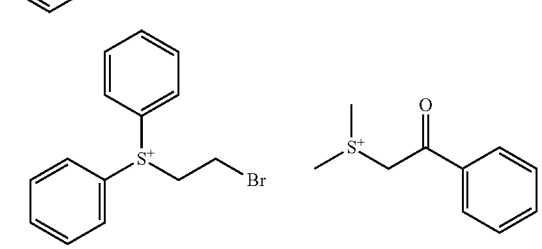
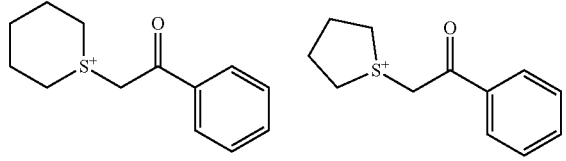
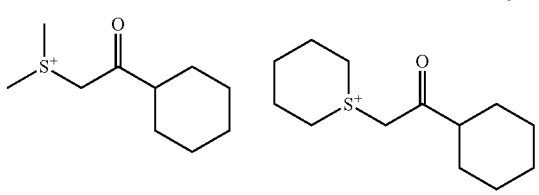
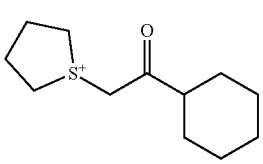
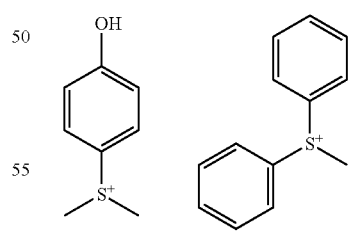
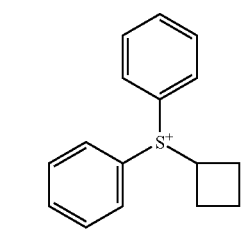
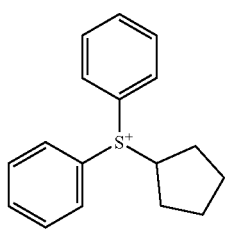

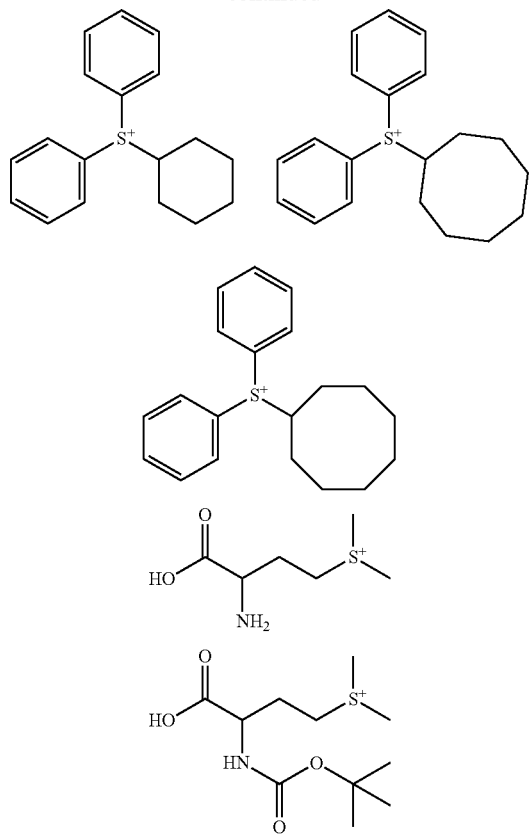
Examples of the cation in the iodonium salt having formula (1-2) are shown below, but not limited thereto.
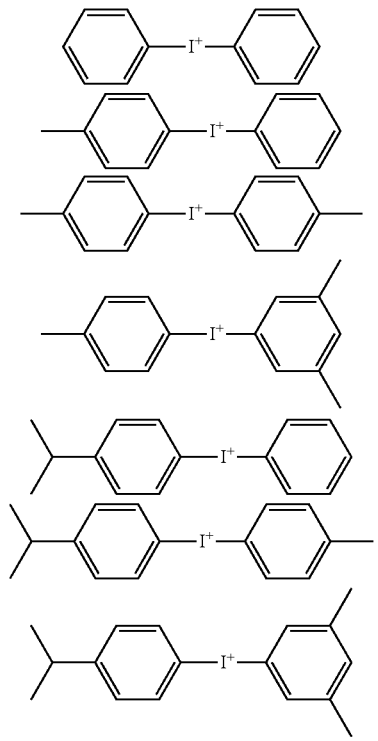
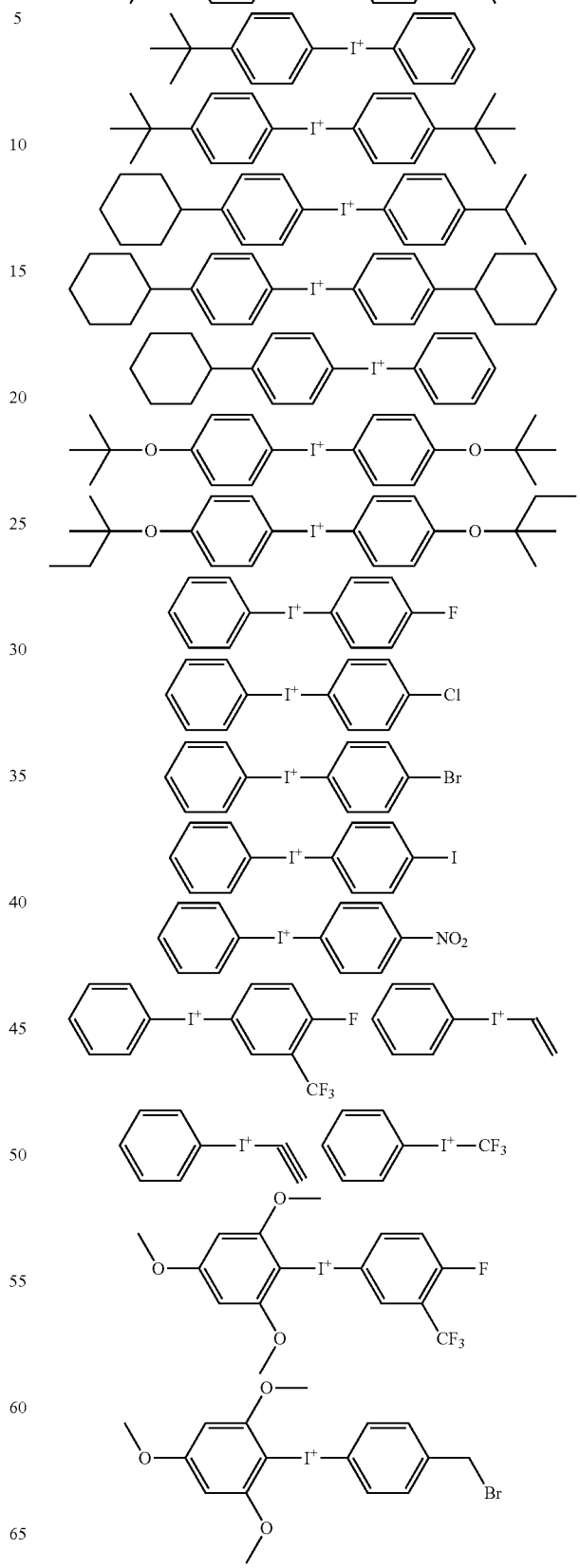

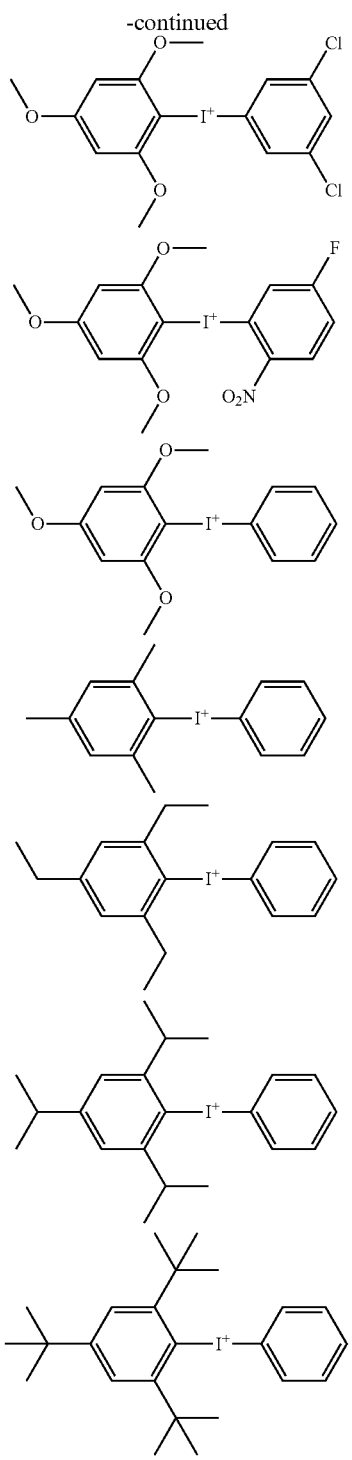

In formulae (1-1) and (1-2), $X_a^-$ is an anion of the following formula (1A), (1B), (1C) or (1D).

$$R^{fa}-CF_2-SO_3^- \quad (1A)$$

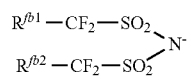
(1B)

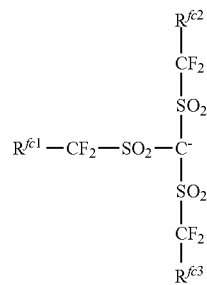
(1C)

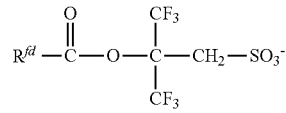
(1D)

In formula (1A), $R^{fa}$ is fluorine or a $C_1$-$C_{40}$ hydrocarbyl group which may contain a heteroatom. The hydrocarbyl group may be saturated or unsaturated and straight, branched or cyclic. Examples thereof are as will be exemplified later for hydrocarbyl group $R^{111}$ in formula (1A').

Of the anions of formula (1A), a structure having formula (1A') is preferred.

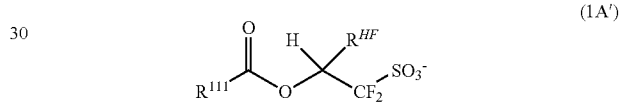
(1A')

In formula (1A'), $R^{HF}$ is hydrogen or trifluoromethyl, preferably trifluoromethyl.

$R^{111}$ is a $C_1$-$C_{38}$ hydrocarbyl group which may contain a heteroatom. Suitable heteroatoms include oxygen, nitrogen, sulfur and halogen, with oxygen being preferred. Of the hydrocarbyl groups, those of 6 to 30 carbon atoms are preferred because a high resolution is available in fine pattern formation. The hydrocarbyl group $R^{111}$ may be saturated or unsaturated and straight, branched or cyclic. Suitable hydrocarbyl groups include $C_1$-$C_{38}$ alkyl groups such as methyl, ethyl, propyl, isopropyl, butyl, isobutyl, sec-butyl, tert-butyl, pentyl, neopentyl, hexyl, heptyl, 2-ethylhexyl, nonyl, undecyl, tridecyl, pentadecyl, heptadecyl, icosanyl; $C_3$-$C_{38}$ cyclic saturated hydrocarbyl groups such as cyclopentyl, cyclohexyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl; $C_2$-$C_{38}$ unsaturated aliphatic hydrocarbyl groups such as allyl and 3-cyclohexenyl; $C_6$-$C_{38}$ aryl groups such as phenyl, 1-naphthyl, 2-naphthyl: $C_7$-$C_{38}$ aralkyl groups such as benzyl and diphenylmethyl; and combinations thereof.

In these groups, some or all of the hydrogen atoms may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxy moiety, fluorine, chlorine, bromine, iodine, cyano moiety, nitro moiety, carbonyl moiety, ether bond, ester bond, sulfonic acid ester bond, carbonate bond, lactone ring, sultone ring, carboxylic anhydride or haloalkyl moiety. Examples of the heteroatom-containing hydrocarbyl group include tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl.

With respect to the synthesis of the sulfonium salt having an anion of formula (1A'), reference is made to JP-A 2007-145797, JP-A 2008-106045, JP-A 2009-007327, and JP-A 2009-258695. Also useful are the sulfonium salts described in JP-A 2010-215608, JP-A 2012-041320, JP-A 2012-106986, and JP-A 2012-153644.

Examples of the anion having formula (1A) are shown below, but not limited thereto.

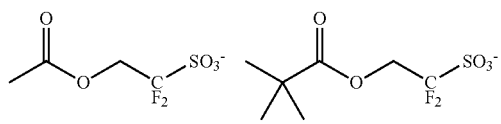
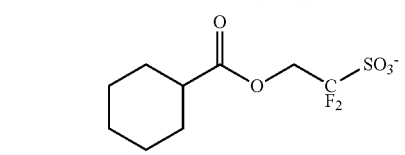
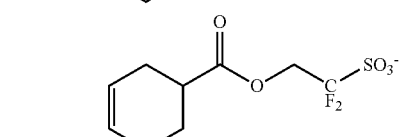
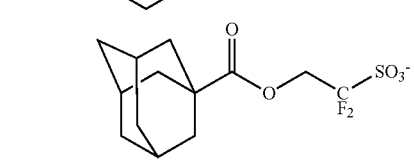
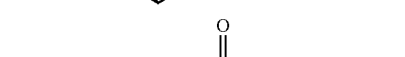
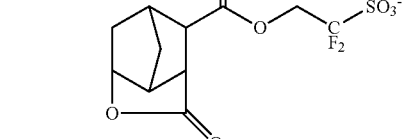
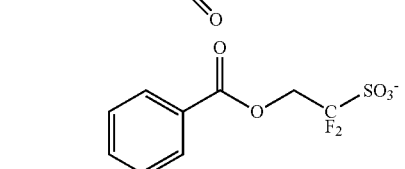
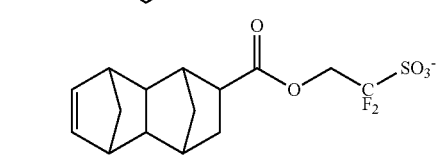
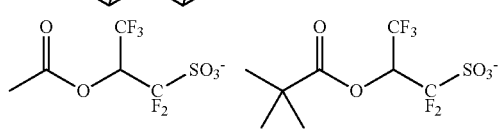
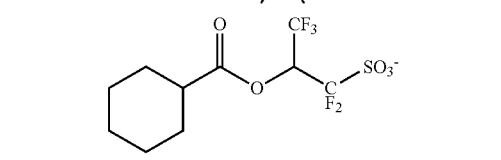

-continued

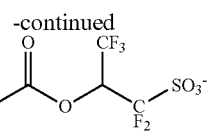
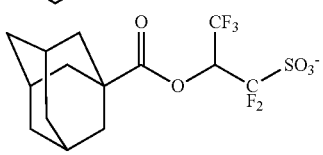
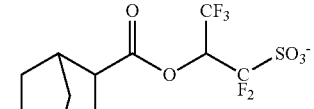
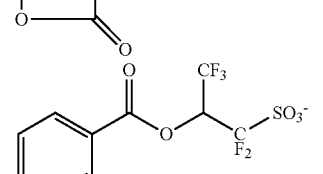
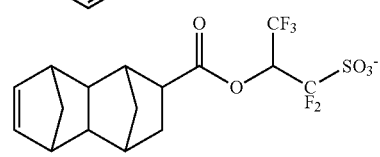
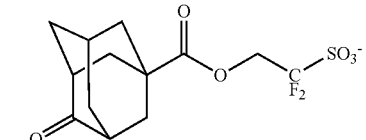
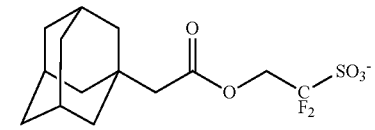
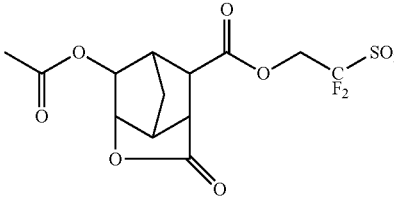
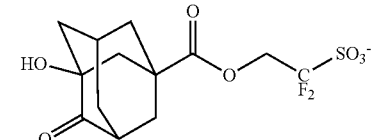
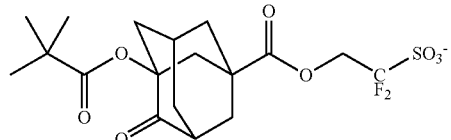
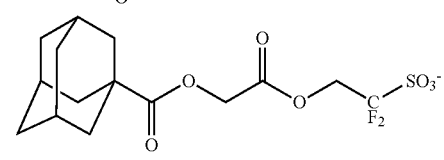

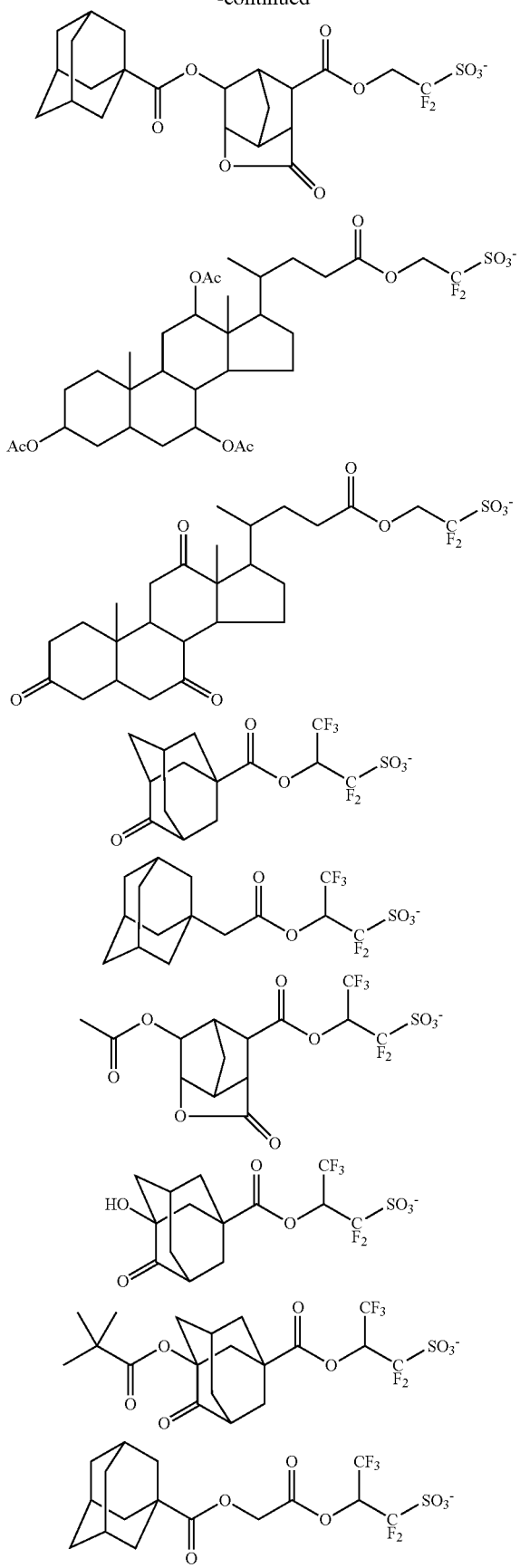

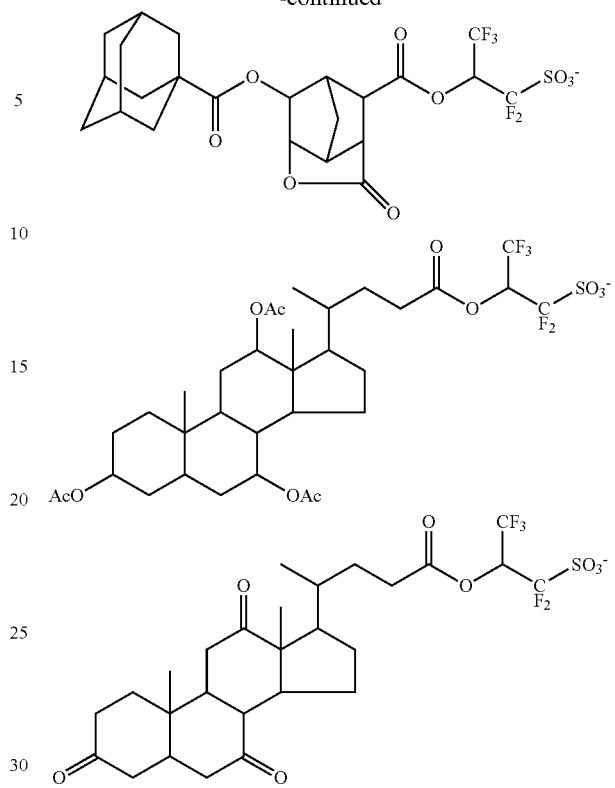

In formula (1B), $R^{fb1}$ and $R^{fb2}$ are each independently fluorine or a $C_1$-$C_{40}$ hydrocarbyl group which may contain a heteroatom. The hydrocarbyl group may be saturated or unsaturated and straight, branched or cyclic. Suitable hydrocarbyl groups are as exemplified above for $R^{111}$ in formula (1A'). Preferably $R^{fb1}$ and $R^{fb2}$ each are fluorine or a straight $C_1$-$C_4$ fluorinated alkyl group. A pair of $R^{fb1}$ and $R^{fb2}$ may bond together to form a ring with the linkage (—$CF_2$—$SO_2$—N—$SO_2$—$CF_2$—) to which they are attached, and the ring-forming pair is preferably a fluorinated ethylene or fluorinated propylene group.

In formula (1C), $R^{fc1}$, $R^{fc2}$ and $R^{fc3}$ are each independently fluorine or a $C_1$-$C_{40}$ hydrocarbyl group which may contain a heteroatom. The hydrocarbyl group may be saturated or unsaturated and straight, branched or cyclic. Suitable hydrocarbyl groups are as exemplified above for $R^{111}$ in formula (1A'). Preferably $R^{fc1}$, $R^{fc2}$ and $R^{fc3}$ each are fluorine or a straight $C_1$-$C_4$ fluorinated alkyl group. A pair of $R^{fc1}$ and $R^{fc2}$ may bond together to form a ring with the linkage (—$CF_2$—$SO_2$—$C^-$—$SO_2$—$CF_2$—) to which they are attached, and the ring-forming pair is preferably a fluorinated ethylene or fluorinated propylene group.

In formula (1D), $R^f$ is a $C_1$-$C_{40}$ hydrocarbyl group which may contain a heteroatom. The hydrocarbyl group may be saturated or unsaturated and straight, branched or cyclic. Suitable hydrocarbyl groups are as exemplified above for $R^{111}$.

With respect to the synthesis of the sulfonium salt having an anion of formula (1D), reference is made to JP-A 2010-215608 and JP-A 2014-133723.

Examples of the anion having formula (1D) are shown below, but not limited thereto.

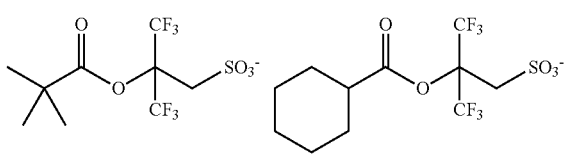
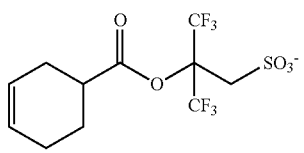
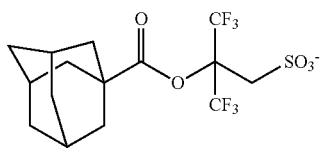
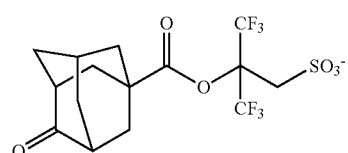
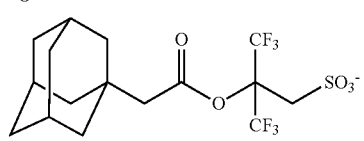
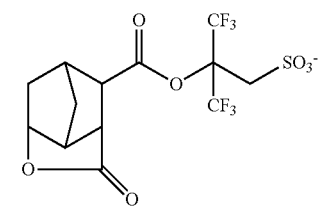
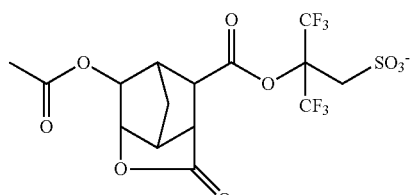
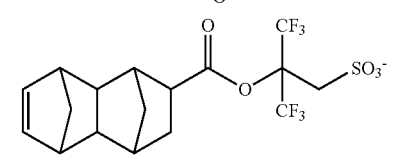
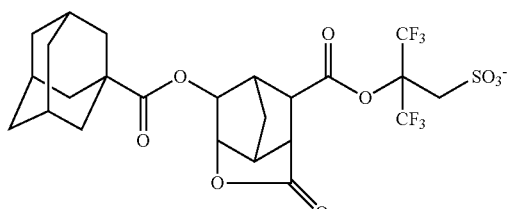

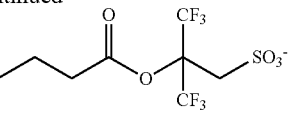

The compound having the anion of formula (1D) has a sufficient acid strength to cleave acid labile groups in the base polymer because it is free of fluorine at α-position of sulfo group, but has two trifluoromethyl groups at β-position. Thus the compound is a useful PAG.

Also compounds having the formula (2) are useful as the PAG.

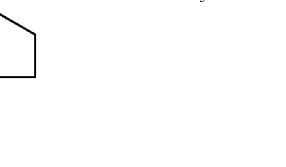

(2)

In formula (2), $R^{201}$ and $R^{202}$ are each independently halogen or a $C_1$-$C_{30}$ hydrocarbyl group which may contain a heteroatom. $R^{203}$ is a $C_1$-$C_{30}$ hydrocarbylene group which may contain a heteroatom. Any two of $R^{201}$, $R^{202}$ and $R^{203}$ may bond together to form a ring with the sulfur atom to which they are attached. Exemplary rings are the same as described above for the ring that $R^{101}$ and $R^{102}$ in formula (1-1), taken together, form with the sulfur atom to which they are attached.

The hydrocarbyl groups $R^{201}$ and $R^{202}$ may be saturated or unsaturated and straight, branched or cyclic. Examples thereof include $C_1$-$C_{30}$ alkyl groups such as methyl, ethyl, propyl, isopropyl, n-butyl, sec-butyl, tert-butyl, n-pentyl, tert-pentyl, n-hexyl, n-octyl, 2-ethylhexyl, n-nonyl, and n-decyl. $C_3$-$C_{30}$ cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, and adamantyl; $C_6$-$C_{30}$ aryl groups such as phenyl, methylphenyl, ethylphenyl, n-propylphenyl, isopropylphenyl, n-butylphenyl, isobutylphenyl, sec-butylphenyl, tert-butylphenyl, naphthyl, methylnaphthyl, ethylnaphthyl, n-propylnaphthyl, isopropylnaphthyl, n-butylnaphthyl, isobutylnaphthyl, sec-butylnaphthyl, tert-butynaphthyl, and anthracenyl; and combinations thereof. In these groups, some or all of the hydrogen atoms may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxy moiety, fluorine, chlorine, bromine, iodine, cyano moiety, nitro moiety, carbonyl moiety, ether bond, ester bond, sulfonic acid ester bond, carbonate bond, lactone ring, sultone ring, carboxylic anhydride or haloalkyl moiety.

The hydrocarbylene group $R^2$ may be saturated or unsaturated and straight, branched or cyclic. Examples thereof include $C_1$-$C_{30}$ alkanediyl groups such as methanediyl, ethane-1,1-diyl, ethane-1,2-diyl, propane-1,3-diyl, butane-1,4- diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, and heptadecane-1,17-diyl; $C_3$-$C_{30}$ cyclic saturated hydrocarbylene groups such as cyclopentanediyl, cyclohexanediyl, norbornanediyl and adamantanediyl; $C_6$-$C_{30}$ arylene groups such as phenylene, methylphenylene, ethylphenylene, n-propylphenylene, isopropylphenylene, n-butylphenylene, isobutylphenylene, sec-butylphenylene, tert-butylphenylene, naphthylene, methylnaphthylene, ethylnaphthylene, n-propylnaphthylene, isopropylnaphthylene, n-butylnaphthylene, isobutylnaphthylene, sec-butylnaphthylene and tert-butylnaphthylene; and combinations thereof. In these groups, some or all of the hydrogen atoms may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxy moiety, fluorine, chlorine, bromine, iodine, cyano moiety, nitro moiety, carbonyl moiety, ether bond, ester bond, sulfonic acid ester bond, carbonate bond, lactone ring, sultone ring, carboxylic anhydride or haloalkyl moiety. Of the heteroatoms, oxygen is preferred.

In formula (2), $L^A$ is a single bond, ether bond or a $C_1$-$C_{20}$ hydrocarbylene group which may contain a heteroatom. The hydrocarbylene group may be saturated or unsaturated and straight, branched or cyclic. Examples thereof are as exemplified above for $R^{203}$.

In formula (2), $X^A$, $X^B$, $X^C$ and $X^D$ are each independently hydrogen, fluorine or trifluoromethyl, with the proviso that at least one of $X^A$, $X^B$, $X^C$ and $X^D$ is fluorine or trifluoromethyl.

In formula (2), k is an integer of 0 to 3.

Of the PAGs having formula (2), those having formula (2') are preferred.

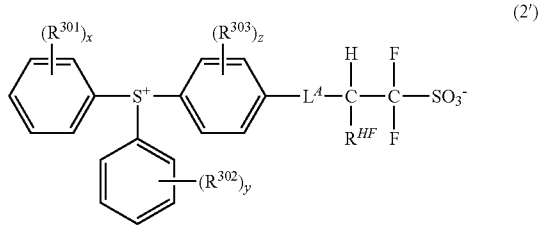

(2')

In formula (2'), $L^A$ is as defined above. $R^{HF}$ is hydrogen or trifluoromethyl, preferably trifluoromethyl. $R^{301}$, $R^{302}$ and $R^{303}$ are each independently hydrogen or a $C_1$-$C_{20}$ hydrocarbyl group which may contain a heteroatom. The hydrocarbyl group may be saturated or unsaturated and straight, branched or cyclic. Examples thereof are as exemplified above for $R^{111}$ in formula (1A'). The subscripts x and y are each independently an integer of 0 to 5, and z is an integer of 0 to 4.

Examples of the PAG having formula (2) are as exemplified for the PAG having formula (2) in JP-A 2017-026980.

Of the foregoing PAGs, those having an anion of formula (1A') or (1D) are especially preferred because of reduced acid diffusion and high solubility in the solvent. Also those having an anion of formula (2') are especially preferred because of extremely reduced acid diffusion.

Also, a sulfonium or iodonium salt having an iodized or brominated aromatic ring-containing anion may be used as the PAG. Suitable are sulfonium and iodonium salts having the formulae (3-1) and (3-2).

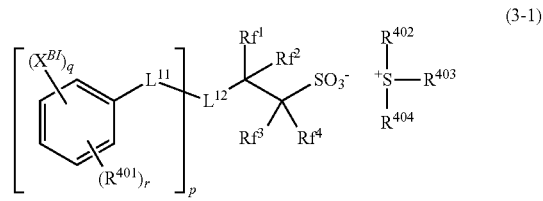

(3-1)

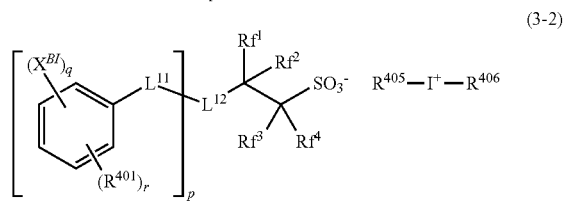

(3-2)

In formulae (3-1) and (3-2), p is an integer of 1 to 3, q is an integer of 1 to 5, and r is an integer of 0 to 3, and 1≤q+r≤5. Preferably, q is an integer of 1 to 3, more preferably 2 or 3, and r is an integer of 0 to 2.

$X^{BI}$ is iodine or bromine, and may be the same or different when p and/or q is 2 or more.

$L^{11}$ s a single bond, ether bond, ester bond, or a $C_1$-$C_6$ saturated hydrocarbylene group which may contain an ether bond or ester bond. The saturated hydrocarbylene group may be straight, branched or cyclic.

$L^{12}$ is a single bond or a $C_1$-$C_{20}$ divalent linking group in case of p=1, and a $C_1$-$C_{20}$ tri- or tetravalent linking group in case of p=2 or 3. The linking group may contain oxygen, sulfur or nitrogen.

$R^{401}$ is a hydroxy group, carboxy group, fluorine, chlorine, bromine, amino group, or a $C_1$-$C_{20}$ saturated hydrocarbyl group, $C_1$-$C_{20}$ saturated hydrocarbyloxy group, $C_2$-$C_{20}$ saturated hydrocarbylcarbonyl group, $C_2$-$C_{20}$ saturated hydrocarbyloxycarbonyl group, $C_2$-$C_{20}$ saturated hydrocarbylcarbonyloxy group or $C_1$-$C_{20}$ saturated hydrocarbylsulfonyloxy group which may contain fluorine, chlorine, bromine, hydroxy moiety, amino moiety or ether bond, or —N($R^{401A}$)($R^{401B}$), —N($R^{401C}$)—C(=O)$R^{401D}$ or —N($R^{401C}$)—C(=O)O—$R^{401D}$. $R^{401A}$ and $R^{401B}$ are each independently hydrogen or a $C_1$-$C_6$ saturated hydrocarbyl group. $R^{401C}$ is hydrogen, or a $C_1$-$C_6$ saturated hydrocarbyl group which may contain halogen, hydroxy, $C_1$-$C_6$ saturated hydrocarbyloxy moiety, $C_2$-$C_6$ saturated hydrocarbylcarbonyl moiety or $C_2$-$C_6$ saturated hydrocarbylcarbonyloxy moiety. $R^{401D}$ is a $C_1$-$C_{16}$ aliphatic hydrocarbyl group, $C_6$-$C_{14}$ aryl group or $C_7$-$C_{15}$ aralkyl group, which may contain halogen, hydroxy, $C_1$-$C_6$ saturated hydrocarbyloxy moiety, $C_2$-$C_6$ saturated hydrocarbylcarbonyl moiety or $C_2$-$C_6$ saturated hydrocarbylcarbonyloxy moiety. The foregoing aliphatic hydrocarbyl groups may be saturated or unsaturated and straight, branched or cyclic.

The saturated hydrocarbyl, saturated hydrocarbyloxy, saturated hydrocarbyloxycarbonyl, saturated hydrocarbylcarbonyl, and saturated hydrocarbylcarbonyloxy groups may be straight, branched or cyclic. The groups $R^{401}$ may be the same or different when r is 2 or more.

Of these, $R^{401}$ is preferably hydroxy, —N($R^{401C}$)—C(=O)—$R^{410D}$, —N($R^{401C}$)—C(=O)—O—$R^{401D}$, fluorine, chlorine, bromine, methyl or methoxy.

$Rf^1$ to $Rf^4$ are each independently hydrogen, fluorine or trifluoromethyl, at least one of $Rf^1$ to $Rf^4$ is fluorine or trifluoromethyl. $Rf^1$ and $Rf^2$, taken together, may form a carbonyl group. Preferably, both $Rf^2$ and $Rf^4$ are fluorine.

$R^{402}$ to $R^{406}$ are each independently halogen or a $C_1$-$C_{20}$ hydrocarbyl group which may contain a heteroatom. The hydrocarbyl group may be saturated or unsaturated and straight, branched or cyclic. Examples thereof are as exemplified above for the hydrocarbyl groups $R^{101}$ to $R^{105}$ in formulae (1-1) and (1-2). In these groups, some or all of the hydrogen atoms may be substituted by hydroxy, carboxy, halogen, cyano, nitro, mercapto, sultone, sulfone, or sulfonium salt-containing moieties, and some carbon may be replaced by an ether bond, ester bond, carbonyl moiety, amide bond, carbonate bond or sulfonic acid ester bond. $R^{402}$ and $R^{403}$ may bond together to form a ring with the sulfur atom to which they are attached. Examples of the ring are as exemplified above for the ring that $R^{101}$ and $R^{102}$ in formula (1-1), taken together, form with the sulfur atom to which they are attached.

Examples of the cation in the sulfonium salt having formula (3-1) include those exemplified above as the cation in the sulfonium salt having formula (1-1). Examples of the cation in the iodonium salt having formula (3-2) include those exemplified above as the cation in the iodonium salt having formula (1-2).

Examples of the anion in the onium salts having formulae (3-1) and (3-2) are shown below, but not limited thereto. Herein $X^{BI}$ is as defined above.

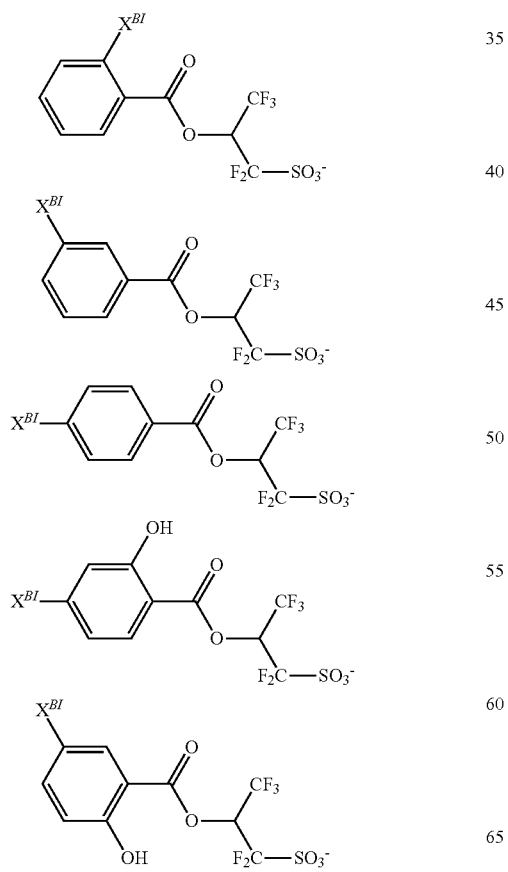

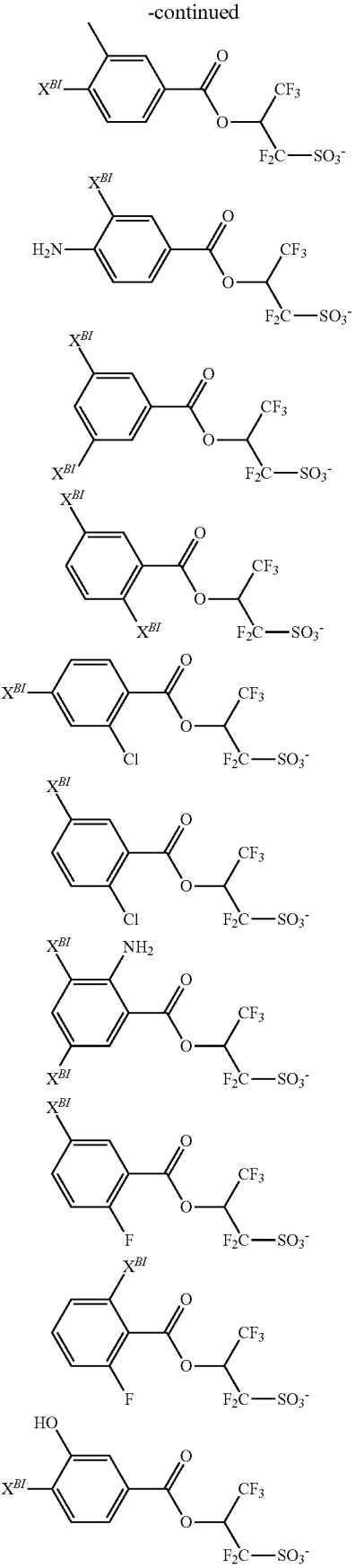

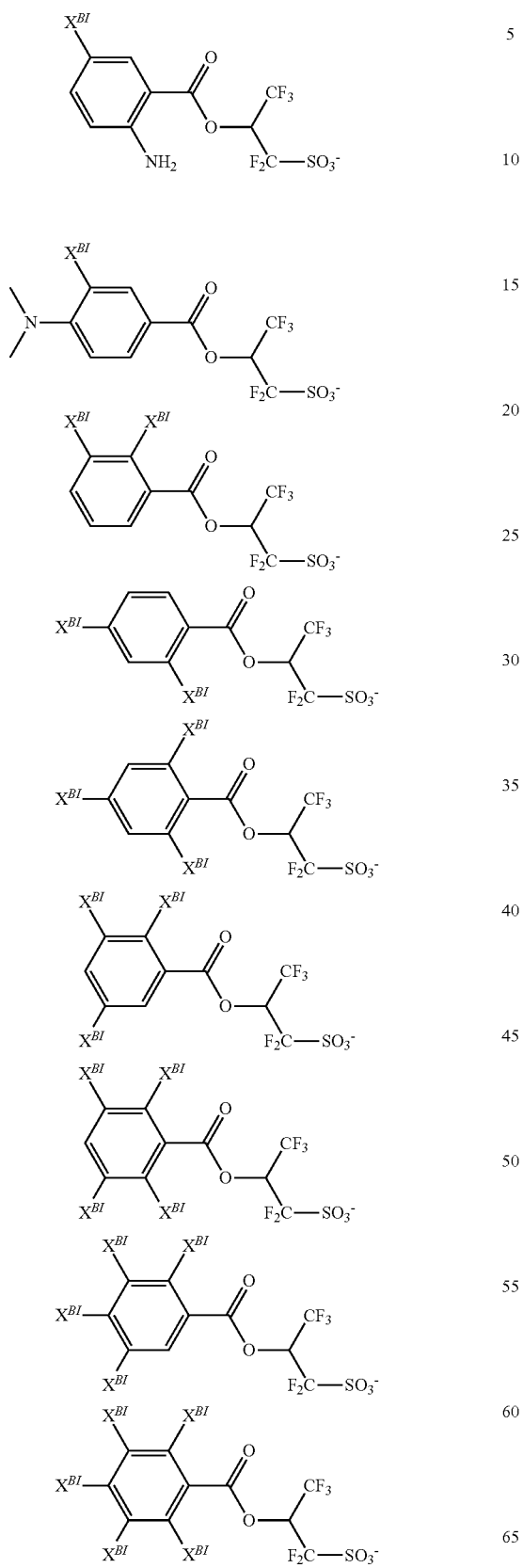
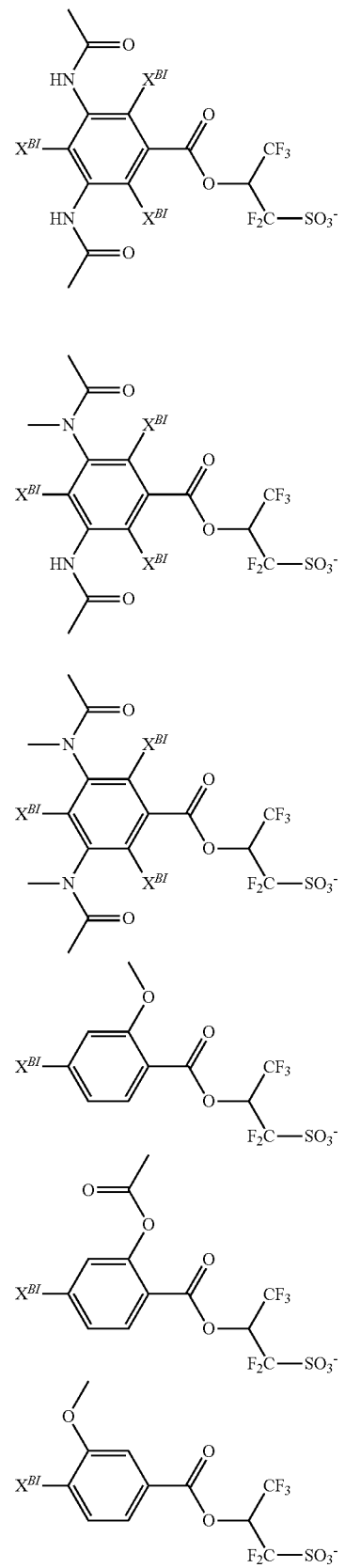

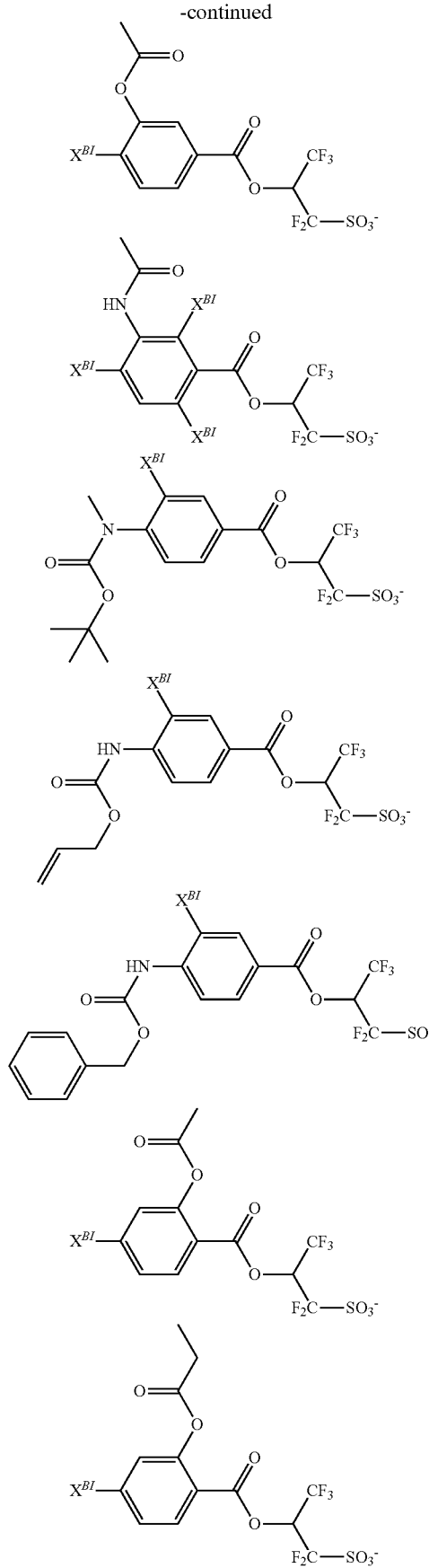
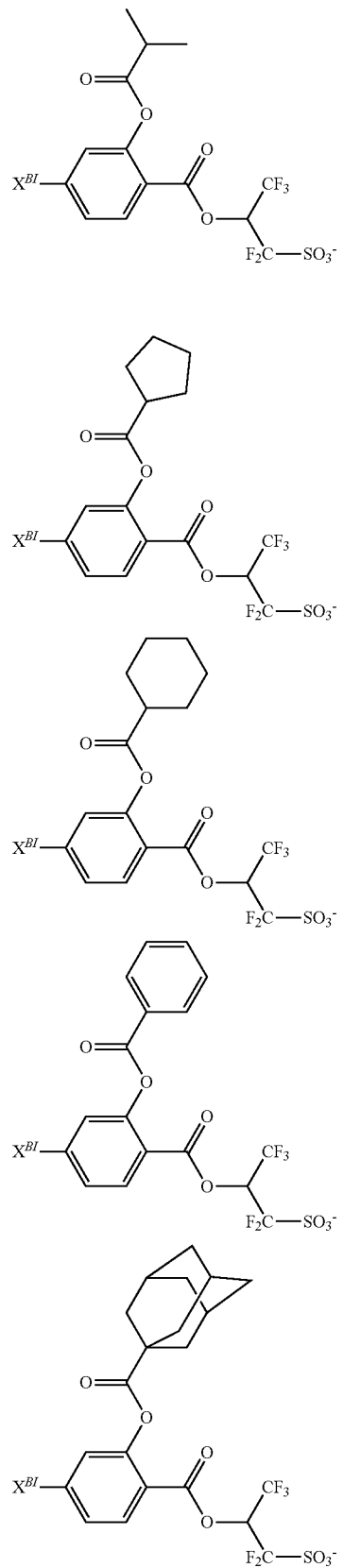

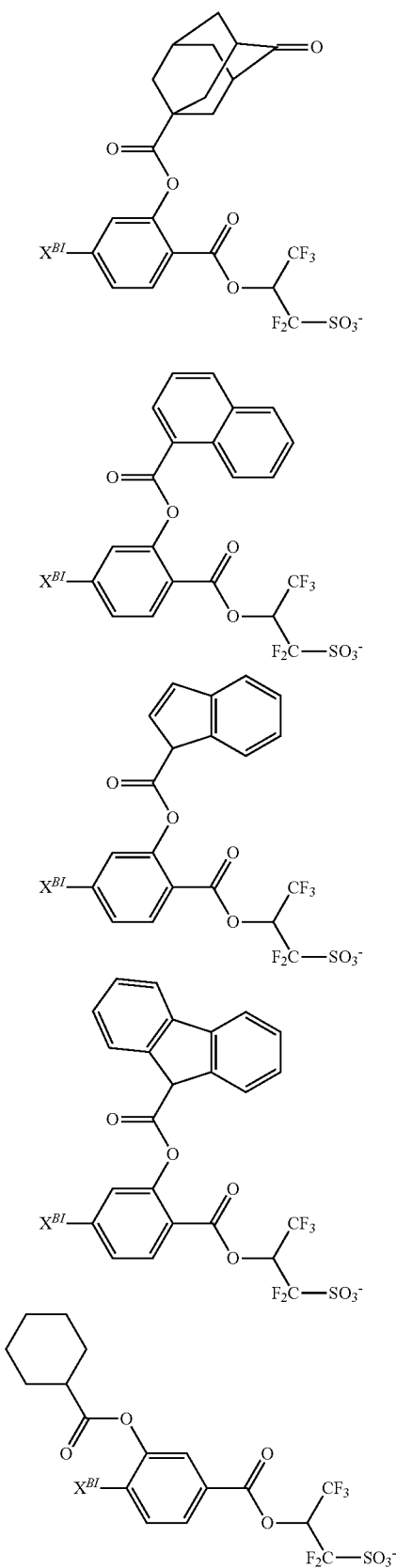
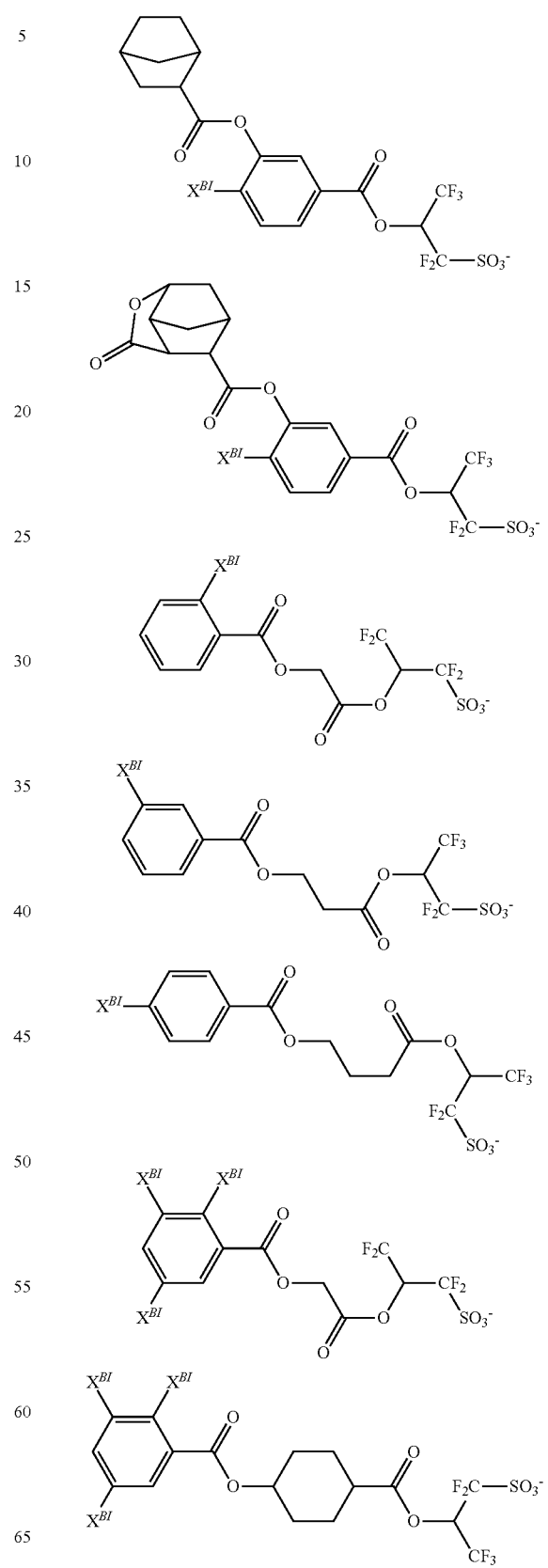

277
-continued
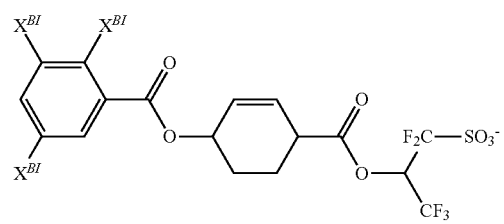
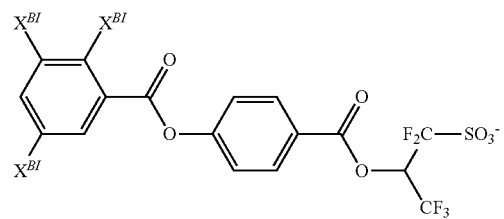
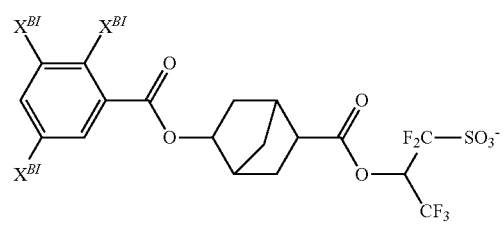
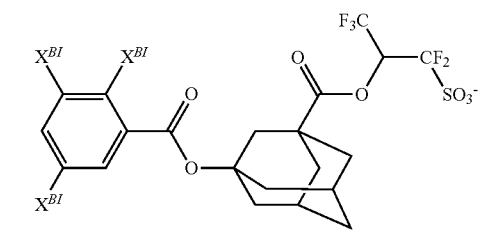
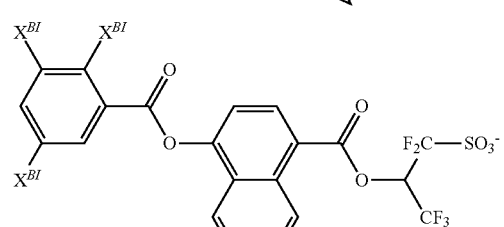
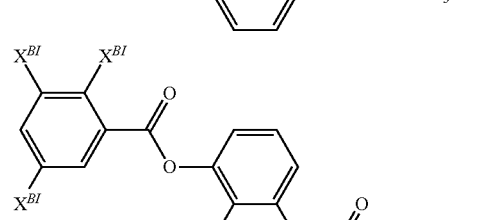
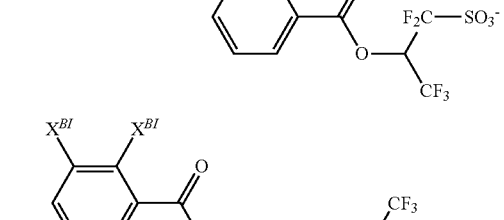
278
-continued
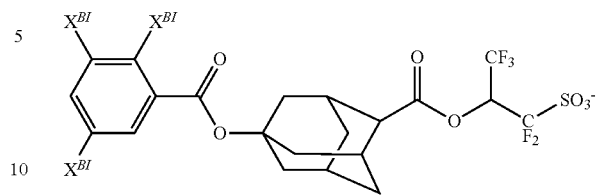
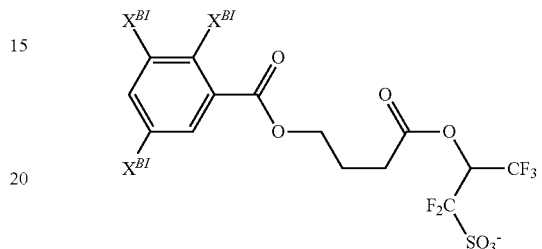
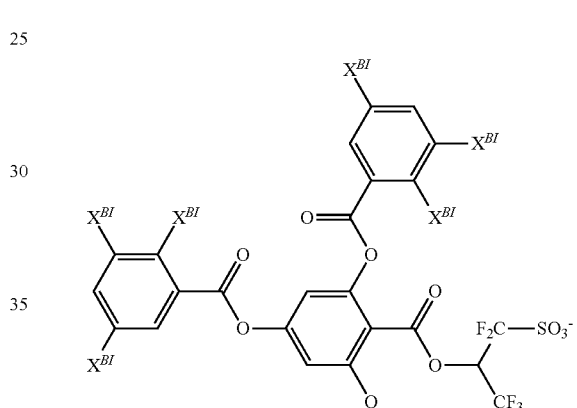
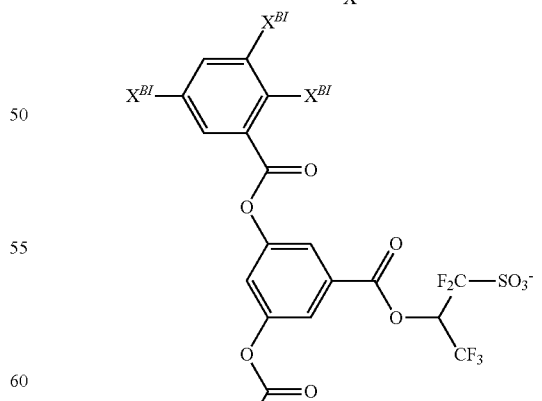

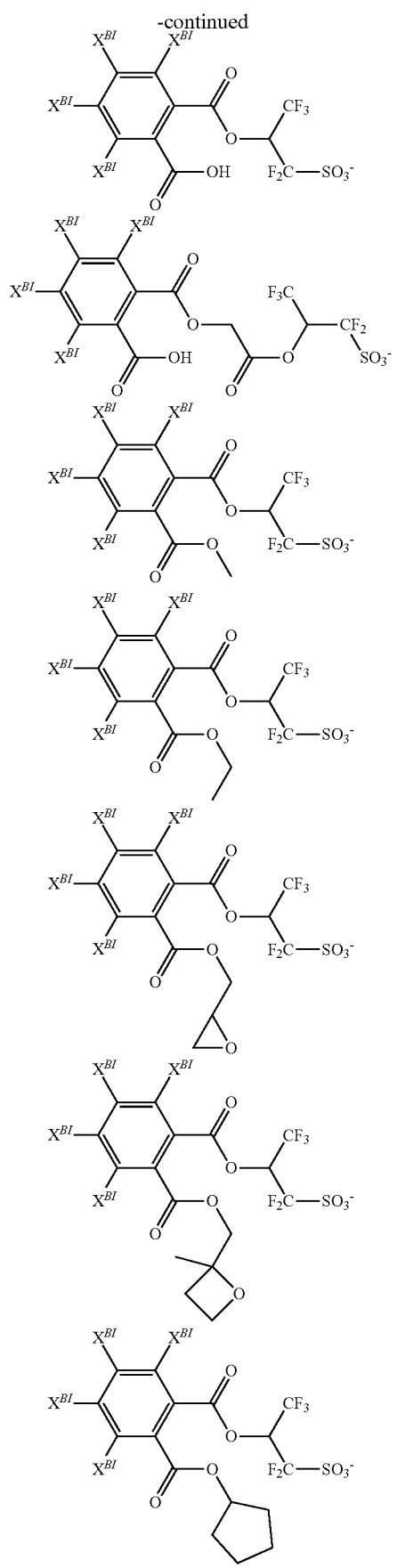
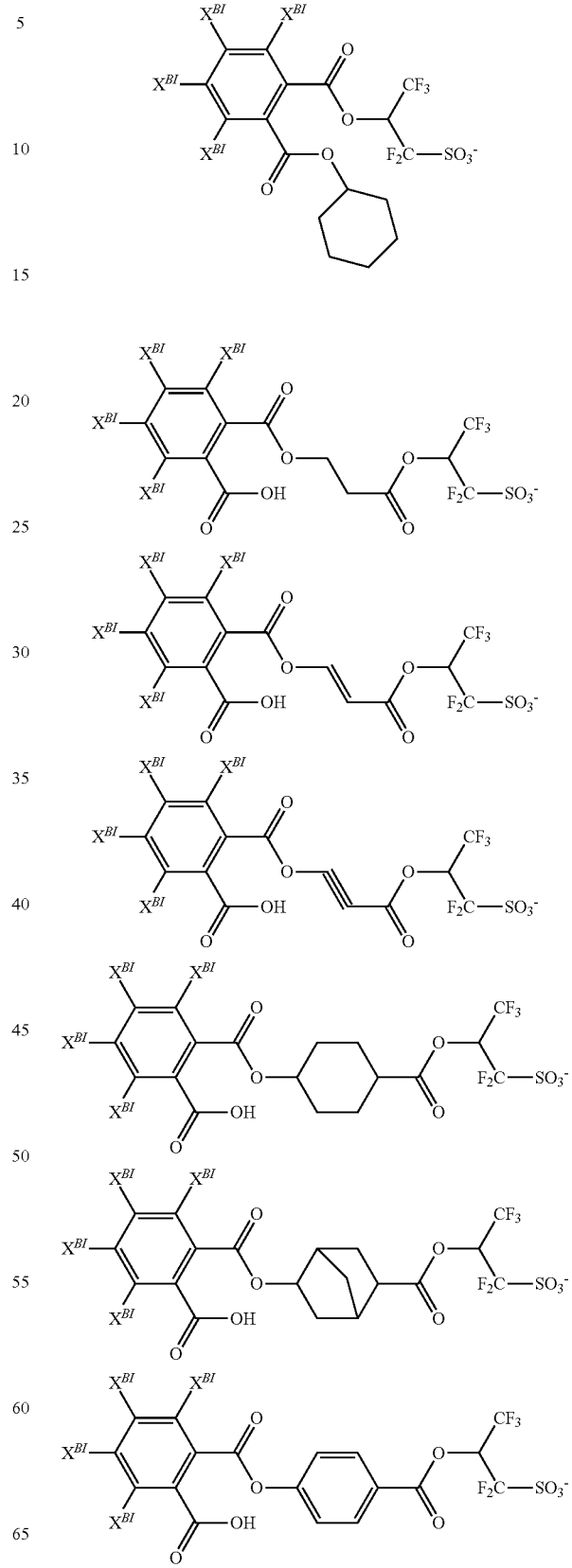

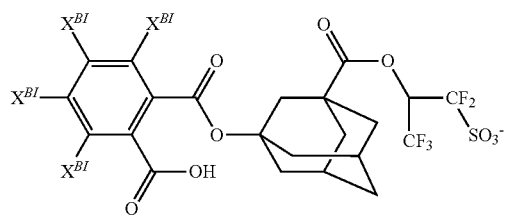
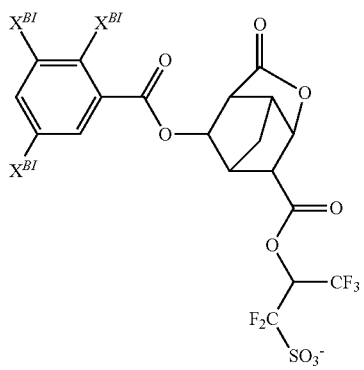
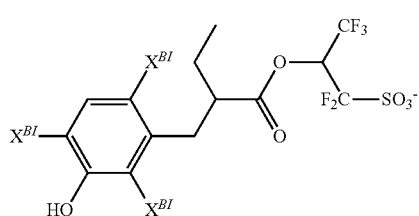
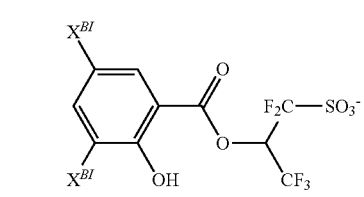
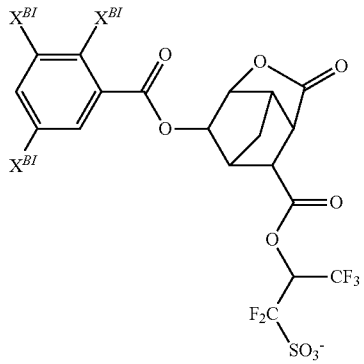
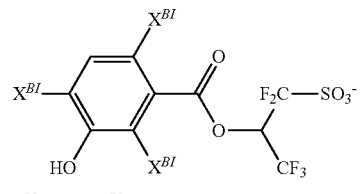
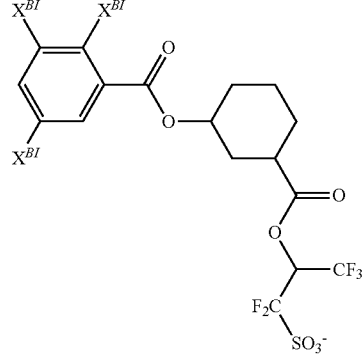
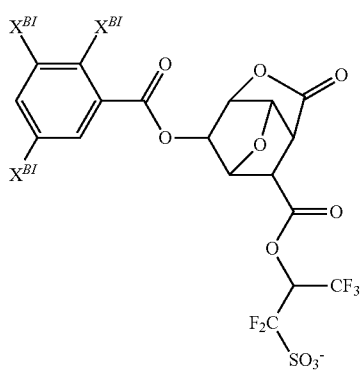
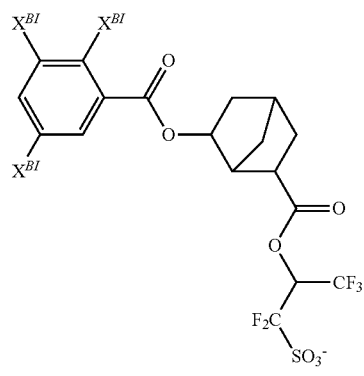
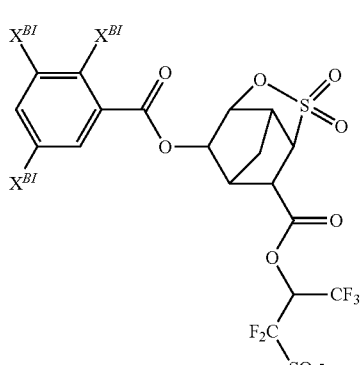

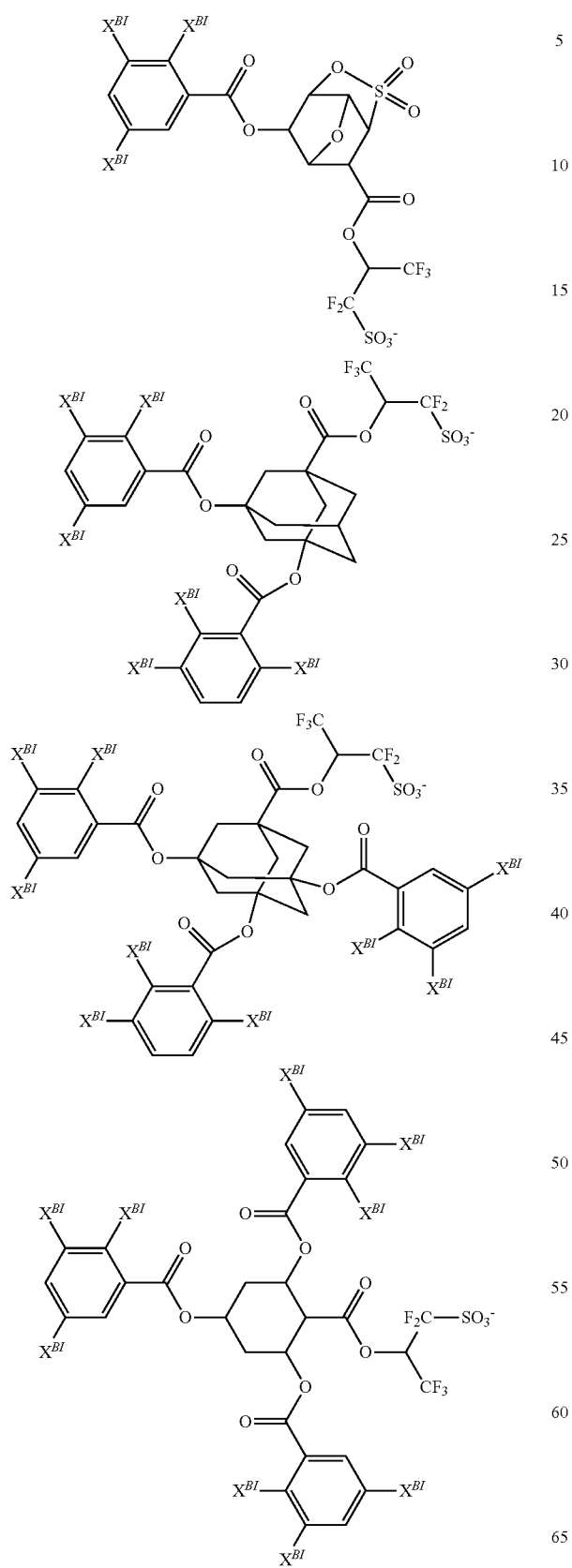
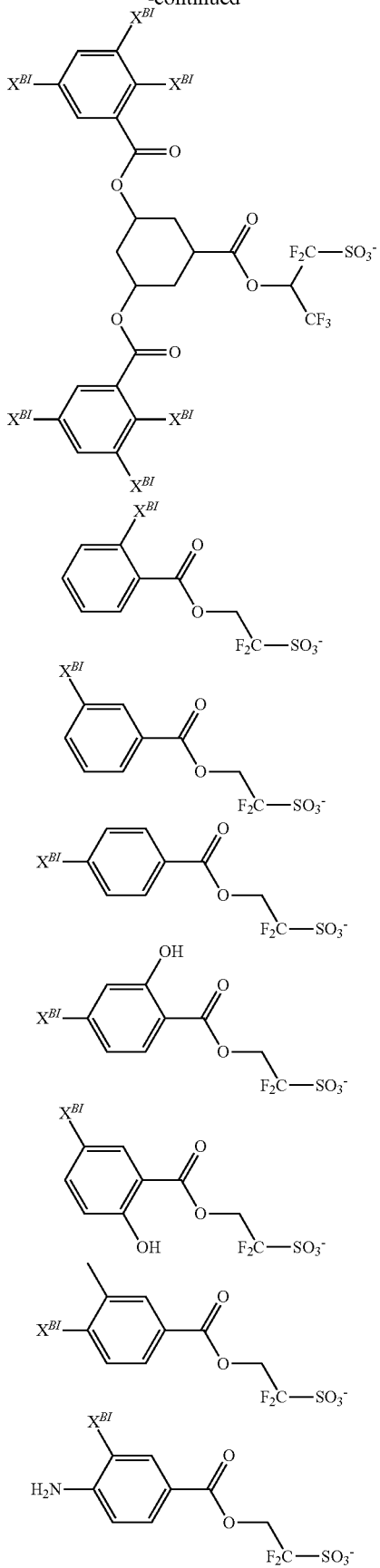

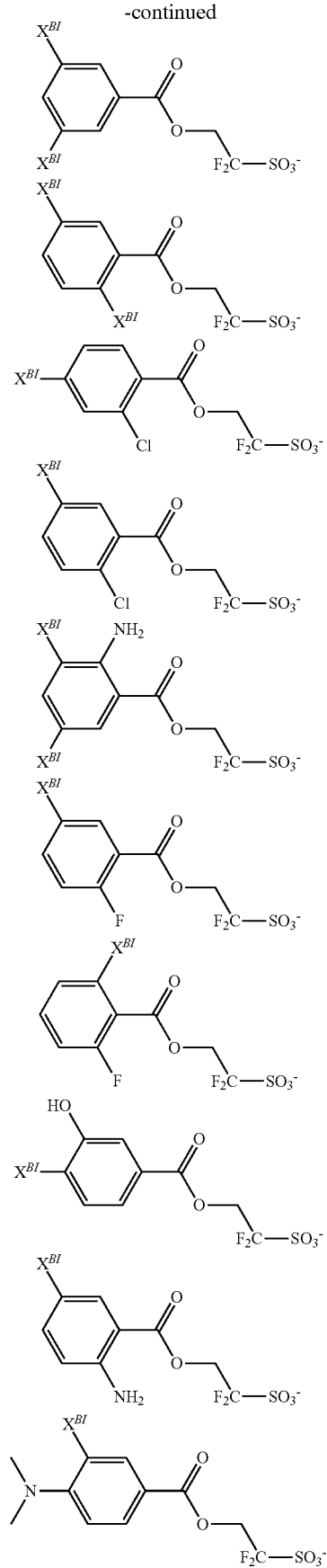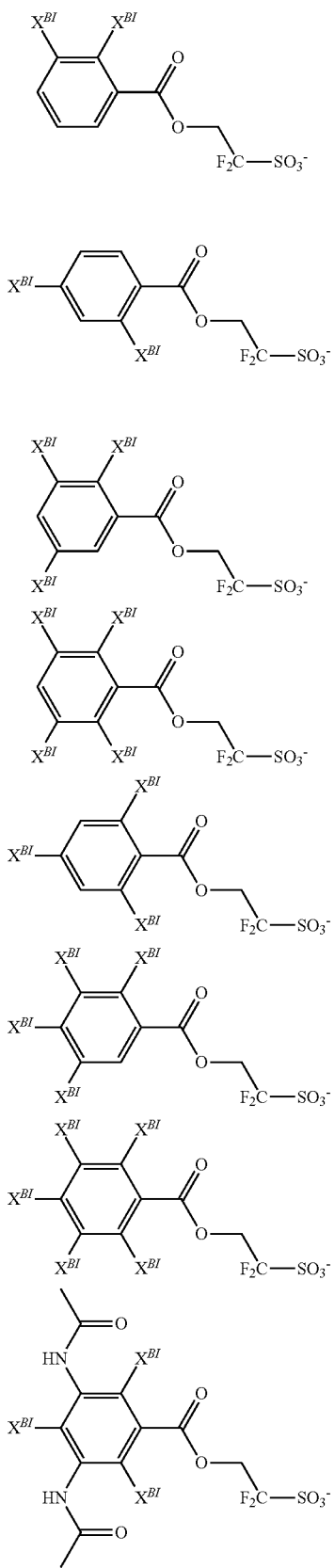

287
-continued
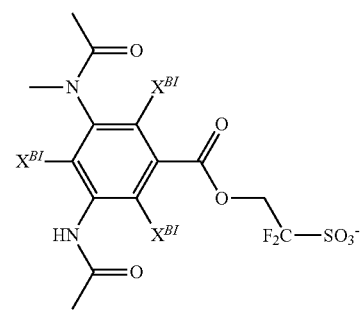
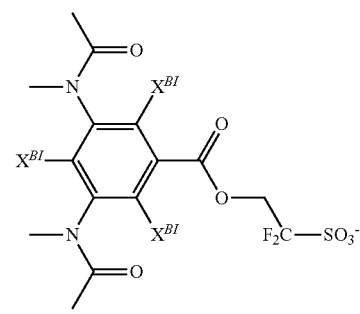
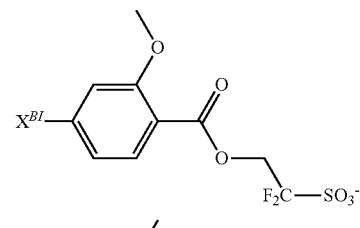
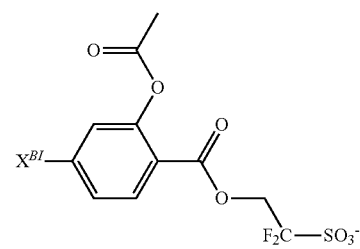
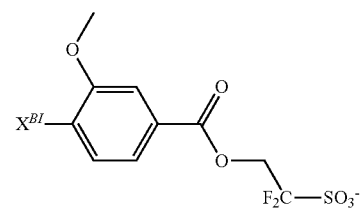
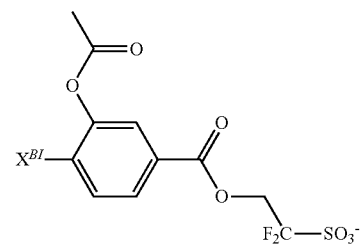
288
-continued
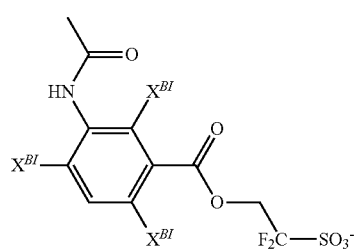
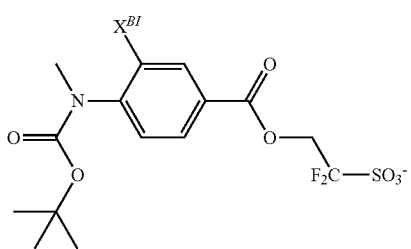
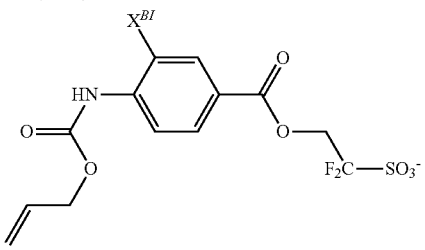
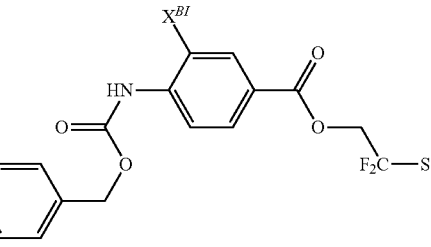
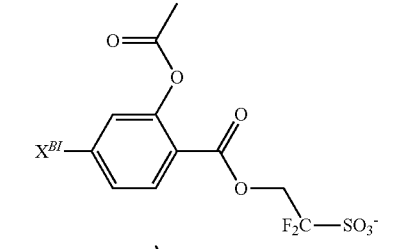
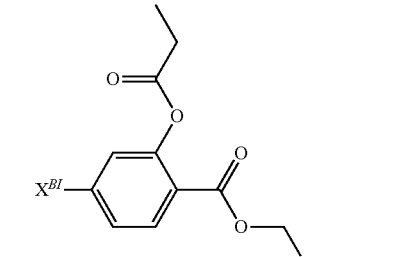

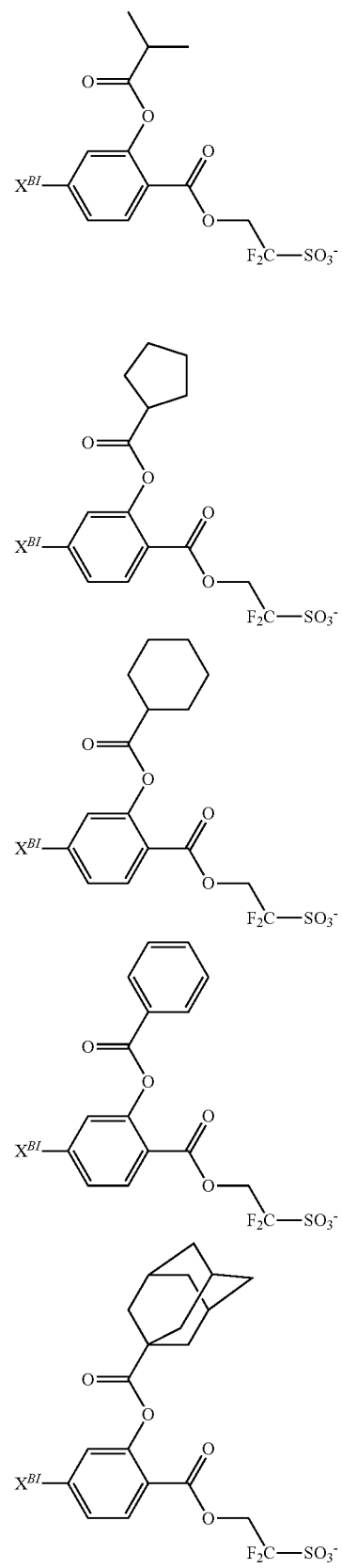
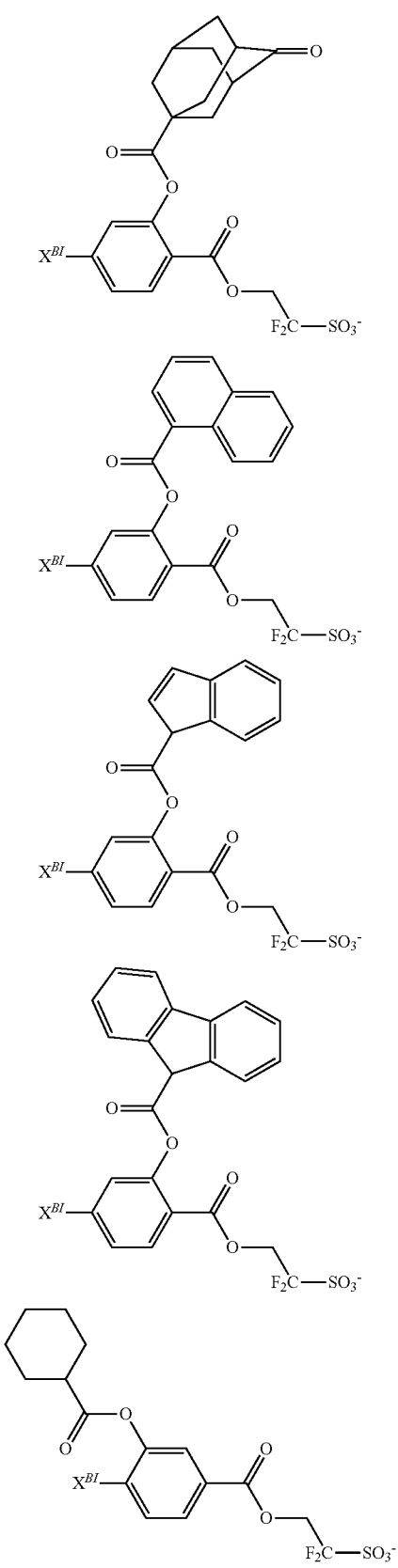

291
-continued
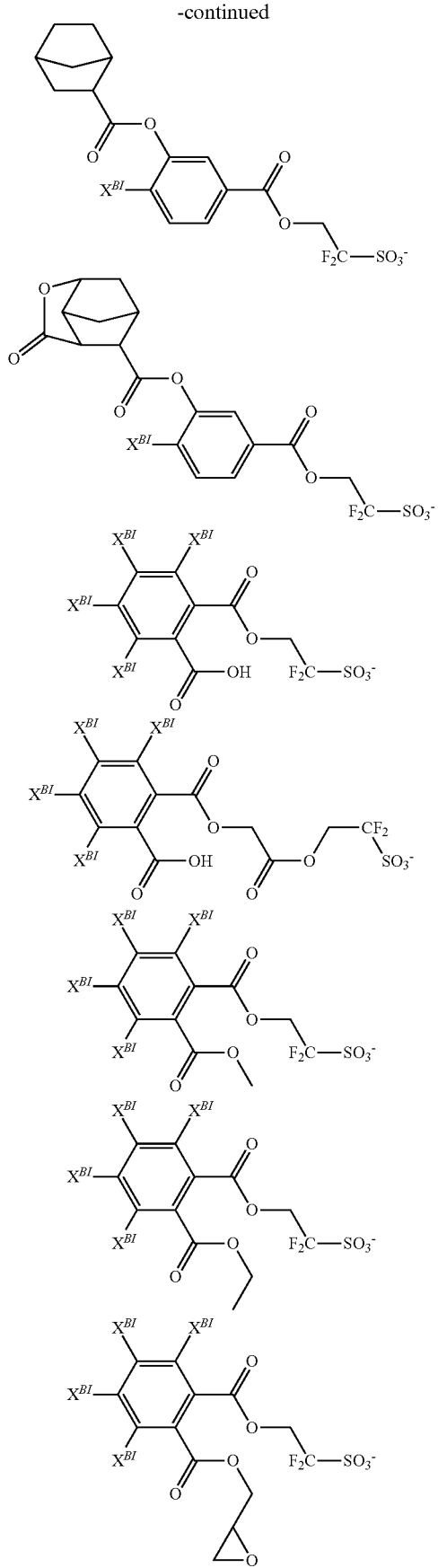
292
-continued
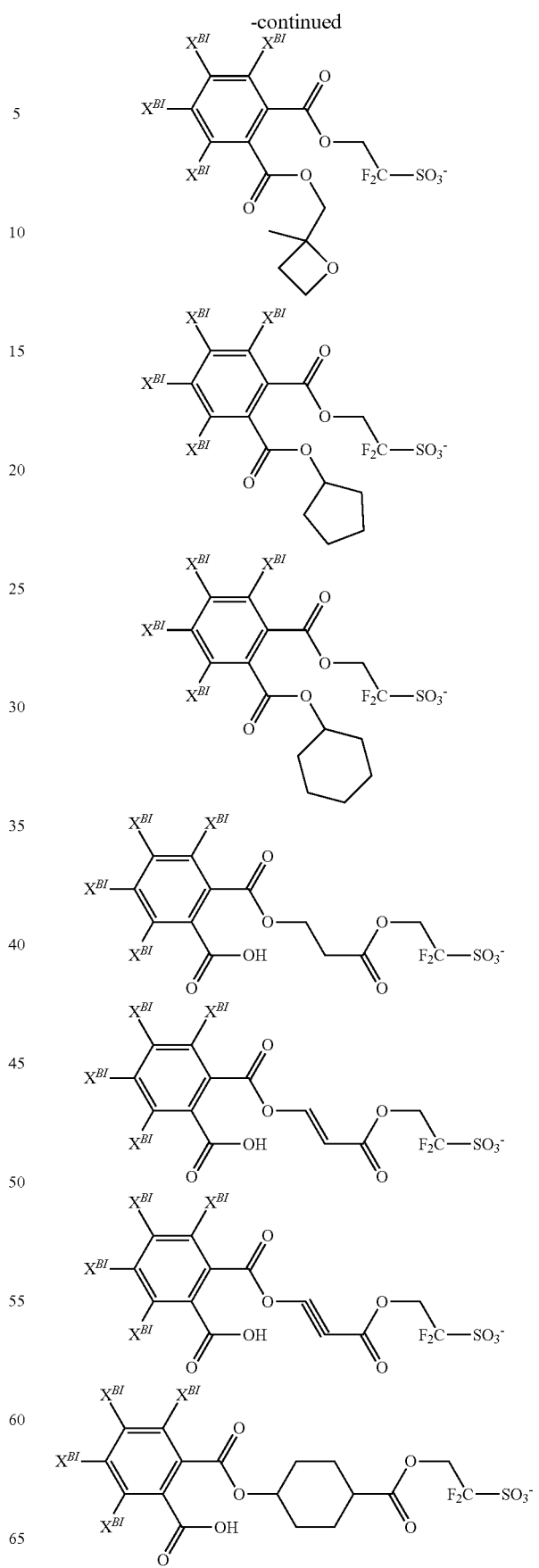

293
-continued
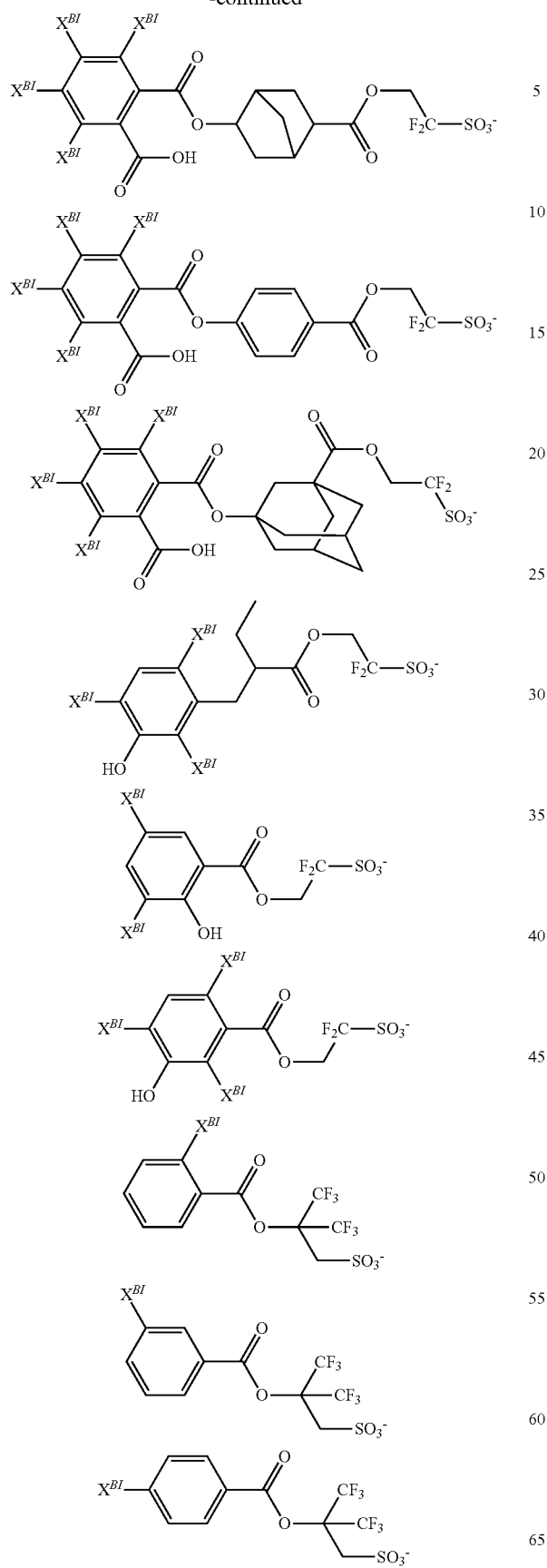
294
-continued
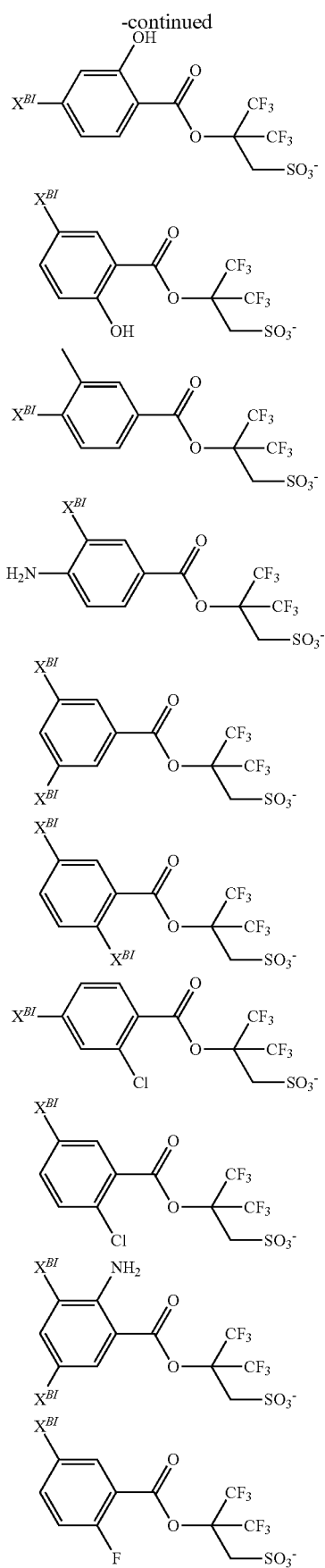

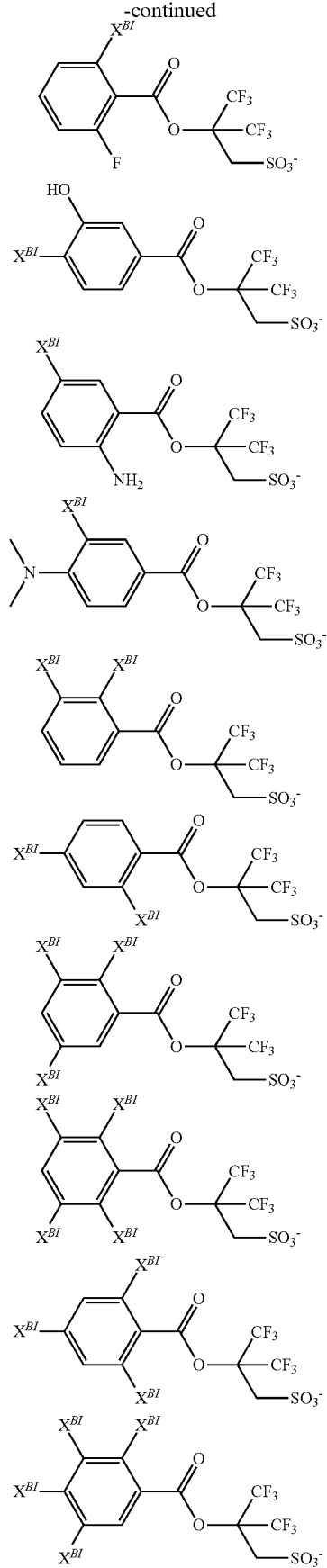
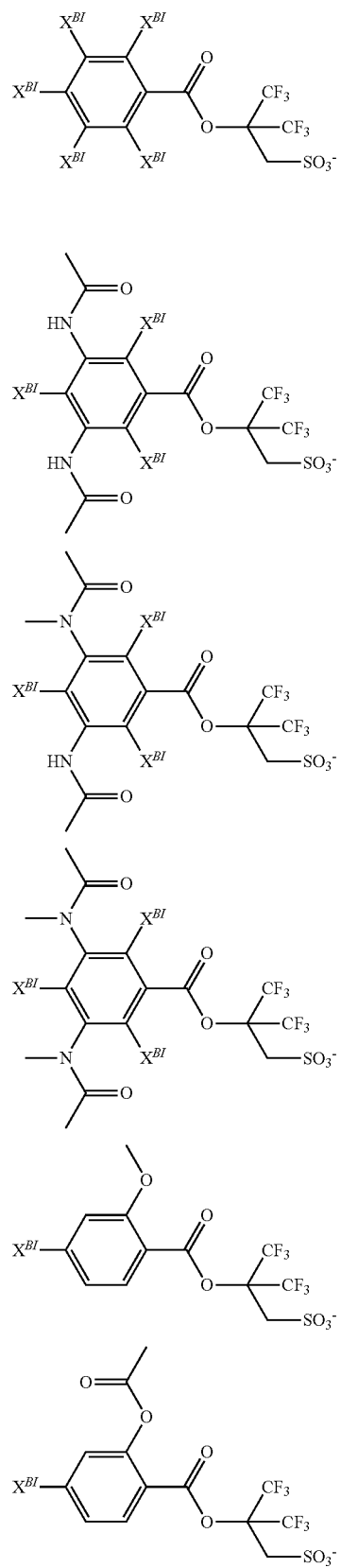

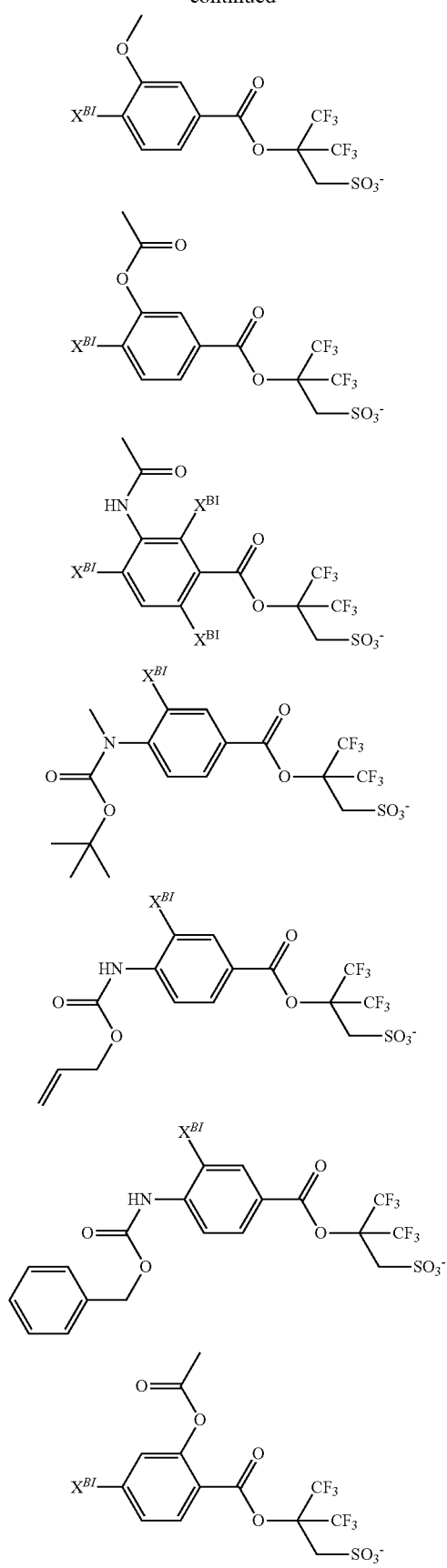
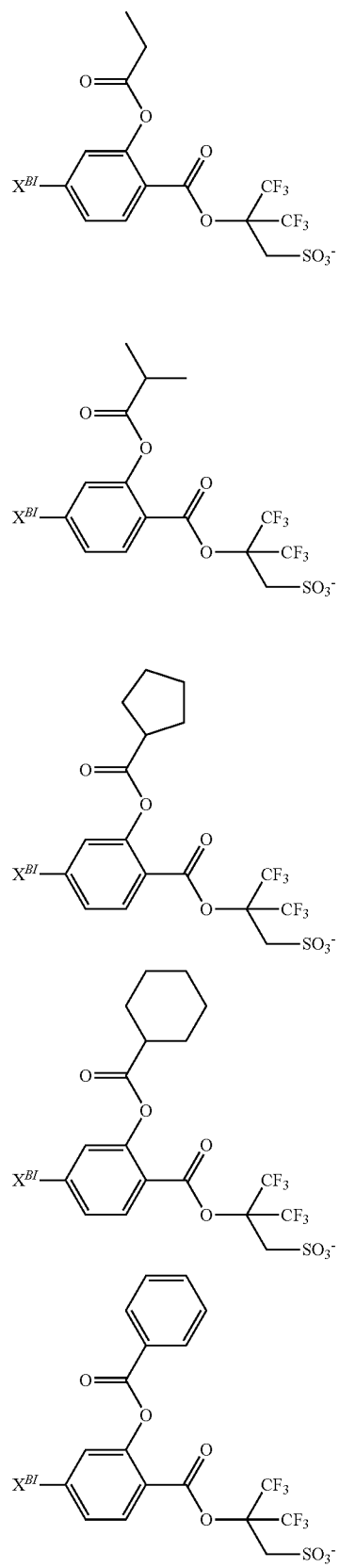

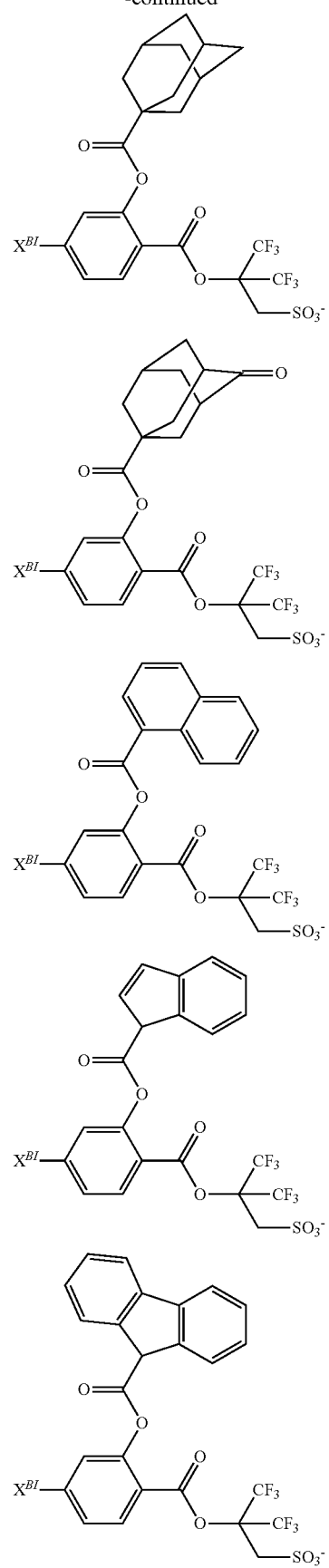

301
-continued
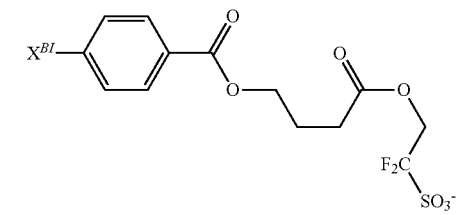
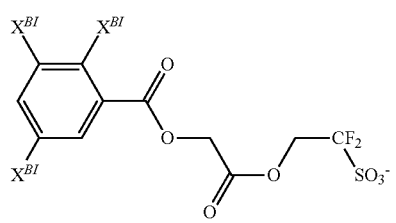
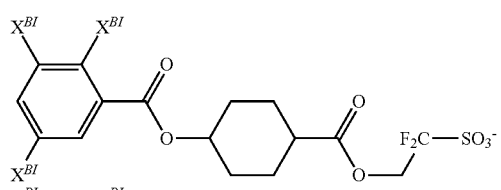
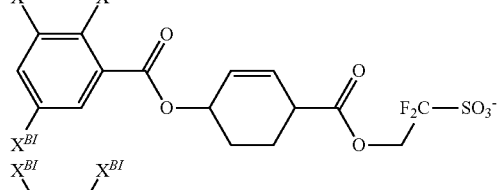
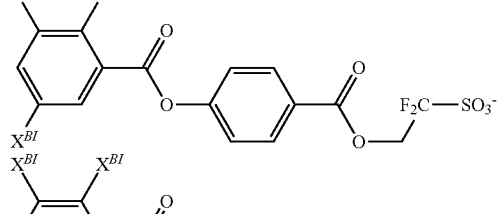
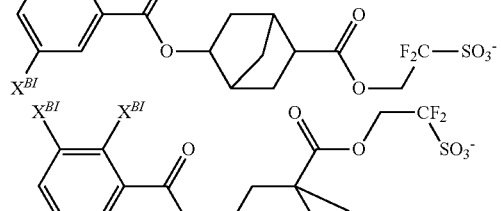
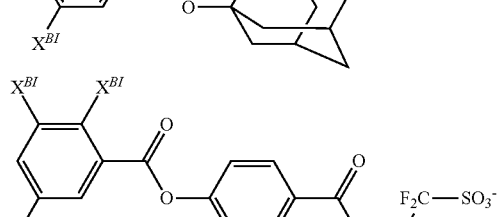
302
-continued
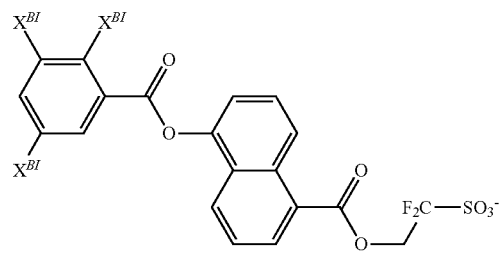
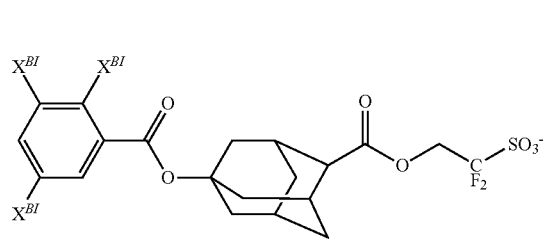
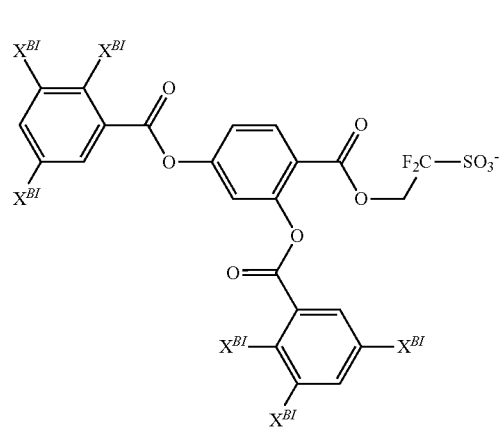
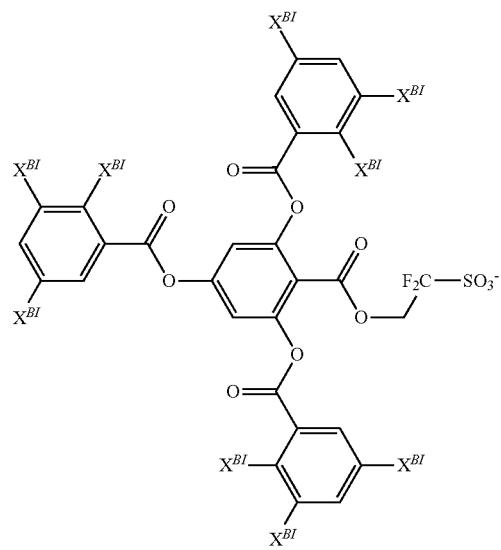

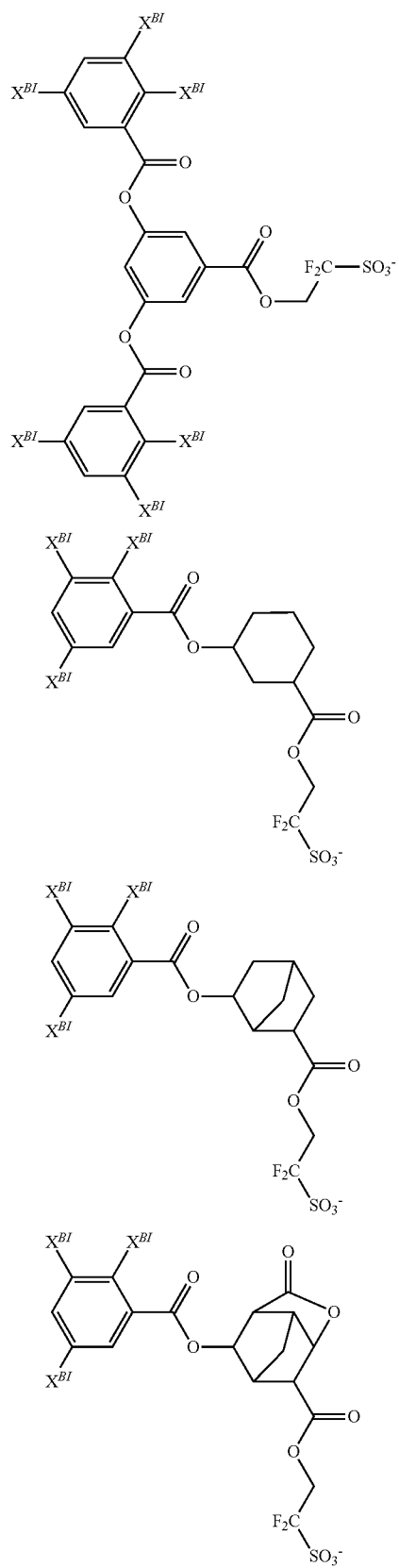
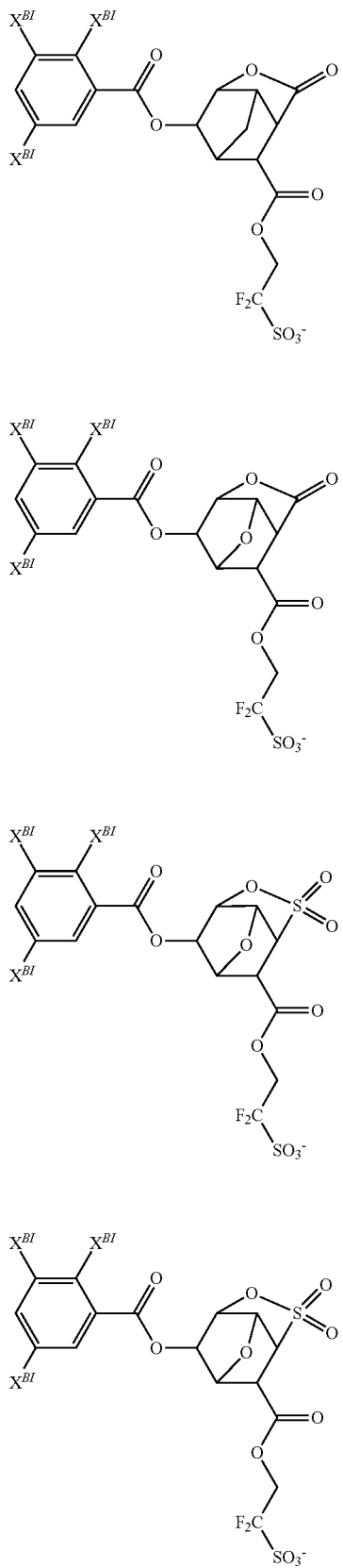

305
-continued
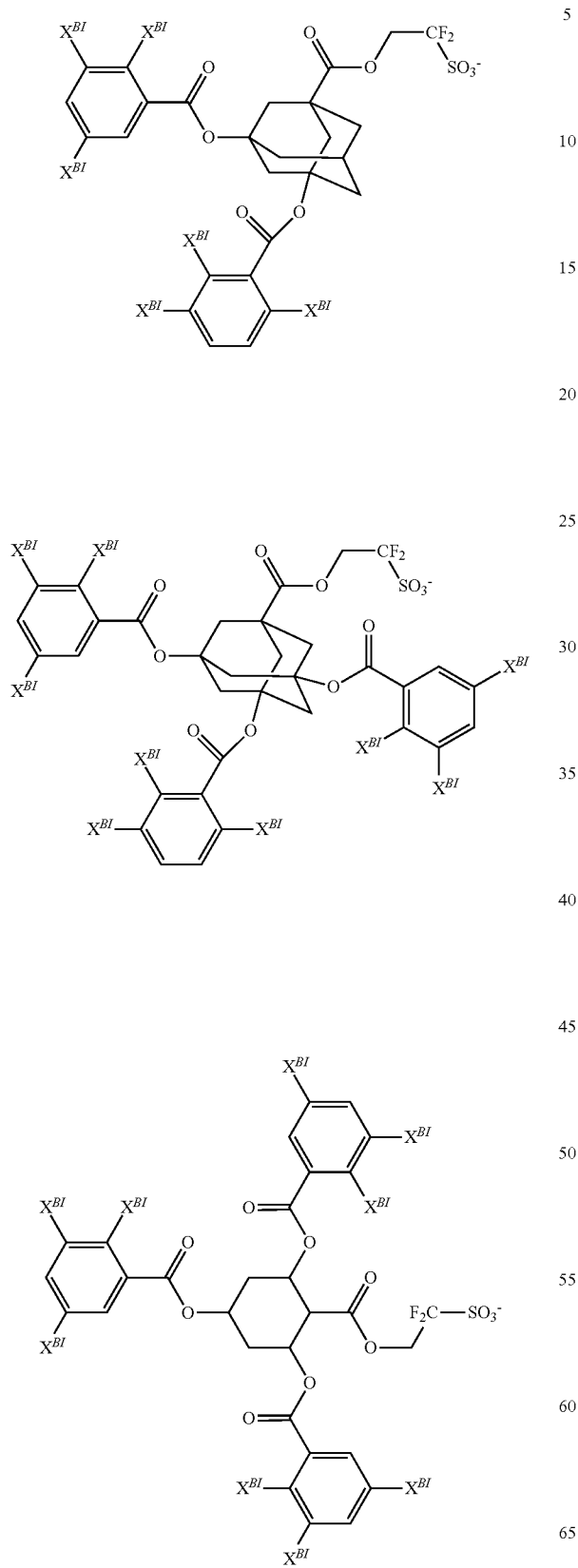
306
-continued
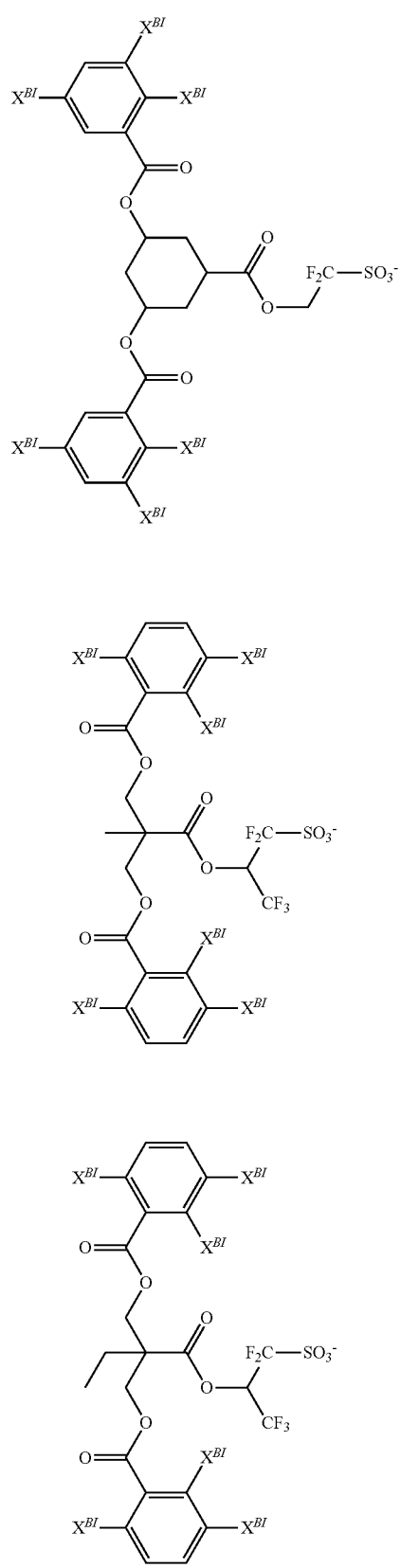

307
-continued
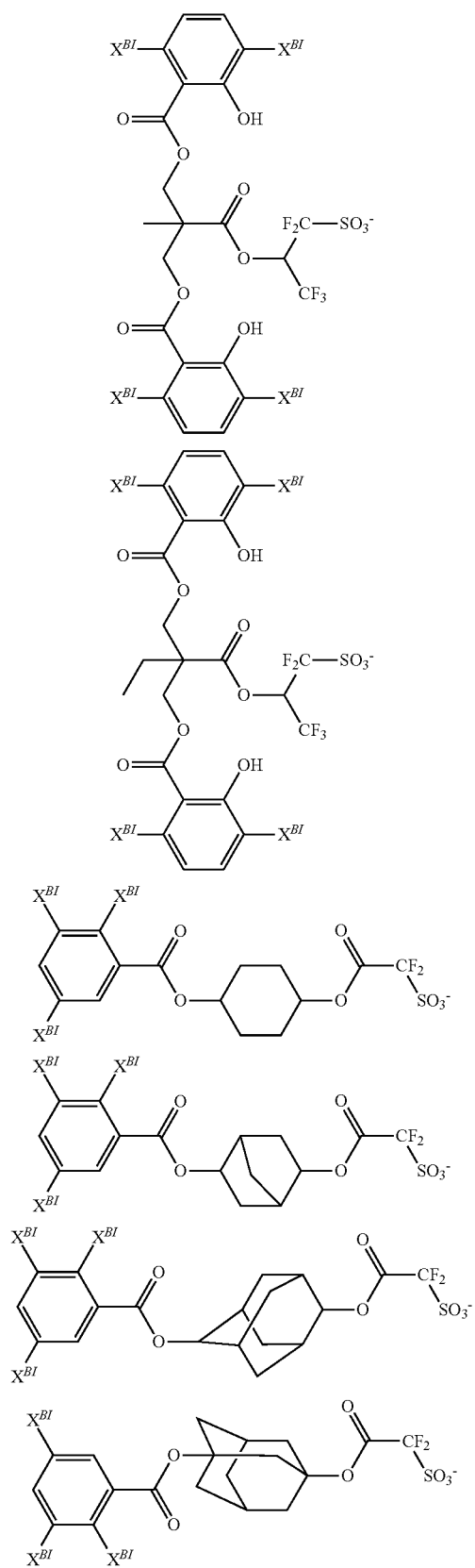
308
-continued
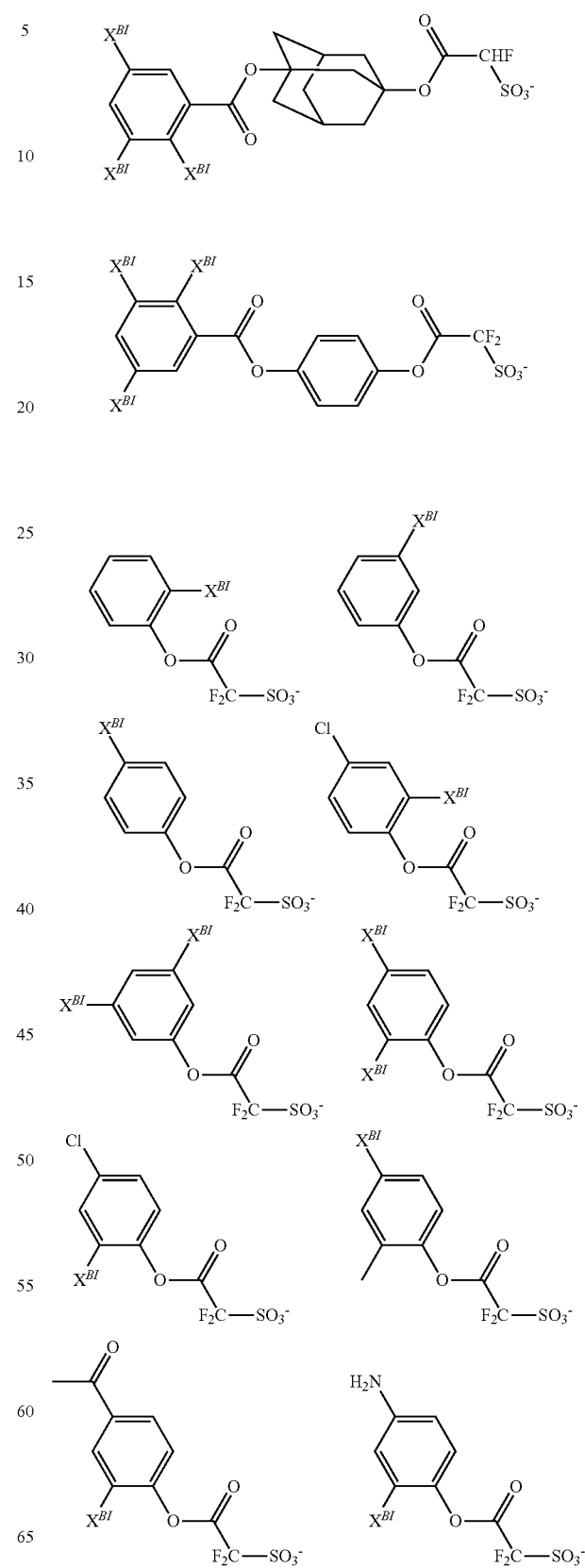

309
-continued
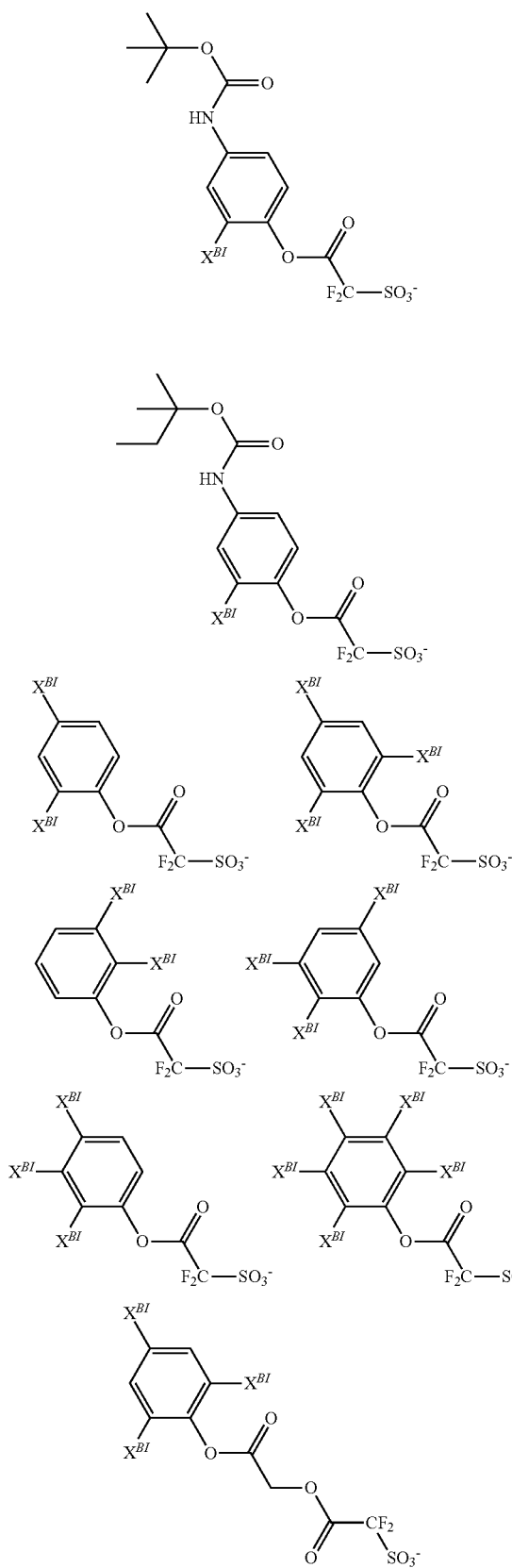
310
-continued
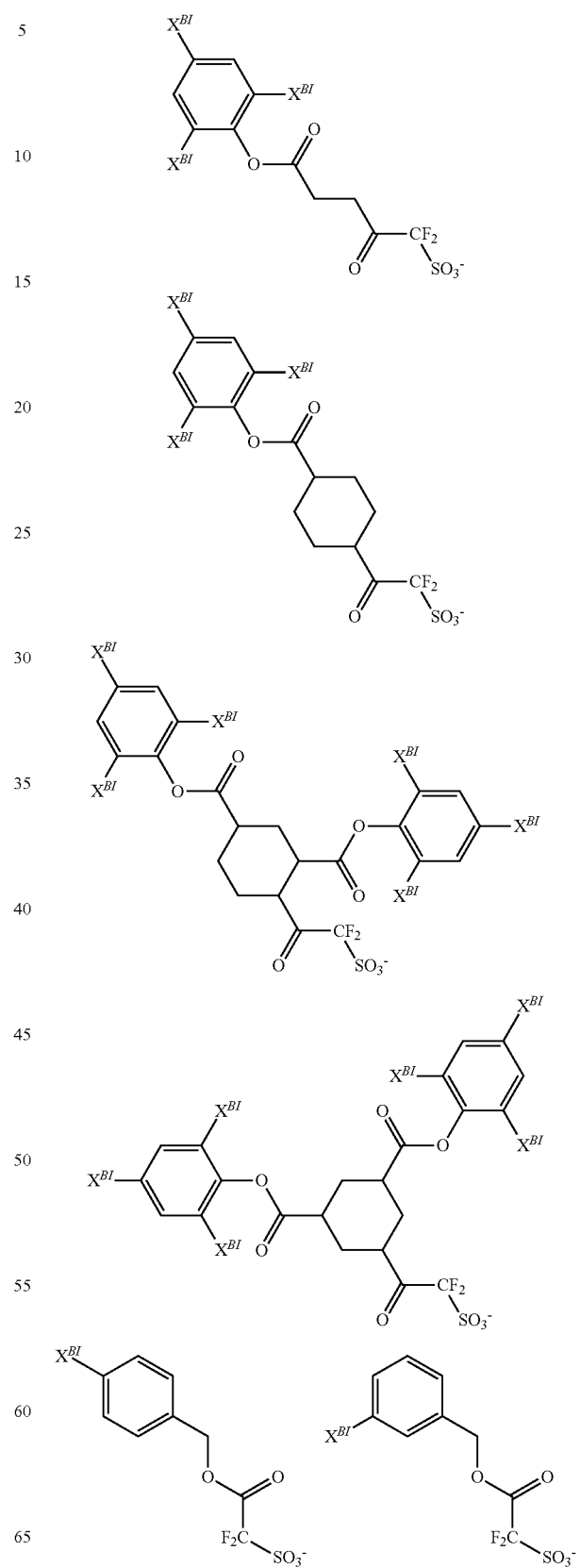

-continued
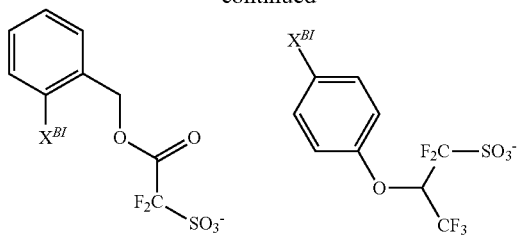
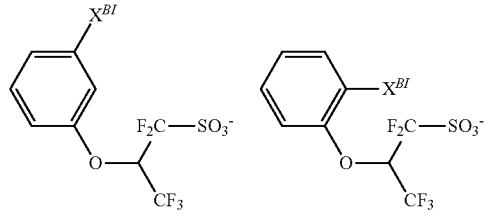
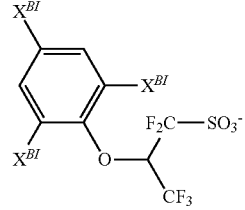
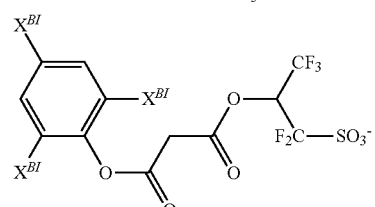
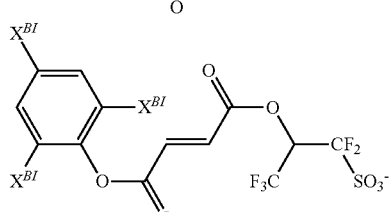
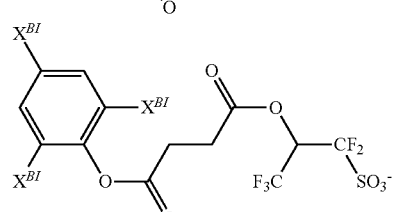
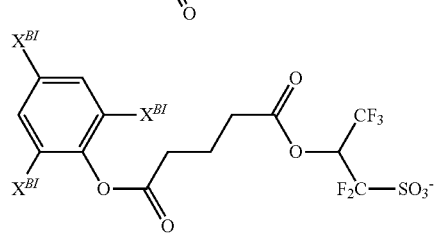
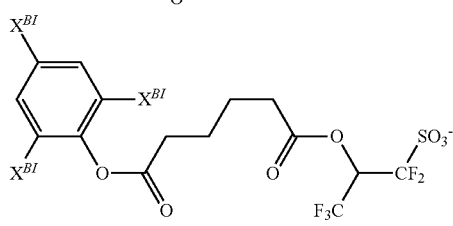
-continued
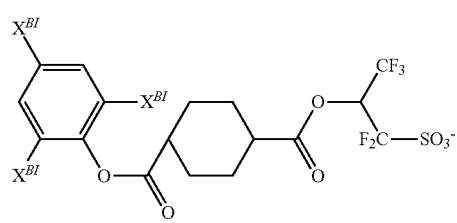
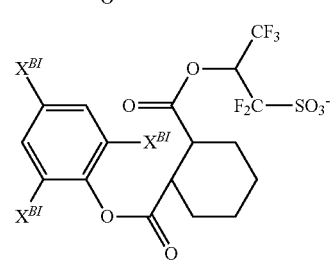
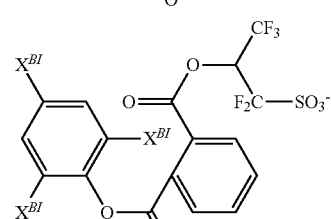
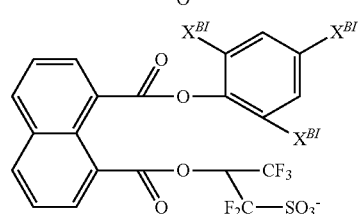
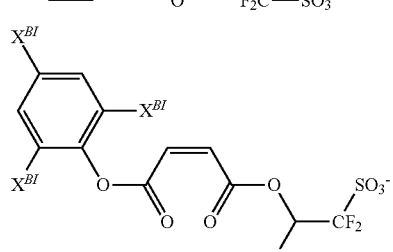
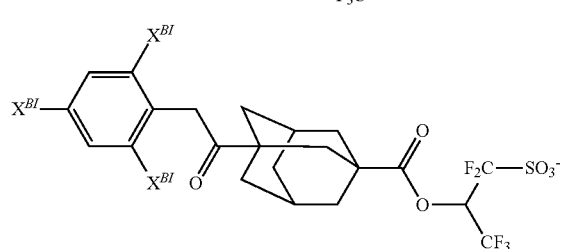
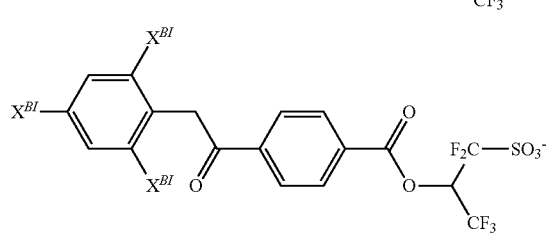

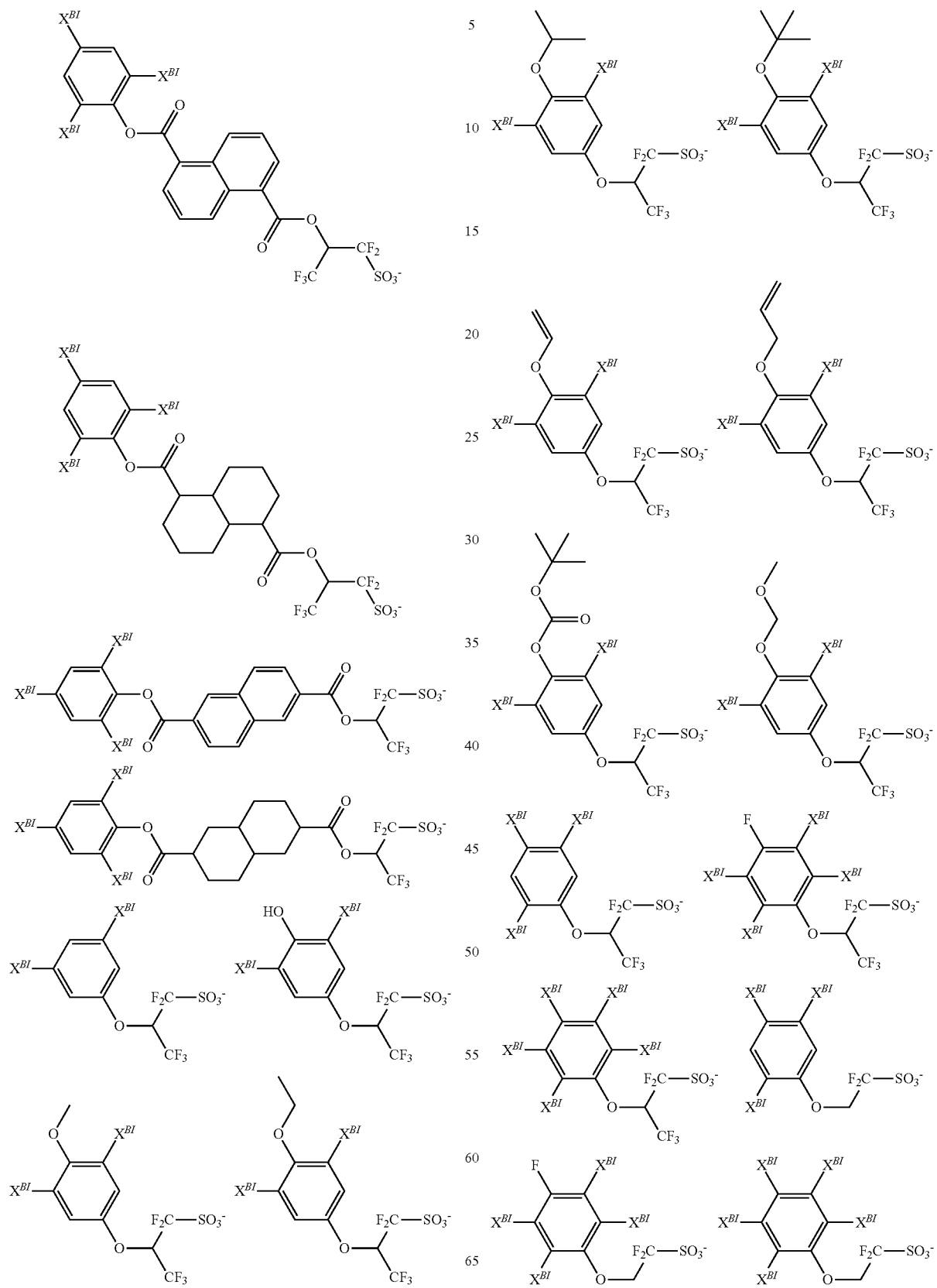

315
-continued
316
-continued
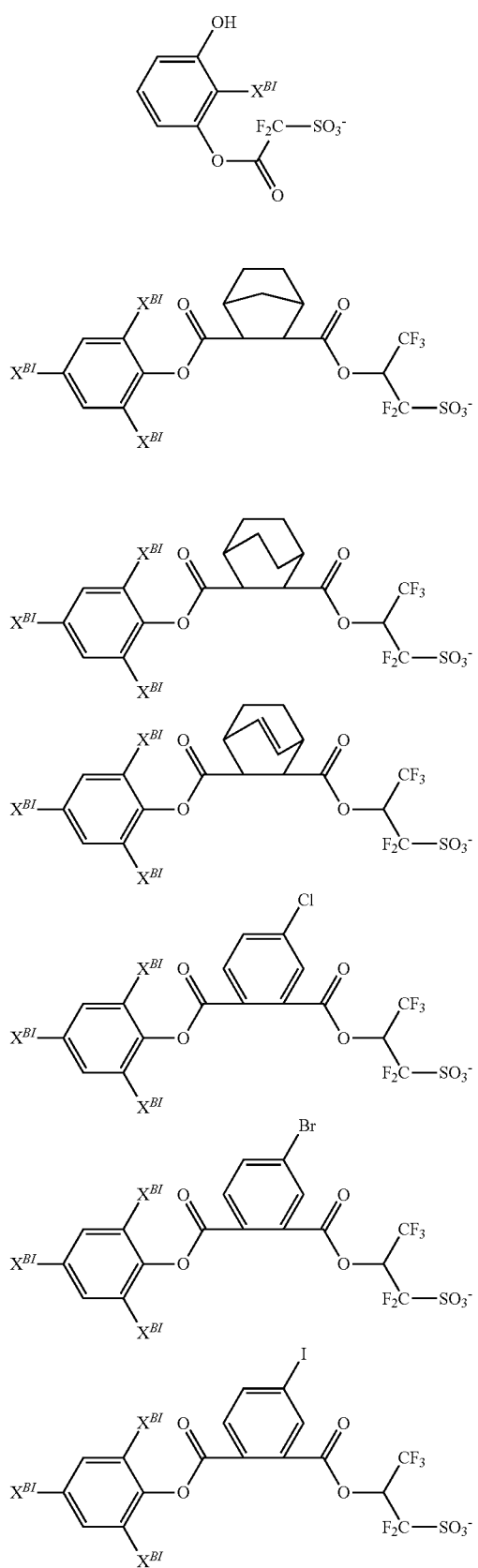
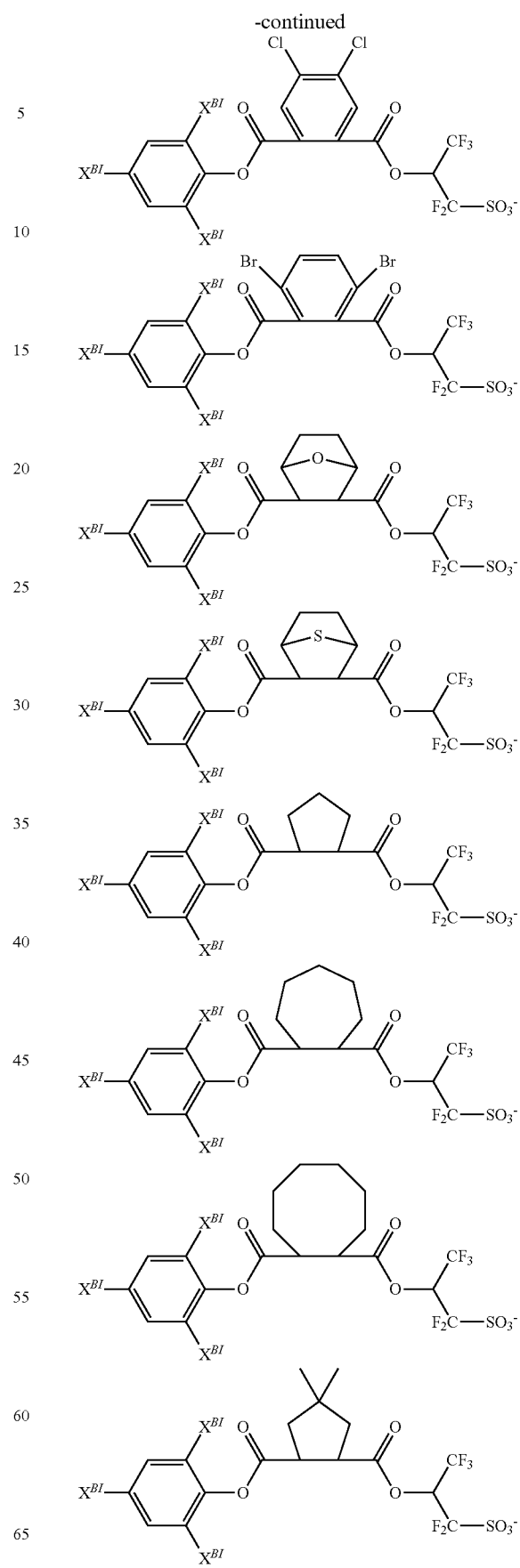

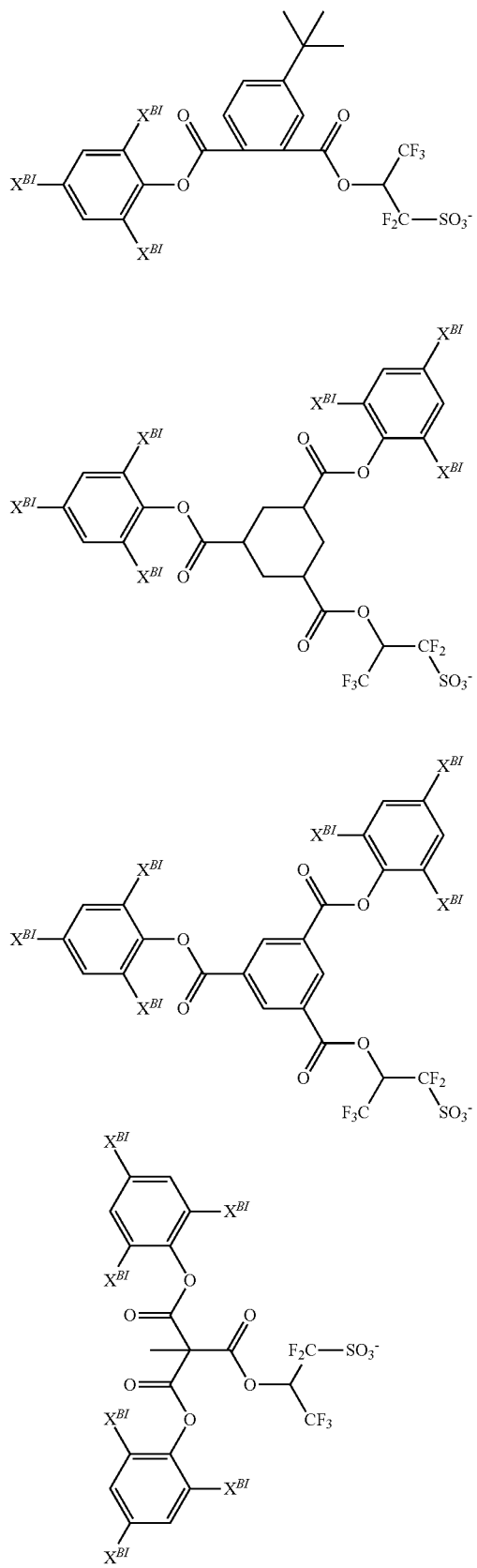
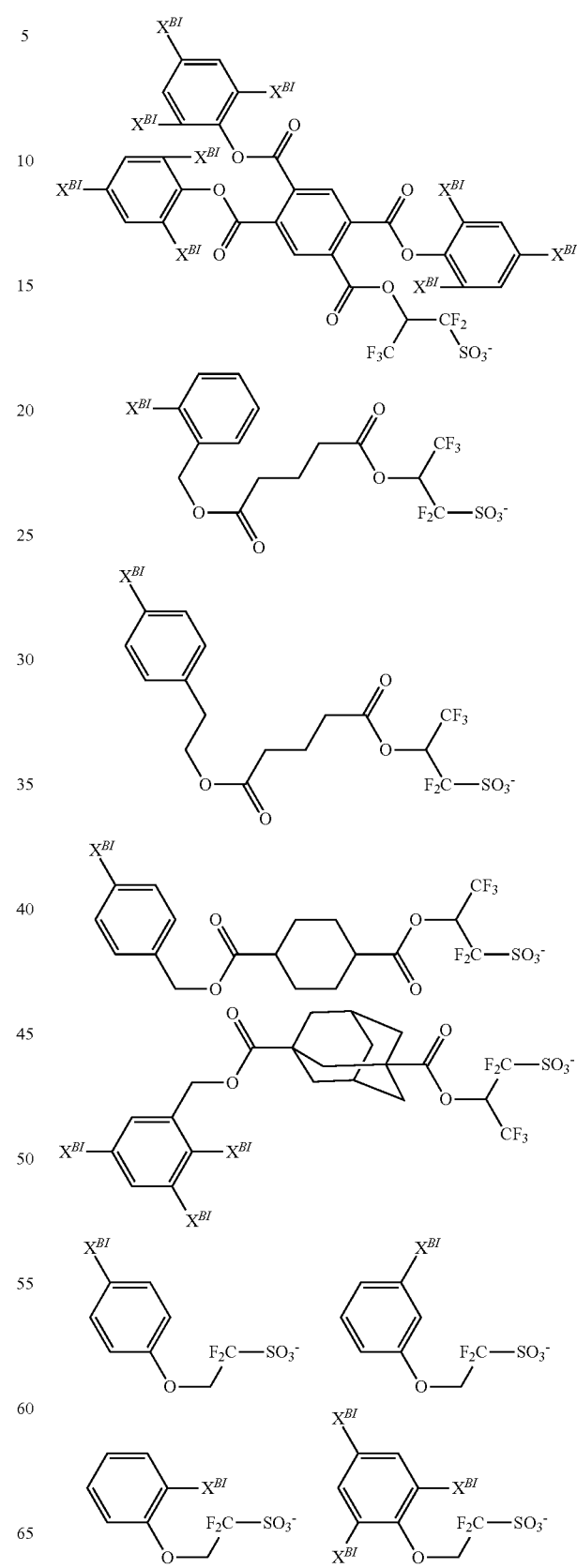

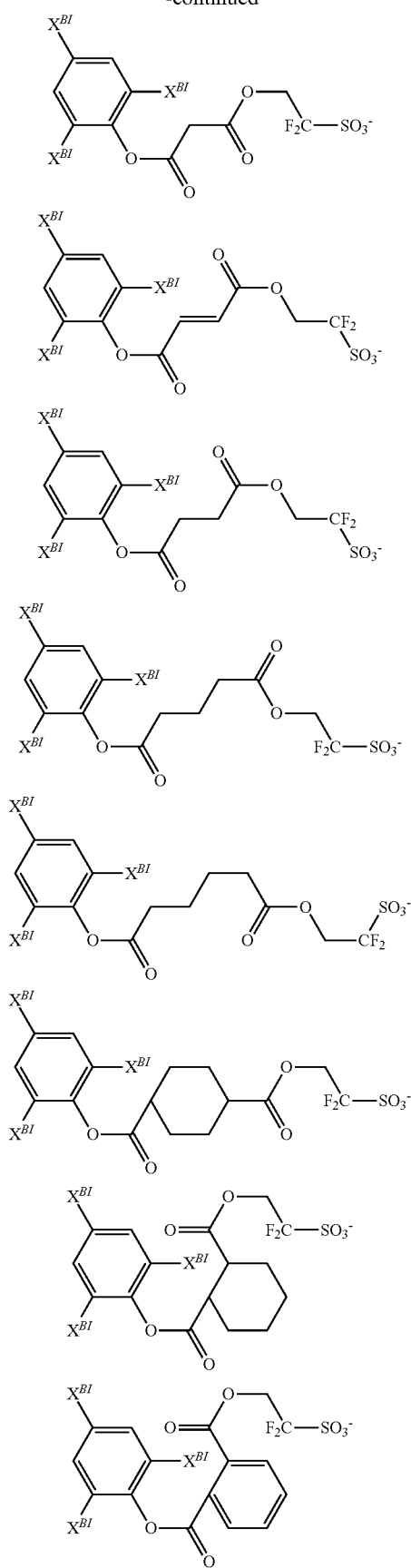
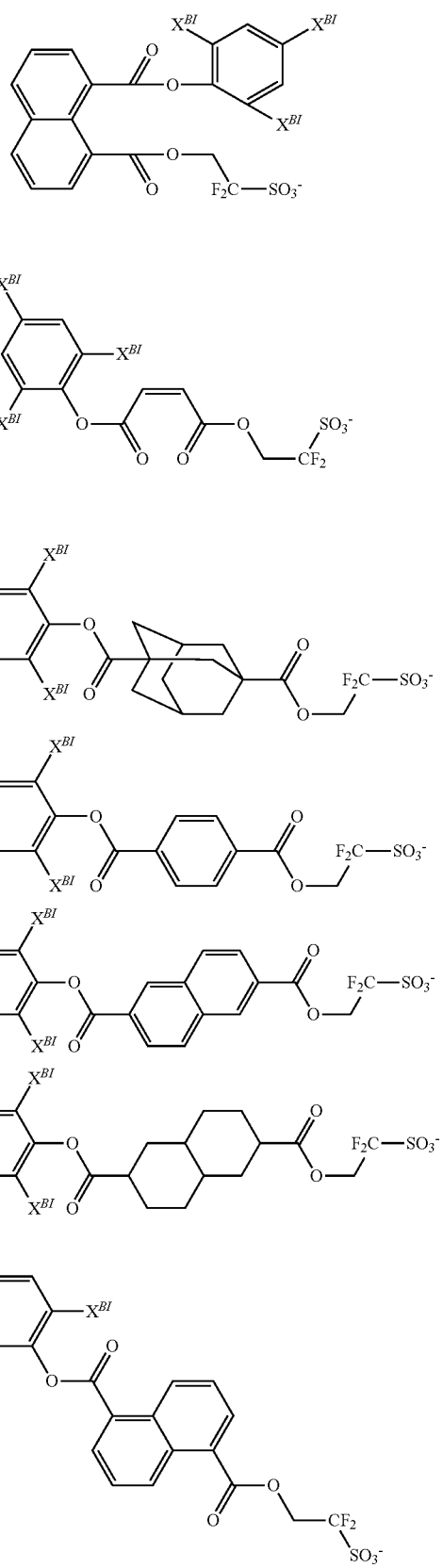

321
-continued
322
-continued
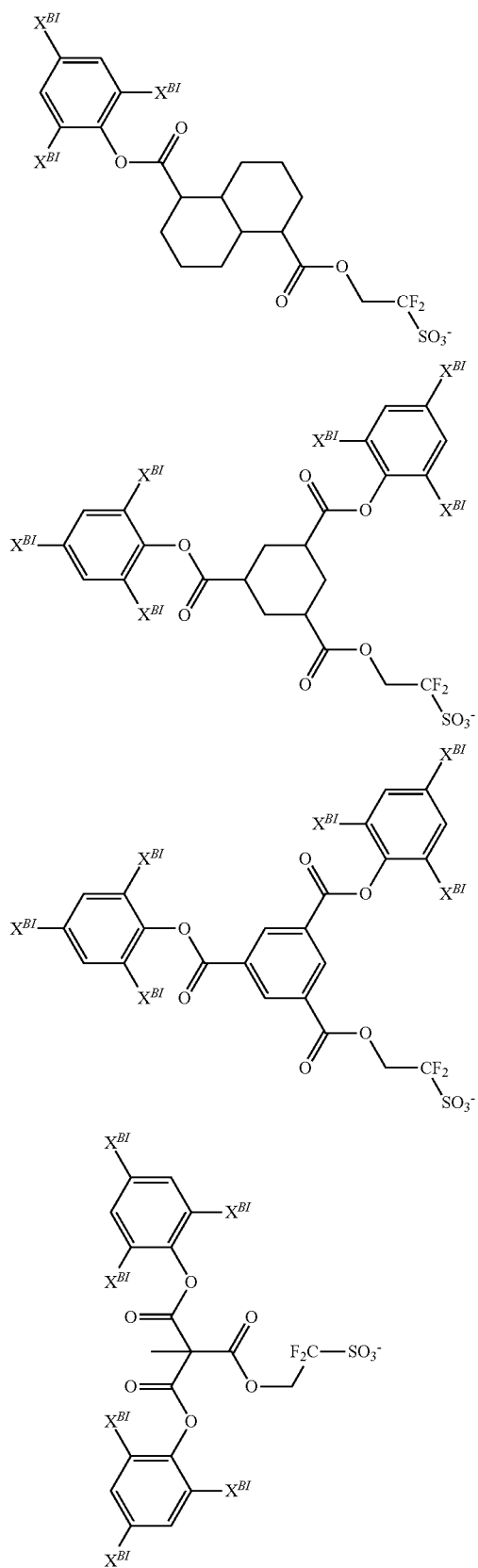
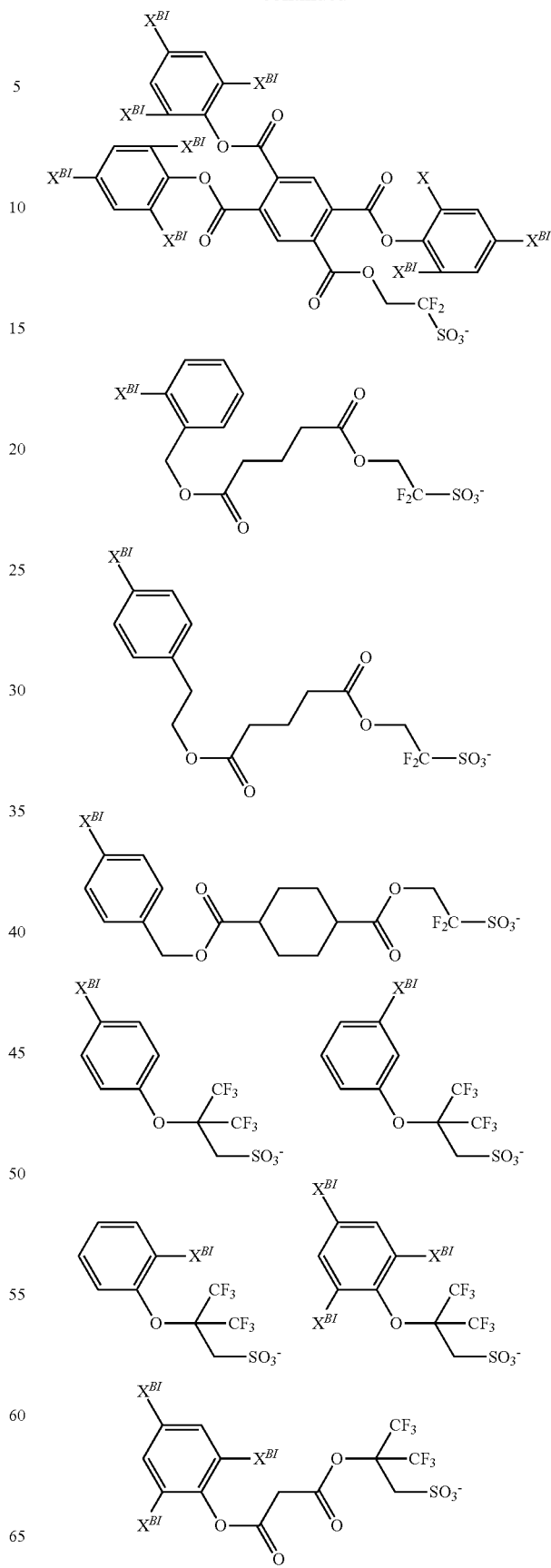

323
-continued
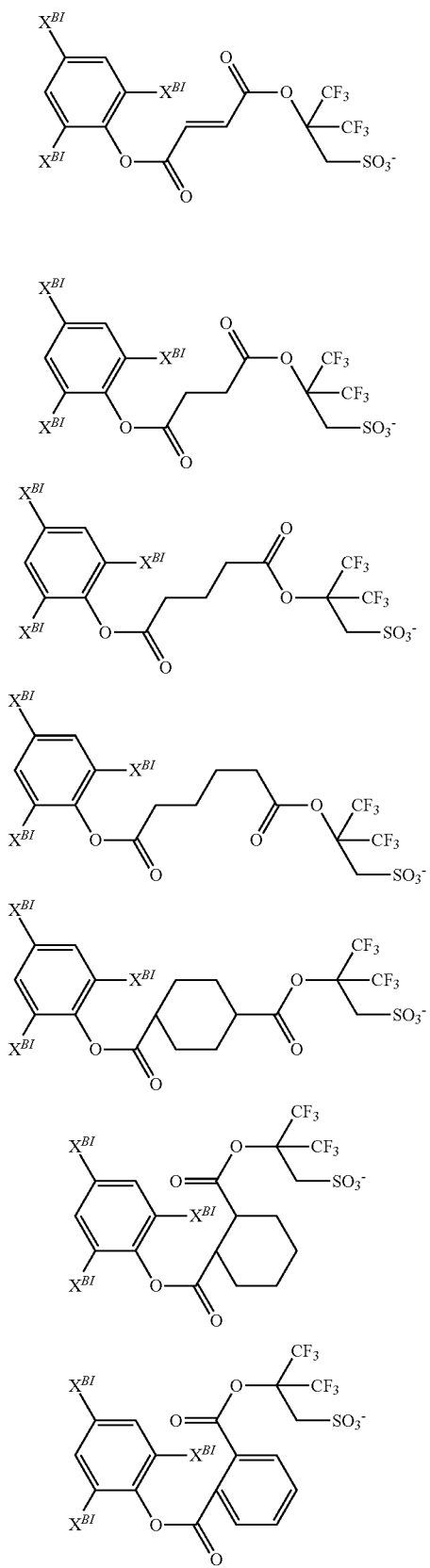
324
-continued
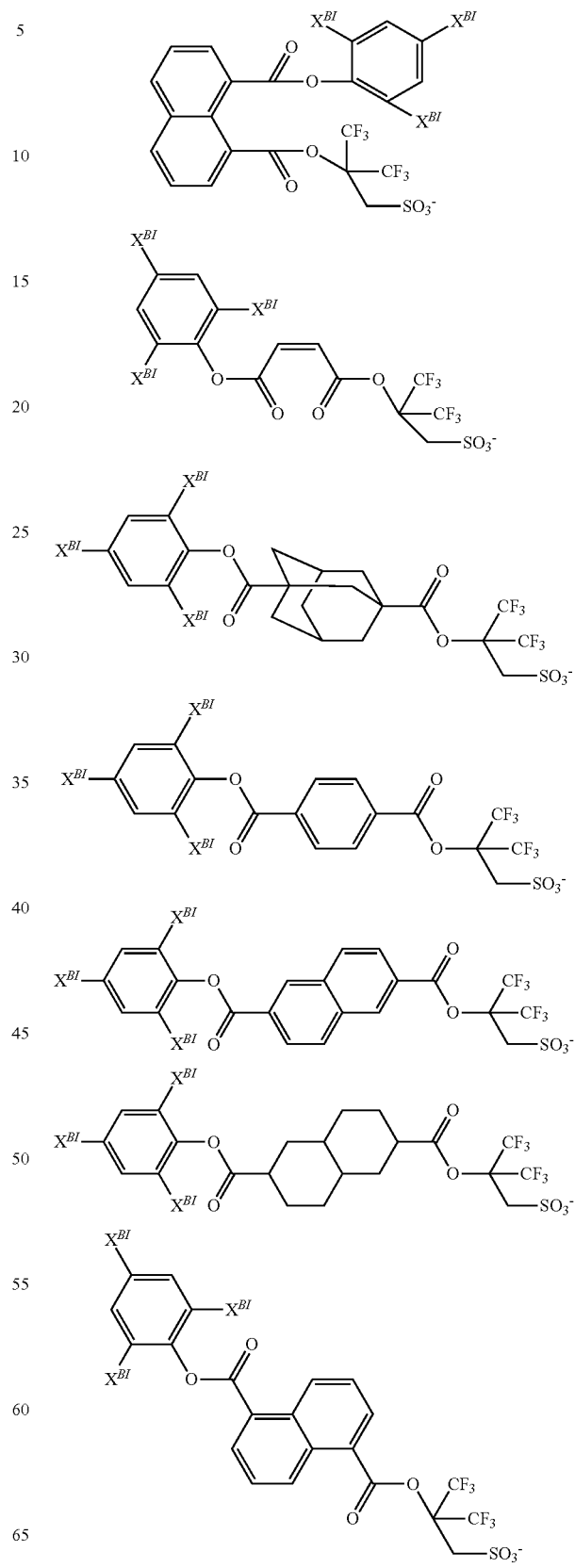

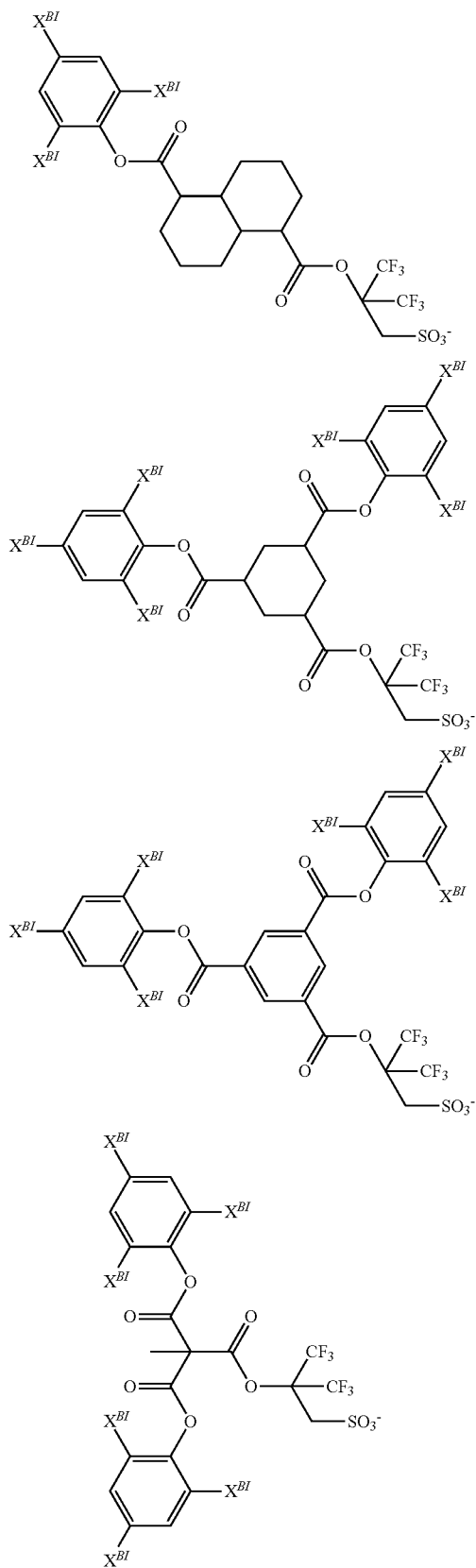

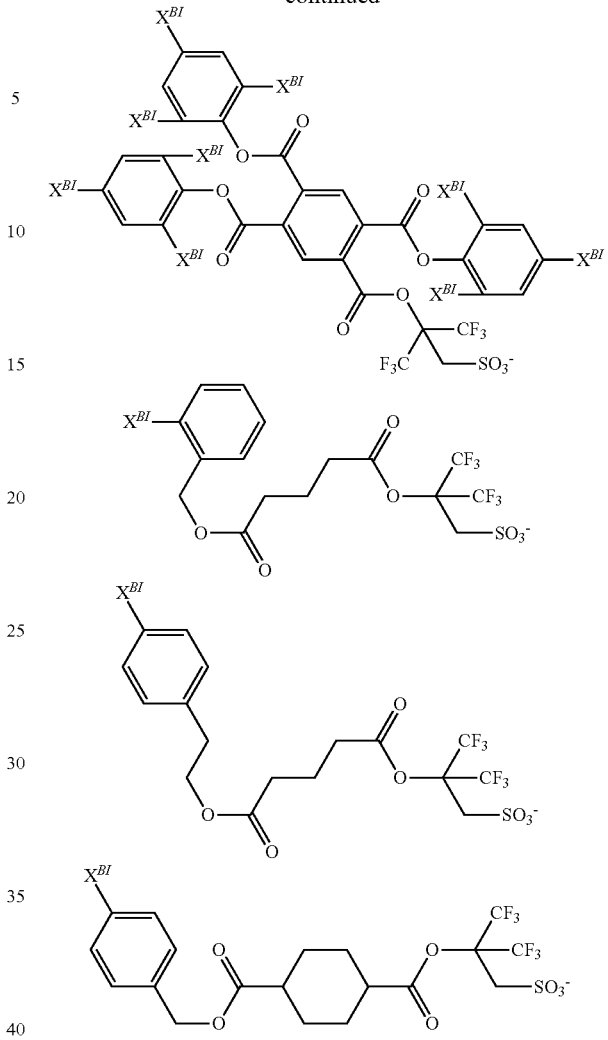

When the resist composition contains the acid generator of addition type, its content is preferably 0.1 to 50 parts by weight, and more preferably 1 to 40 parts by weight per 100 parts by weight of the base polymer. When the base polymer contains repeat units (f) and/or the resist composition contains the acid generator of addition type, the resist composition functions as a chemically amplified resist composition.

Organic Solvent

An organic solvent may be added to the resist composition. The organic solvent used herein is not particularly limited as long as the foregoing and other components are soluble therein. Examples of the organic solvent are described in JP-A 2008-111103, paragraphs [0144]-[0145] (U.S. Pat. No. 7,537,880). Exemplary solvents include ketones such as cyclohexanone, cyclopentanone, methyl-2-n-pentyl ketone and 2-heptanone; alcohols such as 3-methoxybutanol, 3-methyl-3-methoxybutanol, 1-methoxy-2-propanol, 1-ethoxy-2-propanol, and diacetone alcohol (DAA): ethers such as propylene glycol monomethyl ether (PGME), ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone, which may be used alone or in admixture.

The organic solvent is preferably added in an amount of 100 to 10,000 parts, and more preferably 200 to 8,000 parts by weight per 100 parts by weight of the base polymer.

Other Components

With the foregoing components, other components such as a surfactant, dissolution inhibitor, crosslinker, and quencher other than the fluorinated cyclic ammonium salt compound may be blended in any desired combination to formulate a chemically amplified positive or negative resist composition. This positive or negative resist composition has a very high sensitivity in that the dissolution rate in developer of the base polymer in exposed areas is accelerated by catalytic reaction. In addition, the resist film has a high dissolution contrast, resolution, exposure latitude, and process adaptability, and provides a good pattern profile after exposure, and minimal proximity bias because of restrained acid diffusion. By virtue of these advantages, the composition is fully useful in commercial application and suited as a pattern-forming material for the fabrication of VLSIs.

Exemplary surfactants are described in JP-A 2008-111103, paragraphs [0165]-[0166]. Inclusion of a surfactant may improve or control the coating characteristics of the resist composition. While the surfactant may be used alone or in admixture, it is preferably added in an amount of 0.0001 to 10 parts by weight per 100 parts by weight of the base polymer.

In the case of positive resist compositions, inclusion of a dissolution inhibitor may lead to an increased difference in dissolution rate between exposed and unexposed areas and a further improvement in resolution. The dissolution inhibitor which can be used herein is a compound having at least two phenolic hydroxy groups on the molecule, in which an average of from 0 to 100 mol % of all the hydrogen atoms on the phenolic hydroxy groups are replaced by acid labile groups or a compound having at least one carboxy group on the molecule, in which an average of 50 to 100 mol % of all the hydrogen atoms on the carboxy groups are replaced by acid labile groups, both the compounds having a molecular weight of 100 to 1.000, and preferably 150 to 800. Typical are bisphenol A, trisphenol, phenolphthalein, cresol novolac, naphthalenecarboxylic acid, adamantanecarboxylic acid, and cholic acid derivatives in which the hydrogen atom on the hydroxy or carboxy group is replaced by an acid labile group, as described in U.S. Pat. No. 7,771,914 (JP-A 2008-122932, paragraphs [0155]-[0178]).

In the positive resist composition, the dissolution inhibitor is preferably added in an amount of 0 to 50 parts, more preferably 5 to 40 parts by weight per 100 parts by weight of the base polymer. The dissolution inhibitor may be used alone or in admixture.

In the case of negative resist compositions, a negative pattern may be formed by adding a crosslinker to reduce the dissolution rate of a resist film in exposed area.

Suitable crosslinkers include epoxy compounds, melamine compounds, guanamine compounds, glycoluril compounds and urea compounds having substituted thereon at least one group selected from among methylol, alkoxymethyl and acyloxymethyl groups, isocyanate compounds, azide compounds, and compounds having a double bond such as an alkenyloxy group. These compounds may be used as an additive or introduced into a polymer side chain as a pendant. Hydroxy-containing compounds may also be used as the crosslinker.

Examples of the epoxy compound include tris(2,3-epoxypropyl) isocyanurate, trimethylolmethane triglycidyl ether, trimethylolpropane triglycidyl ether, and triethylolethane triglycidyl ether. Examples of the melamine compound include hexamethylol melamine, hexamethoxymethyl melamine, hexamethylol melamine compounds having 1 to 6 methylol groups methoxymethylated and mixtures thereof, hexamethoxyethyl melamine, hexaacyloxymethyl melamine, hexamethylol melamine compounds having 1 to 6 methylol groups acyloxymethylated and mixtures thereof. Examples of the guanamine compound include tetramethylol guanamine, tetramethoxymethyl guanamine, tetramethylol guanamine compounds having 1 to 4 methylol groups methoxymethylated and mixtures thereof, tetramethoxyethyl guanamine, tetraacyloxyguanamine, tetramethylol guanamine compounds having 1 to 4 methylol groups acyloxymethylated and mixtures thereof. Examples of the glycoluril compound include tetramethylol glycoluril, tetramethoxyglycoluril, tetramethoxymethyl glycoluril, tetramethylol glycoluril compounds having 1 to 4 methylol groups methoxymethylated and mixtures thereof, tetramethylol glycoluril compounds having 1 to 4 methylol groups acyloxymethylated and mixtures thereof. Examples of the urea compound include tetramethylol urea, tetramethoxymethyl urea, tetramethylol urea compounds having 1 to 4 methylol groups methoxymethylated and mixtures thereof, and tetramethoxyethyl urea.

Suitable isocyanate compounds include tolylene diisocyanate, diphenylmethane diisocyanate, hexamethylene diisocyanate and cyclohexane diisocyanate. Suitable azide compounds include 1,1'-biphenyl-4,4'-bisazide, 4,4'-methylidenebisazide, and 4,4'-oxybisazide. Examples of the alkenyloxy group-containing compound include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylol propane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylol propane trivinyl ether.

In the negative resist composition, the crosslinker is preferably added in an amount of 0.1 to 50 parts, more preferably 1 to 40 parts by weight per 100 parts by weight of the base polymer. The crosslinker may be used alone or in admixture.

The other quencher is typically selected from conventional basic compounds. Conventional basic compounds include primary, secondary, and tertiary aliphatic amines, mixed amines, aromatic amines, heterocyclic amines, nitrogen-containing compounds with carboxy group, nitrogen-containing compounds with sulfonyl group, nitrogen-containing compounds with hydroxy group, nitrogen-containing compounds with hydroxyphenyl group, alcoholic nitrogen-containing compounds, amide derivatives, imide derivatives, and carbamate derivatives. Also included are primary, secondary, and tertiary amine compounds, specifically amine compounds having a hydroxy group, ether bond, ester bond, lactone ring, cyano group, or sulfonic acid ester bond as described in JP-A 2008-111103, paragraphs [0146]-[0164], and compounds having a carbamate group as described in JP 3790649. Addition of a basic compound may be effective for further suppressing the diffusion rate of acid in the resist film or correcting the pattern profile.

Onium salts such as sulfonium salts, iodonium salts and ammonium salts of sulfonic acids which are not fluorinated at α-position as described in U.S. Pat. No. 8,795,942 (JP-A 2008-158339) and similar onium salts of carboxylic acid may also be used as the other quencher. While an α-fluorinated sulfonic acid, imide acid, and methide acid are necessary to deprotect the acid labile group of carboxylic acid ester, an α-non-fluorinated sulfonic acid and a carboxylic acid are released by salt exchange with an α-non-fluorinated onium salt. An α-non-fluorinated sulfonic acid and a carboxylic acid function as a quencher because they do not induce deprotection reaction.

Also useful are quenchers of polymer type as described in U.S. Pat. No. 7,598,016 (JP-A 2008-239918). The polymeric quencher segregates at the resist film surface and thus enhances the rectangularity of resist pattern. When a protective film is applied as is often the case in the immersion lithography, the polymeric quencher is also effective for preventing a film thickness loss of resist pattern or rounding of pattern top.

The other quencher is preferably added in an amount of 0 to 5 parts, more preferably 0 to 4 parts by weight per 100 parts by weight of the base polymer. The other quencher may be used alone or in admixture.

To the resist composition, a water repellency improver may also be added for improving the water repellency on surface of a resist film. The water repellency improver may be used in the topcoatless immersion lithography. Suitable water repellency improvers include polymers having a fluoroalkyl group and polymers having a specific structure with a 1,1,1,3,3,3-hexafluoro-2-propanol residue and are described in JP-A 2007-297590 and JP-A 2008-111103, for example. The water repellency improver to be added to the resist composition should be soluble in the alkaline developer and organic solvent developer.

The water repellency improver of specific structure with a 1,1,1,3,3,3-hexafluoro-2-propanol residue is well soluble in the developer. A polymer having an amino group or amine salt copolymerized as repeat units may serve as the water repellent additive and is effective for preventing evaporation of acid during PEB, thus preventing any hole pattern opening failure after development. An appropriate amount of the water repellency improver is 0 to 20 parts, more preferably 0.5 to 10 parts by weight per 100 parts by weight of the base polymer. The water repellency improver may be used alone or in admixture.

Also, an acetylene alcohol may be blended in the resist composition. Suitable acetylene alcohols are described in JP-A 2008-122932, paragraphs [0179]-[0182]. An appropriate amount of the acetylene alcohol blended is 0 to 5 parts by weight per 100 parts by weight of the base polymer. The acetylene alcohol may be used alone or in admixture.

Pattern Forming Process

The resist composition is used in the fabrication of various integrated circuits. Pattern formation using the resist composition may be performed by well-known lithography processes. The process generally involves the steps of applying the resist composition to form a resist film on a substrate, exposing the resist film to high-energy radiation, and developing the exposed resist film in a developer. If necessary, any additional steps may be added.

Specifically, the resist composition is first applied onto a substrate on which an integrated circuit is to be formed (e.g., Si, $SiO_2$, SiN, SiON, TiN, WSi, BPSG, SOG, or organic antireflective coating) or a substrate on which a mask circuit is to be formed (e.g., Cr, CrO, CrON, $MoSi_2$, or $SiO_2$) by a suitable coating technique such as spin coating, roll coating, flow coating, dipping, spraying or doctor coating. The coating is prebaked on a hot plate at a temperature of 60 to 150° C. for 10 seconds to 30 minutes, preferably at 80 to 120° C. for 30 seconds to 20 minutes. The resulting resist film is generally 0.01 to 2 µm thick.

The resist film is then exposed to a desired pattern of high-energy radiation such as UV, deep-UV, EB, EUV of wavelength 3 to 15 nm, x-ray, soft x-ray, excimer laser light, γ-ray or synchrotron radiation. When UV, deep-UV, EUV, x-ray, soft x-ray, excimer laser light, γ-ray or synchrotron radiation is used as the high-energy radiation, the resist film is exposed thereto directly or through a mask having a desired pattern in a dose of preferably about 1 to 200 $mJ/cm^2$, more preferably about 10 to 100 mJ/cm. When EB is used as the high-energy radiation, the resist film is exposed thereto directly or through a mask having a desired pattern in a dose of preferably about 0.1 to 100 $\mu C/cm^2$, more preferably about 0.5 to 50 $\mu C/cm^2$. It is appreciated that the inventive resist composition is suited in micropatterning using i-line of wavelength 365 nm, KrF excimer laser, ArF excimer laser, EB. EUV, x-ray, soft x-ray. γ-ray or synchrotron radiation, especially in micropatterning using EB or EUV.

After the exposure, the resist film may or may not be baked (PEB) on a hot plate or in an oven at 30 to 150° C. for 10 seconds to 30 minutes, preferably at 50 to 120° C. for 30 seconds to 20 minutes.

After the exposure or PEB, the resist film is developed in a developer in the form of an aqueous base solution for 3 seconds to 3 minutes, preferably 5 seconds to 2 minutes by conventional techniques such as dip, puddle and spray techniques. A typical developer is a 0.1 to 10 wt %, preferably 2 to 5 wt % aqueous solution of tetramethylammoniun hydroxide (TMAH), tetraethylammonium hydroxide (TEAH), tetrapropylammonium hydroxide (TPAH), or tetrabutylammonium hydroxide (TBAH). In the case of positive resist, the resist film in the exposed area is dissolved in the developer whereas the resist film in the unexposed area is not dissolved. In this way, the desired positive pattern is formed on the substrate. Inversely in the case of negative resist, the exposed area of resist film is insolubilized whereas the unexposed area is dissolved in the developer.

In an alternative embodiment, a negative pattern may be formed via organic solvent development using a positive resist composition comprising a base polymer having an acid labile group. The developer used herein is preferably selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alcohols of 3 to 10 carbon atoms include n-propyl alcohol, isopropyl alcohol, 1-butyl alcohol, 2-butyl alcohol, isobutyl alcohol, tert-butyl alcohol, 1-pentanol, 2-pentanol, 3-pentanol, tert-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-sec-butyl ether, di-n-pentyl ether, diisopentyl ether, di-sec-pentyl ether, di-tert-pentyl ether, and di-n-hexyl ether. Suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable aromatic solvents include toluene, xylene, ethylbenzene, isopropylbenzene, tert-butylbenzene and mesitylene. The solvents may be used alone or in admixture.

Rinsing is effective for minimizing the risks of resist pattern collapse and defect formation. However, rinsing is not essential. If rinsing is omitted, the amount of solvent used may be reduced.

A hole or trench pattern after development may be shrunk by the thermal flow, RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

EXAMPLES

Examples of the invention are given below by way of illustration and not by way of limitation. The abbreviation "pbw" is parts by weight.

Synthesis Example 1-1

Synthesis of Quencher Q-1
(1) Synthesis of Intermediate In-1

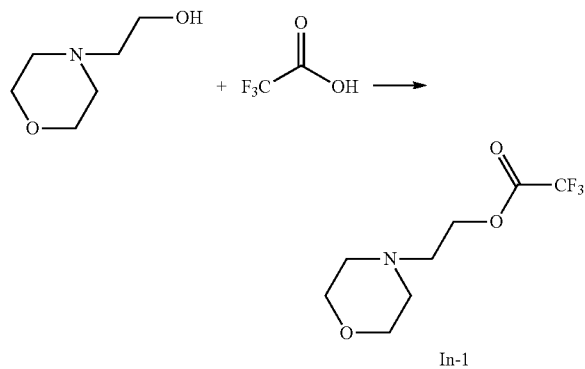

In nitrogen atmosphere, a flask in an ice bath was charged with 5.0 g of 4-(2-hydroxyethyl)morpholine and 100 g of methylene chloride, to which 11.4 g of trifluoroacetic acid was added dropwise. At the end of addition, the reaction system was warmed up to room temperature and aged for 17 hours. At the end of aging, the solvent and the excess of trifluoroacetic acid were distilled off, leaving a fluorinated cyclic amine compound (Intermediate In-1) as oily matter (amount 8.7 g, yield 100%).

(2) Synthesis of Quencher Q-1

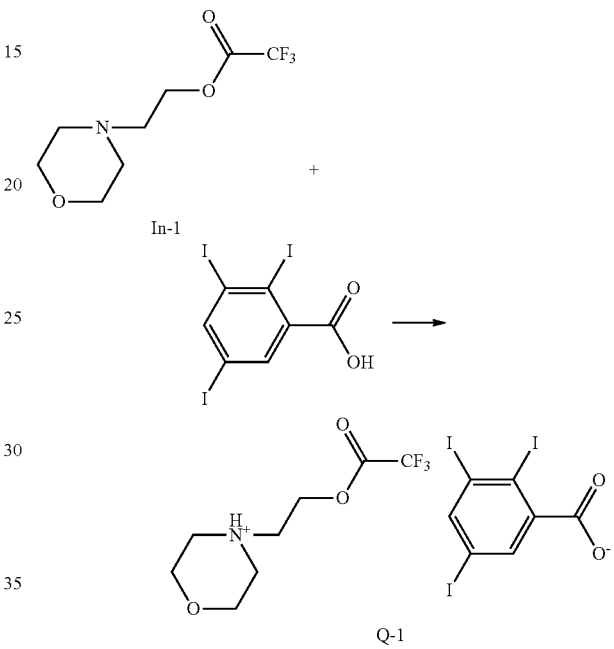

In nitrogen atmosphere, a flask was charged with 1.0 g of Intermediate In-1, 2.2 g of 2,3,5-triiodobenzoic acid, and 5 g of tetrahydrofuran (THF), which were stirred at room temperature for 30 minutes. The solvent was distilled off, leaving Quencher Q-1 as solids (amount 3.3 g, yield 100%).

Quencher Q-1 was analyzed by IR spectroscopy and TOF-MS, with the results shown below. FIGURE is the $^1$H-NMR/DMSO-$d_6$ spectrum of Quencher Q-1. In the $^1$H-NMR, a trace of residual solvent (THF) was observed.

IR (D-ATR): ν=3062, 1780, 1707, 1595, 1543, 1520, 1410, 1392, 1374, 1361, 1276, 1222, 1197, 1108, 1066, 1017, 1002, 911, 871, 839, 799, 778, 723, 706, 688, 677, 595, 509, 457 cm$^{-1}$

TOF-MS (MALDI): positive M$^+$ 228 (corresponding to $C_8H_{13}F_3NO_3^+$)

Synthesis Examples 1-2 to 1-35

Synthesis of Quenchers Q-2 to Q-35

Quenchers Q-2 to Q-35 were synthesized as in Synthesis Example 1-1 by mixing a fluorinated cyclic amine compound with a carboxylic acid compound, sulfonamide compound, halogenated phenol compound or hydrogen halide compound in a molar ratio of 1:1. Quenchers Q-1 to Q-35 have the structure shown below.

333
Q-1
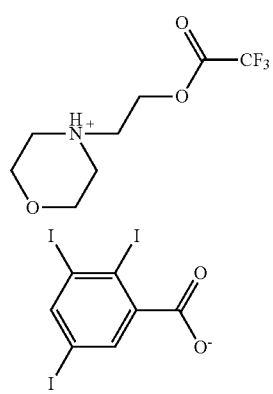
Q-2
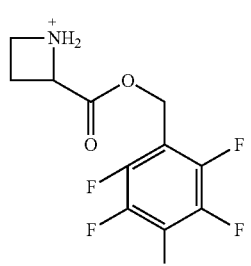
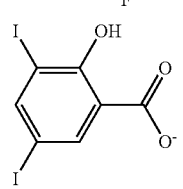
Q-3
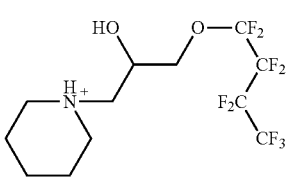
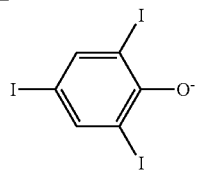
Q-4
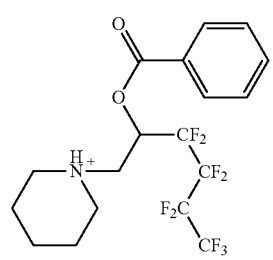
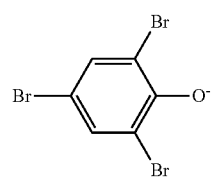
334
-continued
Q-5
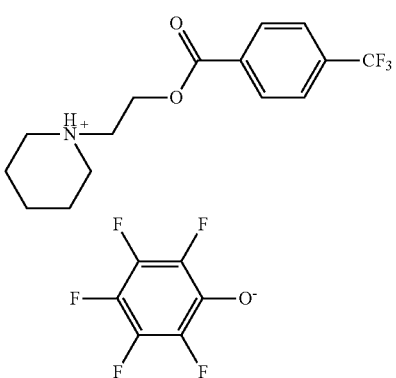
Q-6
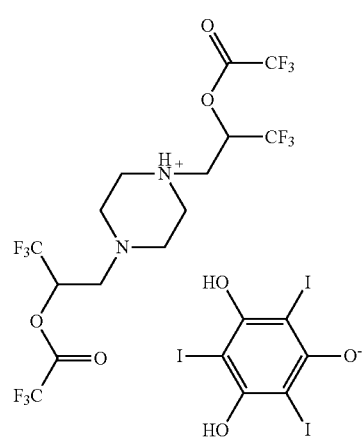
Q-7
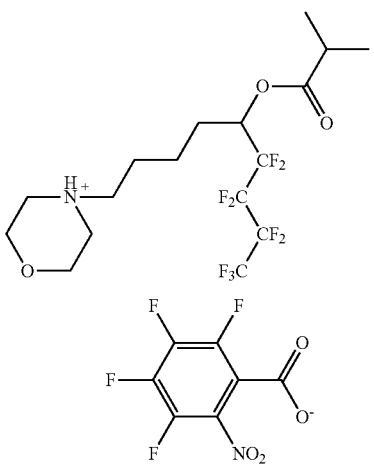

-continued
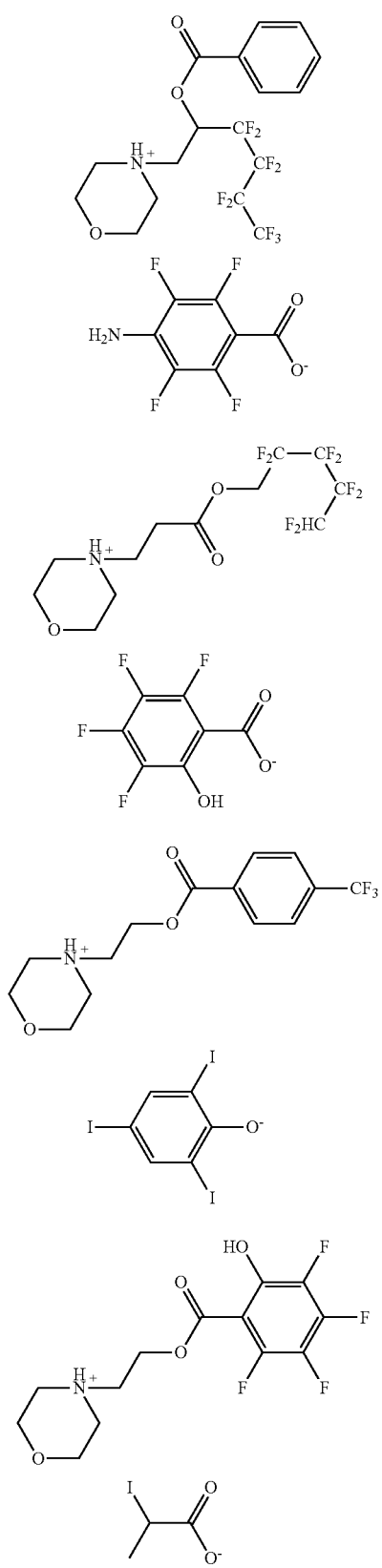
Q-8
Q-9
Q-10
Q-11
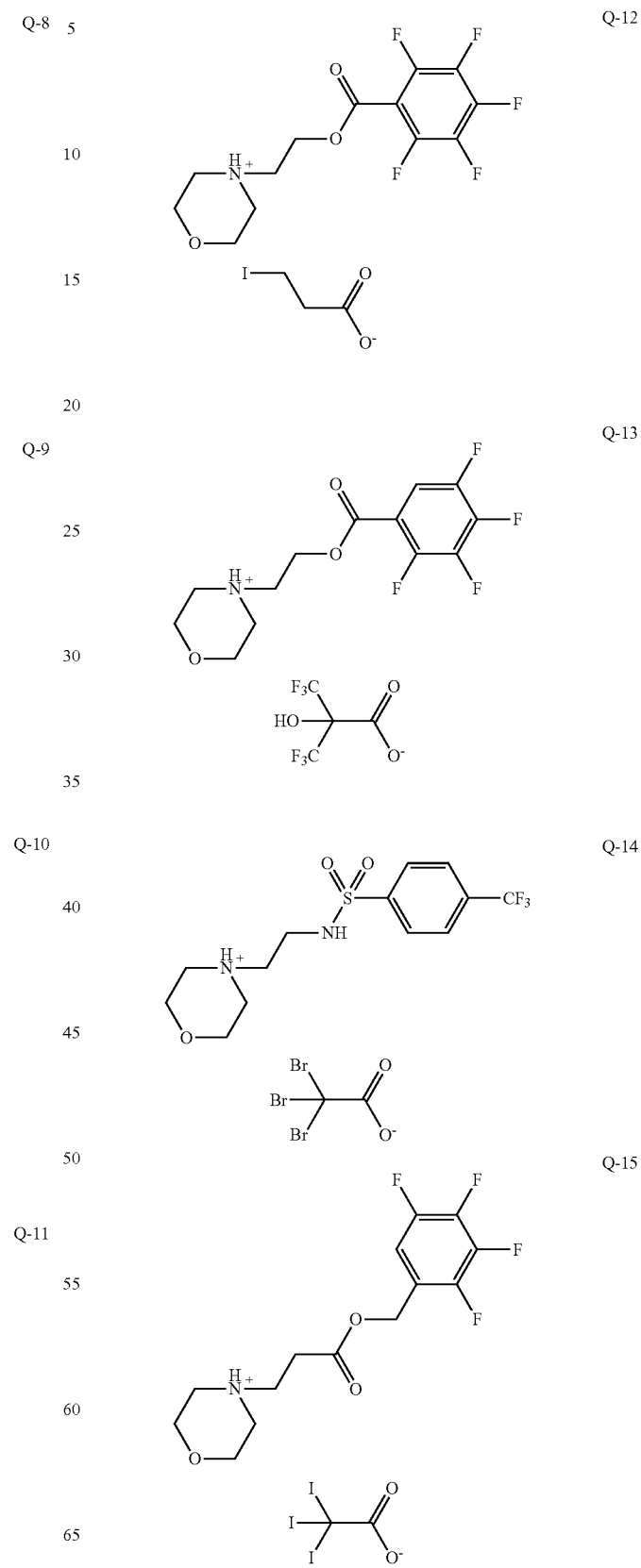
Q-12
Q-13
Q-14
Q-15

-continued
Q-16
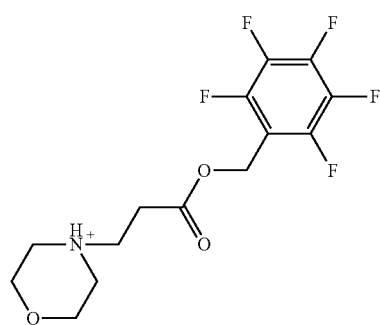
Q-17
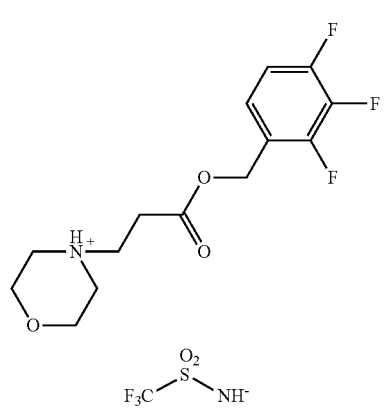
Q-18
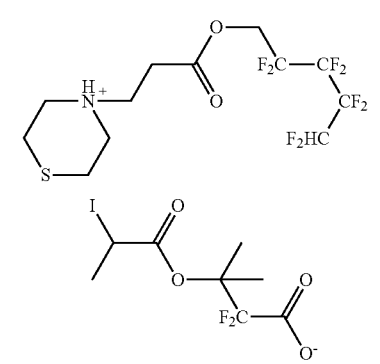
Q-19
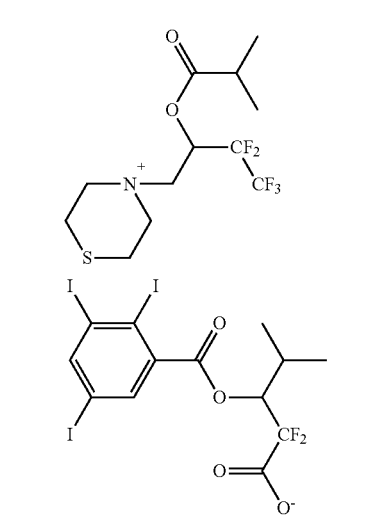
-continued
Q-20
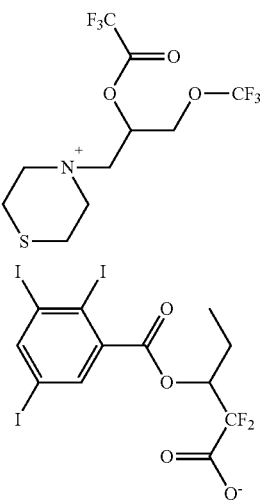
Q-21
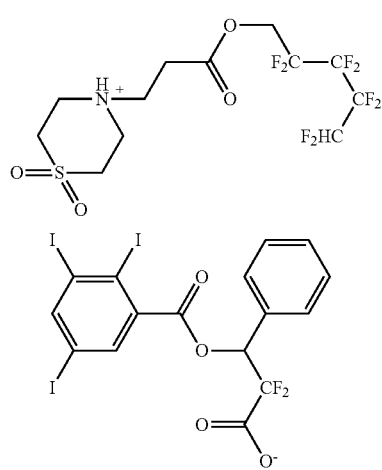
Q-22
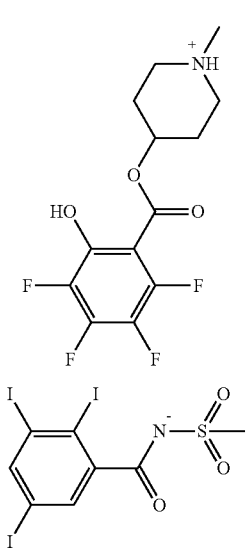

-continued
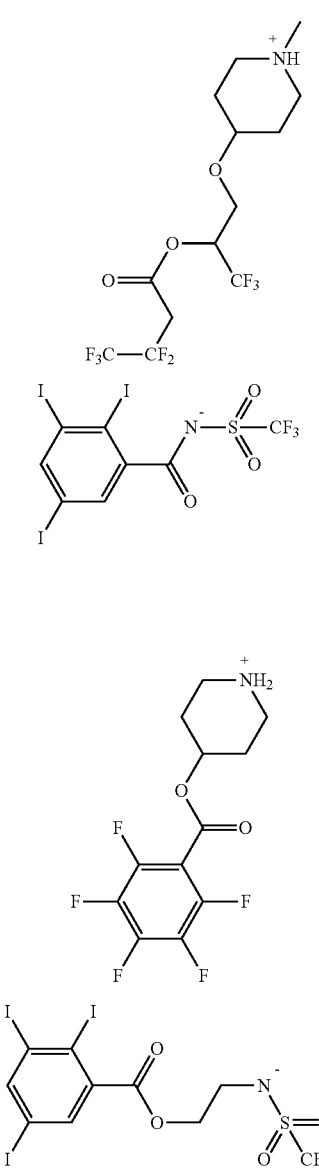
Q-23
Q-24
Q-25
-continued
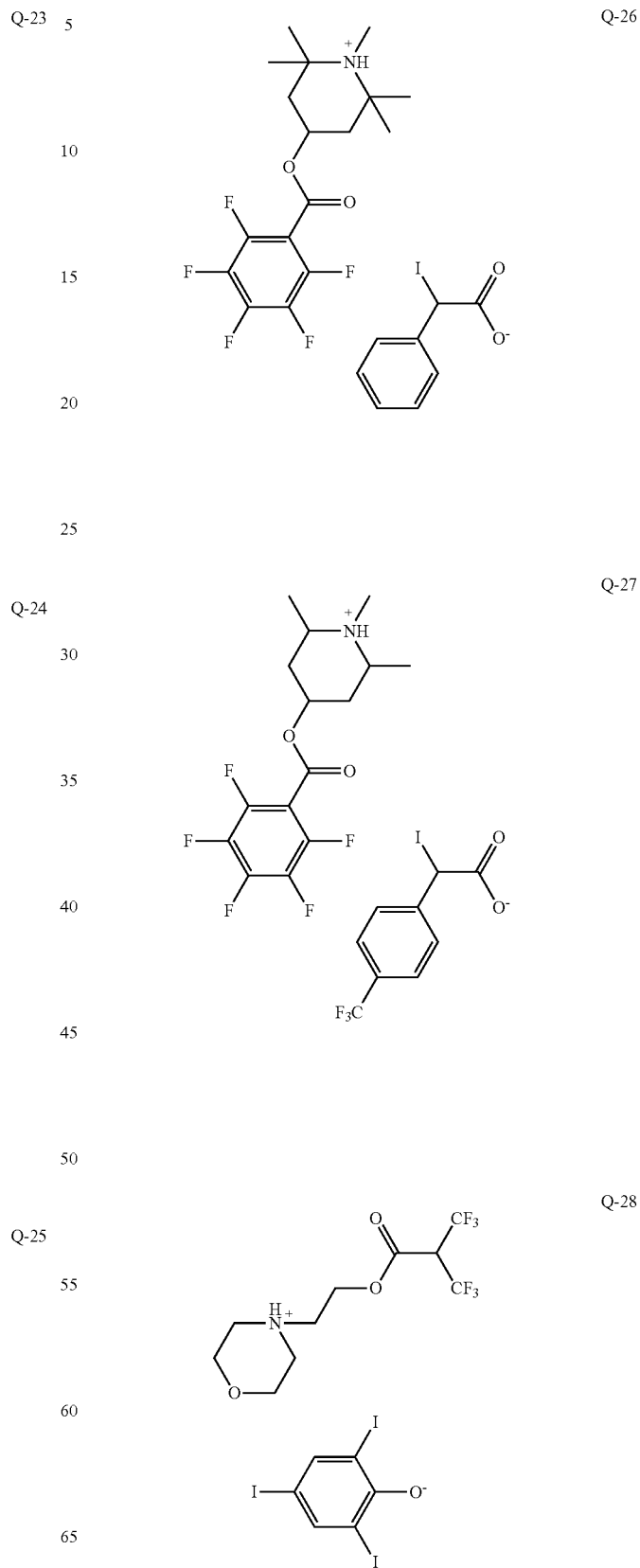
Q-26
Q-27
Q-28

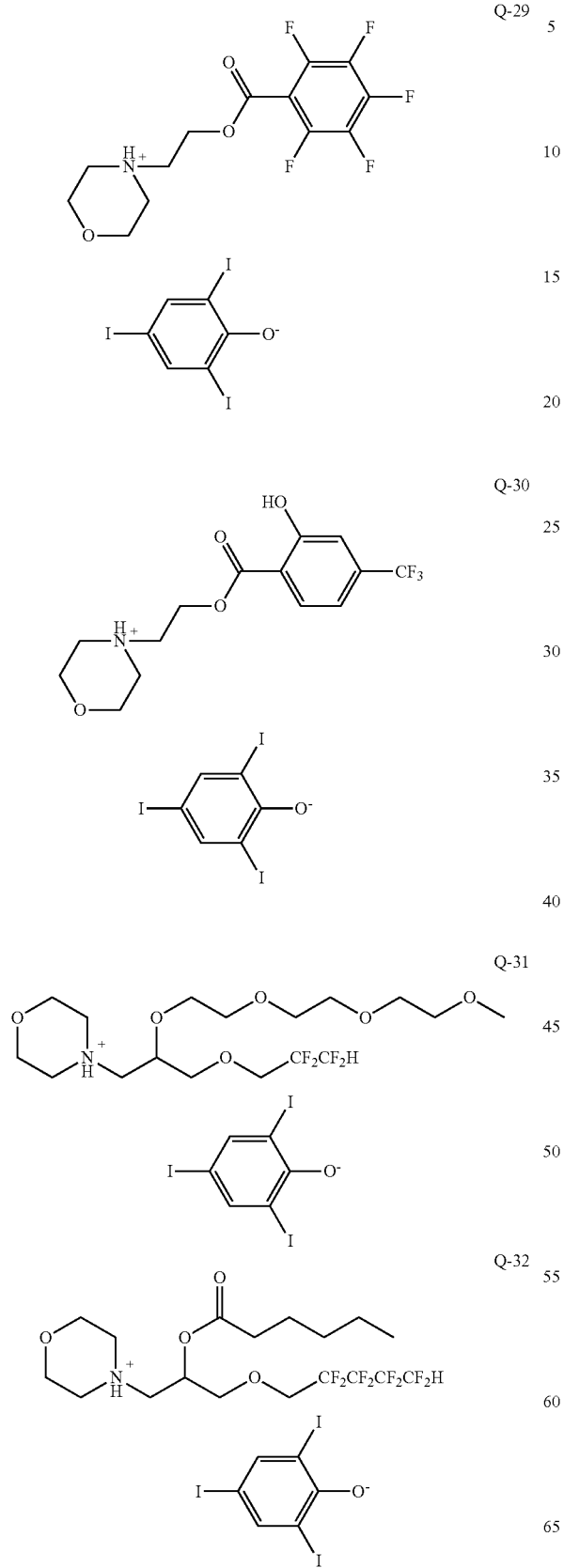
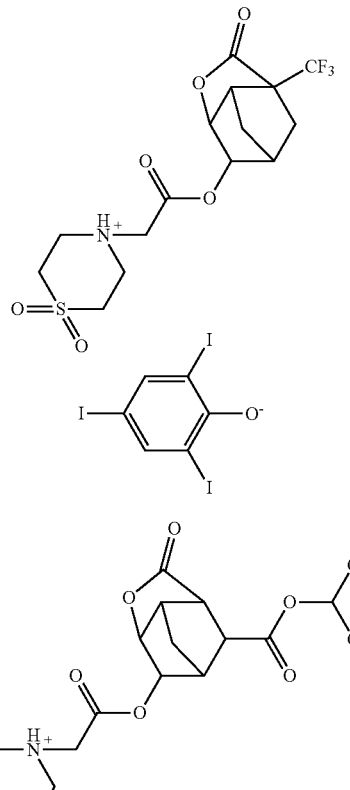
Synthesis Examples 2-4 to 2-4
Synthesis of base polymers (Polymers P-1 to P-4)
Base polymers (Polymers P-1 to P-4) were prepared by combining suitable monomers, effecting copolymerization reaction thereof in THF solvent, pouring the reaction solution into methanol for crystallization, repeatedly washing the solid precipitate with hexane, isolation, and drying. The resulting polymers were analyzed for composition by ¹H-NMR spectroscopy, and for Mw and Mw/Mn by GPC versus polystyrene standards using THF solvent.

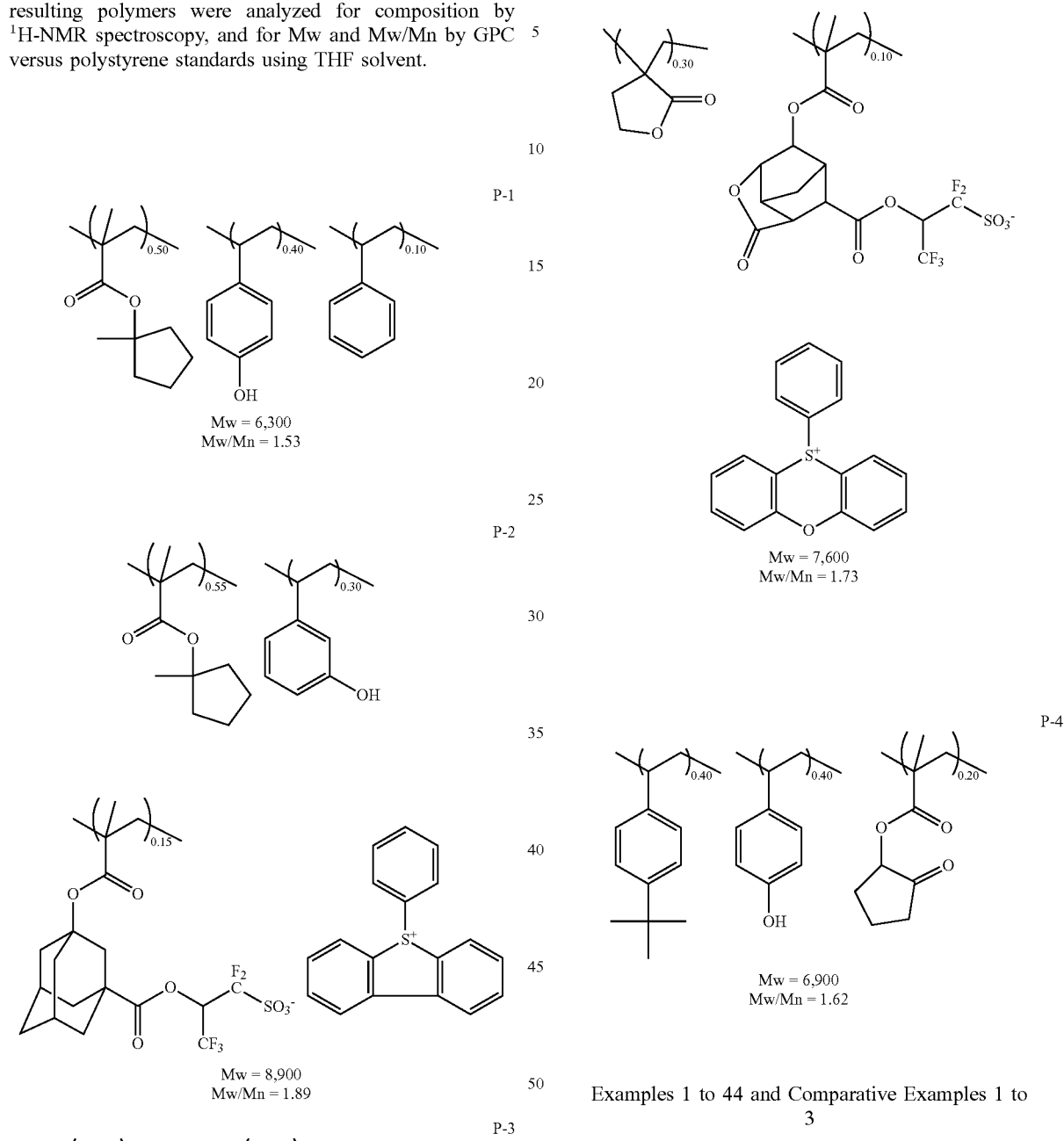

Examples 1 to 44 and Comparative Examples 1 to 3

(1) Preparation of Resist Compositions

Resist compositions were prepared by dissolving various components in a solvent in accordance with the recipe shown in Tables 1 to 3, and filtering through a filter having a pore size of 0.2 μm. The resist compositions of Examples 1 to 21, 23 to 44 and Comparative Examples 1, 2 were of positive tone whereas the resist compositions of Example 22 and Comparative Example 3 were of negative tone.

The components in Tables 1 to 3 are as identified below.

Organic Solvent:

PGMEA (propylene glycol monomethyl ether acetate)

DAA (diacetone alcohol)

Acid generator: PAG-1 to PAG-4 of the following structural formulae
PAG-1
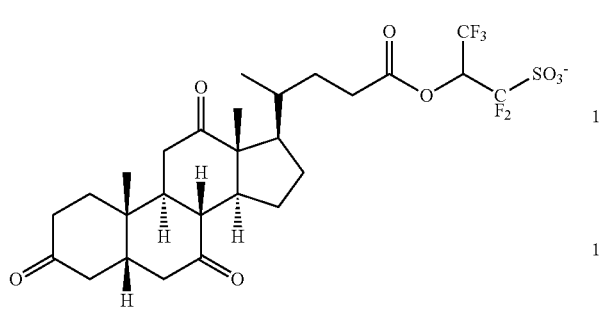
PAG-2
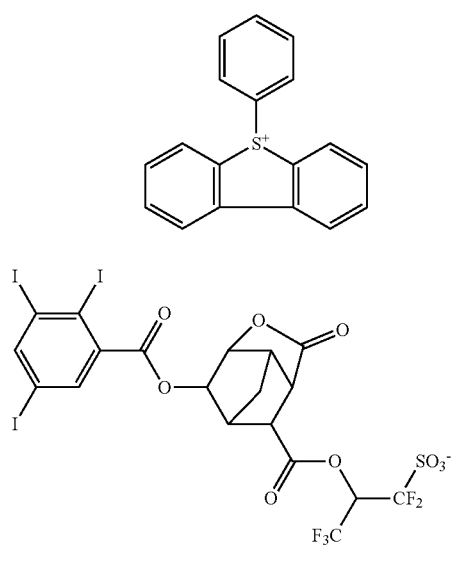
PAG-3
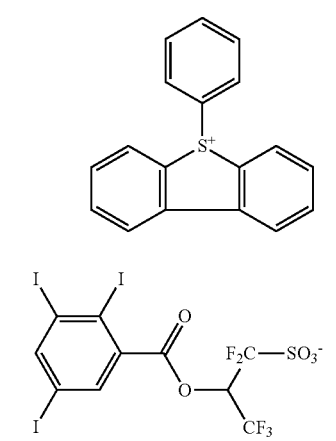
-continued
PAG-4
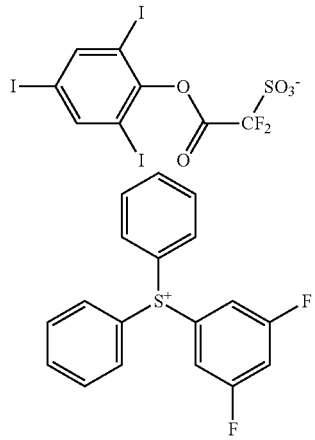
Blend Quenchers bQ-1 to bQ-3 of the following structural formulae
bQ-1
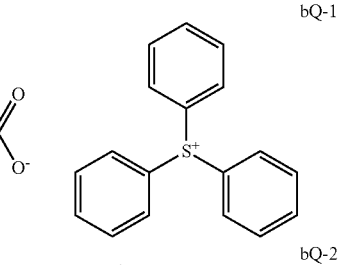
bQ-2
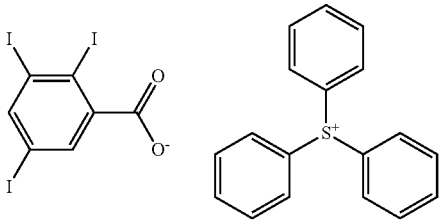
bQ-3
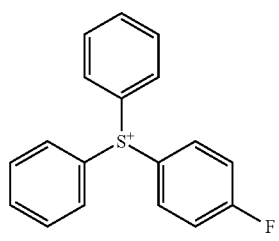
Comparative Quenchers cQ-1 and cQ-2 of the following structural formulae
cQ-1
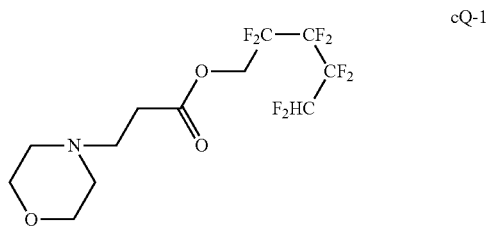

-continued

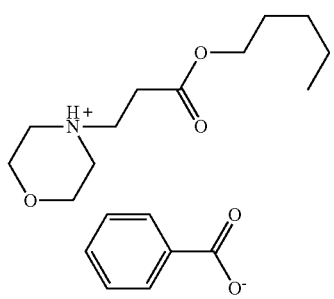

cQ-2

(2) EUV Lithography Test

Each of the resist compositions in Tables 1 to 3 was spin coated on a silicon substrate having a 20-nm coating of silicon-containing spin-on hard mask SHB-A940 (Shin-Etsu Chemical Co., Ltd., silicon content 43 wt %) and prebaked on a hotplate at 100° C. for 60 seconds to form a resist film of 50 nm thick. Using an EUV scanner NXE3300 (ASML, NA 0.33, σ 0.9/0.6, quadrupole illumination), the resist film was exposed to EUV through a mask bearing a hole pattern at a pitch 44 nm (on-wafer size) and +20% bias. The resist film was baked (PEB) on a hotplate at the temperature shown in Tables 1 to 3 for 60 seconds and developed in a 2.38 wt % TMAH aqueous solution for 30 seconds to form a hole pattern having a size of 22 nm in Examples 1 to 21, 23 to 44, and Comparative Examples 1, 2 or a dot pattern having a size of 22 nm in Example 22 and Comparative Example 3.

The resist pattern was evaluated using CD-SEM (CG6300, Hitachi High-Technologies Corp.). The exposure dose that provides a hole or dot pattern having a size of 22 nm is reported as sensitivity. The size of 50 holes or dots in that dose was measured, from which a 3-fold value (3σ) of standard deviation (σ) was computed and reported as a size variation or CDU.

The resist composition is shown in Tables 1 to 3 together with the sensitivity and CDU of EUV lithography.

TABLE 1

| Example | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|
| 1 | P-1 (100) | PAG-1 (30) | Q-1 (7.80) | PGMEA (3,000) DAA (500) | 85 | 36 | 1.3 |
| 2 | P-1 (100) | PAG-2 (30) | Q-2 (6.71) | PGMEA (3,000) DAA (500) | 85 | 31 | 3.2 |
| 3 | P-1 (100) | PAG-2 (30) | Q-3 (8.49) | PGMEA (3,000) DAA (500) | 85 | 32 | 3.2 |
| 4 | P-1 (100) | PAG-2 (30) | Q-4 (7.82) | PGMEA (3,000) DAA (500) | 85 | 33 | 3.3 |
| 5 | P-1 (100) | PAG-2 (30) | Q-5 (4.85) | PGMEA (3,000) DAA (500) | 85 | 35 | 3.3 |
| 6 | P-1 (100) | PAG-2 (30) | Q-6 (10.05) | PGMEA (3,000) DAA (500) | 85 | 36 | 3.1 |
| 7 | P-1 (100) | PAG-2 (30) | Q-7 (7.02) | PGMEA (3,000) DAA (500) | 85 | 37 | 1.4 |
| 8 | P-1 (100) | PAG-2 (30) | Q-8 (6.62) | PGMEA (3,000) DAA (500) | 85 | 38 | 3.2 |
| 9 | P-1 (100) | PAG-2 (30) | Q-9 (5.85) | PGMEA (3,000) DAA (500) | 85 | 36 | 3.6 |
| 10 | P-1 (100) | PAG-2 (30) | Q-10 (735) | PGMEA (3,000) DAA (500) | 85 | 34 | 3.4 |
| 11 | P-1 (100) | PAG-2 (30) | Q-11 (5.23) | PGMEA (3,000) DAA (500) | 85 | 36 | 3.6 |
| 12 | P-1 (100) | PAG-2 (30) | Q-12 (5.25) | PGMEA (3,000) DAA (500) | 85 | 36 | 3.4 |
| 13 | P-1 (100) | PAG-2 (30) | Q-13 (5.19) | PGMEA (3,000) DAA (500) | 85 | 36 | 3.1 |
| 14 | P-1 (100) | PAG-2 (30) | Q-14 (6.35) | PGMEA (3,000) DAA (500) | 85 | 36 | 3.4 |
| 15 | P-1 (100) | PAG-2 (30) | Q-15 (7.59) | PGMEA (3,000) DAA (500) | 85 | 31 | 1.6 |
| 16 | P-1 (100) | PAG-2 (30) | Q-16 (4.67) | PGMEA (3,000) DAA (500) | 85 | 29 | 3.7 |
| 17 | P-1 (100) | PAG-2 (30) | Q-17 (4.52) | PGMEA (3,000) DAA (500) | 85 | 36 | 3.2 |
| 18 | P-2 (100) | — | Q-10 (7.75) | PGMEA (3,000) DAA (500) | 90 | 35 | 1.2 |
| 19 | P-3 (100) | — | Q-10 (7.75) | PGMEA (3,000) DAA (500) | 90 | 32 | 3.4 |
| 20 | P-3 (100) | PAG-3 (4) | Q-10 (7.75) | PGMEA (3,000) DAA (500) | 90 | 30 | 3.5 |

TABLE 2

| Example | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|
| 21 | P-3 (100) | PAG-4 (4) | Q-10 (7.75) | PGMEA (3.000) DAA (500) | 90 | 31 | 1.5 |
| 22 | P-4 (100) | PAG-2 (30) | Q-10 (7.75) | PGMEA (3.000) DAA (500) | 110 | 39 | 3.9 |

TABLE 2-continued

| Example | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|
| 23 | P-1 (100) | PAG-2 (30) | Q-18 (7.25) | PGMEA (3,000) DAA (500) | 85 | 34 | 1.5 |
| 24 | P-1 (100) | PAG-2 (30) | Q-19 (9.85) | PGMEA (3,000) DAA (500) | 85 | 33 | 3.6 |
| 25 | P-1 (100) | PAG-2 (30) | Q-20 (9.77) | PGMEA (3,000) D.AA (500) | 85 | 34 | 3.4 |
| 26 | P-1 (100) | PAG-2 (30) | Q-21 (11.05) | PGMEA (3,000) DAA (500) | 85 | 36 | 3.6 |
| 27 | P-1 (100) | PAG-2 (30) | Q-22 (8.84) | PGMEA (3,000) DAA (500) | 85 | 36 | 3.2 |
| 28 | P-1 (100) | PAG-2 (30) | Q-23 (10.17) | PGMEA (3,000) DAA (500) | 8.5 | 33 | 1.4 |
| 29 | P-1 (100) | PAG-2 (30) | Q-24 (9.70) | PGMEA (3,000) DAA (500) | 85 | 33 | 3.2 |
| 30 | p-1 (100) | PAG-2 (30) | Q-25 (6.31) | PGMEA (3,000) DAA (500) | 85 | 34 | 3.4 |
| 31 | P-1 (100) | PAG-2 (30) | Q-26 (6.09) | PGMEA (3,000) DAA (500) | 85 | 36 | 3.4 |
| 32 | P-1 (100) | PAG-2 (30) | Q-27 (6.67) | PGMEA (3,000) DAA (500) | 85 | 37 | 1.3 |
| 33 | P-1 (100) | PAG-2 (30) | eQ-1 (3.73) 2,3,5-triiodobenzoic acid (5.00) | PGMEA (3,000) DAA (500) | 85 | 35 | 3.5 |
| 34 | P-1 (100) | PAG-2 (30) | bQ-1 (2.36) Q-10 (3.87) | PGMEA (3,000) DAA (500) | 85 | 34 | 3.2 |
| 35 | P-1 (100) | PAG-2 (30) | bQ-2 (2.36) Q-10 (3.87) | PGMEA (3,000) DAA (500) | 8.5 | 35 | 1.0 |
| 36 | P-1 (100) | PAG-2 (30) | bQ-3 (3.81) Q-10 (3.87) | PGMEA (3,000) DAA (500) | 85 | 12 | 3.3 |
| 37 | P-1 (100) | PAG-2 (30) | bQ-2 (2.36) Q-28 (3.90) | PGMEA (3,000) DAA (500) | 85 | 33 | 3.1 |
| 38 | P-1 (100) | PAG-2 (30) | bQ-2 (2.36) Q-29 (3.98) | PGMEA (3,000) DAA (500) | 85 | 34 | 3.1 |
| 39 | P-1 (100) | PAG-2 (30) | bQ-2 (2.39) Q-30 (3.95) | PGMEA (3,000) DAA (500) | 8.5 | 35 | 1.2 |
| 40 | P-1 (100) | PAG-2 (30) | bQ-2 (2.36) Q-31 (4.46) | PGMEA (3.000) DAA (500) | 85 | 32 | 3.3 |
| 41 | P-1 (100) | PAG-2 (30) | bQ-2 (2.36) Q-32 (4.72) | PGMEA (3,000) DAA (500) | 85 | 31 | 3.3 |
| 42 | P-1 (100) | PAG-2 (30) | bQ-2 (2.36) Q-33 (4.35) | PGMEA (3,000) DAA (500) | 85 | 34 | 3.0 |
| 43 | P-1 (100) | PAG-2 (30) | bQ-2 (2.36) Q-34 (4.74) | PGMEA (3,000) DAA (500) | 85 | 32 | 3.0 |
| 44 | P-1 (100) | PAG-2 (30) | bQ-2 (2.36) Q-35 (4.10) | PGMEA (3.000) DAA (500) | 85 | 31 | 3.1 |

TABLE 3

| Comparative Example | Polymer (pbw) | Acid generator (pbw) | Quencher (pbw) | Organic solvent (pbw) | PEB temp (° C.) | Sensitivity (mJ/cm$^2$) | CDU (nm) |
|---|---|---|---|---|---|---|---|
| 1 | P-1 (100) | PAG-2 (30) | cQ-1 (3.73) | PGMEA (3,000) DAA (500) | 85 | 37 | 4.5 |
| 2 | P-1 (100) | PAG-2 (30) | cQ-2 (3.51) | PGMEA (3,000) DAA (500) | 85 | 42 | 4.2 |
| 3 | P-4 (100) | PAG-1 (20) | cQ-1 (3.73) | PGMEA (3,000) DAA (500) | 110 | 14 | 5.1 |

It is demonstrated in Tables 1 to 3 that resist compositions comprising fluorinated cyclic ammonium salt compounds have a high sensitivity and form patterns with a reduced value of CDU.

Japanese Patent Application Nos. 2020-132114 and 2021-041923 are incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A resist composition comprising a base polymer and a quencher, said quencher comprising a salt compound having the formula (A):

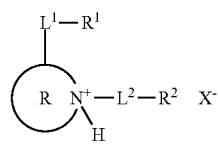
(A)

wherein the ring R is a $C_2$-$C_{12}$ alicyclic group containing the nitrogen atom, the ring may contain an ether bond, thioether bond, carbonyl group, —N(R')— or sulfonyl group, R' is hydrogen, a $C_1$-$C_6$ saturated hydrocarbyl group or -$L^3$-$R^3$, $L^1$, $L^2$ and $L^3$ are each independently a single bond, ester bond, sulfonyl group, or $C_1$-$C_6$ alkanediyl group, some hydrogen in the alkanediyl group may be substituted by a hydroxy moiety, optionally fluorinated $C_1$-$C_{12}$ hydrocarbyloxy moiety, or optionally fluorinated $C_2$-$C_{12}$ hydrocarbylcarbonyloxy moiety, and any methylene constituent in the alkanediyl group may be replaced by an ether bond, ester bond, amide bond, sulfonyl moiety, sulfonate bond, or sulfonamide bond, with the proviso that $L^1$, $L^2$ and $L^3$ do not contain a tertiary ester structure, $R^1$, $R^2$ and $R^3$ are each independently hydrogen, a $C_1$-$C_{16}$ saturated hydrocarbyl group, $C_6$-$C_{10}$ aryl group, $C_1$-$C_{16}$ saturated hydrocarbyl group substituted with at least three fluorine atoms, $C_6$-$C_{10}$ aryl group substituted with at least three fluorine atoms, or a combination thereof, one or both of $R^1$ and $R^2$ have at least three fluorine atoms, and $X^-$ is a carboxylate, sulfonamide, halogenated phenoxide or halide anion.

2. The resist composition of claim 1 wherein $X^-$ is a fluorinated or brominated carboxylate, fluorinated or brominated sulfonamide, or fluorinated or brominated phenoxide anion.

3. The resist composition of claim 1, further comprising an acid generator capable of generating a sulfonic acid, imide acid or methide acid.

4. The resist composition of claim 1, further comprising an organic solvent.

5. The resist composition of claim 1 wherein the base polymer comprises repeat units having the formula (a1) or repeat units having the formula (a2):

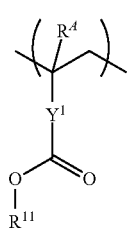
(a1)

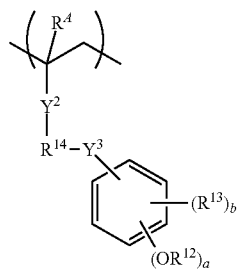
(a2)

wherein $R^A$ is each independently hydrogen or methyl,
$Y^1$ is a single bond, phenylene, naphthylene, or a $C_1$-$C_{12}$ linking group containing an ester bond and % or lactone ring,
$Y^2$ is a single bond or ester bond,
$Y^3$ is a single bond, ether bond or ester bond,
$R^{11}$ and $R^{12}$ are each independently an acid labile group,
$R^{13}$ is fluorine, trifluoromethyl, cyano or $C_1$-$C_6$ saturated hydrocarbyl group,
$R^{14}$ is a single bond or a $C_1$-$C_6$ alkanediyl group in which some carbon may be replaced by an ether bond or ester bond,
a is 1 or 2, b is an integer of 0 to 4, and $1 \leq a+b \leq 5$.

6. The resist composition of claim 5 which is a chemically amplified positive resist composition.

7. The resist composition of claim 1 wherein the base polymer is free of an acid labile group.

8. The resist composition of claim 7 which is a chemically amplified negative resist composition.

9. The resist composition of claim 1, further comprising a surfactant.

10. The resist composition of claim 1 wherein the base polymer comprises repeat units of at least one type selected from repeat units having the formulae (f1) to (f3):

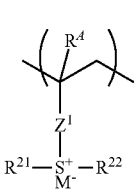
(f1)

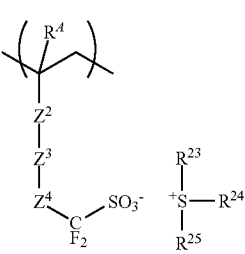
(f2)

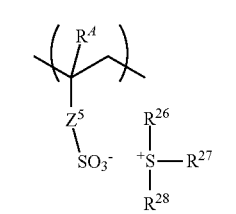
(f3)

wherein $R^4$ is each independently hydrogen or methyl, $Z^1$ is a single bond, a $C_1$-$C_6$ aliphatic hydrocarbylene group, phenylene group, naphthylene group, or $C_7$-$C_{18}$ group obtained by combining the foregoing, or —O—$Z^{11}$—, —C(=O)—O—$Z^{11}$— or —C(=O)—NH—$Z^{11}$—, $Z^{11}$ is a $C_1$-$C_6$ aliphatic hydrocarbylene group, phenylene group, naphthylene group, or $C_7$-$C_{18}$ group obtained by combining the foregoing, which may contain a carbonyl moiety, ester bond, ether bond or hydroxy moiety, $Z^2$ is a single bond or ester bond, $Z^3$ is a single bond, —$Z^{31}$—C(=O)—O—, —$Z^{31}$—O— or —$Z^{31}$—O—C(=O)—, $Z^{31}$ is a $C_1$-$C_{12}$ hydrocarbylene group, phenylene group, or $C_7$-$C_{18}$ group obtained by combining the foregoing, which may contain a carbonyl moiety, ester bond, ether bond, iodine or bromine, $Z^4$ is a methylene, 2,2,2-trifluoro-1,1-ethanediyl or carbonyl group, $Z^5$ is a single bond, methylene, ethylene, phenylene, fluorinated phenylene, trifluoromethyl-substituted phenylene group, —O—$Z^{51}$—, —C(=O)—O—$Z^{51}$— or —C(=O)—NH—$Z^{51}$—, $Z^{51}$ is a $C_1$-$C_6$ aliphatic hydrocarbylene group, phenylene group, fluorinated phenylene group, or trifluoromethyl-substituted phenylene group, which may contain a carbonyl moiety, ester bond, ether bond or hydroxy moiety, $R^{21}$ to $R^{28}$ are each independently halogen or a $C_1$-$C_{20}$ hydrocarbyl group which may contain a heteroatom, a pair of $R^{23}$ and $R^{24}$ or $R^{26}$ and $R^{27}$ may bond together to form a ring with the sulfur atom to which they are attached, and $M^-$ is a non-nucleophilic counter ion.

11. A pattern forming process comprising the steps of applying the resist composition of claim 1 to form a resist film on a substrate, exposing the resist film to high-energy radiation, and developing the exposed resist film in a developer.

12. The process of claim 11 wherein the high-energy radiation is i-line of wavelength 365 nm, ArF excimer laser of wavelength 193 nm or KrF excimer laser of wavelength 248 nm.

13. The process of claim 11 wherein the high-energy radiation is EB or EUV of wavelength 3 to 15 nm.

14. A salt compound having the formula (A'):

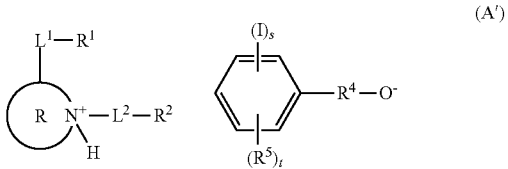

wherein the ring R is a $C_2$-$C_{12}$ alicyclic group containing the nitrogen atom, the ring may contain an ether bond, thioether bond, carbonyl group, —N(R')— or sulfonyl group, R' is hydrogen, a $C_1$-$C_6$ saturated hydrocarbyl group or -$L^3$-$R^3$, $L^1$, $L^2$ and $L^3$ are each independently a single bond, ester bond, sulfonyl group, or $C_1$-$C_6$ alkanediyl group, some hydrogen in the alkanediyl group may be substituted by a hydroxy moiety, optionally fluorinated $C_1$-$C_{12}$ hydrocarbyloxy moiety, or optionally fluorinated $C_2$-$C_{12}$ hydrocarbylcarbonyloxy moiety, and any methylene constituent in the alkanediyl group may be replaced by an ether bond, ester bond, amide bond, sulfonyl moiety, sulfonate bond, or sulfonamide bond, with the proviso that $L^1$, $L^2$ and $L^3$ do not contain a tertiary ester structure, $R^1$, $R^2$ and $R^3$ are each independently hydrogen, a $C_1$-$C_{16}$ saturated hydrocarbyl group, $C_6$-$C_{10}$ aryl group, $C_1$-$C_{16}$ saturated hydrocarbyl group substituted with at least three fluorine atoms, $C_6$-$C_{10}$ aryl group substituted with at least three fluorine atoms, or a combination thereof, one or both of $R^1$ and $R^2$ have at least three fluorine atoms, $R^4$ is a single bond or carbonyl group, $R^5$ is hydrogen, hydroxy group, optionally halogenated $C_1$-$C_6$ saturated hydrocarbyl group, optionally halogenated $C_1$-$C_6$ saturated hydrocarbyloxy group, optionally halogenated $C_2$-$C_7$ saturated hydrocarbylcarbonyloxy group, optionally halogenated $C_1$-$C_4$ saturated hydrocarbylsulfonyloxy group, fluorine, chlorine, bromine, amino group, nitro group, cyano group, —N($R^{51}$)—C(=O)—$R^{52}$, or —N($R^{51}$)—C(=O)—O—$R^{52}$, $R^{51}$ is hydrogen or a $C_1$-$C_6$ saturated hydrocarbyl group, $R^{52}$ is a $C_1$-$C_6$ saturated hydrocarbyl group or $C_2$-$C_8$ unsaturated aliphatic hydrocarbyl group, s is an integer of 1 to 5, t is an integer of 0 to 3, and $1 \leq s+t \leq 5$.

* * * * *